(12) United States Patent
Liao et al.

(10) Patent No.: US 9,150,889 B2
(45) Date of Patent: Oct. 6, 2015

(54) ELECTRO-AUTOTROPHIC SYNTHESIS OF HIGHER ALCOHOLS

(75) Inventors: James C. Liao, Los Angeles, CA (US); Kwang Myung Cho, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 506 days.

(21) Appl. No.: 13/522,288

(22) PCT Filed: Jan. 15, 2011

(86) PCT No.: PCT/US2011/021436
§ 371 (c)(1),
(2), (4) Date: Jan. 14, 2013

(87) PCT Pub. No.: WO2011/088425
PCT Pub. Date: Jul. 21, 2011

(65) Prior Publication Data
US 2013/0130341 A1 May 23, 2013

Related U.S. Application Data

(60) Provisional application No. 61/295,656, filed on Jan. 15, 2010.

(51) Int. Cl.
| | | |
|---|---|---|
| C12P 7/22 | (2006.01) | |
| C12P 7/16 | (2006.01) | |
| C12N 9/04 | (2006.01) | |
| C12N 9/88 | (2006.01) | |
| C12P 7/04 | (2006.01) | |

(52) U.S. Cl.
CPC ............... *C12P 7/16* (2013.01); *C12N 9/0006* (2013.01); *C12N 9/88* (2013.01); *C12P 7/04* (2013.01); *C12P 7/22* (2013.01); *Y02E 50/10* (2013.01)

(58) Field of Classification Search
CPC ............................... C12N 9/0006; C12N 9/88
USPC .................................................. 435/156, 160
See application file for complete search history.

(56) References Cited

U.S. PATENT DOCUMENTS

| 4,551,433 A | 11/1985 | DeBoer |
| 4,683,202 A | 7/1987 | Mullis |
| 5,426,039 A | 6/1995 | Wallace |
| 6,015,891 A | 1/2000 | Adang |
| 2009/0081746 A1 | 3/2009 | Liao |
| 2009/0139134 A1 | 6/2009 | Yoshikuni |
| 2009/0155869 A1 | 6/2009 | Buelter |

FOREIGN PATENT DOCUMENTS

WO 2008098227 A2 8/2008

OTHER PUBLICATIONS

Arnheim, N., and C.H. Levenson, "Polymerase Chain Reaction," Chemical & Engineering News 68(40):36-47, Oct. 1990.
Atsumi, S., et al., "Direct Photosynthetic Recycling of Carbon Dioxide to Isobutyraldehyde," Nature Biotechnology 27(12):1177-1180, Dec. 2009.
Baba, T., et al., "Construction of *Escherichia coli* K-12 In-Frame Single-Gene Knockout Mutants: The Keio Collection," Molecular Systems Biology, Feb. 2006, vol. 2, Article 2006.0008, 11 pages.
Barringer, K.J., et al., "Blunt-End and Single-Strand Ligations by *Escherichia coli* Ligase: Influence on an In Vitro Amplification Scheme," Gene 89(1):117-122, Apr. 1990.
Black, L.K., et al., "Sequences and Characterization of hupU and hupV Genes of *Bradyrhizobium japonicum* Encoding a Possible Nickel-Sensing Complex Involved in Hydrogenase Expression," Journal of Bacteriology 176(22):7102-7106, Nov. 1994.
Buchanan, B.B., and Y. Balmer, "Redox Regulation: A Broadening Horizon," Annual Review of Plant Biology 56:187-220, Jun. 2005.
Buchanan, B.B., et al., "The Ferredoxin/Thioredoxin System: From Discovery to Molecular Structures and Beyond," Photosynthesis Research 73(1-3):215-222, Jul. 2002.
Buhrke, T., et al., "Oxygen Tolerance of the $H_2$-Sensing [NiFe] Hydrogenase From Ralstonia eutropha H16 Is Based on Limited Access of Oxygen to the Active Site," Journal of Biological Chemistry 280(25):23791-23796, Jun. 2005.
Buhrke, T., et al., "Reduction of Unusual Iron-Sulfur Clusters in the $H_2$-Sensing Regulatory Ni-Fe Hydrogenase From Ralstonia eutropha H16," Journal of Biological Chemistry 280(20):19488-19495, May 2005.
Burton, S.G., "Oxidizing Enzymes as Biocatalysts," Trends in Biotechnology 21(12):543-549, Dec. 2003.
Cheng, S., et al., "Long PCR," Nature 369(6482):684-685, Jun. 1994.
Cramm, R., "Genomic View of Energy Metabolism in Ralstonia eutropha H16," Journal of Molecular Microbiology and Biotechnology 16(1-2):38-52, 2009 (published online Oct. 2008).
Dalphin, M.E., et al., "TransTerm: A Database of Translational Signals," Nucleic Acids Research 24(1):216-218, Jan. 1996.
Datsenko, K.A., and B.L. Wanner, "One-Step Inactivation of Chromosomal Genes in *Escherichia coli* K-12 Using PCR Products," Proceedings of the National Academy of Sciences of the United States of America (PNAS) 97(12):6640-6645, Jun. 2000.
Elsen, S., et al., "The hupTUV Operon Is Involved in Negative Control of Hydrogenase Synthesis in *Rhodobacter capsulatus*," Journal of Bacteriology 178(17):5174-5181, Sep. 1996.
Golden, S.S., "Light-Responsive Gene Expression in Cyanobacteria," Journal of Bacteriology 177(7):1651-1654, Apr. 1995.

(Continued)

*Primary Examiner* — Tekchand Saidha
(74) *Attorney, Agent, or Firm* — Christensen O'Connor Johnson Kindness PLLC

(57) ABSTRACT

The disclosure provides a process that converts $CO_2$ to higher alcohols (e.g. isobutanol) using electricity as the energy source. This process stores electricity (e.g. from solar energy, nuclear energy, and the like) in liquid fuels that can be used as high octane number gasoline substitutes. Instead of deriving reducing power from photosynthesis, this process derives reducing power from electrically generated mediators, either $H_2$ or formate. $H_2$ can be derived from electrolysis of water. Formate can be generated by electrochemical reduction of $CO_2$. After delivering the reducing power in the cell, formate becomes $CO_2$ and recycles back. Therefore, the biological $CO_2$ fixation process can occur in the dark.

35 Claims, 31 Drawing Sheets

(56) References Cited

OTHER PUBLICATIONS

Guatelli, J.C., et al., "Isothermal, In Vitro Amplification of Nucleic Acids by a Multienzyme Reaction Modeled After Retroviral Replication," Proceedings of the National Academy of Sciences of the United States of America (PNAS) 87(5):1874-1878, Mar. 1990.

Hummel, W., and M.R. Kula, "Dehydrogenases for the Synthesis of Chiral Compounds," European Journal of Biochemistry/FEBS 184(1):1-13, Sep. 1989.

Innis, M.A., and D.H. Gelfand, "Optimization of PCRs," in M.A. Innis et al. (eds.), "PCR Protocols: A Guide to Methods and Applications," Academic Press, Jan. 1990, Chap. 1, pp. 1-12.

Ishiura, M., et al., "Expression of a Gene Cluster kaiABC as a Circadian Feedback Process in Cyanobacteria," Science 281(5382):1519-1523, Sep. 1998.

Ishizaki, A., et al., "Microbial Production of Poly-D-3-hydroxybutyrate From $CO_2$," Applied Microbiology and Biotechnology 57(1-2):6-12, Oct. 2001.

Ito, H., et al., "Cyanobacterial Daily Life With Kai-Based Circadian and Diurnal Genome-Wide Transcriptional Control in *Synechococcus elongatus*," Proceedings of the National Academy of Sciences of the United States of America (PNAS) 106(33):14168-14173, Aug. 2009.

Ivleva, N. B., et al., "Quinone Sensing by the Circadian Input Kinase of the Cyanobacterial Circadian Clock," Proceedings of the National Academy of Sciences of the United States of America (PNAS) 103(46):17468-17473, Nov. 2006.

Johnson, C.H., et al., "Structural Insights Into a Circadian Oscillator," Science 322(5902):697-701, Oct. 2008 (Author Manuscript provided, PMCID:PMC2588432, available in PMC Oct. 31,2009, 11 pages).

Kleihues, L., et al., "The $H_2$ Sensor of *Ralstonia eutropha* Is a Member of the Subclass of Regulatory (NiFe) Hydrogenases," Journal of Bacteriology 182(10):2716-2724, May 2000.

Kovács, K.L., et al., "The Hydrogenases of Thiocapsa roseopersicina," Biochemical Society Transactions 33(Pt. 1):61-3, Feb. 2005.

Kwoh, D.Y., et al., "Transcription-Based Amplification System and Detection of Amplified Human Immunodeficiency Virus Type 1 With a Bead-Based Sandwich Hybridization Format," Proceedings of the National Academy of Sciences of the United States of America (PNAS) 86(4):1173-1177, Feb. 1989.

Landegren, U., et al., "A Ligase-Mediated Gene Detection Technique," Science 241(4869):1077-1080, Aug. 1988.

Larimer, F.W., et al., "Complete Genome Sequence of the Metabolically Versatile Photosynthetic Bacterium *Rhodopseudomonas palustris*," Nature Biotechnology 22(1):55-61, Jan. 2004.

Lenz, O., and B. Friedrich, "A Novel Multicomponent Regulatory System Mediates $H_2$ Sensing in *Alcaligenes eutrophus*," Proceedings of the National Academy of Sciences of the United States of America (PNAS) 95(21):12474-12479, Oct. 1998.

Lindahl, M., and F.J. Florencio, "Thioredoxin-Linked Processes in Cyanobacteria Are as Numerous as in Chloroplasts, but Targets Are Different," Proceedings of the National Academy of Sciences of the United States of America (PNAS) 100(26):16107-16112, Dec. 2003.

Liu, Y., et al., "Circadian Orchestration of Gene Expression in Cyanobacteria," Genes & Development 9(12):1469-1478, Jun. 1995.

Lomeli, H., et al., "Quantitative Assays Based on the Use of Replicatable Hybridization Probes," Clinical Chemistry 35(9):1826-1831, Sep. 1989.

Marcus, Y., et al., "Dual Role of Cysteine 172 in Redox Regulation of Ribulose 1,5-Bisphosphate Carboxylase/Oxygenase Activity and Degradation," Journal of Bacteriology 185(5):1509-1517, Mar. 2003.

Massanz, C., et al., "Subforms and In Vitro Reconstitution of the NAD-Reducing Hydrogenase of *Alcaligenes eutrophus*," Journal of Bacteriology 180(5):1023-1029, Mar. 1998.

Miyagawa, Y., et al., "Overexpression of a Cyanobacterial Fructose-1,6-/sedoheptulose-1,7-bisphosphatase in Tobacco Enhances Photosynthesis and Growth," Nature Biotechnology 19(10):965-969, Oct. 2001.

Murray, E.E., et al., "Codon Usage in Plant Genes," Nucleic Acids Research 17(2):477-498, Jan. 1989.

Nakahira, Y., et al., "Global Gene Repression by KaiC as a Master Process of Prokaryotic Circadian System," Proceedings of the National Academy of Sciences of the United States of America (PNAS) 101(3):881-885, Jan. 2004.

Ohshima, T., et al., "Improvement for L-Leucine Production in a Continuously Operated Enzyme Membrane Reactor," Biotechnology and Bioengineering 27(11):1616-1618, Nov. 1985.

Pfannschmidt, T., et al., "The Multisubunit Chloroplast RNA Polymerase A From Mustard (*Sinapis alba* L.): Integration of a Prokaryotic Core Into a Larger Complex With Organelle-Specific Functions," European Journal of Biochemistry/FEBS 267(1):253-261, Jan. 2000.

Pohlmann, A., et al., "Genome Sequence of the Bioplastic-Producing 'Knallgas' Bacterium *Ralstonia eutropha* H16," Nature Biotechnology 24(10):1257-1262, Oct. 2006.

Rey, F.E., et al., "Regulation of Uptake Hydrogenase and Effects of Hydrogen Utilization on Gene Expression in *Rhodopseudomonas palustris*," Journal of Bacteriology 188(17):6143-6152, Sep. 2006.

Romagnoli, S., and F.R. Tabita, "Phosphotransfer Reactions of the CbbRRS Three-Protein Two-Component System from Rhodopseudomonas palustris CGA010 Appear to Be Controlled by an Internal Molecular Switch on the Sensor Kinase," Journal of Bacteriology 189(2):325-335, Jan. 2007.

Schink, B., and H.G. Schlegel, "The Membrane-Bound Hydrogenase of *Alcaligenes eutrophus*. I. Solubilization, Purification, and Biochemical Properties," Biochimica et Biophysica Acta 567(2):315-324, Apr. 1979.

Schneider, K., and H.G. Schlegel, "Purification and Properties of Soluble Hydrogenase From *Alcaligenes eutrophus* H 16," Biochimica et Biophysica Acta 452(1):66-80, Nov. 1976.

Schultz, M.G., et al., "Air Pollution and Climate-Forcing Impacts of a Global Hydrogen Economy," Science 302(5645):624-627, Oct. 2003.

Schwartz, E., et al., "Transcriptional Regulation of *Alcaligenes eutrophus* Hydrogenase Genes," Journal of Bacteriology 180(12):3197-3204, Jun. 1998.

Siefert, E., and N. Pfennig, "Hydrogen Metabolism and Nitrogen Fixation in Wild Type and Nif⁻ Mutants of *Rhodopseudomonas acidophila*," Biochimie 60(3):261-265, Jun. 1978.

Slusarczyk, H., et al., "Stabilization of NAD-Dependent Formate Dehydrogenase From *Candida boidinii* by Site-Directed Mutagenesis of Cysteine Residues," European Journal of Biochemistry/FEBS 267(5):1280-1289, Mar. 2000.

Smith, R.M., and S.B. Williams, "Circadian Rhythms in Gene Transcription Imparted by Chromosome Compaction in the Cyanobacterium *Synechococcus elongatus*," Proceedings of the National Academy of Sciences of the United States of America (PNAS) 103(22):8564-8569, May 2006.

Sooknanan, R., and L.T. Malek, "NASBA: A Detection and Amplification System Uniquely Suited for RNA," Nature Biotechnology, 13:563-564, Jun. 1995.

Tamoi, M., et al., "Acquisition of a New Type of Fructose-1,6-bisphosphatase With Resistance to Hydrogen Peroxide in Cyanobacteria: Molecular Characterization of the Enzyme From Synechocystis PCC 6803," Biochimica et Biophysica Acta 1383(2):232-244, Apr. 1998.

Tamoi, M., et al., "The Calvin Cycle in Cyanobacteria Is Regulated by CP12 via the NAD (H)/NADP(H) Ratio Under Light/Dark Conditions," Plant Journal 42(4):504-513, May 2005.

Tamoi, M., et al., "Molecular Characterization and Resistance to Hydrogen Peroxide of Two Fructose-1,6-bisphosphatases From *Synechococcus* PCC 7942," Archives of Biochemistry and Biophysics 334(1):27-36, Oct. 1996.

Van Brunt, J., "Amplifying Genes: PCR and Its Alternatives," Bio/technology 8(4):291-294, Apr. 1990.

Vignais, P.M., and B. Billoud, "Occurrence, Classification, and Biological Function of Hydrogenases: An Overview," Chemical Reviews 107(10):4206-4272, Oct. 2007.

Wedel, N., and J. Soll, "Evolutionary Conserved Light Regulation of Calvin Cycle Activity by NADPH-Mediated Reversible Phosphoribulokinase/CP12/glyceraldehyde-3-phosphate

(56) References Cited

OTHER PUBLICATIONS

Dehydrogenase Complex Dissociation," Proceedings of the National Academy of Sciences of the United States of America (PNAS) 95(16):9699-9704, Aug. 1998.

Wichmann, R., and D. Vasic-Racki, "Cofactor Regeneration at the Lab Scale," Advancements in Biochemical Engineering/Biotechnology 92:225-260, 2005.

Wu, D.Y., and R.B. Wallace, "The Ligation Amplification Reaction (LAR)—Amplification of Specific DNA Sequences Using Sequential Rounds of Template-Dependent Ligation," Genomics 4(4):560-569, May 1989.

International Search Report mailed Sep. 30, 2011, issued in corresponding International Application No. PCT/US2011/021436, filed Jan. 15, 2011.

International Preliminary Report on Patentability and Written Opinion mailed Jul. 17, 2012, issued in corresponding International Application No. PCT/US2011/021436, filed Jan. 15, 2011.

Communication Pursuant to Rules 70(2) and 70a(2) EPC and Supplementary European Search Report mailed Dec. 17, 2013, issued in corresponding European Application No. 11733505.9, filed Jan. 15, 2011, 6 pages.

Communication Pursuant to Article 94(3) EPC mailed Jul. 8, 2015, issued in corresponding European Application No. EP 11 733 505.9, filed Jan. 15, 2011, 4 pages.

Tsuge, T., et al., "Biosynthesis and Compositional Regulation of Poly[(3-hydroxybutyrate)-co-(3-hydroxyhexanoate)] in Recombinant Ralstonia eutropha Expressing Mutated Polyhydroxyalkanoate Synthase Genes," Macromolecular Bioscience 4(3):238-242, Mar. 2004.

FIGURE 2A-B

*kivd*: pyruvate decarboxylase (*Lactococcus lactis*) (SEQ ID NO:1)

atgtatacagtaggagattacctattagaccgattacacgagttaggaattgaagaaattt
ttggagtccctggagactataacttacaattttagatcaaattatttcccgcaaggatat
gaaatgggtcggaaatgctaatgaattaaatgcttcatatatggctgatggctatgctcgt
actaaaaaagctgccgcatttcttacaacctttggagtaggtgaattgagtgcagttaatg
gattagcaggaagttacgccgaaaatttaccagtagtagaaatagtgggatcacctacatc
aaaagttcaaaatgaaggaaaatttgttcatcatacgctggctgacggtgattttaaacac
tttatgaaaatgcacgaacctgttacagcagctcgaactttactgacagcagaaaatgcaa
ccgttgaaattgaccgagtactttctgcactattaaaagaagaaacctgtctatatcaa
cttaccagttgatgttgctgctgcaaaagcagagaaaccctcactccctttgaaaaagaa
aactcaacttcaaatacaagtgaccaagagatcttgaacaaaattcaagaaagcttgaaaa
atgccaaaaaccaatcgtgattacaggacatgaataattagttttggcttagaaaaaac
agtctctcaatttatttcaaagacaaaactacctattacgacattaaactttggaaaagt
tcagttgatgaagctctcccttcattttaggaatctataatggtaaactctcagagccta
atcttaaagaattcgtggaatcagccgacttcatcctgatgcttggagttaaactcacaga
ctcttcaacaggagccttcactcatcatttaaatgaaataaaatgatttcactgaatata
gatgaaggaaaaatatttaacgaaagcatccaaaattttgatttgaatccctcatctcct
ctctcttagacctaagcgaaatagaatacaaaggaaaatatcgataaaaagcaagaaga
ctttgttccatcaaatgcgcttttatcacaagaccgcctatggcaagcagttgaaaaccta
actcaaagcaatgaaacaatcgttgctgaacaagggacatcattctttggcgcttcatcaa
ttttcttaaaaccaaagagtcattttattggtcaacccttatggggatcaattggatatac
attcccagcagcattaggaagccaaattgcagataaagaaagcagacaccttttatttatt
ggtgatggttcacttcaacttacggtgcaagaattaggattagcaatcagagaaaaaatta
atccaatttgctttattatcaataatgatggttatacagtcgaaagagaaattcatggacc
aaatcaaagctacaatgatattccaatgtggaattactcaaaattaccagaatcatttgga
gcaacagaagaacgagtagtctcgaaaatcgttagaactgaaaatgaatttgtgtctgtca
tgaaagaagctcaagcagatccaaatagaatgtactggattgagttaatttttggcaaaga
agatgcaccaaaagtactgaaaaaaatgggcaaactatttgctgaacaaaataaatcataa

FIGURE 3

*PDC6 (Saccharomyces cerevisiae)* (SEQ ID NO:3)

```
atgtctgaaattactcttggaaaatacttatttgaaagattgaagcaagttaatgttaaca
ccattttttgggctaccaggcgacttcaacttgtccctattggacaagatttacgaggtaga
tggattgagatgggctggtaatgcaaatgagctgaacgccgcctatgccgccgatggttac
gcacgcatcaagggtttatctgtgctggtaactacttttggcgtaggtgaattatccgcct
tgaatggtattgcaggatcgtatgcagaacacgtcggtgtactgcatgttgttggtgtccc
ctctatctccgctcaggctaagcaattgttgttgcatcataccttgggtaacggtgatttt
accgttttcacagaatgtccgccaatatctcagaaactacatcaatgattacagacattg
ctacagccccttcagaaatcgataggttgatcaggacaacatttataacacaaaggcctag
ctacttggggttgccagcgaatttggtagatctaaaggttcctggttctcttttggaaaaa
ccgattgatctatcattaaaacctaacgatcccgaagctgaaaggaagttattgataccg
tactagaattgatccagaattcgaaaaccctgttatactatcggatgcctgtgcttctag
gcacaacgttaaaaaagaaacccagaagttaattgatttgacgcaattcccagcttttgtg
acacctctaggtaaagggtcaatagatgaacagcatcccagatatggcggtgtttatgtgg
gaacgctgtccaaacaagacgtgaaacaggccgttagtcggctgatttgatcctttcggt
cggtgctttgctctctgattttaacacaggttcgttttcctactcctacaagactaaaaat
gtagtggagtttcattccgattacgtaaaggtgaagaacgctacgttcctcggtgtacaaa
tgaaatttgcactacaaaacttactgaaggttattcccgatgttgttaagggctacaagag
cgttcccgtaccaaccaaaactcccgcaaacaaaggtgtacctgctagcacgcccttgaaa
caagagtggttgtggaacgaattgtccaaattcttgcaagaaggtgatgttatcatttccg
agaccggcacgtctgccttcggtatcaatcaaactatctttcctaaggacgcctacggtat
ctcgcaggtgttgtgggggtccatcggttttacaacaggagcaactttaggtgctgccttt
gccgctgaggagattgaccccaacaagagagtcatcttattcataggtgacgggtctttgc
agttaaccgtccaagaaatctccaccatgatcagatgggggttaaagccgtatctttttgt
ccttaacaacgacggctacactatcgaaaagctgattcatgggcctcacgcagagtacaac
gaaatccagacctgggatcacctcgccctgttgccgcatttggtgcgaaaaagtacgaaa
atcacaagatcgccactacgggtgagtgggatgccttaaccactgattcagagttccagaa
aaactcggtgatcagactaattgaactgaaactgcccgtctttgatgctccggaaagtttg
atcaaacaagcgcaattgactgccgctacaaatgccaaacaataa
```

FIGURE 4

*ARO10 (Saccharomyces cerevisiae)* (SEQ ID NO:5)

atggcacctgttacaattgaaaagttcgtaaatcaagaagaacgacaccttgtttccaacc
gatcagcaacaattccgtttggtgaatacatatttaaaagattgttgtccatcgatacgaa
atcagttttcggtgttcctggtgacttcaacttatctctattagaatatctctattcacct
agtgttgaatcagctggcctaagatgggtcggcacgtgtaatgaactgaacgccgcttatg
cggccgacggatattcccgttactctaataagattggctgtttaataaccacgtatggcgt
tggtgaattaagcgccttgaacggtatagccggttcgttcgctgaaaatgtcaagttttg
cacattgttggtgtggccaagtccatagattcgcgttcaagtaactttagtgatcggaacc
tacatcatttggtcccacagctacatgattcaaattttaaagggccaaatcataaagtata
tcatgatatggtaaaagatagagtcgcttgctcggtagcctacttggaggatattgaaact
gcatgtgaccaagtcgataatgttatccgcgatatttacaagtattctaaacctggttata
ttttgttcctgcagattttgcggatatgtctgttacatgtgataatttggttaatgttcc
acgtatatctcaacaagattgtatagtataccttctgaaaaccaattgtctgacataatc
aacaagattactagttggatatattccagtaaaacacctgcgatccttggagacgtactga
ctgataggtatggtgtgagtaacttttgaacaagcttatctgcaaaactgggatttggaa
tttttccactgttatgggaaaatctgtaattgatgagtcaaacccaacttatatgggtcaa
tataatggtaaagaaggtttaaaacaagtctatgaacattttgaactgtgcgacttggtct
tgcattttggagtcgacatcaatgaattaataatgggcattatacttttacttataaacc
aaatgctaaaatcattcaatttcatccgaattatattcgccttgtggacactaggcagggc
aatgagcaaatgttcaaggaatcaattttgcccctatttttaaaagaactatacaagcgca
ttgacgtttctaaactttctttgcaatatgattcaaatgtaactcaatatacgaacgaaac
aatgcggttagaagatcctaccaatggacaatcaagcattattacacaagttcacttacaa
aagacgatgcctaaattttgaaccctggtgatgttgtcgtttgtgaaacaggctcttttc
aattctctgttcgtgatttcgcgtttccttcgcaattaaaatatatatcgcaaggatttt
cctttccattggcatggcccttcctgccgccctaggtgttggaattgccatgcaagaccac
tcaaacgctcacatcaatggtggcaacgtaaaagaggactataagccaagattaattttgt
ttgaaggtgacggtgcagcacagatgacaatccaagaactgagcaccattctgaagtgcaa
tattccactagaagttatcatttggaacaataacggctacactattgaaagagccatcatg
ggccctaccaggtcgtataacgacgttatgtcttggaaatggaccaaactatttgaagcat
tcggagacttcgacggaaagtatactaatagcactctcattcaatgtccctctaaattagc
actgaaattggaggagcttaagaattcaaacaaaagaagcgggatagaacttttagaagtc
aaattaggcgaattggatttccccgaacagctaaagtgcatggttgaagcagcggcactta
aaagaaataaaaatag

FIGURE 5

*THI3 (Saccharomyces cerevisiae)* (SEQ ID NO:7)

atgaattctagctatacacagagatatgcactgccgaagtgtatagcaatatcagattatc
ttttccatcggctcaaccagctgaacatacataccatatttggactctccggagaatttag
catgccgttgctggataaactatacaacattccgaacttacgatgggccggtaattctaat
gagttaaatgctgcctacgcagcagatggatactcacgactaaaaggcttgggatgtctca
taacaacctttggtgtaggcgaattatcggcaatcaatggcgtggccggatcttacgctga
acatgtaggaatacttcacatagtgggtatgccgccaacaagtgcacaaacgaaacaacta
ctactgcatcatactctgggcaatggtgatttcacggtatttcatagaatagccagtgatg
tagcatgctatacaacattgattattgactctgaattatgtgccgacgaagtcgataagtg
catcaaaaaggcttggatagaacagaggccagtatacatgggcatgcctgtcaaccaggta
aatctcccgattgaatcagcaaggcttaatacacctctggatttacaattgcataaaaacg
acccagacgtagagaaagaagttatttctcgaatattgagttttatatacaaaagccagaa
tccggcaatcatcgtagatgcatgtactagtcgacagaatttaatcgaggagactaaagag
ctttgtaataggcttaaatttccagttttgttacacctatgggtaagggtacagtaaacg
aaacagacccgcaatttggggcgtattcacgggctcgatatcagccccagaagtaagaga
agtagttgattttgccgattttatcatcgtcattggttgcatgctctccgaattcagcacg
tcaacttccacttccaatataaaactaagaattgtgcgctactatattctacatctgtga
aattgaaaaatgccacatatcctgacttgagcattaaattactacagaaaatattagc
aaatcttgatgaatctaaactgtcttaccaaccaagcgaacaacccagtatgatggttcca
agaccttacccagcaggaaatgtcctcttgagacaagaatgggtctggaatgaaatatccc
attggttccaaccaggtgacataatcataacagaaactggtgcttctgcatttggagttaa
ccagaccagatttccggtaaatacactaggtatttcgcaagctctttggggatctgtcgga
tatacaatgggggcgtgtcttggggcagaatttgctgttcaagagataaacaaggataaat
tccccgcaactaaacatagagttattctgtttatgggtgacggtgctttccaattgacagt
tcaagaattatccacaattgttaagtggggattgacaccttatatttttgtgatgaataac
caaggttactctgtggacaggttttttgcatcacaggtcagatgctagttattacgatatcc
aaccttggaactacttgggattattgcgagtatttggttgcacgaactacgaaacgaaaaa
aattattactgttggagaattcagatccatgatcagtgacccaaactttgcgaccaatgac
aaaattcggatgatagagattatgctaccaccaagggatgttccacaggctctgcttgaca
ggtgggtggtagaaaagaacagagcaaacaagtgcaagaggagaacgaaaattctagcgc
agtaaatacgccaactccagaattccaaccacttctaaaaaaaaatcaagttggatactga

FIGURE 6

*pdc* (*Clostridium acetobutylicum*) (SEQ ID NO:9)

ttgaagagtgaatacacaattggaagatatttgttagaccgtttatcagagttgggtattc
ggcatatctttggtgtacctggagattacaatctatccttttagactatataatggagta
caaagggatagattgggttggaaattgcaatgaattgatgctgggtatgctgctgatgga
tatgcaagaataaatggaattggagccatacttacaacatttggtgttggagaattaagtg
ccattaacgcaattgctggggcatacgctgagcaagttccagttgttaaaattacaggtat
ccccacagcaaaagttagggacaatggattatatgtacaccacacattaggtgacggaagg
tttgatcacttttttgaaatgtttagagaagtaacagttgctgaggcattactaagcgaag
aaaatgcagcacaagaaattgatcgtgttcttatttcatgctggagacaaaaacgtcctgt
tcttataaatttaccgattgatgtatatgataaaccaattaacaaaccattaaagccatta
ctcgattatactatttcaagtaacaaagaggctgcatgtgaatttgttacagaaatagtac
ctataataaatagggcaaaaaagcctgttattcttgcagattatggagtatatcgttacca
agttcaacatgtgcttaaaaacttggccgaaaaaaccggatttcctgtggctacactaagt
atgggaaaggtgttttcaatgaagcacaccctcaatttattggtgtttataatggtgatg
taagttctccttatttaaggcagcgagttgatgaagcagactgcattattagcgttggtgt
aaaattgacggattcaaccacaggggatttctcatggattttctaaaaggaatgtaatt
cacattgatccttttcaataaaggcaaaggtaaaaaatatgcacctattacgatgaaag
atgctttaacagaattaacaagtaaattgagcatagaactttgaggatttagatataaa
gccttacaaatcagataatcaaagtattttgcaaagagaagccaattacacaaaaacgt
tttttgagcgtattgctcactttataaaagaaaaagatgtattattagcagaacagggta
catgcttttttggtgcgtcaaccatacaactacccaaagatgcaacttttattggtcaacc
tttatggggatctattggatacacacttcctgctttattaggttcacaattagctgatcaa
aaaaggcgtaatattcttttaattggggatggtgcatttcaaatgacagcacaagaattt
caacaatgcttcgtttacaaatcaaacctattatttttaattaataacgatggttatac
aattgaacgtgctattcatggtagagaacaagtatataacaatattcaaatgtggcgatat
cataatgttccaaaggttttaggtcctaaagaatgcagcttaacctttaaagtacaagtg
aaactgaacttgaaaaggctctttttagtggcagataaggattgtgaacatttgattttat
agaagttgttatggatcgttatgataaacccgagcctttagaacgtctttcgaacgtttt
gcaaatcaaaataattag

FIGURE 7

*ADH2*: alcohol dehydrogenase (*Saccharomyces cerevisiae*) (SEQ ID NO:11)

atgccttcgcaagtcattcctgaaaaacaaaaggctattgtcttttatgagacagatggaa
aattggaatataaagacgtcacagttccggaacctaagcctaacgaaattttagtccacgt
taaatattctggtgtttgtcatagtgacttgcacgcgtggcacggtgattggccatttcaa
ttgaaatttccattaatcggtggtcacgaaggtgctggtgttgttgttaagttgggatcta
acgttaagggctggaaagtcggtgattttgcaggtataaaatggttgaatgggacttgcat
gtcctgtgaatattgtgaagtaggtaatgaatctcaatgtccttatttggatggtactggc
ttcacacatgatggtacttttcaagaatacgcaactgccgatgccgttcaagctgcccata
ttccaccaaacgtcaatcttgctgaagttgcccaatcttgtgtgcaggtatcactgttta
taaggcgttgaaaagagccaatgtgataccaggccaatgggtcactatatccggtgcatgc
ggtggcttgggttctctggcaatccaatacgcccttgctatgggttacagggtcattggta
tcgatggtggtaatgccaagcgaaagttatttgaacaattaggcggagaaatattcatcga
tttcacggaagaaaaagacattgttggtgctataataaaggccactaatggcggttctcat
ggagttattaatgtgtctgtttctgaagcagctatcgaggcttctacgaggtattgtaggc
ccaatggtactgtcgtcctggttggtatgccagctcatgcttactgcaattccgatgtttt
caatcaagttgtaaaatcaatctccatcgttggatcttgtgttggaaatagagctgataca
agggaggctttagatttcttcgccagaggtttgatcaaatctccgatccacttagctggcc
tatcggatgttcctgaaattttgcaaagatggagaagggtgaaattgttggtagatatgt
tgttgagacttctaaatga

FIGURE 8

*ilvI: (E.coli)* (SEQ ID NO:13)

atggagatgttgtctggagccgagatggtcgtccgatcgcttatcgatcagggcgttaaac
aagtattcggttatcccggaggcgcagtccttgatatttatgatgcattgcataccgtggg
tggtattgatcatgtattagttcgtcatgagcaggcggcggtgcatatggccgatggcctg
gcgcgcgcgaccggggaagtcggcgtcgtgctggtaacgtcgggtccagggcgaccaatg
cgattactggcatcgccaccgcttatatggattccattccattagttgtcctttccgggca
ggtagcgacctcgttgataggttacgatgcctttcaggagtgcgacatggtgggatttcg
cgaccggtggttaaacacagttttctggttaagcaaacggaagacattccgcaggtgctga
aaaaggctttctggctggcggcaagtggtcgcccaggaccagtagtcgttgatttaccgaa
agatattcttaatccggcgaacaaattaccctatgtctggccggagtcggtcagtatgcgt
tcttacaatcccactactaccggacataaagggcaaattaagcgtgctctgcaaacgctgg
tagcggcaaaaaaaccggttgtctacgtaggcggtgggggcaatcacggcgggctgccatca
gcagttgaaagaaacggtggaggcgttgaatctgcccgttgtttgctcattgatggggctg
ggggcgtttccggcaacgcatcgtcaggcactgggcatgctgggaatgcacggtacctacg
aagccaatatgacgatgcataacgcggatgtgattttcgccgtcggggtacgatttgatga
ccgaacgacgaacaatctggcaaagtactgcccaaatgccactgttctgcatatcgatatt
gatcctacttccatttctaaaaccgtgactgcggatatcccgattgtggggatgctcgcc
aggtcctcgaacaaatgcttgaactcttgtcgcaagaatccgcccatcaaccactggatga
gatccgcgactggtggcagcaaattgaacagtggcgcgctcgtcagtgcctgaaatatgac
actcacagtgaaaagattaaaccgcaggcggtgatcgagactctttggcggttgacgaagg
gagacgcttacgtgacgtccgatgtcgggcagcaccagatgtttgctgcactttattatcc
attcgacaaaccgcgtcgctggatcaattccggtggcctcggcacgatgggttttggttta
cctgcggcactgggcgtcaaaatggcgttgccagaagaaaccgtggtttgcgtcactggcg
acggcagtattcagatgaacatccaggaactgtctaccgcgttgcaatacgagttgcccgt
actggtggtgaatctcaataaccgctatctggggatggtgaagcagtggcaggacatgatc
tattccggccgtcattcacaatcttatatgcaatcgctacccgatttcgtccgtctggcgg
aagcctatgggcatgtcgggatccagatttctcatccgcatgagctggaaagcaaacttag
cgaggcgctggaacaggtgcgcaataatcgcctggtgtttgttgatgttaccgtcgatggc
agcgagcacgtctacccgatgcagattcgcggggcggaatggatgaaatgtggttaagca
aaacggagagaacctga

FIGURE 9

*ilvH*: (*E.coli*) (SEQ ID NO:15)

```
atgcgccggatattatcagtcttactcgaaaatgaatcaggcgcgttatcccgcgtgattg
gccttttttcccagcgtggctacaacattgaaagcctgaccgttgcgccaaccgacgatcc
gacattatcgcgtatgaccatccagaccgtgggcgatgaaaaagtacttgagcagatcgaa
aagcaattacacaaactggtcgatgtcttgcgcgtgagtgagttggggcagggcgcgcatg
ttgagcgggaaatcatgctggtgaaaattcaggccagcggttacgggcgtgacgaagtgaa
acgtaatacggaaatattccgtgggcaaattatcgatgtcacaccctcgctttataccgtt
caattagcaggcaccagcggtaagcttgatgcattttttagcatcgattcgcgatgtggcga
aaattgtggaggttgctcgctctggtgtggtcggactttcgcgcggcgataaaataatgcg
ttga
```

FIGURE 10 ilvC: (E.coli) (SEQ ID NO:17)

atggctaactacttcaatacactgaatctgcgccagcagctggcacagctgggcaaatgtc
gctttatgggccgcgatgaattcgccgatggcgcgagctaccttcagggtaaaaaagtagt
catcgtcggctgtggcgcacagggtctgaaccagggcctgaacatgcgtgattctggtctc
gatatctcctacgctctgcgtaaagaagcgattgccgagaagcgcgcgtcctggcgtaaag
cgaccgaaaatggttttaaagtgggtacttacgaagaactgatcccacaggcggatctggt
gattaacctgacgccggacaagcagcactctgatgtagtgcgcaccgtacagccactgatg
aaagacggcgcggcgctgggctactcgcacggtttcaacatcgtcgaagtgggcgagcaga
tccgtaaagatatcaccgtagtgatggttgcgccgaaatgcccaggcaccgaagtgcgtga
agagtacaaacgtgggttcggcgtaccgacgctgattgccgttcacccggaaaacgatccg
aaaggcgaaggcatggcgattgccaaagcctgggcggctgcaaccggtggtcaccgtgcgg
gtgtgctggaatcgtccttcgttgcggaagtgaaatctgacctgatgggcgagcaaaccat
cctgtgcggtatgttgcaggctggctctctgctgtgcttcgacaagctggtggaagaaggt
accgatccagcatacgcagaaaaactgattcagttcggttgggaaaccatcaccgaagcac
tgaaacagggcggcatcaccctgatgatggaccgtctctctaaccggcgaaactgcgtgc
ttatgcgctttctgaacagctgaaagagatcatggcacccctgttccagaaacatatggac
gacatcatctccggcgaattctcttccggtatgatggcggactgggccaacgatgataaga
aactgctgacctggcgtgaagagaccggcaaaaccgcgtttgaaaccgcgccgcagtatga
aggcaaaatcggcgagcaggagtacttcgataaggcgtactgatgattgcgatggtgaaa
gcgggcgttgaactggcgttcgaaaccatggtcgattccggcatcattgaagagtctgcat
attatgaatcactgcacgagctgccgctgattgccaacaccatcgcccgtaagcgtctgta
cgaaatgaacgtggttatctctgataccgctgagtacggtaactatctgttctcttacgct
tgtgtgccgttgctgaaaccgtttatggcagagctgcaaccgggcgacctgggtaaagcta
ttccggaaggcgcggtagataacggcaactgcgtgatgtgaacgaagcgattcgcagcca
tgcgattgagcaggtaggtaagaaactgcgcggctatatgacagatatgaaacgtattgct
gttgcgggttaa

FIGURE 11 ilvD: (*E.coli*) (SEQ ID NO:19)

atgcctaagtaccgttccgccaccaccactcatggtcgtaatatggcgggtgctcgtgcgc
tgtggcgcgccaccggaatgaccgacgccgatttcggtaagccgattatcgcggttgtgaa
ctcgttcacccaatttgtaccgggtcacgtccatctgcgcgatctcggtaaactggtcgcc
gaacaaattgaagcggctggcggcgttgccaaagagttcaacaccattgcggtggatgatg
ggattgccatgggccacggggggatgctttattcactgccatctcgcgaactgatcgctga
ttccgttgagtatatggtcaacgccactgcgccgacgccatggtctgcatctctaactgc
gacaaaatcaccccggggatgctgatggcttccctgcgcctgaatattccggtgatctttg
tttccggcggcccgatggaggccgggaaaaccaaactttccgatcagatcatcaagctcga
tctggttgatgcgatgatccagggcgcagacccgaaagtatctgactcccagagcgatcag
gttgaacgttccgcgtgtccgacctgcggttcctgctccgggatgtttaccgctaactcaa
tgaactgcctgaccgaagcgctgggcctgtcgcagccgggcaacggctcgctgctggcaac
ccacgccgaccgtaagcagctgttccttaatgctggtaaacgcattgttgaattgaccaaa
cgttattacgagcaaaacgacgaaagtgcactgccgcgtaatatcgccagtaaggcggcgt
ttgaaaacgccatgacgctggatatcgcgatggtggatcgactaacaccgtacttcacct
gctggcggcggcgcaggaagcggaaatcgacttcaccatgagtgatatcgataagctttcc
cgcaaggttccacagctgtgtaaagttgcgccgagcacccagaaataccatatggaagatg
ttcaccgtgctggtggtgttatcggtattctcggcgaactggatcgcgcggggttactgaa
ccgtgatgtgaaaaacgtacttggcctgacgttgccgcaaacgctggaacaatacgacgtt
atgctgacccaggatgacgcggtaaaaaatatgttccgcgcaggtcctgcaggcattcgta
ccacacaggcattctcgcaagattgccgttgggatacgctggacgacgatcgcgccaatgg
ctgtatccgctcgctggaacacgcctacagcaaagacggcggcctggcggtgctctacggt
aactttgcggaaaacggctgcatcgtgaaaacggcaggcgtcgatgacagcatcctcaaat
tcaccggcccggcgaaagtgtacgaaagccaggacgatgcggtagaagcgattctcggcgg
taaagttgtcgccggagatgtggtagtaattcgctatgaaggcccgaaaggcggtccgggg
atgcaggaaatgctctacccaaccagcttcctgaaatcaatgggtctcggcaaagcctgtg
cgctgatcaccgacggtcgtttctctggtggcacctctggtctttccatcggccacgtctc
accggaagcggcaagcggcggcagcattggcctgattgaagatggtgacctgatcgctatc
gacatcccgaaccgtggcattcagttacaggtaagcgatgccgaactggcggcgcgtcgtg
aagcgcaggacgctcgaggtgacaaagcctggacgccgaaaaatcgtgaacgtcaggtctc
ctttgccctgcgtgcttatgccagcctggcaaccagcgccgacaaaggcgcggtgcgcgat
aaatcgaaactgggggggttaa

FIGURE 12 ilvA: (*E.coli*) (SEQ ID NO:21)

atggctgactcgcaacccctgtccggtgctccggaaggtgccgaatatttaagagcagtgc
tgcgcgcgccggtttacgaggcggcgcaggttacgccgctacaaaaaatggaaaaactgtc
gtcgcgtcttgataacgtcattctggtgaagcgcgaagatcgccagccagtgcacagcttt
aagctgcgcggcgcatacgccatgatggcgggcctgacggaagaacagaaagcgcacggcg
tgatcactgcttctgcgggtaaccacgcgcagggcgtcgcgttttcttctgcgcggttagg
cgtgaaggccctgatcgttatgccaaccgccaccgccgacatcaaagtcgacgcggtgcgc
ggcttcggcggcgaagtgctgctccacggcgcgaactttgatgaagcgaaagccaaagcga
tcgaactgtcacagcagcaggggttcacctgggtgccgccgttcgaccatccgatggtgat
tgccgggcaaggcacgctggcgctggaactgctccagcaggacgcccatctcgaccgcgta
tttgtgccagtcggcggcggcggtctggctgctggcgtggcggtgctgatcaaacaactga
tgccgcaaatcaaagtgatcgccgtagaagcggaagactccgcctgcctgaaagcagcgct
ggatgcgggtcatccggttgatctgccgcgcgtagggctatttgctgaaggcgtagcggta
aaacgcatcggtgacgaaaccttccgtttatgccaggagtatctcgacgacatcatcaccg
tcgatagcgatgcgatctgtgcggcgatgaaggatttattcgaagatgtgcgcgcggtggc
ggaaccctctggcgcgctggcgctggcgggaatgaaaaaatatatcgccctgcacaacatt
cgcggcgaacggctggcgcatattctttccggtgccaacgtgaacttccacggcctgcgct
acgtctcagaacgctgcgaactgggcgaacagcgtgaagcgttgttggcggtgaccattcc
ggaagaaaaggcagcttcctcaaattctgccaactgcttggcgggcgttcggtcaccgag
ttcaactaccgttttgccgatgccaaaaacgcctgcatctttgtcggtgtgcgcctgagcc
gcggcctcgaagagcgcaaagaaattttgcagatgctcaacgacggcggctacagcgtggt
tgatctctccgacgacgaaatggcgaagctacacgtgcgctatatggtcggcggacgtcca
tcgcatccgttgcaggaacgcctctacagcttcgaattcccggaatcaccgggcgcgctgc
tgcgcttcctcaacacgctgggtacgtactggaacatttctttgttccactatcgcagcca
tggcaccgactacgggcgcgtactggcggcgttcgaacttggcgaccatgaaccggatttc
gaaacccggctgaatgagctgggctacgattgccacgacgaaaccaataaccggcgttca
ggttcttttggcgggttag

FIGURE 13 leuA: (SEQ ID NO:23)

```
atgagccagcaagtcattattttcgataccacattgcgcgacggtgaacaggcgttacagg
caagcttgagtgtgaaagaaaaactgcaaattgcgctggcccttgagcgtatgggtgttga
cgtgatggaagtcggtttccccgtctcttcgcgggcgattttgaatcggtgcaaaccatc
gcccgccaggttaaaaacagccgcgtatgtgcgttagctcgctgcgtggaaaaagatatcg
acgtggcggccgaatccctgaaagtcgccgaagccttccgtattcatacctttattgccac
ttcgccaatgcacatcgccaccaagctgcgcagcacgctggacgaggtgatcgaacgcgct
atctatatggtgaaacgcgccgtaattacaccgatgatgttgaattttcttgcgaagatg
ccgggcgtacacccattgccgatctggcgcgagtggtcgaagcggcgattaatgccggtgc
caccaccatcaacattccggacaccgtgggctacaccatgccgtttgagttcgccggaatc
atcagcggcctgtatgaacgcgtgcctaacatcgacaaagccattatctccgtacatacc
acgacgatttgggcctggcggtcggaaactcactggcggcggtacatgccggtgcacgcca
ggtggaaggcgcaatgaacgggatcggcgagcgtgccggaaactgttccctggaagaagtc
atcatggcgatcaaagttcgtaaggatattctcaacgtccacaccgccattaatcaccagg
agatatggcgcaccagccagttagttagccagatttgtaatatgccgatcccggcaaacaa
agccattgttggcagcggcgcattcgcacactcctccggtatacaccaggatggcgtgctg
aaaaaccgcgaaaactacgaaatcatgacaccagaatctattggtctgaaccaaatccagc
tgaatctgacctctcgttcggggcgtgcggcggtgaaacatcgcatggatgagatggggta
taaagaaagtgaatataatttagacaatttgtacgatgctttcctgaagctggcggacaaa
aaaggtcaggtgtttgattacgatctggaggcgctggccttcatcggtaagcagcaagaag
agccggagcatttccgtctggattacttcagcgtgcagtctggctctaacgatatcgccac
cgccgccgtcaaactggcctgtggcgaagaagtcaaagcagaagccgccaacggtaacggt
ccggtcgatgccgtctatcaggcaattaaccgcatcactgaatataacgtcgaactggtga
atacagcctgaccgccaaaggccacggtaaagatgcgctgggtcaggtggatatcgtcgc
taactacaacggtcgccgcttccacggcgtcggcctggctaccgatattgtcgagtcatct
gccaaagccatggtgcacgttctgaacaatatctggcgtgccgcagaagtcgaaaaagagt
tgcaacgcaaagctcaacacaacgaaaacaacaaggaaaccgtgtga
```

FIGURE 14

*leuB*: (SEQ ID NO:25)

gtgatgtcgaagaattaccatattgccgtattgccgggggacggtattggtccggaagtga
tgacccaggcgctgaaagtgctggatgccgtgcgcaaccgctttgcgatgcgcatcaccac
cagccattacgatgtaggcggcgcagccattgataaccacgggcaaccactgccgcctgcg
acggttgaaggttgtgagcaagccgatgccgtgctgtttggctcggtaggcggcccgaagt
gggaacatttaccaccagaccagcaaccagaacgcggcgcgctgctgcctctgcgtaagca
cttcaaattattcagcaacctgcgcccggcaaaactgtatcaggggctggaagcattctgt
ccgctgcgtgcagacattgccgcaaacggcttcgacatcctgtgtgtgcgcgaactgaccg
gcggcatctatttcggtcagccaaaaggccgcgaaggtagcggacaatatgaaaaagcctt
tgataccgaggtgtatcaccgttttgagatcgaacgtatcgcccgcatcgcgtttgaatct
gctcgcaagcgtcgccacaaagtgacgtcgatcgataaagccaacgtgctgcaatcctcta
ttttatggcgggagatcgttaacgagatcgccacggaatacccggatgtcgaactggcgca
tatgtacatcgacaacgccaccatgcagctgattaaagatccatcacagtttgacgttctg
ctgtgctccaacctgtttggcgacattctgtctgacgagtgcgcaatgatcactggctcga
tggggatgttgccttccgccagcctgaacgagcaaggttttggactgtatgaaccggcggg
cggctcggcaccagatatcgcaggcaaaaacatcgccaacccgattgcacaaatcctttcg
ctggcactgctgctgcgttacagcctggatgccgatgatgcggcttgcgccattgaacgcg
ccattaaccgcgcattagaagaaggcattcgcaccggggatttagcccgtggcgctgccgc
cgttagtaccgatgaaatgggcgatatcattgcccgctatgtagcagaaggggtgtaa

FIGURE 15 leuC: (SEQ ID NO:27)

atggctaagacgttatacgaaaaattgttcgacgctcacgttgtgtacgaagccgaaaacg
aaaccccactgttatatatcgaccgccacctggtgcatgaagtgacctcaccgcaggcgtt
cgatggtctgcgcgcccacggtcgcccggtacgtcagccgggcaaaaccttcgctaccatg
gatcacaacgtctctacccagaccaaagacattaatgcctgcggtgaaatggcgcgtatcc
agatgcaggaactgatcaaaaactgcaaagaatttggcgtcgaactgtatgacctgaatca
cccgtatcaggggatcgtccacgtaatggggccggaacagggcgtcaccttgccggggatg
accattgtctgcggcgactcgcataccgccacccacggcgcgtttggcgcactggcctttg
gtatcggcacttccgaagttgaacacgtactggcaacgcaaaccctgaaacagggccgcgc
aaaaaccatgaaaattgaagtccagggcaaagccgcgccgggcattaccgcaaaagatatc
gtgctggcaattatcggtaaaaccggtagcgcaggcggcaccgggcatgtggtggagtttt
gcggcgaagcaatccgtgatttaagcatggaaggtcgtatgaccctgtgcaatatggcaat
cgaaatgggcgcaaaagccggtctggttgcaccggacgaaaccacctttaactatgtcaaa
ggccgtctgcatgcgccgaaaggcaaagatttcgacgacgccgttgcctactggaaaaccc
tgcaaaccgacgaaggcgcaactttcgataccgttgtcactctgcaagcagaagaaatttc
accgcaggtcacctggggcaccaatcccggccaggtgatttccgtgaacgacaatattccc
gatccggcttcgtttgccgatccggttgaacgcgcgtcggcagaaaaagcgctggcctata
tggggctgaaaccgggtattccgctgaccgaagtggctatcgacaaagtgtttatcggttc
ctgtaccaactcgcgcattgaagatttacgcgcggcagcggagatcgccaaagggcgaaaa
gtcgcgccaggcgtgcaggcactggtggttcccggctctggcccggtaaaagcccaggcgg
aagcggaaggtctggataaaatctttattgaagccggttttgaatggcgcttgcctggctg
ctcaatgtgtctggcgatgaacaacgaccgtctgaatccgggcgaacgttgtgcctccacc
agcaaccgtaactttgaaggccgccaggggcgcggcgggcgcacgcatctggtcagccgg
caatggctgccgctgctgctgtgaccggacatttcgccgacattcgcaacattaaataa

FIGURE 16 leuD: (SEQ ID NO:29)

atggcagagaaatttatcaaacacacaggcctggtggttccgctggatgccgccaatgtcg
ataccgatgcaatcatcccgaaacagttttgcagaaagtgacccgtacgggttttggcgc
gcatctgtttaacgactggcgttttctggatgaaaaaggccaacagccaaacccggacttc
gtgctgaacttcccgcagtatcagggcgcttccatttgctggcacgagaaaacttcggct
gtggctcttcgcgtgagcacgcgccctgggcattgaccgactacggtttaaagtggtgat
tgcgccgagttttgctgacatcttctacggcaatagctttaacaaccagctgctgccggtg
aaattaagcgatgcagaagtggacgaactgtttgcgctggtgaaagctaatccggggatcc
atttcgacgtggatctggaagcgcaagaggtgaaagcgggagagaaaacctatcgctttac
catcgatgccttccgccgccactgcatgatgaacggtctggacagtattgggcttaccttg
cagcacgacgacgccattgccgcttatgaagcaaaacaacctgcgtttatgaattaa

FIGURE 17 cimA (*Methanocaldococcus jannaschii*): (SEQ ID NO:31)

```
atgatggtaaggatatttgatacaacacttagagatggagagcaaacaccaggagtttctt
taacaccaaatgataagttagagatagcaaaaaaattggatgagcttggagttgatgttat
agaggcaggttcagctataacttcaaaaggagagagagaaggaataaaattaataacaaaa
gaaggtttaaatgcagaaatctgctcatttgttagagctttacctgtagatattgatgctg
ccttagaatgtgatgtagatagtgtccatttagtagtgccaacatctccaatacacatgaa
atataagcttagaaaaacagaagatgaggttttagagacagctttaaaggctgtagagtat
gctaaagaacatggattgattgttgagttatctgcagaggatgcaacaagaagtgatgtaa
atttcttaataaaactatttaatgaaggggaaaaggttggagcagacagagtttgtgtttg
tgacacagtaggagttttaactccacaaaagagtcaggaattatttaaaaaaataactgaa
aatgttaatttaccggtctcagttcattgccacaacgactttggaatggctactgctaata
cttgctcagcagttttaggtggagctgttcagtgccacgtaacagttaatggtattggaga
gagagcaggaaatgcctcattggaagaggttgttgctgctttaaaaatactctatggctat
gatactaagataaagatggaaagttatatgaggtttcaagaattgtctcaagattgatga
acttcctgttccaccaaataaagcaattgttggggacaatgcatttgctcatgaagcagg
aatacatgttgatggattaataaaaaatactgaaacctatgagccaataaaaccagaaatg
gttgggaatagaagaagaattattttgggtaagcattctggtagaaaagctttaaaataca
aacttgatttgatgggcataaacgttagtgatgagcaattaaataaaatatatgaaagagt
taaagaatttggggatttgggtaaatacatttcagacgctgatttgttggctatagttaga
gaagttactggaaaattggtagaagagaaaatcaaattagatgaattaactgttgtatctg
gaaataaaataacaccaattgcatctgttaaactccattataaggagaagatataacttt
aatagaaactgcttatggtgttggaccggtagatgcagcaataaatgctgtgagaaaggca
ataagtggagttgcagatattaagttggtagagtatagagttgaagcaattggtggaggaa
ctgatgcgttaatagaggttgttgttaaattaagaaaaggaactgaaattgttgaagttag
aaaatcagacgctgatataataaggggcttctgtagatgctgtaatggaaggaatcaatatg
ttattgaattaa
```

FIGURE 18

*ilvM*: (SEQ ID NO:33)

atgatgcaacatcaggtcaatgtatcggctcgcttcaatccagaaaccttagaacgtgttt
tacgcgtggtgcgtcatcgtggtttccacgtctgctcaatgaatatggccgccgccagcga
tgcacaaaatataaatatcgaattgaccgttgccagcccacggtcggtcgacttactgttt
agtcagttaaataaactggtggacgtcgcacacgttgccatctgccagagcacaaccacat
cacaacaaatccgcgcctga

FIGURE 19

*ilvG*: (SEQ ID NO:35)

ttgttgttaaaacaactgtcggatcgtaaacctgcggattgcgtcgtgaccacagatgtgg
ggcagcaccagatgtgggctgcgcagcacatcgcccacactcgcccggaaaatttcatcac
ctccagcggtttaggtaccatgggttttggtttaccggcggcggttggcgcacaagtcgcg
cgaccgaacgataccgttgtctgtatctccggtgacggctcttttcatgatgaatgtgcaag
agctgggcaccgtaaaacgcaagcagttaccgttgaaaatcgtcttactcgataaccaacg
gttagggatggttcgacaatggcagcaactgttttttcaggaacgatacagcgaaaccacc
cttactgataaccccgatttcctcatgttagccagcgccttcggcatccatggccaacaca
tcacccggaagaccaggttgaagcggcactcgacaccatgctgaacagtgatgggccata
cctgcttcatgtctcaatcgacgaacttgagaacgtctggccgctggtgccgcctggcgcc
agtaattcagaaatgttggagaaattatcatga

FIGURE 20

*ilvN*: (SEQ ID NO:37)

atgcaaaacacaactcatgacaacgtaattctggagctcaccgttcgcaaccatccgggcg
taatgacccacgtttgtggcctttttgcccgccgcgcttttaacgttgaaggcattctttg
tctgccgattcaggacagcgacaaaagccatatctggctactggtcaatgacgaccagcgt
ctggagcagatgataagccaaatcgataagctggaagatgtcgtgaaagtgcagcgtaatc
agtccgatccgacgatgtttaacaagatcgcggtgttttttcagtaa

FIGURE 21

*ilvB*: (SEQ ID NO:39)

atggcaagttcgggcacaacatcgacgcgtaagcgctttaccggcgcagaatttatcgttc
atttcctggaacagcagggcattaagattgtgacaggcattccgggcggttctatcctgcc
tgtttacgatgccttaagccaaagcacgcaaatccgccatattctggcccgtcatgaacag
ggcgcgggctttatcgctcagggaatggcgcgcaccgacggtaaaccggcggtctgtatgg
cctgtagcggaccgggtgcgactaacctggtgaccgccattgccgatgcgcggctggactc
catcccgctgatttgcatcactggtcaggttcccgcctcgatgatcggcaccgacgccttc
caggaagtggacacctacggcatctctatccccatcaccaaacacaactatctggtcagac
atatcgaagaactcccgcaggtcatgagcgatgccttccgcattgcgcaatcaggccgccc
aggcccggtgtggatagacattcctaaggatgtgcaaacggcagtttttgagattgaaaca
cagcccgctatggcagaaaaagccgccgcccccgcctttagcgaagaaagcattcgtgacg
cagcggcgatgattaacgctgccaaacgcccggtgctttatctgggcggcggtgtgatcaa
tgcgcccgcacgggtgcgtgaactggcggagaaagcgcaactgcctaccaccatgacttta
atggcgctgggcatgttgccaaaagcgcatccgttgtcgctgggtatgctggggatgcacg
gcgtgcgcagcaccaactatattttgcaggaggcggatttgttgatagtgctcggtgcgcg
ttttgatgaccgggcgattggcaaaaccgagcagttctgtccgaatgccaaaatcattcat
gtcgatatcgaccgtgcagagctgggtaaaatcaagcagccgcacgtggcgattcaggcgg
atgttgatgacgtgctggcgcagttgatcccgctggtggaagcgcaaccgcgtgcagagtg
gcaccagttggtagcggatttgcagcgtgagtttccgtgtccaatcccgaaagcgtgcgat
ccgttaagccattacggcctgatcaacgccgttgccgctgtgtcgatgacaatgcaatta
tcaccaccgacgttggtcagcatcagatgtggaccgcgcaagcttatccgctcaatcgccc
acgccagtggctgacctccggtgggctgggcacgatgggttttggcctgcctgcggcgatt
ggcgctgcgctggcgaacccggatcgcaaagtgttgtgtttctccggcgacggcagcctga
tgatgaatattcaggagatggcgaccgccagtgaaaatcagctggatgtcaaaatcattct
gatgaacaacgaagcgctgggctggtgcatcagcaacagagtctgttctacgagcaaggc
gttttttgccgccacctatccgggcaaaatcaactttatgcagattgccgccggattcggcc
tcgaaacctgtgatttgaataacgaagccgatccgcaggcttcattgcaggaaatcatcaa
tcgccctggcccggcgctgatccatgtgcgcattgatgccgaagaaaagtttacccgatg
gtgccgccaggtgcggcgaatactgaaatggtgggggaataa

FIGURE 22

*adhE2 (Clostridium acetobutylicum):* (SEQ ID NO:41)

```
atgaaagttacaaatcaaaagaactaaaacaaaagctaaatgaattgagagaagcgcaaa
agaagtttgcaacctatactcaagagcaagttgataaaattttaaacaatgtgccatagc
cgcagctaaagaaagaataaacttagctaaattagcagtagaagaaacaggaataggtctt
gtagaagataaaattataaaaaatcattttgcagcagaatatatatacaataaatataaaa
atgaaaaaacttgtggcataatagaccatgacgattctttaggcataacaaaggttgctga
accaattggaattgttgcagccatagttcctactactaatccaacttccacagcaattttc
aaatcattaatttctttaaaaacaagaaacgcaatattcttttcaccacatccacgtgcaa
aaaaatctacaattgctgcagcaaaattaattttagatgcagctgttaaagcaggagcacc
taaaaatataataggctggatagatgagccatcaatagaactttctcaagatttgatgagt
gaagctgatataatattagcaacaggaggtccttcaatggttaaagcggcctattcatctg
gaaacctgcaattggtgttggagcaggaaatacaccagcaataatagatgagagtgcaga
tatagatatggcagtaagctccataatttatcaagacttatgacaatggagtaatatgc
gcttctgaacaatcaatattagttatgaattcaatatacgaaaaagttaaagaggaatttg
taaaacgaggatcatatatactcaatcaaaatgaaatagctaaaataaaagaaactatgtt
taaaaatggagctattaatgctgacatagttggaaaatctgcttatataattgctaaaatg
gcaggaattgaagttcctcaaactacaaagatacttataggcgaagtacaatctgttgaaa
aaagcgagctgttctcacatgaaaaactatcaccagtacttgcaatgtataaagttaagga
ttttgatgaagctctaaaaaaggcacaaaggctaatagaattaggtggaagtggacacacg
tcatctttatatatagattcacaaaacaataaggataaagttaaagaatttggattagcaa
tgaaaacttcaaggacatttattaacatgccttcttcacagggagcaagcggagatttata
caattttgcgatagcaccatcatttactcttggatgcggcacttggggaggaaactctgta
tcgcaaaatgtagagcctaaacatttattaaatattaaaagtgttgctgaaagaagggaaa
atatgctttggtttaaagtgccacaaaaaatatattttaaatatggatgtcttagatttgc
attaaaagaattaaaagatatgaataagaaaagagcctttatagtaacagataaagatctt
tttaaacttggatatgttaataaaataacaaaggtactagatgagatagatattaaataca
gtatatttacagatattaaatctgatccaactattgattcagtaaaaaaaggtgctaaaga
aatgcttaactttgaacctgatactataatctctattggtggtggatcgccaatggatgca
gcaaaggttatgcacttgttatatgaatatccagaagcagaaattgaaaatctagctataa
actttatggatataagaaagagaatatgcaatttccctaaattaggtacaaaggcgatttc
agtagctattcctacaactgctggtaccggttcagaggcaacacctttgcagttataact
aatgatgaaacaggaatgaaatacccttaacttcttatgaattgacccaaacatggcaa
taatagatactgaattaatgttaaatatgcctagaaaattaacagcagcaactggaataga
tgcattagttcatgctatagaagcatatgtttcggttatggctacggattatactgatgaa
ttagccttaagagcaataaaaatgatatttaaatatttgcctagagcctataaaaatggga
ctaacgacattgaagcaagagaaaaaatggcacatgcctctaatattgcggggatggcatt
tgcaaatgctttcttaggtgtatgccattcaatggctcataaacttggggcaatgcatcac
gttccacatggaattgcttgtgctgtattaatagaagaagttattaaatataacgctacag
actgtccaacaaagcaaacagcattccctcaatataaatctcctaatgctaagagaaaata
tgctgaaattgcagagtatttgaatttaaagggtactagcgataccgaaaaggtaacagcc
ttaatagaagctatttcaaagttaaagatagatttgagtattccacaaaatataagtgccg
ctggaataaataaaaaagattttttataatacgctagataaaatgtcagagcttgcttttga
tgaccaatgtacaacagctaatcctaggtatccacttataagtgaacttaaggatatctat
ataaaatcatttttaa
```

FIGURE 23

Li-*cimA* (*Leptospira interrogans*): (SEQ ID NO:43)

atgacaaaagtagaaactcgattggaaattttagacgtaactttgagagacggggagcaga
ccagaggggtcagttttctccacttccgaaaaactaaatatcgcaaaatttctattacaaaa
actaaatgtagatcgggtagagattgcgtctgcaagagtttctaaaggggaattggaaacg
gtccaaaaaatcatggaatgggctgcaacagaacagcttacggaaagaatcgaaatcttag
gttttgtagacgggaataaaaccgtagattggatcaaagatagtgggctaaggttttaaa
tcttttgactaagggatcgcttcatcatttagaaaaacaattaggcaaaactccgaaagaa
ttctttacagacgtttcttttgtaatagaatacgcgatcaaaagcggacttaaaataaacg
tatatttagaagattggtccaacggtttcagaaacagtccagattacgtcaaatcgctcgt
agaacatctaagtaaagaacatatagaaagaattttcttccagacacgttaggcgttctt
tcgccagaagagacgtttcaaggagtggattcactcattcaaaaatacccggatattcatt
ttgaatttcacggacataacgactacgatctttccgtggcaaatagtcttcaagcgattcg
tgccggagtcaaaggtcttcacgcttctataaatggtctcggagaaagagccggaaatact
ccgttggaagcactcgtaaccacgattcatgataagtctaactctaaaacgaacataaacg
aaattgcaattacggaagcaagccgtcttgtagaagtattcagcggaaaaagaatttctgc
aaatagaccgatcgtaggagaagacgtgtttactcagaccgcgggagtacacgcagacgga
gacaaaaaggaaatttatacgcaaatcctattttaccggaaagatttggtaggaaaagaa
gttacgcgttaggcaaacttgcaggtaaggcgagtatctccgaaaatgtaaaacaactcgg
aatggttttaagtgaagtggttttacaaaaggttttagaagggtgatcgaattaggagat
cagaataaactagtgacacctgaagatcttccatttatcattgcggacgtttctggaagaa
ccggagaaaaggtacttacaatcaaatcttgtaatattcattccggaattggaattcgtcc
tcacgcacaaattgaattggaatatcagggaaagattcataaggaaatttctgaaggagac
ggagggtatgatgcgtttatgaatgcacttactaaaattacgaatcgcctcggtattagta
ttcctaaattgatagattacgaagtaaggattcctcctggtggaaaaacagatgcacttgt
agaaactaggatcacctggaacaagtccttagatttagaagaggaccagactttcaaaacg
atgggagttcatccggatcaaacggttgcagcggttcatgcaactgaaagatgctcaatc
aaattctacaaccatggcaaatctaa

FIGURE 24

Li-*leuC* (*Leptospira interrogans*): (SEQ ID NO:45)

atgaagacaatgttcgaaaaaatttgggaagatcatctagtcggagaactagatgctggat
cctatctaatctatatagatcgccatctcattcatgaagttacaagtcctcaggcgtttga
aggacttaaacttgcaggcagaaaggttcgtcgtcctgaagctacttttgccacaatggat
cataacgtttctactagaacacgtgatttaagtctggccgatcctgtttccgcaattcaaa
tgcagactttaaaaaagaactgcgacgaaaacggaatccgcgtttatgattttcaaaaccc
tgaccaaggaatcattcacgtaatcgctcctgaaatgggactgactcatcctggaatgaca
atcgtatgcggagattctcatacttctacacacggtgcgtttggtgcgcttgctttcggga
tcggaaccagcgaagtagagcacgttcttgcgactcaaaccttagttcaaaaaagagcaaa
aacaatggagattagagtcgatggaaaactttccgataaggtcacagcaaaagacatcatt
cttgcgatcattggaaaaattggaaccgcaggtgcgacaggttatgtgatcgaatatagag
gttctgcaattcaagccctcagtatggaagctagaatgactatttgtaatatgtctatcga
agcgggagctagagcaggtttaatcgcaccagatgaaactacttttaattatattcaagga
aaggactttctccaaaaggagtcgaatgggatcttgcggtcaaaaaatggaaacactatg
taacggacgaaggtgctaaatttgatagaaccgtaattcttcatgcagatgaaatcgctcc
tatggtaacttggggaacttctcccagtcaggttgtttcgataaaaggagtcgttccagat
ccaaaagatgcaaatgatccggtggaaaaaattggaattgagtctgcgcttaaatatatgg
atctcaaatcgggccagaagatagaagacatttcaattaataaagtgtttatcggttcctg
tactaattctagaatcgaagatttaagagcggccgctgctaccgtaaaaggaaaaaaagtt
tcctctaaggttcaggcgattgtggttcccggttcaggcagagtcaaacgtcaggcggaac
aagaaggtctggataaaatttttaccgcggccggttttgaatggagaaatccaggctgttc
tatgtgtcttgcgatgaacgacgacgtattagaaccgggagatcgttgtgcttctacttct
aaccgaaactttgaaggtcgtcaaggaaaaggtggaagaacccatctagtaggaccggaaa
tggccgccgccgcggctatcgaaggccatttttgtggatattcgaaactggaaataa

FIGURE 25

Li-*leuD* (*Leptospira interrogans*): (SEQ ID NO:47)

```
atgaaaccctttactatattaaatggaattgccgccttactggacagacccaacgtggata
cggatcagatcattccaaaacaattttacggaagatagaacgaaccggtttcggagttca
tctgtttcacgattggagatacttagacgacgcgggtaccaaactcaatcctgattttcc
ctcaatcaagaacgatataagggagcttctatccttatcaccagagataactttggttgtg
gatcttccagagaacacgctccttgggctttagaagactacgggtttagggcaatcattgc
tccttcttacgcggatattttttcaacaactgctttaaaaacggaatgcttccagtcatt
ttaaaatcggaagaagtagaagagctgttccatttggtttcgactaacgtaggagcgaaag
tcatagtggatctggacaaacaaactgtaaccggaccgactggaaaaatatattatttga
agtggattcttttcgtaaatactgtctttataacggacttgatgacataggtctaactcta
aaacaagaaagtaaaattggagagtttgaaaaaagcagaagaagttgaaccttggttat
acgccatataa
```

FIGURE 26

Li-*leuB* (*Leptospira interrogans*): (SEQ ID NO:49)

atgaagaatgtagcagtactttcaggagacggaatcggaccggaagtcatggagatagcca
tctccgttttgaaaaaggctctcggtgcaaaagtttccgagtttcaatttaaagaaggatt
tgtaggtggaatcgcaatcgataaaactggacacccacttccaccggaaactcttaaacta
tgtgaagaatcttccgcaattcttttcggaagtgtgggaggtcctaaatgggaaacactcc
ctccggaaaaacaaccggaacgagggcacttctacctttgagaaaacatttgatctatt
tgcaaacttaagacctgcgatcatttatccagagttgaaaaatgcttctccagttcgttct
gatattattggaaacggattagatattctcatattaagagagttaaccggaggaatttatt
ttggacaaccaaaaggaagagaaggatcaggtcaggaagaatttgcatacgacacgatgaa
gtattccagaagagaaatcgaaggattgctaaagtcgcattccaggcggccagaaaaaga
aataataaagtgactagtatcgataaagcaaacgtcttgactacttccgttttttggaagg
aagtagtaatcgaattgcataagaagaattttcagacgtccaattgaatcatctttatgt
ggacaatgcggcgatgcagttaatcgtaaatccgaaacaattcgacgtggttctttgtgag
aatatgtttggtgatattctttcggacgaggcttccatcattacgggttcaatcggaatgc
ttccttctgcctctctttccgaatctggatttggattgtatgaaccttctggtggttctgc
gccggacatagccggaaaaggagtggcaaatccgattgctcaagtattgagtgcggcgttg
atgttacgttattcttttctatggaagaagaagcaaacaagatagaaaccgccgtgcgta
aaacgattgcctccggaaaaagaaccagagacatagcggaagtaggatctacgatcgtagg
aactaaagaaatcggtcaattgatcgaatcctttctctaa

FIGURE 27

*pheA*: (SEQ ID NO:51)

```
atgacatcggaaaacccgttactggcgctgcgagagaaaatcagcgcgctggatgaaaat
tattagcgttactggcagaacggcgcgaactggccgtcgaggtgggaaaagccaaactgct
ctcgcatcgcccggtacgtgatattgatcgtgaacgcgatttgctggaaagattaattacg
ctcggtaaagcgcaccatctggacgcccattacattactcgcctgttccagctcatcattg
aagattccgtattaactcagcaggctttgctccaacaacatctcaataaaattaatccgca
ctcagcacgcatcgcttttctcggccccaaaggttcttattccatcttgcggcgcgccag
tatgctgcccgtcactttgagcaattcattgaaagtggctgcgccaaatttgccgatattt
ttaatcaggtggaaaccggccaggccgactatgccgtcgtaccgattgaaaataccagctc
cggtgccataaacgacgtttacgatctgctgcaacataccagcttgtcgattgttggcgag
atgacgttaactatcgaccattgtttgttggtctccggcactactgatttatccaccatca
atacggtctacagccatccgcagccattccagcaatgcagcaaattccttaatcgttatcc
gcactggaagattgaatataccgaaagtacgtctgcggcaatggaaaaggttgcacaggca
aaatcaccgcatgttgctgcgttgggaagcgaagctggcggcactttgtacggtttgcagg
tactggagcgtattgaagcaaatcagcgacaaaacttcaccgatttgtggtgttggcgcg
taaagccattaacgtgtctgatcaggttccggcgaaaaccacgttgttaatggcgaccggg
caacaagccggtgcgctggttgaagcgttgctggtactgcgcaaccacaatctgattatga
cccgtctggaatcacgcccgattcacggtaatccatgggaagagatgttctatctggatat
tcaggccaatcttgaatcagcggaaatgcaaaaagcattgaaagagttaggggaaatcacc
cgttcaatgaaggtattgggctgttacccaagtgagaacgtagtgcctgttgatccaacct
                                                              ga
```

FIGURE 28

*TyrA:* (SEQ ID NO:53)

atggttgctgaattgaccgcattacgcgatcaaattgatgaagtcgataaagcgctgctga
atttattagcgaagcgtctggaactggttgctgaagtgggcgaggtgaaaagccgctttgg
actgcctatttatgttccggagcgcgaggcatctatgttggcctcgcgtcgtgcagaggcg
gaagctctgggtgtaccgccagatctgattgaggatgttttgcgtcgggtgatgcgtgaat
cttactccagtgaaaacgacaaaggatttaaaacactttgtccgtcactgcgtccggtggt
tatcgtcggcggtggcggtcagatgggacgccgttcgagaagatgctgaccctctcgggt
tatcaggtgcggattctggagcaacatgactgggatcgagcggctgatattgttgccgatg
ccggaatggtgattgttagtgtgccaatccacgttactgagcaagttattggcaaattacc
gcctttaccgaaagattgtattctggtcgatctggcatcagtgaaaaatgggccattacag
gccatgctggtggcgcatgatggtccggtgctggggctacacccgatgttcggtccggaca
gcggtagcctggcaaagcaagttgtggtctggtgtgatggacgtaaaccggaagcatacca
atggtttctggagcaaattcaggtctgggcgctcggctgcatcgtattagcgccgtcgag
cacgatcagaatatggcgtttattcaggcactgcgccactttgctactttgcttacgggc
tgcacctggcagaagaaaatgttcagcttgagcaacttctggcgctctcttcgccgattta
ccgccttgagctggcgatggtcgggcgactgtttgctcaggatccgcagctttatgccgac
atcattatgtcgtcagagcgtaatctggcgttaatcaaacgttactataagcgtttcggcg
aggcgattgagttgctggagcagggcgataagcaggcgtttattgacagtttccgcaaggt
ggagcactggttcggcgattacgcacagcgttttcagagtgaaagccgcgtgttattgcgt
caggcgaatgacaatcgccagtaa

FIGURE 29

*alsS*: acetolactate synthase (*Bacillus subtilis subsp. subtilis*) (SEQ ID NO: 55)

atgttgacaaaagcaacaaaagaacaaaaatcccttgtgaaaaacagaggggcggagcttg
ttgttgattgcttagtggagcaaggtgtcacacatgtatttggcattccaggtgcaaaaat
tgatgcggtatttgacgctttacaagataaaggacctgaaattatcgttgcccggcacgaa
caaaacgcagcattcatggcccaagcagtcggccgtttaactggaaaaccgggagtcgtgt
tagtcacatcaggaccgggtgcctctaacttggcaacaggcctgctgacagcgaacactga
aggagaccctgtcgttgcgcttgctggaaacgtgatccgtgcagatcgtttaaaacggaca
catcaatctttggataatgcggcgctattccagccgattacaaaatacagtgtagaagttc
aagatgtaaaaaatataccggaagctgttacaaatgcatttaggatagcgtcagcagggca
ggctggggccgcttttgtgagctttccgcaagatgttgtgaatgaagtcacaaatacgaaa
aacgtgcgtgctgttgcagcgccaaaactcggtcctgcagcagatgatgcaatcagtgcgg
ccatagcaaaaatccaaacagcaaaacttcctgtcgttttggtcggcatgaaaggcggaag
accggaagcaattaaagcggttcgcaagcttttgaaaaaggttcagcttccatttgttgaa
acatatcaagctgccggtacccttctagagatttagaggatcaatattttggccgtatcg
gtttgttccgcaaccagcctggcgatttactgctagagcaggcagatgttgttctgacgat
cggctatgacccgattgaatatgatccgaaattctggaatatcaatggagaccggacaatt
atccatttagacgagattatcgctgacattgatcatgcttaccagcctgatcttgaattga
tcggtgacattccgtccacgatcaatcatatcgaacacgatgctgtgaaagtggaatttgc
agagcgtgagcagaaaatcctttctgatttaaaacaatatatgcatgaaggtgagcaggtg
cctgcagattggaaatcagacagagcgcaccctcttgaaatcgttaaagagttgcgtaatg
cagtcgatgatcatgttacagtaacttgcgatatcggttcgcacgccatttggatgtcacg
ttatttccgcagctacgagccgttaacattaatgatcagtaacggtatgcaaacactcggc
gttgcgcttccttgggcaatcggcgcttcattggtgaaaccgggagaaaaagtggtttctg
tctctggtgacggcggtttcttattctcagcaatggaattagagacagcagttcgactaaa
agcaccaattgtacacattgtatggaacgacagcacatatgacatggttgcattccagcaa
ttgaaaaaatataaccgtacatctgcggtcgatttcggaaatatcgatatcgtgaaatatg
cggaaagcttcggagcaactggcttgcgcgtagaatcaccagaccagctggcagatgttct
gcgtcaaggcatgaacgctgaaggtcctgtcatcatcgatgtcccggttgactacagtgat
aacattaatttagcaagtgacaagcttccgaaagaattcggggaactcatgaaaacgaaag
ctctctag

FIGURE 30

SEQUENCE LISTING

```
<160> NUMBER OF SEQ ID NOS: 56

<210> SEQ ID NO 1
<211> LENGTH: 1647
<212> TYPE: DNA
<213> ORGANISM: Lactococcus lactis
<220> FEATURE:
<221> NAME/KEY: CDS
<222> LOCATION: (1)..(1647)

<400> SEQUENCE: 1 atg tat aca gta gga gat tac cta tta gac cga tta cac gag tta gga      48
Met Tyr Thr Val Gly Asp Tyr Leu Leu Asp Arg Leu His Glu Leu Gly
1               5                   10                  15 att gaa gaa att ttt gga gtc cct gga gac tat aac tta caa ttt tta      96
Ile Glu Glu Ile Phe Gly Val Pro Gly Asp Tyr Asn Leu Gln Phe Leu
            20                  25                  30 gat caa att att tcc cgc aag gat atg aaa tgg gtc gga aat gct aat     144
Asp Gln Ile Ile Ser Arg Lys Asp Met Lys Trp Val Gly Asn Ala Asn
        35                  40                  45 gaa tta aat gct tca tat atg gct gat ggc tat gct cgt act aaa aaa     192
Glu Leu Asn Ala Ser Tyr Met Ala Asp Gly Tyr Ala Arg Thr Lys Lys
```

```
                50                   55                   60
gct gcc gca ttt ctt aca acc ttt gga gta ggt gaa ttg agt gca gtt         240
Ala Ala Ala Phe Leu Thr Thr Phe Gly Val Gly Glu Leu Ser Ala Val
 65                  70                  75                  80 aat gga tta gca gga agt tac gcc gaa aat tta cca gta gta gaa ata         288
Asn Gly Leu Ala Gly Ser Tyr Ala Glu Asn Leu Pro Val Val Glu Ile
                 85                  90                  95 gtg gga tca cct aca tca aaa gtt caa aat gaa gga aaa ttt gtt cat         336
Val Gly Ser Pro Thr Ser Lys Val Gln Asn Glu Gly Lys Phe Val His
            100                 105                 110 cat acg ctg gct gac ggt gat ttt aaa cac ttt atg aaa atg cac gaa         384
His Thr Leu Ala Asp Gly Asp Phe Lys His Phe Met Lys Met His Glu
        115                 120                 125 cct gtt aca gca gct cga act tta ctg aca gca gaa aat gca acc gtt         432
Pro Val Thr Ala Ala Arg Thr Leu Leu Thr Ala Glu Asn Ala Thr Val
    130                 135                 140 gaa att gac cga gta ctt tct gca cta tta aaa gaa aga aaa cct gtc         480
Glu Ile Asp Arg Val Leu Ser Ala Leu Leu Lys Glu Arg Lys Pro Val
145                 150                 155                 160 tat atc aac tta cca gtt gat gtt gct gct gca aaa gca gag aaa ccc         528
Tyr Ile Asn Leu Pro Val Asp Val Ala Ala Ala Lys Ala Glu Lys Pro
                165                 170                 175 tca ctc cct ttg aaa aaa gaa aac tca act tca aat aca agt gac caa         576
Ser Leu Pro Leu Lys Lys Glu Asn Ser Thr Ser Asn Thr Ser Asp Gln
            180                 185                 190 gag atc ttg aac aaa att caa gaa agc ttg aaa aat gcc aaa aaa cca         624
Glu Ile Leu Asn Lys Ile Gln Glu Ser Leu Lys Asn Ala Lys Lys Pro
        195                 200                 205 atc gtg att aca gga cat gaa ata att agt ttt ggc tta gaa aaa aca         672
Ile Val Ile Thr Gly His Glu Ile Ile Ser Phe Gly Leu Glu Lys Thr
    210                 215                 220 gtc tct caa ttt att tca aag aca aaa cta cct att acg aca tta aac         720
Val Ser Gln Phe Ile Ser Lys Thr Lys Leu Pro Ile Thr Thr Leu Asn
225                 230                 235                 240 ttt gga aaa agt tca gtt gat gaa gct ctc cct tca ttt tta gga atc         768
Phe Gly Lys Ser Ser Val Asp Glu Ala Leu Pro Ser Phe Leu Gly Ile
                245                 250                 255 tat aat ggt aaa ctc tca gag cct aat ctt aaa gaa ttc gtg gaa tca         816
Tyr Asn Gly Lys Leu Ser Glu Pro Asn Leu Lys Glu Phe Val Glu Ser
            260                 265                 270 gcc gac ttc atc ctg atg ctt gga gtt aaa ctc aca gac tct tca aca         864
Ala Asp Phe Ile Leu Met Leu Gly Val Lys Leu Thr Asp Ser Ser Thr
        275                 280                 285 gga gcc ttc act cat cat tta aat gaa aat aaa atg att tca ctg aat         912
Gly Ala Phe Thr His His Leu Asn Glu Asn Lys Met Ile Ser Leu Asn
    290                 295                 300 ata gat gaa gga aaa ata ttt aac gaa agc atc caa aat ttt gat ttt         960
Ile Asp Glu Gly Lys Ile Phe Asn Glu Ser Ile Gln Asn Phe Asp Phe
305                 310                 315                 320 gaa tcc ctc atc tcc tct ctc tta gac cta agc gaa ata gaa tac aaa        1008
Glu Ser Leu Ile Ser Ser Leu Leu Asp Leu Ser Glu Ile Glu Tyr Lys
                325                 330                 335 gga aaa tat atc gat aaa aag caa gaa gac ttt gtt cca tca aat gcg        1056
Gly Lys Tyr Ile Asp Lys Lys Gln Glu Asp Phe Val Pro Ser Asn Ala
            340                 345                 350 ctt tta tca caa gac cgc cta tgg caa gca gtt gaa aac cta act caa        1104
Leu Leu Ser Gln Asp Arg Leu Trp Gln Ala Val Glu Asn Leu Thr Gln
        355                 360                 365 agc aat gaa aca atc gtt gct gaa caa ggg aca tca ttc ttt ggc gct        1152
Ser Asn Glu Thr Ile Val Ala Glu Gln Gly Thr Ser Phe Phe Gly Ala
```

```
Ser Asn Glu Thr Ile Val Ala Glu Gln Gly Thr Ser Phe Phe Gly Ala
    370                 375                 380 tca tca att ttc tta aaa cca aag agt cat ttt att ggt caa ccc tta        1200
Ser Ser Ile Phe Leu Lys Pro Lys Ser His Phe Ile Gly Gln Pro Leu
385                 390                 395                 400 tgg gga tca att gga tat aca ttc cca gca gca tta gga agc caa att        1248
Trp Gly Ser Ile Gly Tyr Thr Phe Pro Ala Ala Leu Gly Ser Gln Ile
                405                 410                 415 gca gat aaa gaa agc aga cac ctt tta ttt att ggt gat ggt tca ctt        1296
Ala Asp Lys Glu Ser Arg His Leu Leu Phe Ile Gly Asp Gly Ser Leu
            420                 425                 430 caa ctt acg gtg caa gaa tta gga tta gca atc aga gaa aaa att aat        1344
Gln Leu Thr Val Gln Glu Leu Gly Leu Ala Ile Arg Glu Lys Ile Asn
        435                 440                 445 cca att tgc ttt att atc aat aat gat ggt tat aca gtc gaa aga gaa        1392
Pro Ile Cys Phe Ile Ile Asn Asn Asp Gly Tyr Thr Val Glu Arg Glu
    450                 455                 460 att cat gga cca aat caa agc tac aat gat att cca atg tgg aat tac        1440
Ile His Gly Pro Asn Gln Ser Tyr Asn Asp Ile Pro Met Trp Asn Tyr
465                 470                 475                 480 tca aaa tta cca gaa tca ttt gga gca aca gaa gaa cga gta gtc tcg        1488
Ser Lys Leu Pro Glu Ser Phe Gly Ala Thr Glu Glu Arg Val Val Ser
                485                 490                 495 aaa atc gtt aga act gaa aat gaa ttt gtg tct gtc atg aaa gaa gct        1536
Lys Ile Val Arg Thr Glu Asn Glu Phe Val Ser Val Met Lys Glu Ala
            500                 505                 510 caa gca gat cca aat aga atg tac tgg att gag tta att ttg gca aaa        1584
Gln Ala Asp Pro Asn Arg Met Tyr Trp Ile Glu Leu Ile Leu Ala Lys
        515                 520                 525 gaa gat gca cca aaa gta ctg aaa aaa atg ggc aaa cta ttt gct gaa        1632
Glu Asp Ala Pro Lys Val Leu Lys Lys Met Gly Lys Leu Phe Ala Glu
    530                 535                 540 caa aat aaa tca taa                                                     1647
Gln Asn Lys Ser
545

<210> SEQ ID NO 2
<211> LENGTH: 548
<212> TYPE: PRT
<213> ORGANISM: Lactococcus lactis

<400> SEQUENCE: 2

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125
```

```
Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
        180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
    210                 215                 220

Val Ser Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Asp Ala Pro Lys Val Leu Lys Lys Met Gly Lys Leu Phe Ala Glu
    530                 535                 540

Gln Asn Lys Ser
```

```
<210> SEQ ID NO 3
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 3 atg tct gaa att act ctt gga aaa tac tta ttt gaa aga ttg aag caa      48
Met Ser Glu Ile Thr Leu Gly Lys Tyr Leu Phe Glu Arg Leu Lys Gln
1               5                   10                  15 gtt aat gtt aac acc att ttt ggg cta cca ggc gac ttc aac ttg tcc      96
Val Asn Val Asn Thr Ile Phe Gly Leu Pro Gly Asp Phe Asn Leu Ser
            20                  25                  30 cta ttg gac aag att tac gag gta gat gga ttg aga tgg gct ggt aat     144
Leu Leu Asp Lys Ile Tyr Glu Val Asp Gly Leu Arg Trp Ala Gly Asn
        35                  40                  45 gca aat gag ctg aac gcc gcc tat gcc gcc gat ggt tac gca cgc atc     192
Ala Asn Glu Leu Asn Ala Ala Tyr Ala Ala Asp Gly Tyr Ala Arg Ile
    50                  55                  60 aag ggt tta tct gtg ctg gta act act ttt ggc gta ggt gaa tta tcc     240
Lys Gly Leu Ser Val Leu Val Thr Thr Phe Gly Val Gly Glu Leu Ser
65                  70                  75                  80 gcc ttg aat ggt att gca gga tcg tat gca gaa cac gtc ggt gta ctg     288
Ala Leu Asn Gly Ile Ala Gly Ser Tyr Ala Glu His Val Gly Val Leu
                85                  90                  95 cat gtt gtt ggt gtc ccc tct atc tcc gct cag gct aag caa ttg ttg     336
His Val Val Gly Val Pro Ser Ile Ser Ala Gln Ala Lys Gln Leu Leu
            100                 105                 110 ttg cat cat acc ttg ggt aac ggt gat ttt acc gtt ttt cac aga atg     384
Leu His His Thr Leu Gly Asn Gly Asp Phe Thr Val Phe His Arg Met
        115                 120                 125 tcc gcc aat atc tca gaa act aca tca atg att aca gac att gct aca     432
Ser Ala Asn Ile Ser Glu Thr Thr Ser Met Ile Thr Asp Ile Ala Thr
    130                 135                 140 gcc cct tca gaa atc gat agg ttg atc agg aca aca ttt ata aca caa     480
Ala Pro Ser Glu Ile Asp Arg Leu Ile Arg Thr Thr Phe Ile Thr Gln
145                 150                 155                 160 agg cct agc tac ttg ggg ttg cca gcg aat ttg gta gat cta aag gtt     528
Arg Pro Ser Tyr Leu Gly Leu Pro Ala Asn Leu Val Asp Leu Lys Val
                165                 170                 175 cct ggt tct ctt ttg gaa aaa ccg att gat cta tca tta aaa cct aac     576
Pro Gly Ser Leu Leu Glu Lys Pro Ile Asp Leu Ser Leu Lys Pro Asn
            180                 185                 190 gat ccc gaa gct gaa aag gaa gtt att gat acc gta cta gaa ttg atc     624
Asp Pro Glu Ala Glu Lys Glu Val Ile Asp Thr Val Leu Glu Leu Ile
        195                 200                 205 cag aat tcg aaa aac cct gtt ata cta tcg gat gcc tgt gct tct agg     672
Gln Asn Ser Lys Asn Pro Val Ile Leu Ser Asp Ala Cys Ala Ser Arg
    210                 215                 220 cac aac gtt aaa aaa gaa acc cag aag tta att gat ttg acg caa ttc     720
His Asn Val Lys Lys Glu Thr Gln Lys Leu Ile Asp Leu Thr Gln Phe
225                 230                 235                 240 cca gct ttt gtg aca cct cta ggt aaa ggg tca ata gat gaa cag cat     768
Pro Ala Phe Val Thr Pro Leu Gly Lys Gly Ser Ile Asp Glu Gln His
                245                 250                 255 ccc aga tat ggc ggt gtt tat gtg gga acg ctg tcc aaa caa gac gtg     816
Pro Arg Tyr Gly Gly Val Tyr Val Gly Thr Leu Ser Lys Gln Asp Val
```

```
            260             265             270
aaa cag gcc gtt gag tcg gct gat ttg atc ctt tcg gtc ggt gct ttg    864
Lys Gln Ala Val Glu Ser Ala Asp Leu Ile Leu Ser Val Gly Ala Leu
            275             280             285 ctc tct gat ttt aac aca ggt tcg ttt tcc tac tcc tac aag act aaa    912
Leu Ser Asp Phe Asn Thr Gly Ser Phe Ser Tyr Ser Tyr Lys Thr Lys
        290             295             300 aat gta gtg gag ttt cat tcc gat tac gta aag gtg aag aac gct acg    960
Asn Val Val Glu Phe His Ser Asp Tyr Val Lys Val Lys Asn Ala Thr
305             310             315             320 ttc ctc ggt gta caa atg aaa ttt gca cta caa aac tta ctg aag gtt   1008
Phe Leu Gly Val Gln Met Lys Phe Ala Leu Gln Asn Leu Leu Lys Val
                325             330             335 att ccc gat gtt gtt aag ggc tac aag agc gtt ccc gta cca acc aaa   1056
Ile Pro Asp Val Val Lys Gly Tyr Lys Ser Val Pro Val Pro Thr Lys
            340             345             350 act ccc gca aac aaa ggt gta cct gct agc acg ccc ttg aaa caa gag   1104
Thr Pro Ala Asn Lys Gly Val Pro Ala Ser Thr Pro Leu Lys Gln Glu
        355             360             365 tgg ttg tgg aac gaa ttg tcc aaa ttc ttg caa gaa ggt gat gtt atc   1152
Trp Leu Trp Asn Glu Leu Ser Lys Phe Leu Gln Glu Gly Asp Val Ile
370             375             380 att tcc gag acc ggc acg tct gcc ttc ggt atc aat caa act atc ttt   1200
Ile Ser Glu Thr Gly Thr Ser Ala Phe Gly Ile Asn Gln Thr Ile Phe
385             390             395             400 cct aag gac gcc tac ggt atc tcg cag gtg ttg tgg ggg tcc atc ggt   1248
Pro Lys Asp Ala Tyr Gly Ile Ser Gln Val Leu Trp Gly Ser Ile Gly
                405             410             415 ttt aca aca gga gca act tta ggt gct gcc ttt gcc gct gag gag att   1296
Phe Thr Thr Gly Ala Thr Leu Gly Ala Ala Phe Ala Ala Glu Glu Ile
            420             425             430 gac ccc aac aag aga gtc atc tta ttc ata ggt gac ggg tct ttg cag   1344
Asp Pro Asn Lys Arg Val Ile Leu Phe Ile Gly Asp Gly Ser Leu Gln
        435             440             445 tta acc gtc caa gaa atc tcc acc atg atc aga tgg ggg tta aag ccg   1392
Leu Thr Val Gln Glu Ile Ser Thr Met Ile Arg Trp Gly Leu Lys Pro
450             455             460 tat ctt ttt gtc ctt aac aac gac ggc tac act atc gaa aag ctg att   1440
Tyr Leu Phe Val Leu Asn Asn Asp Gly Tyr Thr Ile Glu Lys Leu Ile
465             470             475             480 cat ggg cct cac gca gag tac aac gaa atc cag acc tgg gat cac ctc   1488
His Gly Pro His Ala Glu Tyr Asn Glu Ile Gln Thr Trp Asp His Leu
                485             490             495 gcc ctg ttg ccc gca ttt ggt gcg aaa aag tac gaa aat cac aag atc   1536
Ala Leu Leu Pro Ala Phe Gly Ala Lys Lys Tyr Glu Asn His Lys Ile
            500             505             510 gcc act acg ggt gag tgg gat gcc tta acc act gat tca gag ttc cag   1584
Ala Thr Thr Gly Glu Trp Asp Ala Leu Thr Thr Asp Ser Glu Phe Gln
        515             520             525 aaa aac tcg gtg atc aga cta att gaa ctg aaa ctg ccc gtc ttt gat   1632
Lys Asn Ser Val Ile Arg Leu Ile Glu Leu Lys Leu Pro Val Phe Asp
530             535             540 gct ccg gaa agt ttg atc aaa caa gcg caa ttg act gcc gct aca aat   1680
Ala Pro Glu Ser Leu Ile Lys Gln Ala Gln Leu Thr Ala Ala Thr Asn
545             550             555             560 gcc aaa caa taa                                                    1692
Ala Lys Gln

<210> SEQ ID NO 4
```

<211> LENGTH: 563
<212> TYPE: PRT
<213> ORGANISM: Saccharomyces cerevisiae

<400> SEQUENCE: 4

```
Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
```

```
Pro Lys Asp Ala Tyr Gly Ile Ser Gln Val Leu Trp Gly Ser Ile Gly
385                 390                 395                 400
            405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
            515                 520                 525

Lys Asn Ser Val Ile Arg Leu Ile Glu Leu Lys Leu Pro Val Phe Asp
            530                 535                 540

Ala Pro Glu Ser Leu Ile Lys Gln Ala Gln Leu Thr Ala Ala Thr Asn
545                 550                 555                 560

Ala Lys Gln
```

<210> SEQ ID NO 5
<211> LENGTH: 1908
<212> TYPE: DNA
<213> ORGANISM: Saccharomyces cerevisiae
<220> FEATURE:
<221> NAME/KEY: CDS
<222> LOCATION: (1)..(1908)

<400> SEQUENCE: 5

```
atg gca cct gtt aca att gaa aag ttc gta aat caa gaa gaa cga cac      48
Met Ala Pro Val Thr Ile Glu Lys Phe Val Asn Gln Glu Glu Arg His
1               5                   10                  15 ctt gtt tcc aac cga tca gca aca att ccg ttt ggt gaa tac ata ttt      96
Leu Val Ser Asn Arg Ser Ala Thr Ile Pro Phe Gly Glu Tyr Ile Phe
            20                  25                  30 aaa aga ttg ttg tcc atc gat acg aaa tca gtt ttc ggt gtt cct ggt     144
Lys Arg Leu Leu Ser Ile Asp Thr Lys Ser Val Phe Gly Val Pro Gly
        35                  40                  45 gac ttc aac tta tct cta tta gaa tat ctc tat tca cct agt gtt gaa     192
Asp Phe Asn Leu Ser Leu Leu Glu Tyr Leu Tyr Ser Pro Ser Val Glu
    50                  55                  60 tca gct ggc cta aga tgg gtc ggc acg tgt aat gaa ctg aac gcc gct     240
Ser Ala Gly Leu Arg Trp Val Gly Thr Cys Asn Glu Leu Asn Ala Ala
65                  70                  75                  80 tat gcg gcc gac gga tat tcc cgt tac tct aat aag att ggc tgt tta     288
Tyr Ala Ala Asp Gly Tyr Ser Arg Tyr Ser Asn Lys Ile Gly Cys Leu
                85                  90                  95 ata acc acg tat ggc gtt ggt gaa tta agc gcc ttg aac ggt ata gcc     336
Ile Thr Thr Tyr Gly Val Gly Glu Leu Ser Ala Leu Asn Gly Ile Ala
            100                 105                 110 ggt tcg ttc gct gaa aat gtc aaa gtt ttg cac att gtt ggt gtg gcc     384
Gly Ser Phe Ala Glu Asn Val Lys Val Leu His Ile Val Gly Val Ala
        115                 120                 125 aag tcc ata gat tcg cgt tca agt aac ttt agt gat cgg aac cta cat     432
Lys Ser Ile Asp Ser Arg Ser Ser Asn Phe Ser Asp Arg Asn Leu His
```

```
                    130                 135                 140
cat ttg gtc cca cag cta cat gat tca aat ttt aaa ggg cca aat cat    480
His Leu Val Pro Gln Leu His Asp Ser Asn Phe Lys Gly Pro Asn His
145                 150                 155                 160 aaa gta tat cat gat atg gta aaa gat aga gtc gct tgc tcg gta gcc    528
Lys Val Tyr His Asp Met Val Lys Asp Arg Val Ala Cys Ser Val Ala
                165                 170                 175 tac ttg gag gat att gaa act gca tgt gac caa gtc gat aat gtt atc    576
Tyr Leu Glu Asp Ile Glu Thr Ala Cys Asp Gln Val Asp Asn Val Ile
            180                 185                 190 cgc gat att tac aag tat tct aaa cct ggt tat att ttt gtt cct gca    624
Arg Asp Ile Tyr Lys Tyr Ser Lys Pro Gly Tyr Ile Phe Val Pro Ala
        195                 200                 205 gat ttt gcg gat atg tct gtt aca tgt gat aat ttg gtt aat gtt cca    672
Asp Phe Ala Asp Met Ser Val Thr Cys Asp Asn Leu Val Asn Val Pro
    210                 215                 220 cgt ata tct caa caa gat tgt ata gta tac cct tct gaa aac caa ttg    720
Arg Ile Ser Gln Gln Asp Cys Ile Val Tyr Pro Ser Glu Asn Gln Leu
225                 230                 235                 240 tct gac ata atc aac aag att act agt tgg ata tat tcc agt aaa aca    768
Ser Asp Ile Ile Asn Lys Ile Thr Ser Trp Ile Tyr Ser Ser Lys Thr
                245                 250                 255 cct gcg atc ctt gga gac gta ctg act gat agg tat ggt gtg agt aac    816
Pro Ala Ile Leu Gly Asp Val Leu Thr Asp Arg Tyr Gly Val Ser Asn
            260                 265                 270 ttt ttg aac aag ctt atc tgc aaa act ggg att tgg aat ttt tcc act    864
Phe Leu Asn Lys Leu Ile Cys Lys Thr Gly Ile Trp Asn Phe Ser Thr
        275                 280                 285 gtt atg gga aaa tct gta att gat gag tca aac cca act tat atg ggt    912
Val Met Gly Lys Ser Val Ile Asp Glu Ser Asn Pro Thr Tyr Met Gly
    290                 295                 300 caa tat aat ggt aaa gaa ggt tta aaa caa gtc tat gaa cat ttt gaa    960
Gln Tyr Asn Gly Lys Glu Gly Leu Lys Gln Val Tyr Glu His Phe Glu
305                 310                 315                 320 ctg tgc gac ttg gtc ttg cat ttt gga gtc gac atc aat gaa att aat   1008
Leu Cys Asp Leu Val Leu His Phe Gly Val Asp Ile Asn Glu Ile Asn
                325                 330                 335 aat ggg cat tat act ttt act tat aaa cca aat gct aaa atc att caa   1056
Asn Gly His Tyr Thr Phe Thr Tyr Lys Pro Asn Ala Lys Ile Ile Gln
            340                 345                 350 ttt cat ccg aat tat att cgc ctt gtg gac act agg cag ggc aat gag   1104
Phe His Pro Asn Tyr Ile Arg Leu Val Asp Thr Arg Gln Gly Asn Glu
        355                 360                 365 caa atg ttc aaa gga atc aat ttt gcc cct att tta aaa gaa cta tac   1152
Gln Met Phe Lys Gly Ile Asn Phe Ala Pro Ile Leu Lys Glu Leu Tyr
    370                 375                 380 aag cgc att gac gtt tct aaa ctt tct ttg caa tat gat tca aat gta   1200
Lys Arg Ile Asp Val Ser Lys Leu Ser Leu Gln Tyr Asp Ser Asn Val
385                 390                 395                 400 act caa tat acg aac gaa aca atg cgg tta gaa gat cct acc aat gga   1248
Thr Gln Tyr Thr Asn Glu Thr Met Arg Leu Glu Asp Pro Thr Asn Gly
                405                 410                 415 caa tca agc att att aca caa gtt cac tta caa aag acg atg cct aaa   1296
Gln Ser Ser Ile Ile Thr Gln Val His Leu Gln Lys Thr Met Pro Lys
            420                 425                 430 ttt ttg aac cct ggt gat gtt gtc gtt tgt gaa aca ggc tct ttt caa   1344
Phe Leu Asn Pro Gly Asp Val Val Val Cys Glu Thr Gly Ser Phe Gln
        435                 440                 445 ttc tct gtt cgt gat ttc gcg ttt cct tcg caa tta aaa tat ata tcg   1392
```

```
                                                                           1440
caa gga ttt ttc ctt tcc att ggc atg gcc ctt cct gcc gcc cta ggt
Gln Gly Phe Phe Leu Ser Ile Gly Met Ala Leu Pro Ala Ala Leu Gly
465             470             475             480 gtt gga att gcc atg caa gac cac tca aac gct cac atc aat ggt ggc    1488
Val Gly Ile Ala Met Gln Asp His Ser Asn Ala His Ile Asn Gly Gly
                485             490             495 aac gta aaa gag gac tat aag cca aga tta att ttg ttt gaa ggt gac    1536
Asn Val Lys Glu Asp Tyr Lys Pro Arg Leu Ile Leu Phe Glu Gly Asp
        500             505             510 ggt gca gca cag atg aca atc caa gaa ctg agc acc att ctg aag tgc    1584
Gly Ala Ala Gln Met Thr Ile Gln Glu Leu Ser Thr Ile Leu Lys Cys
    515             520             525 aat att cca cta gaa gtt atc att tgg aac aat aac ggc tac act att    1632
Asn Ile Pro Leu Glu Val Ile Ile Trp Asn Asn Asn Gly Tyr Thr Ile
530             535             540 gaa aga gcc atc atg ggc cct acc agg tcg tat aac gac gtt atg tct    1680
Glu Arg Ala Ile Met Gly Pro Thr Arg Ser Tyr Asn Asp Val Met Ser
545             550             555             560 tgg aaa tgg acc aaa cta ttt gaa gca ttc gga gac ttc gac gga aag    1728
Trp Lys Trp Thr Lys Leu Phe Glu Ala Phe Gly Asp Phe Asp Gly Lys
                565             570             575 tat act aat agc act ctc att caa tgt ccc tct aaa tta gca ctg aaa    1776
Tyr Thr Asn Ser Thr Leu Ile Gln Cys Pro Ser Lys Leu Ala Leu Lys
                580             585             590 ttg gag gag ctt aag aat tca aac aaa aga agc ggg ata gaa ctt tta    1824
Leu Glu Glu Leu Lys Asn Ser Asn Lys Arg Ser Gly Ile Glu Leu Leu
        595             600             605 gaa gtc aaa tta ggc gaa ttg gat ttc ccc gaa cag cta aag tgc atg    1872
Glu Val Lys Leu Gly Glu Leu Asp Phe Pro Glu Gln Leu Lys Cys Met
    610             615             620 gtt gaa gca gcg gca ctt aaa aga aat aaa aaa tag                    1908
Val Glu Ala Ala Ala Leu Lys Arg Asn Lys Lys
625             630             635

<210> SEQ ID NO 6
<211> LENGTH: 635
<212> TYPE: PRT
<213> ORGANISM: Saccharomyces cerevisiae

<400> SEQUENCE: 6

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125
```

```
Lys Ser Ile Asp Ser Arg Ser Ser Asn Phe Ser Asp Arg Asn Leu His
    130                 135                 140
His Leu Val Pro Gln Leu His Asp Ser Asn Phe Lys Gly Pro Asn His
145                 150                 155                 160
Lys Val Tyr His Asp Met Val Lys Asp Arg Val Ala Cys Ser Val Ala
                165                 170                 175
Tyr Leu Glu Asp Ile Glu Thr Ala Cys Asp Gln Val Asp Asn Val Ile
            180                 185                 190
Arg Asp Ile Tyr Lys Tyr Ser Lys Pro Gly Tyr Ile Phe Val Pro Ala
        195                 200                 205
Asp Phe Ala Asp Met Ser Val Thr Cys Asp Asn Leu Val Asn Val Pro
    210                 215                 220
Arg Ile Ser Gln Gln Asp Cys Ile Val Tyr Pro Ser Glu Asn Gln Leu
225                 230                 235                 240
Ser Asp Ile Ile Asn Lys Ile Thr Ser Trp Ile Tyr Ser Ser Lys Thr
                245                 250                 255
Pro Ala Ile Leu Gly Asp Val Leu Thr Asp Arg Tyr Gly Val Ser Asn
            260                 265                 270
Phe Leu Asn Lys Leu Ile Cys Lys Thr Gly Ile Trp Asn Phe Ser Thr
        275                 280                 285
Val Met Gly Lys Ser Val Ile Asp Glu Ser Asn Pro Thr Tyr Met Gly
    290                 295                 300
Gln Tyr Asn Gly Lys Glu Gly Leu Lys Gln Val Tyr Glu His Phe Glu
305                 310                 315                 320
Leu Cys Asp Leu Val Leu His Phe Gly Val Asp Ile Asn Glu Ile Asn
                325                 330                 335
Asn Gly His Tyr Thr Phe Thr Tyr Lys Pro Asn Ala Lys Ile Ile Gln
            340                 345                 350
Phe His Pro Asn Tyr Ile Arg Leu Val Asp Thr Arg Gln Gly Asn Glu
        355                 360                 365
Gln Met Phe Lys Gly Ile Asn Phe Ala Pro Ile Leu Lys Glu Leu Tyr
    370                 375                 380
Lys Arg Ile Asp Val Ser Lys Leu Ser Leu Gln Tyr Asp Ser Asn Val
385                 390                 395                 400
Thr Gln Tyr Thr Asn Glu Thr Met Arg Leu Glu Asp Pro Thr Asn Gly
                405                 410                 415
Gln Ser Ser Ile Ile Thr Gln Val His Leu Gln Lys Thr Met Pro Lys
            420                 425                 430
Phe Leu Asn Pro Gly Asp Val Val Cys Glu Thr Gly Ser Phe Gln
        435                 440                 445
Phe Ser Val Arg Asp Phe Ala Phe Pro Ser Gln Leu Lys Tyr Ile Ser
    450                 455                 460
Gln Gly Phe Phe Leu Ser Ile Gly Met Ala Leu Pro Ala Ala Leu Gly
465                 470                 475                 480
Val Gly Ile Ala Met Gln Asp His Ser Asn Ala His Ile Asn Gly Gly
                485                 490                 495
Asn Val Lys Glu Asp Tyr Lys Pro Arg Leu Ile Leu Phe Glu Gly Asp
            500                 505                 510
Gly Ala Ala Gln Met Thr Ile Gln Glu Leu Ser Thr Ile Leu Lys Cys
        515                 520                 525
Asn Ile Pro Leu Glu Val Ile Trp Asn Asn Gly Tyr Thr Ile
    530                 535                 540
Glu Arg Ala Ile Met Gly Pro Thr Arg Ser Tyr Asn Asp Val Met Ser
```

```
                 545                 550                 555                 560
Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
                580                 585                 590

Leu Glu Glu Leu Lys Asn Ser Asn Lys Arg Ser Gly Ile Glu Leu Leu
                595                 600                 605

Glu Val Lys Leu Gly Glu Leu Asp Phe Pro Gln Leu Lys Cys Met
610                 615                 620

Val Glu Ala Ala Ala Leu Lys Arg Asn Lys Lys
625                 630                 635

<210> SEQ ID NO 7
<211> LENGTH: 1830
<212> TYPE: DNA
<213> ORGANISM: Saccharomyces cerevisiae
<220> FEATURE:
<221> NAME/KEY: CDS
<222> LOCATION: (1)..(1830)

<400> SEQUENCE: 7 atg aat tct agc tat aca cag aga tat gca ctg ccg aag tgt ata gca        48
Met Asn Ser Ser Tyr Thr Gln Arg Tyr Ala Leu Pro Lys Cys Ile Ala
1               5                   10                  15 ata tca gat tat ctt ttc cat cgg ctc aac cag ctg aac ata cat acc        96
Ile Ser Asp Tyr Leu Phe His Arg Leu Asn Gln Leu Asn Ile His Thr
                20                  25                  30 ata ttt gga ctc tcc gga gaa ttt agc atg ccg ttg ctg gat aaa cta       144
Ile Phe Gly Leu Ser Gly Glu Phe Ser Met Pro Leu Leu Asp Lys Leu
            35                  40                  45 tac aac att ccg aac tta cga tgg gcc ggt aat tct aat gag tta aat       192
Tyr Asn Ile Pro Asn Leu Arg Trp Ala Gly Asn Ser Asn Glu Leu Asn
        50                  55                  60 gct gcc tac gca gca gat gga tac tca cga cta aaa ggc ttg gga tgt       240
Ala Ala Tyr Ala Ala Asp Gly Tyr Ser Arg Leu Lys Gly Leu Gly Cys
65                  70                  75                  80 ctc ata aca acc ttt ggt gta ggc gaa tta tcg gca atc aat ggc gtg       288
Leu Ile Thr Thr Phe Gly Val Gly Glu Leu Ser Ala Ile Asn Gly Val
                85                  90                  95 gcc gga tct tac gct gaa cat gta gga ata ctt cac ata gtg ggt atg       336
Ala Gly Ser Tyr Ala Glu His Val Gly Ile Leu His Ile Val Gly Met
                100                 105                 110 ccg cca aca agt gca caa acg aaa caa cta cta ctg cat cat act ctg       384
Pro Pro Thr Ser Ala Gln Thr Lys Gln Leu Leu Leu His His Thr Leu
            115                 120                 125 ggc aat ggt gat ttc acg gta ttt cat aga ata gcc agt gat gta gca       432
Gly Asn Gly Asp Phe Thr Val Phe His Arg Ile Ala Ser Asp Val Ala
        130                 135                 140 tgc tat aca aca ttg att att gac tct gaa tta tgt gcc gac gaa gtc       480
Cys Tyr Thr Thr Leu Ile Ile Asp Ser Glu Leu Cys Ala Asp Glu Val
145                 150                 155                 160 gat aag tgc atc aaa aag gct tgg ata gaa cag agg cca gta tac atg       528
Asp Lys Cys Ile Lys Lys Ala Trp Ile Glu Gln Arg Pro Val Tyr Met
                165                 170                 175 ggc atg cct gtc aac cag gta aat ctc ccg att gaa tca gca agg ctt       576
Gly Met Pro Val Asn Gln Val Asn Leu Pro Ile Glu Ser Ala Arg Leu
                180                 185                 190 aat aca cct ctg gat tta caa ttg cat aaa aac gac cca gac gta gag       624
Asn Thr Pro Leu Asp Leu Gln Leu His Lys Asn Asp Pro Asp Val Glu
            195                 200                 205
```

-continued

| | |
|---|---|
| aaa gaa gtt att tct cga ata ttg agt ttt ata tac aaa agc cag aat<br>Lys Glu Val Ile Ser Arg Ile Leu Ser Phe Ile Tyr Lys Ser Gln Asn<br>210                       215                        220 | 672 |
| ccg gca atc atc gta gat gca tgt act agt cga cag aat tta atc gag<br>Pro Ala Ile Ile Val Asp Ala Cys Thr Ser Arg Gln Asn Leu Ile Glu<br>225                      230                       235                   240 | 720 |
| gag act aaa gag ctt tgt aat agg ctt aaa ttt cca gtt ttt gtt aca<br>Glu Thr Lys Glu Leu Cys Asn Arg Leu Lys Phe Pro Val Phe Val Thr<br>                     245                       250                   255 | 768 |
| cct atg ggt aag ggt aca gta aac gaa aca gac ccg caa ttt ggg ggc<br>Pro Met Gly Lys Gly Thr Val Asn Glu Thr Asp Pro Gln Phe Gly Gly<br>           260                       265                      270 | 816 |
| gta ttc acg ggc tcg ata tca gcc cca gaa gta aga gaa gta gtt gat<br>Val Phe Thr Gly Ser Ile Ser Ala Pro Glu Val Arg Glu Val Val Asp<br>275                       280                       285 | 864 |
| ttt gcc gat ttt atc atc gtc att ggt tgc atg ctc tcc gaa ttc agc<br>Phe Ala Asp Phe Ile Ile Val Ile Gly Cys Met Leu Ser Glu Phe Ser<br>        290                       295                   300 | 912 |
| acg tca act ttc cac ttc caa tat aaa act aag aat tgt gcg cta cta<br>Thr Ser Thr Phe His Phe Gln Tyr Lys Thr Lys Asn Cys Ala Leu Leu<br>305                     310                       315                   320 | 960 |
| tat tct aca tct gtg aaa ttg aaa aat gcc aca tat cct gac ttg agc<br>Tyr Ser Thr Ser Val Lys Leu Lys Asn Ala Thr Tyr Pro Asp Leu Ser<br>                     325                       330                   335 | 1008 |
| att aaa tta cta cta cag aaa ata tta gca aat ctt gat gaa tct aaa<br>Ile Lys Leu Leu Leu Gln Lys Ile Leu Ala Asn Leu Asp Glu Ser Lys<br>           340                       345                      350 | 1056 |
| ctg tct tac caa cca agc gaa caa ccc agt atg atg gtt cca aga cct<br>Leu Ser Tyr Gln Pro Ser Glu Gln Pro Ser Met Met Val Pro Arg Pro<br>355                       360                       365 | 1104 |
| tac cca gca gga aat gtc ctc ttg aga caa gaa tgg gtc tgg aat gaa<br>Tyr Pro Ala Gly Asn Val Leu Leu Arg Gln Glu Trp Val Trp Asn Glu<br>        370                       375                   380 | 1152 |
| ata tcc cat tgg ttc caa cca ggt gac ata atc ata aca gaa act ggt<br>Ile Ser His Trp Phe Gln Pro Gly Asp Ile Ile Ile Thr Glu Thr Gly<br>385                       390                       395                   400 | 1200 |
| gct tct gca ttt gga gtt aac cag acc aga ttt ccg gta aat aca cta<br>Ala Ser Ala Phe Gly Val Asn Gln Thr Arg Phe Pro Val Asn Thr Leu<br>                     405                       410                   415 | 1248 |
| ggt att tcg caa gct ctt tgg gga tct gtc gga tat aca atg ggg gcg<br>Gly Ile Ser Gln Ala Leu Trp Gly Ser Val Gly Tyr Thr Met Gly Ala<br>           420                       425                      430 | 1296 |
| tgt ctt ggg gca gaa ttt gct gtt caa gag ata aac aag gat aaa ttc<br>Cys Leu Gly Ala Glu Phe Ala Val Gln Glu Ile Asn Lys Asp Lys Phe<br>435                       440                       445 | 1344 |
| ccc gca act aaa cat aga gtt att ctg ttt atg ggt gac ggt gct ttc<br>Pro Ala Thr Lys His Arg Val Ile Leu Phe Met Gly Asp Gly Ala Phe<br>        450                       455                   460 | 1392 |
| caa ttg aca gtt caa gaa tta tcc aca att gtt aag tgg gga ttg aca<br>Gln Leu Thr Val Gln Glu Leu Ser Thr Ile Val Lys Trp Gly Leu Thr<br>465                     470                       475                   480 | 1440 |
| cct tat att ttt gtg atg aat aac caa ggt tac tct gtg gac agg ttt<br>Pro Tyr Ile Phe Val Met Asn Asn Gln Gly Tyr Ser Val Asp Arg Phe<br>                     485                       490                   495 | 1488 |
| ttg cat cac agg tca gat gct agt tat tac gat atc caa cct tgg aac<br>Leu His His Arg Ser Asp Ala Ser Tyr Tyr Asp Ile Gln Pro Trp Asn<br>           500                       505                      510 | 1536 |
| tac ttg gga tta ttg cga gta ttt ggt tgc acg aac tac gaa acg aaa<br>Tyr Leu Gly Leu Leu Arg Val Phe Gly Cys Thr Asn Tyr Glu Thr Lys | 1584 |

```
                515                 520                 525
aaa att att act gtt gga gaa ttc aga tcc atg atc agt gac cca aac    1632
Lys Ile Ile Thr Val Gly Glu Phe Arg Ser Met Ile Ser Asp Pro Asn
    530                 535                 540 ttt gcg acc aat gac aaa att cgg atg ata gag att atg cta cca cca    1680
Phe Ala Thr Asn Asp Lys Ile Arg Met Ile Glu Ile Met Leu Pro Pro
545                 550                 555                 560 agg gat gtt cca cag gct ctg ctt gac agg tgg gtg gta gaa aaa gaa    1728
Arg Asp Val Pro Gln Ala Leu Leu Asp Arg Trp Val Val Glu Lys Glu
                565                 570                 575 cag agc aaa caa gtg caa gag gag aac gaa aat tct agc gca gta aat    1776
Gln Ser Lys Gln Val Gln Glu Glu Asn Glu Asn Ser Ser Ala Val Asn
            580                 585                 590 acg cca act cca gaa ttc caa cca ctt cta aaa aaa aat caa gtt gga    1824
Thr Pro Thr Pro Glu Phe Gln Pro Leu Leu Lys Lys Asn Gln Val Gly
        595                 600                 605 tac tga                                                            1830
Tyr
```

<210> SEQ ID NO 8
<211> LENGTH: 609
<212> TYPE: PRT
<213> ORGANISM: Saccharomyces cerevisiae

<400> SEQUENCE: 8

```
Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
    50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
    130                 135                 140

Cys Tyr Thr Thr Leu Ile Ile Asp Ser Glu Leu Cys Ala Asp Glu Val
145                 150                 155                 160

Asp Lys Cys Ile Lys Lys Ala Trp Ile Glu Gln Arg Pro Val Tyr Met
                165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
        195                 200                 205

Lys Glu Val Ile Ser Arg Ile Leu Ser Phe Ile Tyr Lys Ser Gln Asn
    210                 215                 220

Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
```

```
            245                 250                 255
Pro Met Gly Lys Gly Thr Val Asn Glu Thr Asp Pro Gln Phe Gly Gly
        260                 265                 270

Val Phe Thr Gly Ser Ile Ser Ala Pro Glu Val Arg Glu Val Val Asp
            275                 280                 285

Phe Ala Asp Phe Ile Ile Val Ile Gly Cys Met Leu Ser Glu Phe Ser
290                 295                 300

Thr Ser Thr Phe His Phe Gln Tyr Lys Thr Lys Asn Cys Ala Leu Leu
305                 310                 315                 320

Tyr Ser Thr Ser Val Lys Leu Lys Asn Ala Thr Tyr Pro Asp Leu Ser
            325                 330                 335

Ile Lys Leu Leu Leu Gln Lys Ile Leu Ala Asn Leu Asp Glu Ser Lys
        340                 345                 350

Leu Ser Tyr Gln Pro Ser Glu Gln Pro Ser Met Met Val Pro Arg Pro
            355                 360                 365

Tyr Pro Ala Gly Asn Val Leu Leu Arg Gln Glu Trp Val Trp Asn Glu
370                 375                 380

Ile Ser His Trp Phe Gln Pro Gly Asp Ile Ile Ile Thr Glu Thr Gly
385                 390                 395                 400

Ala Ser Ala Phe Gly Val Asn Gln Thr Arg Phe Pro Val Asn Thr Leu
            405                 410                 415

Gly Ile Ser Gln Ala Leu Trp Gly Ser Val Gly Tyr Thr Met Gly Ala
        420                 425                 430

Cys Leu Gly Ala Glu Phe Ala Val Gln Glu Ile Asn Lys Asp Lys Phe
            435                 440                 445

Pro Ala Thr Lys His Arg Val Ile Leu Phe Met Gly Asp Gly Ala Phe
450                 455                 460

Gln Leu Thr Val Gln Glu Leu Ser Thr Ile Val Lys Trp Gly Leu Thr
465                 470                 475                 480

Pro Tyr Ile Phe Val Met Asn Asn Gln Gly Tyr Ser Val Asp Arg Phe
            485                 490                 495

Leu His His Arg Ser Asp Ala Ser Tyr Tyr Asp Ile Gln Pro Trp Asn
        500                 505                 510

Tyr Leu Gly Leu Leu Arg Val Phe Gly Cys Thr Asn Tyr Glu Thr Lys
            515                 520                 525

Lys Ile Ile Thr Val Gly Glu Phe Arg Ser Met Ile Ser Asp Pro Asn
        530                 535                 540

Phe Ala Thr Asn Asp Lys Ile Arg Met Ile Glu Ile Met Leu Pro Pro
545                 550                 555                 560

Arg Asp Val Pro Gln Ala Leu Leu Asp Arg Trp Val Val Glu Lys Glu
            565                 570                 575

Gln Ser Lys Gln Val Gln Glu Glu Asn Ser Ser Ala Val Asn
        580                 585                 590

Thr Pro Thr Pro Glu Phe Gln Pro Leu Leu Lys Lys Asn Gln Val Gly
            595                 600                 605

Tyr

<210> SEQ ID NO 9
<211> LENGTH: 1665
<212> TYPE: DNA
<213> ORGANISM: Clostridium acetobutylicum
<220> FEATURE:
<221> NAME/KEY: CDS
<222> LOCATION: (1)..(1665)
```

<400> SEQUENCE: 9

```
ttg aag agt gaa tac aca att gga aga tat ttg tta gac cgt tta tca      48
Leu Lys Ser Glu Tyr Thr Ile Gly Arg Tyr Leu Leu Asp Arg Leu Ser
  1               5                  10                  15 gag ttg ggt att cgg cat atc ttt ggt gta cct gga gat tac aat cta      96
Glu Leu Gly Ile Arg His Ile Phe Gly Val Pro Gly Asp Tyr Asn Leu
             20                  25                  30 tcc ttt tta gac tat ata atg gag tac aaa ggg ata gat tgg gtt gga    144
Ser Phe Leu Asp Tyr Ile Met Glu Tyr Lys Gly Ile Asp Trp Val Gly
         35                  40                  45 aat tgc aat gaa ttg aat gct ggg tat gct gct gat gga tat gca aga    192
Asn Cys Asn Glu Leu Asn Ala Gly Tyr Ala Ala Asp Gly Tyr Ala Arg
 50                  55                  60 ata aat gga att gga gcc ata ctt aca aca ttt ggt gtt gga gaa tta    240
Ile Asn Gly Ile Gly Ala Ile Leu Thr Thr Phe Gly Val Gly Glu Leu
 65                  70                  75                  80 agt gcc att aac gca att gct ggg gca tac gct gag caa gtt cca gtt    288
Ser Ala Ile Asn Ala Ile Ala Gly Ala Tyr Ala Glu Gln Val Pro Val
                 85                  90                  95 gtt aaa att aca ggt atc ccc aca gca aaa gtt agg gac aat gga tta    336
Val Lys Ile Thr Gly Ile Pro Thr Ala Lys Val Arg Asp Asn Gly Leu
            100                 105                 110 tat gta cac cac aca tta ggt gac gga agg ttt gat cac ttt ttt gaa    384
Tyr Val His His Thr Leu Gly Asp Gly Arg Phe Asp His Phe Phe Glu
        115                 120                 125 atg ttt aga gaa gta aca gtt gct gag gca tta cta agc gaa gaa aat    432
Met Phe Arg Glu Val Thr Val Ala Glu Ala Leu Leu Ser Glu Glu Asn
    130                 135                 140 gca gca caa gaa att gat cgt gtt ctt att tca tgc tgg aga caa aaa    480
Ala Ala Gln Glu Ile Asp Arg Val Leu Ile Ser Cys Trp Arg Gln Lys
145                 150                 155                 160 cgt cct gtt ctt ata aat tta ccg att gat gta tat gat aaa cca att    528
Arg Pro Val Leu Ile Asn Leu Pro Ile Asp Val Tyr Asp Lys Pro Ile
                165                 170                 175 aac aaa cca tta aag cca tta ctc gat tat act att tca agt aac aaa    576
Asn Lys Pro Leu Lys Pro Leu Leu Asp Tyr Thr Ile Ser Ser Asn Lys
            180                 185                 190 gag gct gca tgt gaa ttt gtt aca gaa ata gta cct ata ata aat agg    624
Glu Ala Ala Cys Glu Phe Val Thr Glu Ile Val Pro Ile Ile Asn Arg
        195                 200                 205 gca aaa aag cct gtt att ctt gca gat tat gga gta tat cgt tac caa    672
Ala Lys Lys Pro Val Ile Leu Ala Asp Tyr Gly Val Tyr Arg Tyr Gln
    210                 215                 220 gtt caa cat gtg ctt aaa aac ttg gcc gaa aaa acc gga ttt cct gtg    720
Val Gln His Val Leu Lys Asn Leu Ala Glu Lys Thr Gly Phe Pro Val
225                 230                 235                 240 gct aca cta agt atg gga aaa ggt gtt ttc aat gaa gca cac cct caa    768
Ala Thr Leu Ser Met Gly Lys Gly Val Phe Asn Glu Ala His Pro Gln
                245                 250                 255 ttt att ggt gtt tat aat ggt gat gta agt tct cct tat tta agg cag    816
Phe Ile Gly Val Tyr Asn Gly Asp Val Ser Ser Pro Tyr Leu Arg Gln
            260                 265                 270 cga gtt gat gaa gca gac tgc att att agc gtt ggt gta aaa ttg acg    864
Arg Val Asp Glu Ala Asp Cys Ile Ile Ser Val Gly Val Lys Leu Thr
        275                 280                 285 gat tca acc aca ggg gga ttt tct cat gga ttt tct aaa agg aat gta    912
Asp Ser Thr Thr Gly Gly Phe Ser His Gly Phe Ser Lys Arg Asn Val
    290                 295                 300 att cac att gat cct ttt tca ata aag gca aaa ggt aaa aaa tat gca    960
```

| | | | | | | | | | | | | | | |
|---|---|---|---|---|---|---|---|---|---|---|---|---|---|---|
| Ile | His | Ile | Asp | Pro | Phe | Ser | Ile | Lys | Ala | Lys | Gly | Lys | Lys | Tyr | Ala |
| 305 | | | | 310 | | | | | 315 | | | | | 320 | |

```
cct att acg atg aaa gat gct tta aca gaa tta aca agt aaa att gag      1008
Pro Ile Thr Met Lys Asp Ala Leu Thr Glu Leu Thr Ser Lys Ile Glu
            325                 330                 335 cat aga aac ttt gag gat tta gat ata aag cct tac aaa tca gat aat      1056
His Arg Asn Phe Glu Asp Leu Asp Ile Lys Pro Tyr Lys Ser Asp Asn
        340                 345                 350 caa aag tat ttt gca aaa gag aag cca att aca caa aaa cgt ttt ttt      1104
Gln Lys Tyr Phe Ala Lys Glu Lys Pro Ile Thr Gln Lys Arg Phe Phe
    355                 360                 365 gag cgt att gct cac ttt ata aaa gaa aaa gat gta tta tta gca gaa      1152
Glu Arg Ile Ala His Phe Ile Lys Glu Lys Asp Val Leu Leu Ala Glu
370                 375                 380 cag ggt aca tgc ttt ttt ggt gcg tca acc ata caa cta ccc aaa gat      1200
Gln Gly Thr Cys Phe Phe Gly Ala Ser Thr Ile Gln Leu Pro Lys Asp
385                 390                 395                 400 gca act ttt att ggt caa cct tta tgg gga tct att gga tac aca ctt      1248
Ala Thr Phe Ile Gly Gln Pro Leu Trp Gly Ser Ile Gly Tyr Thr Leu
            405                 410                 415 cct gct tta tta ggt tca caa tta gct gat caa aaa agg cgt aat att      1296
Pro Ala Leu Leu Gly Ser Gln Leu Ala Asp Gln Lys Arg Arg Asn Ile
        420                 425                 430 ctt tta att ggg gat ggt gca ttt caa atg aca gca caa gaa att tca      1344
Leu Leu Ile Gly Asp Gly Ala Phe Gln Met Thr Ala Gln Glu Ile Ser
    435                 440                 445 aca atg ctt cgt tta caa atc aaa cct att att ttt tta att aat aac      1392
Thr Met Leu Arg Leu Gln Ile Lys Pro Ile Ile Phe Leu Ile Asn Asn
450                 455                 460 gat ggt tat aca att gaa cgt gct att cat ggt aga gaa caa gta tat      1440
Asp Gly Tyr Thr Ile Glu Arg Ala Ile His Gly Arg Glu Gln Val Tyr
465                 470                 475                 480 aac aat att caa atg tgg cga tat cat aat gtt cca aag gtt tta ggt      1488
Asn Asn Ile Gln Met Trp Arg Tyr His Asn Val Pro Lys Val Leu Gly
            485                 490                 495 cct aaa gaa tgc agc tta acc ttt aaa gta caa agt gaa act gaa ctt      1536
Pro Lys Glu Cys Ser Leu Thr Phe Lys Val Gln Ser Glu Thr Glu Leu
        500                 505                 510 gaa aag gct ctt tta gtg gca gat aag gat tgt gaa cat ttg att ttt      1584
Glu Lys Ala Leu Leu Val Ala Asp Lys Asp Cys Glu His Leu Ile Phe
    515                 520                 525 ata gaa gtt gtt atg gat cgt tat gat aaa ccc gag cct tta gaa cgt      1632
Ile Glu Val Val Met Asp Arg Tyr Asp Lys Pro Glu Pro Leu Glu Arg
530                 535                 540 ctt tcg aaa cgt ttt gca aat caa aat aat tag                          1665
Leu Ser Lys Arg Phe Ala Asn Gln Asn Asn
545                 550

<210> SEQ ID NO 10
<211> LENGTH: 554
<212> TYPE: PRT
<213> ORGANISM: Clostridium acetobutylicum

<400> SEQUENCE: 10

Leu Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45
```

```
Asn Cys Asn Glu Leu Asn Ala Gly Tyr Ala Ala Asp Gly Tyr Ala Arg
     50                  55                  60

Ile Asn Gly Ile Gly Ala Ile Leu Thr Thr Phe Gly Val Gly Glu Leu
 65              70                  75                      80

Ser Ala Ile Asn Ala Ile Ala Gly Ala Tyr Ala Glu Gln Val Pro Val
             85                  90                  95

Val Lys Ile Thr Gly Ile Pro Thr Ala Lys Val Arg Asp Asn Gly Leu
            100                 105                 110

Tyr Val His His Thr Leu Gly Asp Gly Arg Phe Asp His Phe Phe Glu
        115                 120                 125

Met Phe Arg Glu Val Thr Val Ala Glu Ala Leu Leu Ser Glu Glu Asn
    130                 135                 140

Ala Ala Gln Glu Ile Asp Arg Val Leu Ile Ser Cys Trp Arg Gln Lys
145             150                 155                     160

Arg Pro Val Leu Ile Asn Leu Pro Ile Asp Val Tyr Asp Lys Pro Ile
                165                 170                 175

Asn Lys Pro Leu Lys Pro Leu Leu Asp Tyr Thr Ile Ser Ser Asn Lys
            180                 185                 190

Glu Ala Ala Cys Glu Phe Val Thr Glu Ile Val Pro Ile Ile Asn Arg
        195                 200                 205

Ala Lys Lys Pro Val Ile Leu Ala Asp Tyr Gly Val Tyr Arg Tyr Gln
    210                 215                 220

Val Gln His Val Leu Lys Asn Leu Ala Glu Lys Thr Gly Phe Pro Val
225             230                 235                     240

Ala Thr Leu Ser Met Gly Lys Gly Val Phe Asn Glu Ala His Pro Gln
                245                 250                 255

Phe Ile Gly Val Tyr Asn Gly Asp Val Ser Ser Pro Tyr Leu Arg Gln
            260                 265                 270

Arg Val Asp Glu Ala Asp Cys Ile Ile Ser Val Gly Val Lys Leu Thr
        275                 280                 285

Asp Ser Thr Thr Gly Gly Phe Ser His Gly Phe Ser Lys Arg Asn Val
    290                 295                 300

Ile His Ile Asp Pro Phe Ser Ile Lys Ala Lys Gly Lys Lys Tyr Ala
305             310                 315                     320

Pro Ile Thr Met Lys Asp Ala Leu Thr Glu Leu Thr Ser Lys Ile Glu
                325                 330                 335

His Arg Asn Phe Glu Asp Leu Asp Ile Lys Pro Tyr Lys Ser Asp Asn
            340                 345                 350

Gln Lys Tyr Phe Ala Lys Glu Lys Pro Ile Thr Gln Lys Arg Phe Phe
        355                 360                 365

Glu Arg Ile Ala His Phe Ile Lys Glu Lys Asp Val Leu Leu Ala Glu
    370                 375                 380

Gln Gly Thr Cys Phe Phe Gly Ala Ser Thr Ile Gln Leu Pro Lys Asp
385             390                 395                     400

Ala Thr Phe Ile Gly Gln Pro Leu Trp Gly Ser Ile Gly Tyr Thr Leu
                405                 410                 415

Pro Ala Leu Leu Gly Ser Gln Leu Ala Asp Gln Lys Arg Arg Asn Ile
            420                 425                 430

Leu Leu Ile Gly Asp Gly Ala Phe Gln Met Thr Ala Gln Glu Ile Ser
        435                 440                 445

Thr Met Leu Arg Leu Gln Ile Lys Pro Ile Ile Phe Leu Ile Asn Asn
    450                 455                 460
```

```
Asp Gly Tyr Thr Ile Glu Arg Ala Ile His Gly Arg Glu Gln Val Tyr
465                 470                 475                 480

Asn Asn Ile Gln Met Trp Arg Tyr His Asn Val Pro Lys Val Leu Gly
                485                 490                 495

Pro Lys Glu Cys Ser Leu Thr Phe Lys Val Gln Ser Glu Thr Glu Leu
            500                 505                 510

Glu Lys Ala Leu Leu Val Ala Asp Lys Asp Cys Glu His Leu Ile Phe
        515                 520                 525

Ile Glu Val Val Met Asp Arg Tyr Asp Lys Pro Pro Leu Glu Arg
    530                 535                 540

Leu Ser Lys Arg Phe Ala Asn Gln Asn Asn
545                 550

<210> SEQ ID NO 11
<211> LENGTH: 1056
<212> TYPE: DNA
<213> ORGANISM: Saccharomyces cerevisiae
<220> FEATURE:
<221> NAME/KEY: CDS
<222> LOCATION: (1)..(1056)

<400> SEQUENCE: 11 atg cct tcg caa gtc att cct gaa aaa caa aag gct att gtc ttt tat      48
Met Pro Ser Gln Val Ile Pro Glu Lys Gln Lys Ala Ile Val Phe Tyr
1               5                   10                  15 gag aca gat gga aaa ttg gaa tat aaa gac gtc aca gtt ccg gaa cct      96
Glu Thr Asp Gly Lys Leu Glu Tyr Lys Asp Val Thr Val Pro Glu Pro
            20                  25                  30 aag cct aac gaa att tta gtc cac gtt aaa tat tct ggt gtt tgt cat     144
Lys Pro Asn Glu Ile Leu Val His Val Lys Tyr Ser Gly Val Cys His
        35                  40                  45 agt gac ttg cac gcg tgg cac ggt gat tgg cca ttt caa ttg aaa ttt     192
Ser Asp Leu His Ala Trp His Gly Asp Trp Pro Phe Gln Leu Lys Phe
    50                  55                  60 cca tta atc ggt ggt cac gaa ggt gct ggt gtt gtt gtt aag ttg gga     240
Pro Leu Ile Gly Gly His Glu Gly Ala Gly Val Val Val Lys Leu Gly
65                  70                  75                  80 tct aac gtt aag ggc tgg aaa gtc ggt gat ttt gca ggt ata aaa tgg     288
Ser Asn Val Lys Gly Trp Lys Val Gly Asp Phe Ala Gly Ile Lys Trp
                85                  90                  95 ttg aat ggg act tgc atg tcc tgt gaa tat tgt gaa gta ggt aat gaa     336
Leu Asn Gly Thr Cys Met Ser Cys Glu Tyr Cys Glu Val Gly Asn Glu
            100                 105                 110 tct caa tgt cct tat ttg gat ggt act ggc ttc aca cat gat ggt act     384
Ser Gln Cys Pro Tyr Leu Asp Gly Thr Gly Phe Thr His Asp Gly Thr
        115                 120                 125 ttt caa gaa tac gca act gcc gat gcc gtt caa gct gcc cat att cca     432
Phe Gln Glu Tyr Ala Thr Ala Asp Ala Val Gln Ala Ala His Ile Pro
    130                 135                 140 cca aac gtc aat ctt gct gaa gtt gcc cca atc ttg tgt gca ggt atc     480
Pro Asn Val Asn Leu Ala Glu Val Ala Pro Ile Leu Cys Ala Gly Ile
145                 150                 155                 160 act gtt tat aag gcg ttg aaa aga gcc aat gtg ata cca ggc caa tgg     528
Thr Val Tyr Lys Ala Leu Lys Arg Ala Asn Val Ile Pro Gly Gln Trp
                165                 170                 175 gtc act ata tcc ggt gca tgc ggt ggc ttg ggt tct ctg gca atc caa     576
Val Thr Ile Ser Gly Ala Cys Gly Gly Leu Gly Ser Leu Ala Ile Gln
            180                 185                 190 tac gcc ctt gct atg ggt tac agg gtc att ggt atc gat ggt ggt aat     624
Tyr Ala Leu Ala Met Gly Tyr Arg Val Ile Gly Ile Asp Gly Gly Asn
```

-continued

```
                   195                 200                 205
gcc aag cga aag tta ttt gaa caa tta ggc gga gaa ata ttc atc gat    672
Ala Lys Arg Lys Leu Phe Glu Gln Leu Gly Gly Glu Ile Phe Ile Asp
210                 215                 220 ttc acg gaa gaa aaa gac att gtt ggt gct ata ata aag gcc act aat    720
Phe Thr Glu Glu Lys Asp Ile Val Gly Ala Ile Ile Lys Ala Thr Asn
225                 230                 235                 240 ggc ggt tct cat gga gtt att aat gtg tct gtt tct gaa gca gct atc    768
Gly Gly Ser His Gly Val Ile Asn Val Ser Val Ser Glu Ala Ala Ile
                245                 250                 255 gag gct tct acg agg tat tgt agg ccc aat ggt act gtc gtc ctg gtt    816
Glu Ala Ser Thr Arg Tyr Cys Arg Pro Asn Gly Thr Val Val Leu Val
            260                 265                 270 ggt atg cca gct cat gct tac tgc aat tcc gat gtt ttc aat caa gtt    864
Gly Met Pro Ala His Ala Tyr Cys Asn Ser Asp Val Phe Asn Gln Val
        275                 280                 285 gta aaa tca atc tcc atc gtt gga tct tgt gtt gga aat aga gct gat    912
Val Lys Ser Ile Ser Ile Val Gly Ser Cys Val Gly Asn Arg Ala Asp
    290                 295                 300 aca agg gag gct tta gat ttc ttc gcc aga ggt ttg atc aaa tct ccg    960
Thr Arg Glu Ala Leu Asp Phe Phe Ala Arg Gly Leu Ile Lys Ser Pro
305                 310                 315                 320 atc cac tta gct ggc cta tcg gat gtt cct gaa att ttt gca aag atg   1008
Ile His Leu Ala Gly Leu Ser Asp Val Pro Glu Ile Phe Ala Lys Met
                325                 330                 335 gag aag ggt gaa att gtt ggt aga tat gtt gtt gag act tct aaa tga   1056
Glu Lys Gly Glu Ile Val Gly Arg Tyr Val Val Glu Thr Ser Lys
            340                 345                 350
```

<210> SEQ ID NO 12
<211> LENGTH: 351
<212> TYPE: PRT
<213> ORGANISM: Saccharomyces cerevisiae

<400> SEQUENCE: 12

```
Met Pro Ser Gln Val Ile Pro Glu Lys Gln Lys Ala Ile Val Phe Tyr
1               5                   10                  15

Glu Thr Asp Gly Lys Leu Glu Tyr Lys Asp Val Thr Val Pro Glu Pro
            20                  25                  30

Lys Pro Asn Glu Ile Leu Val His Val Lys Tyr Ser Gly Val Cys His
        35                  40                  45

Ser Asp Leu His Ala Trp His Gly Asp Trp Pro Phe Gln Leu Lys Phe
    50                  55                  60

Pro Leu Ile Gly Gly His Glu Gly Ala Gly Val Val Lys Leu Gly
65                  70                  75                  80

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175
```

```
Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 13
<211> LENGTH: 1725
<212> TYPE: DNA
<213> ORGANISM: Escherichia coli
<220> FEATURE:
<221> NAME/KEY: CDS
<222> LOCATION: (1)..(1725)

<400> SEQUENCE: 13 atg gag atg ttg tct gga gcc gag atg gtc gtc cga tcg ctt atc gat    48
Met Glu Met Leu Ser Gly Ala Glu Met Val Val Arg Ser Leu Ile Asp
1               5                   10                  15 cag ggc gtt aaa caa gta ttc ggt tat ccc gga ggc gca gtc ctt gat    96
Gln Gly Val Lys Gln Val Phe Gly Tyr Pro Gly Gly Ala Val Leu Asp
            20                  25                  30 att tat gat gca ttg cat acc gtg ggt ggt att gat cat gta tta gtt   144
Ile Tyr Asp Ala Leu His Thr Val Gly Gly Ile Asp His Val Leu Val
        35                  40                  45 cgt cat gag cag gcg gcg gtg cat atg gcc gat ggc ctg gcg cgc gcg   192
Arg His Glu Gln Ala Ala Val His Met Ala Asp Gly Leu Ala Arg Ala
    50                  55                  60 acc ggg gaa gtc ggc gtc gtg ctg gta acg tcg ggt cca ggg gcg acc   240
Thr Gly Glu Val Gly Val Val Leu Val Thr Ser Gly Pro Gly Ala Thr
65                  70                  75                  80 aat gcg att act ggc atc gcc acc gct tat atg gat tcc att cca tta   288
Asn Ala Ile Thr Gly Ile Ala Thr Ala Tyr Met Asp Ser Ile Pro Leu
                85                  90                  95 gtt gtc ctt tcc ggg cag gta gcg acc tcg ttg ata ggt tac gat gcc   336
Val Val Leu Ser Gly Gln Val Ala Thr Ser Leu Ile Gly Tyr Asp Ala
            100                 105                 110 ttt cag gag tgc gac atg gtg ggg att tcg cga ccg gtg gtt aaa cac   384
Phe Gln Glu Cys Asp Met Val Gly Ile Ser Arg Pro Val Val Lys His
        115                 120                 125 agt ttt ctg gtt aag caa acg gaa gac att ccg cag gtg ctg aaa aag   432
Ser Phe Leu Val Lys Gln Thr Glu Asp Ile Pro Gln Val Leu Lys Lys
    130                 135                 140
```

```
gct ttc tgg ctg gcg gca agt ggt cgc cca gga cca gta gtc gtt gat      480
Ala Phe Trp Leu Ala Ala Ser Gly Arg Pro Gly Pro Val Val Val Asp
145                 150                 155                 160 tta ccg aaa gat att ctt aat ccg gcg aac aaa tta ccc tat gtc tgg      528
Leu Pro Lys Asp Ile Leu Asn Pro Ala Asn Lys Leu Pro Tyr Val Trp
                165                 170                 175 ccg gag tcg gtc agt atg cgt tct tac aat ccc act act acc gga cat      576
Pro Glu Ser Val Ser Met Arg Ser Tyr Asn Pro Thr Thr Thr Gly His
            180                 185                 190 aaa ggg caa att aag cgt gct ctg caa acg ctg gta gcg gca aaa aaa      624
Lys Gly Gln Ile Lys Arg Ala Leu Gln Thr Leu Val Ala Ala Lys Lys
        195                 200                 205 ccg gtt gtc tac gta ggc ggt ggg gca atc acg gcg ggc tgc cat cag      672
Pro Val Val Tyr Val Gly Gly Gly Ala Ile Thr Ala Gly Cys His Gln
    210                 215                 220 cag ttg aaa gaa acg gtg gag gcg ttg aat ctg ccc gtt gtt tgc tca      720
Gln Leu Lys Glu Thr Val Glu Ala Leu Asn Leu Pro Val Val Cys Ser
225                 230                 235                 240 ttg atg ggg ctg ggg gcg ttt ccg gca acg cat cgt cag gca ctg ggc      768
Leu Met Gly Leu Gly Ala Phe Pro Ala Thr His Arg Gln Ala Leu Gly
                245                 250                 255 atg ctg gga atg cac ggt acc tac gaa gcc aat atg acg atg cat aac      816
Met Leu Gly Met His Gly Thr Tyr Glu Ala Asn Met Thr Met His Asn
            260                 265                 270 gcg gat gtg att ttc gcc gtc ggg gta cga ttt gat gac cga acg acg      864
Ala Asp Val Ile Phe Ala Val Gly Val Arg Phe Asp Asp Arg Thr Thr
        275                 280                 285 aac aat ctg gca aag tac tgc cca aat gcc act gtt ctg cat atc gat      912
Asn Asn Leu Ala Lys Tyr Cys Pro Asn Ala Thr Val Leu His Ile Asp
    290                 295                 300 att gat cct act tcc att tct aaa acc gtg act gcg gat atc ccg att      960
Ile Asp Pro Thr Ser Ile Ser Lys Thr Val Thr Ala Asp Ile Pro Ile
305                 310                 315                 320 gtg ggg gat gct cgc cag gtc ctc gaa caa atg ctt gaa ctc ttg tcg     1008
Val Gly Asp Ala Arg Gln Val Leu Glu Gln Met Leu Glu Leu Leu Ser
                325                 330                 335 caa gaa tcc gcc cat caa cca ctg gat gag atc cgc gac tgg tgg cag     1056
Gln Glu Ser Ala His Gln Pro Leu Asp Glu Ile Arg Asp Trp Trp Gln
            340                 345                 350 caa att gaa cag tgg cgc gct cgt cag tgc ctg aaa tat gac act cac     1104
Gln Ile Glu Gln Trp Arg Ala Arg Gln Cys Leu Lys Tyr Asp Thr His
        355                 360                 365 agt gaa aag att aaa ccg cag gcg gtg atc gag act ctt tgg cgg ttg     1152
Ser Glu Lys Ile Lys Pro Gln Ala Val Ile Glu Thr Leu Trp Arg Leu
    370                 375                 380 acg aag gga gac gct tac gtg acg tcc gat gtc ggg cag cac cag atg     1200
Thr Lys Gly Asp Ala Tyr Val Thr Ser Asp Val Gly Gln His Gln Met
385                 390                 395                 400 ttt gct gca ctt tat tat cca ttc gac aaa ccg cgt cgc tgg atc aat     1248
Phe Ala Ala Leu Tyr Tyr Pro Phe Asp Lys Pro Arg Arg Trp Ile Asn
                405                 410                 415 tcc ggt ggc ctc ggc acg atg ggt ttt ggt tta cct gcg gca ctg ggc     1296
Ser Gly Gly Leu Gly Thr Met Gly Phe Gly Leu Pro Ala Ala Leu Gly
            420                 425                 430 gtc aaa atg gcg ttg cca gaa gaa acc gtg gtt tgc gtc act ggc gac     1344
Val Lys Met Ala Leu Pro Glu Glu Thr Val Val Cys Val Thr Gly Asp
        435                 440                 445 ggc agt att cag atg aac atc cag gaa ctg tct acc gcg ttg caa tac     1392
Gly Ser Ile Gln Met Asn Ile Gln Glu Leu Ser Thr Ala Leu Gln Tyr
```

```
                 450                 455                 460
gag ttg ccc gta ctg gtg gtg aat ctc aat aac cgc tat ctg ggg atg    1440
Glu Leu Pro Val Leu Val Val Asn Leu Asn Asn Arg Tyr Leu Gly Met
465                 470                 475                 480 gtg aag cag tgg cag gac atg atc tat tcc ggc cgt cat tca caa tct    1488
Val Lys Gln Trp Gln Asp Met Ile Tyr Ser Gly Arg His Ser Gln Ser
                485                 490                 495 tat atg caa tcg cta ccc gat ttc gtc cgt ctg gcg gaa gcc tat ggg    1536
Tyr Met Gln Ser Leu Pro Asp Phe Val Arg Leu Ala Glu Ala Tyr Gly
            500                 505                 510 cat gtc ggg atc cag att tct cat ccg cat gag ctg gaa agc aaa ctt    1584
His Val Gly Ile Gln Ile Ser His Pro His Glu Leu Glu Ser Lys Leu
        515                 520                 525 agc gag gcg ctg gaa cag gtg cgc aat aat cgc ctg gtg ttt gtt gat    1632
Ser Glu Ala Leu Glu Gln Val Arg Asn Asn Arg Leu Val Phe Val Asp
    530                 535                 540 gtt acc gtc gat ggc agc gag cac gtc tac ccg atg cag att cgc ggg    1680
Val Thr Val Asp Gly Ser Glu His Val Tyr Pro Met Gln Ile Arg Gly
545                 550                 555                 560 ggc gga atg gat gaa atg tgg tta agc aaa acg gag aga acc tga        1725
Gly Gly Met Asp Glu Met Trp Leu Ser Lys Thr Glu Arg Thr
                565                 570

<210> SEQ ID NO 14
<211> LENGTH: 574
<212> TYPE: PRT
<213> ORGANISM: Escherichia coli

<400> SEQUENCE: 14

Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110

Phe Gln Glu Cys Asp Met Val Gly Ile Ser Arg Pro Val Val Lys His
        115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Ala Ala Lys Lys
        195                 200                 205

Pro Val Val Tyr Val Gly Gly Gly Ala Ile Thr Ala Gly Cys His Gln
    210                 215                 220
```

| | | | | | | | | | | | | | | |
|---|---|---|---|---|---|---|---|---|---|---|---|---|---|---|
| Gln | Leu | Lys | Glu | Thr | Val | Glu | Ala | Leu | Asn | Leu | Pro | Val | Val | Cys | Ser |
| 225 | | | | 230 | | | | 235 | | | | 240 | | | |

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
            245                 250                 255

Met Leu Gly Met His Gly Thr Tyr Glu Ala Asn Met Thr Met His Asn
        260                 265                 270

Ala Asp Val Ile Phe Ala Val Gly Val Arg Phe Asp Asp Arg Thr Thr
    275                 280                 285

Asn Asn Leu Ala Lys Tyr Cys Pro Asn Ala Thr Val Leu His Ile Asp
290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
            340                 345                 350

Gln Ile Glu Gln Trp Arg Ala Arg Gln Cys Leu Lys Tyr Asp Thr His
        355                 360                 365

Ser Glu Lys Ile Lys Pro Gln Ala Val Ile Glu Thr Leu Trp Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Met Ala Leu Pro Glu Glu Thr Val Val Cys Val Thr Gly Asp
        435                 440                 445

Gly Ser Ile Gln Met Asn Ile Gln Glu Leu Ser Thr Ala Leu Gln Tyr
    450                 455                 460

Glu Leu Pro Val Leu Val Asn Leu Asn Asn Arg Tyr Leu Gly Met
465                 470                 475                 480

Val Lys Gln Trp Gln Asp Met Ile Tyr Ser Gly Arg His Ser Gln Ser
            485                 490                 495

Tyr Met Gln Ser Leu Pro Asp Phe Val Arg Leu Ala Glu Ala Tyr Gly
        500                 505                 510

His Val Gly Ile Gln Ile Ser His Pro His Glu Leu Glu Ser Lys Leu
    515                 520                 525

Ser Glu Ala Leu Glu Gln Val Arg Asn Asn Arg Leu Val Phe Val Asp
530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
            565                 570

<210> SEQ ID NO 15
<211> LENGTH: 492
<212> TYPE: DNA
<213> ORGANISM: Escherichia coli
<220> FEATURE:
<221> NAME/KEY: CDS
<222> LOCATION: (1)..(492)

<400> SEQUENCE: 15 atg cgc cgg ata tta tca gtc tta ctc gaa aat gaa tca ggc gcg tta         48

```
Met Arg Arg Ile Leu Ser Val Leu Leu Glu Asn Glu Ser Gly Ala Leu
1               5                   10                  15 tcc cgc gtg att ggc ctt ttt tcc cag cgt ggc tac aac att gaa agc        96
Ser Arg Val Ile Gly Leu Phe Ser Gln Arg Gly Tyr Asn Ile Glu Ser
            20                  25                  30 ctg acc gtt gcg cca acc gac gat ccg aca tta tcg cgt atg acc atc       144
Leu Thr Val Ala Pro Thr Asp Asp Pro Thr Leu Ser Arg Met Thr Ile
                35                  40                  45 cag acc gtg ggc gat gaa aaa gta ctt gag cag atc gaa aag caa tta       192
Gln Thr Val Gly Asp Glu Lys Val Leu Glu Gln Ile Glu Lys Gln Leu
    50                  55                  60 cac aaa ctg gtc gat gtc ttg cgc gtg agt gag ttg ggg cag ggc gcg       240
His Lys Leu Val Asp Val Leu Arg Val Ser Glu Leu Gly Gln Gly Ala
65                  70                  75                  80 cat gtt gag cgg gaa atc atg ctg gtg aaa att cag gcc agc ggt tac       288
His Val Glu Arg Glu Ile Met Leu Val Lys Ile Gln Ala Ser Gly Tyr
                85                  90                  95 ggg cgt gac gaa gtg aaa cgt aat acg gaa ata ttc cgt ggg caa att       336
Gly Arg Asp Glu Val Lys Arg Asn Thr Glu Ile Phe Arg Gly Gln Ile
            100                 105                 110 atc gat gtc aca ccc tcg ctt tat acc gtt caa tta gca ggc acc agc       384
Ile Asp Val Thr Pro Ser Leu Tyr Thr Val Gln Leu Ala Gly Thr Ser
                115                 120                 125 ggt aag ctt gat gca ttt tta gca tcg att cgc gat gtg gcg aaa att       432
Gly Lys Leu Asp Ala Phe Leu Ala Ser Ile Arg Asp Val Ala Lys Ile
    130                 135                 140 gtg gag gtt gct cgc tct ggt gtg gtc gga ctt tcg cgc ggc gat aaa       480
Val Glu Val Ala Arg Ser Gly Val Val Gly Leu Ser Arg Gly Asp Lys
145                 150                 155                 160 ata atg cgt tga                                                        492
Ile Met Arg <210> SEQ ID NO 16
<211> LENGTH: 163
<212> TYPE: PRT
<213> ORGANISM: Escherichia coli

<400> SEQUENCE: 16

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
                35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
                115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160
```

Ile Met Arg

<210> SEQ ID NO 17
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 17

| | | | | | | | | | | | | | | | | |
|---|---|---|---|---|---|---|---|---|---|---|---|---|---|---|---|---|
| atg | gct | aac | tac | ttc | aat | aca | ctg | aat | ctg | cgc | cag | cag | ctg | gca | cag | 48 |
| Met | Ala | Asn | Tyr | Phe | Asn | Thr | Leu | Asn | Leu | Arg | Gln | Gln | Leu | Ala | Gln | |
| 1 | | | | 5 | | | | | 10 | | | | | 15 | | |

| ctg | ggc | aaa | tgt | cgc | ttt | atg | ggc | cgc | gat | gaa | ttc | gcc | gat | ggc | gcg | 96 |
|---|---|---|---|---|---|---|---|---|---|---|---|---|---|---|---|---|
| Leu | Gly | Lys | Cys | Arg | Phe | Met | Gly | Arg | Asp | Glu | Phe | Ala | Asp | Gly | Ala | |
| | | | 20 | | | | | 25 | | | | | 30 | | | |

| agc | tac | ctt | cag | ggt | aaa | aaa | gta | gtc | atc | gtc | ggc | tgt | ggc | gca | cag | 144 |
|---|---|---|---|---|---|---|---|---|---|---|---|---|---|---|---|---|
| Ser | Tyr | Leu | Gln | Gly | Lys | Lys | Val | Val | Ile | Val | Gly | Cys | Gly | Ala | Gln | |
| | | | 35 | | | | | 40 | | | | | 45 | | | |

| ggt | ctg | aac | cag | ggc | ctg | aac | atg | cgt | gat | tct | ggt | ctc | gat | atc | tcc | 192 |
|---|---|---|---|---|---|---|---|---|---|---|---|---|---|---|---|---|
| Gly | Leu | Asn | Gln | Gly | Leu | Asn | Met | Arg | Asp | Ser | Gly | Leu | Asp | Ile | Ser | |
| | 50 | | | | | 55 | | | | | 60 | | | | | |

| tac | gct | ctg | cgt | aaa | gaa | gcg | att | gcc | gag | aag | cgc | gcg | tcc | tgg | cgt | 240 |
|---|---|---|---|---|---|---|---|---|---|---|---|---|---|---|---|---|
| Tyr | Ala | Leu | Arg | Lys | Glu | Ala | Ile | Ala | Glu | Lys | Arg | Ala | Ser | Trp | Arg | |
| 65 | | | | | 70 | | | | | 75 | | | | | 80 | |

| aaa | gcg | acc | gaa | aat | ggt | ttt | aaa | gtg | ggt | act | tac | gaa | gaa | ctg | atc | 288 |
|---|---|---|---|---|---|---|---|---|---|---|---|---|---|---|---|---|
| Lys | Ala | Thr | Glu | Asn | Gly | Phe | Lys | Val | Gly | Thr | Tyr | Glu | Glu | Leu | Ile | |
| | | | | 85 | | | | | 90 | | | | | 95 | | |

| cca | cag | gcg | gat | ctg | gtg | att | aac | ctg | acg | ccg | gac | aag | cag | cac | tct | 336 |
|---|---|---|---|---|---|---|---|---|---|---|---|---|---|---|---|---|
| Pro | Gln | Ala | Asp | Leu | Val | Ile | Asn | Leu | Thr | Pro | Asp | Lys | Gln | His | Ser | |
| | | | 100 | | | | | 105 | | | | | 110 | | | |

| gat | gta | gtg | cgc | acc | gta | cag | cca | ctg | atg | aaa | gac | ggc | gcg | gcg | ctg | 384 |
|---|---|---|---|---|---|---|---|---|---|---|---|---|---|---|---|---|
| Asp | Val | Val | Arg | Thr | Val | Gln | Pro | Leu | Met | Lys | Asp | Gly | Ala | Ala | Leu | |
| | | 115 | | | | | 120 | | | | | 125 | | | | |

| ggc | tac | tcg | cac | ggt | ttc | aac | atc | gtc | gaa | gtg | ggc | gag | cag | atc | cgt | 432 |
|---|---|---|---|---|---|---|---|---|---|---|---|---|---|---|---|---|
| Gly | Tyr | Ser | His | Gly | Phe | Asn | Ile | Val | Glu | Val | Gly | Glu | Gln | Ile | Arg | |
| | 130 | | | | | 135 | | | | | 140 | | | | | |

| aaa | gat | atc | acc | gta | gtg | atg | gtt | gcg | ccg | aaa | tgc | cca | ggc | acc | gaa | 480 |
|---|---|---|---|---|---|---|---|---|---|---|---|---|---|---|---|---|
| Lys | Asp | Ile | Thr | Val | Val | Met | Val | Ala | Pro | Lys | Cys | Pro | Gly | Thr | Glu | |
| 145 | | | | | 150 | | | | | 155 | | | | | 160 | |

| gtg | cgt | gaa | gag | tac | aaa | cgt | ggg | ttc | ggc | gta | ccg | acg | ctg | att | gcc | 528 |
|---|---|---|---|---|---|---|---|---|---|---|---|---|---|---|---|---|
| Val | Arg | Glu | Glu | Tyr | Lys | Arg | Gly | Phe | Gly | Val | Pro | Thr | Leu | Ile | Ala | |
| | | | | 165 | | | | | 170 | | | | | 175 | | |

| gtt | cac | ccg | gaa | aac | gat | ccg | aaa | ggc | gaa | ggc | atg | gcg | att | gcc | aaa | 576 |
|---|---|---|---|---|---|---|---|---|---|---|---|---|---|---|---|---|
| Val | His | Pro | Glu | Asn | Asp | Pro | Lys | Gly | Glu | Gly | Met | Ala | Ile | Ala | Lys | |
| | | | 180 | | | | | 185 | | | | | 190 | | | |

| gcc | tgg | gcg | gct | gca | acc | ggt | ggt | cac | cgt | gcg | ggt | gtg | ctg | gaa | tcg | 624 |
|---|---|---|---|---|---|---|---|---|---|---|---|---|---|---|---|---|
| Ala | Trp | Ala | Ala | Ala | Thr | Gly | Gly | His | Arg | Ala | Gly | Val | Leu | Glu | Ser | |
| | 195 | | | | | 200 | | | | | 205 | | | | | |

| tcc | ttc | gtt | gcg | gaa | gtg | aaa | tct | gac | ctg | atg | ggc | gag | caa | acc | atc | 672 |
|---|---|---|---|---|---|---|---|---|---|---|---|---|---|---|---|---|
| Ser | Phe | Val | Ala | Glu | Val | Lys | Ser | Asp | Leu | Met | Gly | Glu | Gln | Thr | Ile | |
| | 210 | | | | | 215 | | | | | 220 | | | | | |

| ctg | tgc | ggt | atg | ttg | cag | gct | ggc | tct | ctg | tgc | ttc | gac | aag | ctg | | 720 |
|---|---|---|---|---|---|---|---|---|---|---|---|---|---|---|---|---|
| Leu | Cys | Gly | Met | Leu | Gln | Ala | Gly | Ser | Leu | Cys | Phe | Asp | Lys | Leu | | |
| 225 | | | | | 230 | | | | | 235 | | | | | 240 | |

| gtg | gaa | gaa | ggt | acc | gat | cca | gca | tac | gca | gaa | aaa | ctg | att | cag | ttc | 768 |
|---|---|---|---|---|---|---|---|---|---|---|---|---|---|---|---|---|
| Val | Glu | Glu | Gly | Thr | Asp | Pro | Ala | Tyr | Ala | Glu | Lys | Leu | Ile | Gln | Phe | |
| | | | | 245 | | | | | 250 | | | | | 255 | | |

| ggt | tgg | gaa | acc | atc | acc | gaa | gca | ctg | aaa | cag | ggc | ggc | atc | acc | ctg | 816 |

```
                                                                        -continued Gly Trp Glu Thr Ile Thr Glu Ala Leu Lys Gln Gly Gly Ile Thr Leu
            260                 265                 270 atg atg gac cgt ctc tct aac ccg gcg aaa ctg cgt gct tat gcg ctt       864
Met Met Asp Arg Leu Ser Asn Pro Ala Lys Leu Arg Ala Tyr Ala Leu
            275                 280                 285 tct gaa cag ctg aaa gag atc atg gca ccc ctg ttc cag aaa cat atg       912
Ser Glu Gln Leu Lys Glu Ile Met Ala Pro Leu Phe Gln Lys His Met
        290                 295                 300 gac gac atc atc tcc ggc gaa ttc tct tcc ggt atg atg gcg gac tgg       960
Asp Asp Ile Ile Ser Gly Glu Phe Ser Ser Gly Met Met Ala Asp Trp
305                 310                 315                 320 gcc aac gat gat aag aaa ctg ctg acc tgg cgt gaa gag acc ggc aaa      1008
Ala Asn Asp Asp Lys Lys Leu Leu Thr Trp Arg Glu Glu Thr Gly Lys
                325                 330                 335 acc gcg ttt gaa acc gcg ccg cag tat gaa ggc aaa atc ggc gag cag      1056
Thr Ala Phe Glu Thr Ala Pro Gln Tyr Glu Gly Lys Ile Gly Glu Gln
            340                 345                 350 gag tac ttc gat aaa ggc gta ctg atg att gcg atg gtg aaa gcg ggc      1104
Glu Tyr Phe Asp Lys Gly Val Leu Met Ile Ala Met Val Lys Ala Gly
        355                 360                 365 gtt gaa ctg gcg ttc gaa acc atg gtc gat tcc ggc atc att gaa gag      1152
Val Glu Leu Ala Phe Glu Thr Met Val Asp Ser Gly Ile Ile Glu Glu
    370                 375                 380 tct gca tat tat gaa tca ctg cac gag ctg ccg ctg att gcc aac acc      1200
Ser Ala Tyr Tyr Glu Ser Leu His Glu Leu Pro Leu Ile Ala Asn Thr
385                 390                 395                 400 atc gcc cgt aag cgt ctg tac gaa atg aac gtg gtt atc tct gat acc      1248
Ile Ala Arg Lys Arg Leu Tyr Glu Met Asn Val Val Ile Ser Asp Thr
                405                 410                 415 gct gag tac ggt aac tat ctg ttc tct tac gct tgt gtg ccg ttg ctg      1296
Ala Glu Tyr Gly Asn Tyr Leu Phe Ser Tyr Ala Cys Val Pro Leu Leu
            420                 425                 430 aaa ccg ttt atg gca gag ctg caa ccg ggc gac ctg ggt aaa gct att      1344
Lys Pro Phe Met Ala Glu Leu Gln Pro Gly Asp Leu Gly Lys Ala Ile
        435                 440                 445 ccg gaa ggc gcg gta gat aac ggg caa ctg cgt gat gtg aac gaa gcg      1392
Pro Glu Gly Ala Val Asp Asn Gly Gln Leu Arg Asp Val Asn Glu Ala
    450                 455                 460 att cgc agc cat gcg att gag cag gta ggt aag aaa ctg cgc ggc tat      1440
Ile Arg Ser His Ala Ile Glu Gln Val Gly Lys Lys Leu Arg Gly Tyr
465                 470                 475                 480 atg aca gat atg aaa cgt att gct gtt gcg ggt taa                      1476
Met Thr Asp Met Lys Arg Ile Ala Val Ala Gly
                485                 490

<210> SEQ ID NO 18
<211> LENGTH: 491
<212> TYPE: PRT
<213> ORGANISM: Escherichia coli

<400> SEQUENCE: 18

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60
```

```
Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
```

```
<210> SEQ ID NO 19
<211> LENGTH: 1851
<212> TYPE: DNA
<213> ORGANISM: Escherichia coli
<220> FEATURE:
<221> NAME/KEY: CDS
<222> LOCATION: (1)..(1851)

<400> SEQUENCE: 19 atg cct aag tac cgt tcc gcc acc acc act cat ggt cgt aat atg gcg      48
Met Pro Lys Tyr Arg Ser Ala Thr Thr Thr His Gly Arg Asn Met Ala
1               5                   10                  15 ggt gct cgt gcg ctg tgg cgc gcc acc gga atg acc gac gcc gat ttc      96
Gly Ala Arg Ala Leu Trp Arg Ala Thr Gly Met Thr Asp Ala Asp Phe
            20                  25                  30 ggt aag ccg att atc gcg gtt gtg aac tcg ttc acc caa ttt gta ccg     144
Gly Lys Pro Ile Ile Ala Val Val Asn Ser Phe Thr Gln Phe Val Pro
        35                  40                  45 ggt cac gtc cat ctg cgc gat ctc ggt aaa ctg gtc gcc gaa caa att     192
Gly His Val His Leu Arg Asp Leu Gly Lys Leu Val Ala Glu Gln Ile
    50                  55                  60 gaa gcg gct ggc ggt gtt gcc aaa gag ttc aac acc att gcg gtg gat     240
Glu Ala Ala Gly Gly Val Ala Lys Glu Phe Asn Thr Ile Ala Val Asp
65                  70                  75                  80 gat ggg att gcc atg ggc cac ggg ggg atg ctt tat tca ctg cca tct     288
Asp Gly Ile Ala Met Gly His Gly Gly Met Leu Tyr Ser Leu Pro Ser
                85                  90                  95 cgc gaa ctg atc gct gat tcc gtt gag tat atg gtc aac gcc cac tgc     336
Arg Glu Leu Ile Ala Asp Ser Val Glu Tyr Met Val Asn Ala His Cys
            100                 105                 110 gcc gac gcc atg gtc tgc atc tct aac tgc gac aaa atc acc ccg ggg     384
Ala Asp Ala Met Val Cys Ile Ser Asn Cys Asp Lys Ile Thr Pro Gly
        115                 120                 125 atg ctg atg gct tcc ctg cgc ctg aat att ccg gtg atc ttt gtt tcc     432
Met Leu Met Ala Ser Leu Arg Leu Asn Ile Pro Val Ile Phe Val Ser
    130                 135                 140 ggc ggc ccg atg gag gcc ggg aaa acc aaa ctt tcc gat cag atc atc     480
Gly Gly Pro Met Glu Ala Gly Lys Thr Lys Leu Ser Asp Gln Ile Ile
145                 150                 155                 160 aag ctc gat ctg gtt gat gcg atg atc cag ggc gca gac ccg aaa gta     528
Lys Leu Asp Leu Val Asp Ala Met Ile Gln Gly Ala Asp Pro Lys Val
                165                 170                 175 tct gac tcc cag agc gat cag gtt gaa cgt tcc gcg tgt ccg acc tgc     576
Ser Asp Ser Gln Ser Asp Gln Val Glu Arg Ser Ala Cys Pro Thr Cys
            180                 185                 190 ggt tcc tgc tcc ggg atg ttt acc gct aac tca atg aac tgc ctg acc     624
Gly Ser Cys Ser Gly Met Phe Thr Ala Asn Ser Met Asn Cys Leu Thr
        195                 200                 205 gaa gcg ctg ggc ctg tcg cag ccg ggc aac ggc tcg ctg ctg gca acc     672
Glu Ala Leu Gly Leu Ser Gln Pro Gly Asn Gly Ser Leu Leu Ala Thr
    210                 215                 220 cac gcc gac cgt aag cag ctg ttc ctt aat gct ggt aaa cgc att gtt     720
His Ala Asp Arg Lys Gln Leu Phe Leu Asn Ala Gly Lys Arg Ile Val
225                 230                 235                 240 gaa ttg acc aaa cgt tat tac gag caa aac gac gaa agt gca ctg ccg     768
Glu Leu Thr Lys Arg Tyr Tyr Glu Gln Asn Asp Glu Ser Ala Leu Pro
                245                 250                 255 cgt aat atc gcc agt aag gcg gcg ttt gaa aac gcc atg acg ctg gat     816
Arg Asn Ile Ala Ser Lys Ala Ala Phe Glu Asn Ala Met Thr Leu Asp
```

```
                260             265             270
atc gcg atg ggt gga tcg act aac acc gta ctt cac ctg ctg gcg gcg     864
Ile Ala Met Gly Gly Ser Thr Asn Thr Val Leu His Leu Leu Ala Ala
            275             280             285 gcg cag gaa gcg gaa atc gac ttc acc atg agt gat atc gat aag ctt     912
Ala Gln Glu Ala Glu Ile Asp Phe Thr Met Ser Asp Ile Asp Lys Leu
        290             295             300 tcc cgc aag gtt cca cag ctg tgt aaa gtt gcg ccg agc acc cag aaa     960
Ser Arg Lys Val Pro Gln Leu Cys Lys Val Ala Pro Ser Thr Gln Lys
305             310             315             320 tac cat atg gaa gat gtt cac cgt gct ggt ggt gtt atc ggt att ctc    1008
Tyr His Met Glu Asp Val His Arg Ala Gly Gly Val Ile Gly Ile Leu
            325             330             335 ggc gaa ctg gat cgc gcg ggg tta ctg aac cgt gat gtg aaa aac gta    1056
Gly Glu Leu Asp Arg Ala Gly Leu Leu Asn Arg Asp Val Lys Asn Val
        340             345             350 ctt ggc ctg acg ttg ccg caa acg ctg gaa caa tac gac gtt atg ctg    1104
Leu Gly Leu Thr Leu Pro Gln Thr Leu Glu Gln Tyr Asp Val Met Leu
            355             360             365 acc cag gat gac gcg gta aaa aat atg ttc cgc gca ggt cct gca ggc    1152
Thr Gln Asp Asp Ala Val Lys Asn Met Phe Arg Ala Gly Pro Ala Gly
370             375             380 att cgt acc aca cag gca ttc tcg caa gat tgc cgt tgg gat acg ctg    1200
Ile Arg Thr Thr Gln Ala Phe Ser Gln Asp Cys Arg Trp Asp Thr Leu
385             390             395             400 gac gac gat cgc gcc aat ggc tgt atc cgc tcg ctg gaa cac gcc tac    1248
Asp Asp Asp Arg Ala Asn Gly Cys Ile Arg Ser Leu Glu His Ala Tyr
            405             410             415 agc aaa gac ggc ggc ctg gcg gtg ctc tac ggt aac ttt gcg gaa aac    1296
Ser Lys Asp Gly Gly Leu Ala Val Leu Tyr Gly Asn Phe Ala Glu Asn
        420             425             430 ggc tgc atc gtg aaa acg gca ggc gtc gat gac agc atc ctc aaa ttc    1344
Gly Cys Ile Val Lys Thr Ala Gly Val Asp Asp Ser Ile Leu Lys Phe
            435             440             445 acc ggc ccg gcg aaa gtg tac gaa agc cag gac gat gcg gta gaa gcg    1392
Thr Gly Pro Ala Lys Val Tyr Glu Ser Gln Asp Asp Ala Val Glu Ala
450             455             460 att ctc ggc ggt aaa gtt gtc gcc gga gat gtg gta gta att cgc tat    1440
Ile Leu Gly Gly Lys Val Val Ala Gly Asp Val Val Val Ile Arg Tyr
465             470             475             480 gaa ggc ccg aaa ggc ggt ccg ggg atg cag gaa atg ctc tac cca acc    1488
Glu Gly Pro Lys Gly Gly Pro Gly Met Gln Glu Met Leu Tyr Pro Thr
            485             490             495 agc ttc ctg aaa tca atg ggt ctc ggc aaa gcc tgt gcg ctg atc acc    1536
Ser Phe Leu Lys Ser Met Gly Leu Gly Lys Ala Cys Ala Leu Ile Thr
        500             505             510 gac ggt cgt ttc tct ggt ggc acc tct ggt ctt tcc atc ggc cac gtc    1584
Asp Gly Arg Phe Ser Gly Gly Thr Ser Gly Leu Ser Ile Gly His Val
            515             520             525 tca ccg gaa gcg gca agc ggc ggc agc att ggc ctg att gaa gat ggt    1632
Ser Pro Glu Ala Ala Ser Gly Gly Ser Ile Gly Leu Ile Glu Asp Gly
530             535             540 gac ctg atc gct atc gac atc ccg aac cgt ggc att cag tta cag gta    1680
Asp Leu Ile Ala Ile Asp Ile Pro Asn Arg Gly Ile Gln Leu Gln Val
545             550             555             560 agc gat gcc gaa ctg gcg gcg cgt cgt gaa gcg cag gac gct cga ggt    1728
Ser Asp Ala Glu Leu Ala Ala Arg Arg Glu Ala Gln Asp Ala Arg Gly
            565             570             575 gac aaa gcc tgg acg ccg aaa aat cgt gaa cgt cag gtc tcc ttt gcc    1776
```

```
                                        Asp Lys Ala Trp Thr Pro Lys Asn Arg Glu Arg Gln Val Ser Phe Ala
                                                        580                 585                 590 ctg cgt gct tat gcc agc ctg gca acc agc gcc gac aaa ggc gcg gtg                        1824
Leu Arg Ala Tyr Ala Ser Leu Ala Thr Ser Ala Asp Lys Gly Ala Val
            595                 600                 605 cgc gat aaa tcg aaa ctg ggg ggt taa                                                    1851
Arg Asp Lys Ser Lys Leu Gly Gly
        610                 615
```

<210> SEQ ID NO 20
<211> LENGTH: 616
<212> TYPE: PRT
<213> ORGANISM: Escherichia coli

<400> SEQUENCE: 20

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320
```

```
Tyr His Met Glu Asp Val His Arg Ala Gly Val Ile Gly Ile Leu
            325                 330                 335

Gly Glu Leu Asp Arg Ala Gly Leu Leu Asn Arg Asp Val Lys Asn Val
        340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Ala Val Glu Ala
        450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615

<210> SEQ ID NO 21
<211> LENGTH: 1545
<212> TYPE: DNA
<213> ORGANISM: Escherichia coli
<220> FEATURE:
<221> NAME/KEY: CDS
<222> LOCATION: (1)..(1545)

<400> SEQUENCE: 21 atg gct gac tcg caa ccc ctg tcc ggt gct ccg gaa ggt gcc gaa tat      48
Met Ala Asp Ser Gln Pro Leu Ser Gly Ala Pro Glu Gly Ala Glu Tyr
1               5                   10                  15 tta aga gca gtg ctg cgc gcg ccg gtt tac gag gcg gcg cag gtt acg      96
Leu Arg Ala Val Leu Arg Ala Pro Val Tyr Glu Ala Ala Gln Val Thr
            20                  25                  30 ccg cta caa aaa atg gaa aaa ctg tcg tcg cgt ctt gat aac gtc att     144
Pro Leu Gln Lys Met Glu Lys Leu Ser Ser Arg Leu Asp Asn Val Ile
        35                  40                  45
```

```
ctg gtg aag cgc gaa gat cgc cag cca gtg cac agc ttt aag ctg cgc    192
Leu Val Lys Arg Glu Asp Arg Gln Pro Val His Ser Phe Lys Leu Arg
     50                  55                  60 ggc gca tac gcc atg atg gcg ggc ctg acg gaa gaa cag aaa gcg cac    240
Gly Ala Tyr Ala Met Met Ala Gly Leu Thr Glu Glu Gln Lys Ala His
 65                  70                  75                  80 ggc gtg atc act gct tct gcg ggt aac cac gcg cag ggc gtc gcg ttt    288
Gly Val Ile Thr Ala Ser Ala Gly Asn His Ala Gln Gly Val Ala Phe
                 85                  90                  95 tct tct gcg cgg tta ggc gtg aag gcc ctg atc gtt atg cca acc gcc    336
Ser Ser Ala Arg Leu Gly Val Lys Ala Leu Ile Val Met Pro Thr Ala
                100                 105                 110 acc gcc gac atc aaa gtc gac gcg gtg cgc ggc ttc ggc ggc gaa gtg    384
Thr Ala Asp Ile Lys Val Asp Ala Val Arg Gly Phe Gly Gly Glu Val
            115                 120                 125 ctc ctc cac ggc gcg aac ttt gat gaa gcg aaa gcc aaa gcg atc gaa    432
Leu Leu His Gly Ala Asn Phe Asp Glu Ala Lys Ala Lys Ala Ile Glu
        130                 135                 140 ctg tca cag cag cag ggg ttc acc tgg gtg ccg ccg ttc gac cat ccg    480
Leu Ser Gln Gln Gln Gly Phe Thr Trp Val Pro Pro Phe Asp His Pro
145                 150                 155                 160 atg gtg att gcc ggg caa ggc acg ctg gcg ctg gaa ctg ctc cag cag    528
Met Val Ile Ala Gly Gln Gly Thr Leu Ala Leu Glu Leu Leu Gln Gln
                165                 170                 175 gac gcc cat ctc gac cgc gta ttt gtg cca gtc ggc ggc ggc ggt ctg    576
Asp Ala His Leu Asp Arg Val Phe Val Pro Val Gly Gly Gly Gly Leu
            180                 185                 190 gct gct ggc gtg gcg gtg ctg atc aaa caa ctg atg ccg caa atc aaa    624
Ala Ala Gly Val Ala Val Leu Ile Lys Gln Leu Met Pro Gln Ile Lys
        195                 200                 205 gtg atc gcc gta gaa gcg gaa gac tcc gcc tgc ctg aaa gca gcg ctg    672
Val Ile Ala Val Glu Ala Glu Asp Ser Ala Cys Leu Lys Ala Ala Leu
    210                 215                 220 gat gcg ggt cat ccg gtt gat ctg ccg cgc gta ggg cta ttt gct gaa    720
Asp Ala Gly His Pro Val Asp Leu Pro Arg Val Gly Leu Phe Ala Glu
225                 230                 235                 240 ggc gta gcg gta aaa cgc atc ggt gac gaa acc ttc cgt tta tgc cag    768
Gly Val Ala Val Lys Arg Ile Gly Asp Glu Thr Phe Arg Leu Cys Gln
                245                 250                 255 gag tat ctc gac gac atc atc acc gtc gat agc gat gcg atc tgt gcg    816
Glu Tyr Leu Asp Asp Ile Ile Thr Val Asp Ser Asp Ala Ile Cys Ala
            260                 265                 270 gcg atg aag gat tta ttc gaa gat gtg cgc gcg gtg gcg gaa ccc tct    864
Ala Met Lys Asp Leu Phe Glu Asp Val Arg Ala Val Ala Glu Pro Ser
        275                 280                 285 ggc gcg ctg gcg ctg gcg gga atg aaa aaa tat atc gcc ctg cac aac    912
Gly Ala Leu Ala Leu Ala Gly Met Lys Lys Tyr Ile Ala Leu His Asn
    290                 295                 300 att cgc ggc gaa cgg ctg gcg cat att ctt tcc ggt gcc aac gtg aac    960
Ile Arg Gly Glu Arg Leu Ala His Ile Leu Ser Gly Ala Asn Val Asn
305                 310                 315                 320 ttc cac ggc ctg cgc tac gtc tca gaa cgc tgc gaa ctg ggc gaa cag   1008
Phe His Gly Leu Arg Tyr Val Ser Glu Arg Cys Glu Leu Gly Glu Gln
                325                 330                 335 cgt gaa gcg ttg ttg gcg gtg acc att ccg gaa gaa aaa ggc agc ttc   1056
Arg Glu Ala Leu Leu Ala Val Thr Ile Pro Glu Glu Lys Gly Ser Phe
            340                 345                 350 ctc aaa ttc tgc caa ctg ctt ggc ggg cgt tcg gtc acc gag ttc aac   1104
Leu Lys Phe Cys Gln Leu Leu Gly Gly Arg Ser Val Thr Glu Phe Asn
```

```
                355                 360                 365
tac cgt ttt gcc gat gcc aaa aac gcc tgc atc ttt gtc ggt gtg cgc      1152
Tyr Arg Phe Ala Asp Ala Lys Asn Ala Cys Ile Phe Val Gly Val Arg
    370                 375                 380 ctg agc cgc ggc ctc gaa gag cgc aaa gaa att ttg cag atg ctc aac      1200
Leu Ser Arg Gly Leu Glu Glu Arg Lys Glu Ile Leu Gln Met Leu Asn
385                 390                 395                 400 gac ggc ggc tac agc gtg gtt gat ctc tcc gac gac gaa atg gcg aag      1248
Asp Gly Gly Tyr Ser Val Val Asp Leu Ser Asp Asp Glu Met Ala Lys
                405                 410                 415 cta cac gtg cgc tat atg gtc ggc gga cgt cca tcg cat ccg ttg cag      1296
Leu His Val Arg Tyr Met Val Gly Gly Arg Pro Ser His Pro Leu Gln
            420                 425                 430 gaa cgc ctc tac agc ttc gaa ttc ccg gaa tca ccg ggc gcg ctg ctg      1344
Glu Arg Leu Tyr Ser Phe Glu Phe Pro Glu Ser Pro Gly Ala Leu Leu
        435                 440                 445 cgc ttc ctc aac acg ctg ggt acg tac tgg aac att tct ttg ttc cac      1392
Arg Phe Leu Asn Thr Leu Gly Thr Tyr Trp Asn Ile Ser Leu Phe His
    450                 455                 460 tat cgc agc cat ggc acc gac tac ggg cgc gta ctg gcg gcg ttc gaa      1440
Tyr Arg Ser His Gly Thr Asp Tyr Gly Arg Val Leu Ala Ala Phe Glu
465                 470                 475                 480 ctt ggc gac cat gaa ccg gat ttc gaa acc cgg ctg aat gag ctg ggc      1488
Leu Gly Asp His Glu Pro Asp Phe Glu Thr Arg Leu Asn Glu Leu Gly
                485                 490                 495 tac gat tgc cac gac gaa acc aat aac ccg gcg ttc agg ttc ttt ttg      1536
Tyr Asp Cys His Asp Glu Thr Asn Asn Pro Ala Phe Arg Phe Phe Leu
            500                 505                 510 gcg ggt tag                                                          1545
Ala Gly <210> SEQ ID NO 22
<211> LENGTH: 514
<212> TYPE: PRT
<213> ORGANISM: Escherichia coli

<400> SEQUENCE: 22

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160
```

```
Met Val Ile Ala Gly Gln Gly Thr Leu Ala Leu Glu Leu Leu Gln Gln
                165                 170                 175
Asp Ala His Leu Asp Arg Val Phe Val Pro Val Gly Gly Gly Gly Leu
            180                 185                 190
Ala Ala Gly Val Ala Val Leu Ile Lys Gln Leu Met Pro Gln Ile Lys
        195                 200                 205
Val Ile Ala Val Glu Ala Glu Asp Ser Ala Cys Leu Lys Ala Ala Leu
    210                 215                 220
Asp Ala Gly His Pro Val Asp Leu Pro Arg Val Gly Leu Phe Ala Glu
225                 230                 235                 240
Gly Val Ala Val Lys Arg Ile Gly Asp Glu Thr Phe Arg Leu Cys Gln
                245                 250                 255
Glu Tyr Leu Asp Asp Ile Ile Thr Val Asp Ser Asp Ala Ile Cys Ala
            260                 265                 270
Ala Met Lys Asp Leu Phe Glu Asp Val Arg Ala Val Ala Glu Pro Ser
        275                 280                 285
Gly Ala Leu Ala Leu Ala Gly Met Lys Lys Tyr Ile Ala Leu His Asn
    290                 295                 300
Ile Arg Gly Glu Arg Leu Ala His Ile Leu Ser Gly Ala Asn Val Asn
305                 310                 315                 320
Phe His Gly Leu Arg Tyr Val Ser Glu Arg Cys Glu Leu Gly Glu Gln
                325                 330                 335
Arg Glu Ala Leu Leu Ala Val Thr Ile Pro Glu Glu Lys Gly Ser Phe
            340                 345                 350
Leu Lys Phe Cys Gln Leu Leu Gly Gly Arg Ser Val Thr Glu Phe Asn
        355                 360                 365
Tyr Arg Phe Ala Asp Ala Lys Asn Ala Cys Ile Phe Val Gly Val Arg
    370                 375                 380
Leu Ser Arg Gly Leu Glu Glu Arg Lys Glu Ile Leu Gln Met Leu Asn
385                 390                 395                 400
Asp Gly Gly Tyr Ser Val Val Asp Leu Ser Asp Asp Glu Met Ala Lys
                405                 410                 415
Leu His Val Arg Tyr Met Val Gly Gly Arg Pro Ser His Pro Leu Gln
            420                 425                 430
Glu Arg Leu Tyr Ser Phe Glu Phe Pro Glu Ser Pro Gly Ala Leu Leu
        435                 440                 445
Arg Phe Leu Asn Thr Leu Gly Thr Tyr Trp Asn Ile Ser Leu Phe His
    450                 455                 460
Tyr Arg Ser His Gly Thr Asp Tyr Gly Arg Val Leu Ala Ala Phe Glu
465                 470                 475                 480
Leu Gly Asp His Glu Pro Asp Phe Glu Thr Arg Leu Asn Glu Leu Gly
                485                 490                 495
Tyr Asp Cys His Asp Glu Thr Asn Asn Pro Ala Phe Arg Phe Phe Leu
            500                 505                 510
Ala Gly

<210> SEQ ID NO 23
<211> LENGTH: 1572
<212> TYPE: DNA
<213> ORGANISM: Escherichia coli
<220> FEATURE:
<221> NAME/KEY: CDS
<222> LOCATION: (1)..(1572)

<400> SEQUENCE: 23
```

-continued

```
atg agc cag caa gtc att att ttc gat acc aca ttg cgc gac ggt gaa    48
Met Ser Gln Gln Val Ile Ile Phe Asp Thr Thr Leu Arg Asp Gly Glu
1               5                   10                  15 cag gcg tta cag gca agc ttg agt gtg aaa gaa aaa ctg caa att gcg    96
Gln Ala Leu Gln Ala Ser Leu Ser Val Lys Glu Lys Leu Gln Ile Ala
            20                  25                  30 ctg gcc ctt gag cgt atg ggt gtt gac gtg atg gaa gtc ggt ttc ccc   144
Leu Ala Leu Glu Arg Met Gly Val Asp Val Met Glu Val Gly Phe Pro
        35                  40                  45 gtc tct tcg ccg ggc gat ttt gaa tcg gtg caa acc atc gcc cgc cag   192
Val Ser Ser Pro Gly Asp Phe Glu Ser Val Gln Thr Ile Ala Arg Gln
    50                  55                  60 gtt aaa aac agc cgc gta tgt gcg tta gct cgc tgc gtg gaa aaa gat   240
Val Lys Asn Ser Arg Val Cys Ala Leu Ala Arg Cys Val Glu Lys Asp
65                  70                  75                  80 atc gac gtg gcg gcc gaa tcc ctg aaa gtc gcc gaa gcc ttc cgt att   288
Ile Asp Val Ala Ala Glu Ser Leu Lys Val Ala Glu Ala Phe Arg Ile
                85                  90                  95 cat acc ttt att gcc act tcg cca atg cac atc gcc acc aag ctg cgc   336
His Thr Phe Ile Ala Thr Ser Pro Met His Ile Ala Thr Lys Leu Arg
            100                 105                 110 agc acg ctg gac gag gtg atc gaa cgc gct atc tat atg gtg aaa cgc   384
Ser Thr Leu Asp Glu Val Ile Glu Arg Ala Ile Tyr Met Val Lys Arg
        115                 120                 125 gcc cgt aat tac acc gat gat gtt gaa ttt tct tgc gaa gat gcc ggg   432
Ala Arg Asn Tyr Thr Asp Asp Val Glu Phe Ser Cys Glu Asp Ala Gly
    130                 135                 140 cgt aca ccc att gcc gat ctg gcg cga gtg gtc gaa gcg gcg att aat   480
Arg Thr Pro Ile Ala Asp Leu Ala Arg Val Val Glu Ala Ala Ile Asn
145                 150                 155                 160 gcc ggt gcc acc acc atc aac att ccg gac acc gtg ggc tac acc atg   528
Ala Gly Ala Thr Thr Ile Asn Ile Pro Asp Thr Val Gly Tyr Thr Met
                165                 170                 175 ccg ttt gag ttc gcc gga atc atc agc ggc ctg tat gaa cgc gtg cct   576
Pro Phe Glu Phe Ala Gly Ile Ile Ser Gly Leu Tyr Glu Arg Val Pro
            180                 185                 190 aac atc gac aaa gcc att atc tcc gta cat acc cac gac gat ttg ggc   624
Asn Ile Asp Lys Ala Ile Ile Ser Val His Thr His Asp Asp Leu Gly
        195                 200                 205 ctg gcg gtc gga aac tca ctg gcg gcg gta cat gcc ggt gca cgc cag   672
Leu Ala Val Gly Asn Ser Leu Ala Ala Val His Ala Gly Ala Arg Gln
    210                 215                 220 gtg gaa ggc gca atg aac ggg atc ggc gag cgt gcc gga aac tgt tcc   720
Val Glu Gly Ala Met Asn Gly Ile Gly Glu Arg Ala Gly Asn Cys Ser
225                 230                 235                 240 ctg gaa gaa gtc atc atg gcg atc aaa gtt cgt aag gat att ctc aac   768
Leu Glu Glu Val Ile Met Ala Ile Lys Val Arg Lys Asp Ile Leu Asn
                245                 250                 255 gtc cac acc gcc att aat cac cag gag ata tgg cgc acc agc cag tta   816
Val His Thr Ala Ile Asn His Gln Glu Ile Trp Arg Thr Ser Gln Leu
            260                 265                 270 gtt agc cag att tgt aat atg ccg atc ccg gca aac aaa gcc att gtt   864
Val Ser Gln Ile Cys Asn Met Pro Ile Pro Ala Asn Lys Ala Ile Val
        275                 280                 285 ggc agc ggc gca ttc gca cac tcc tcc ggt ata cac cag gat ggc gtg   912
Gly Ser Gly Ala Phe Ala His Ser Ser Gly Ile His Gln Asp Gly Val
    290                 295                 300 ctg aaa aac cgc gaa aac tac gaa atc atg aca cca gaa tct att ggt   960
Leu Lys Asn Arg Glu Asn Tyr Glu Ile Met Thr Pro Glu Ser Ile Gly
305                 310                 315                 320
```

```
ctg aac caa atc cag ctg aat ctg acc tct cgt tcg ggg cgt gcg gcg      1008
Leu Asn Gln Ile Gln Leu Asn Leu Thr Ser Arg Ser Gly Arg Ala Ala
                325                 330                 335 gtg aaa cat cgc atg gat gag atg ggg tat aaa gaa agt gaa tat aat      1056
Val Lys His Arg Met Asp Glu Met Gly Tyr Lys Glu Ser Glu Tyr Asn
        340                 345                 350 tta gac aat ttg tac gat gct ttc ctg aag ctg gcg gac aaa aaa ggt      1104
Leu Asp Asn Leu Tyr Asp Ala Phe Leu Lys Leu Ala Asp Lys Lys Gly
    355                 360                 365 cag gtg ttt gat tac gat ctg gag gcg ctg gcc ttc atc ggt aag cag      1152
Gln Val Phe Asp Tyr Asp Leu Glu Ala Leu Ala Phe Ile Gly Lys Gln
370                 375                 380 caa gaa gag ccg gag cat ttc cgt ctg gat tac ttc agc gtg cag tct      1200
Gln Glu Glu Pro Glu His Phe Arg Leu Asp Tyr Phe Ser Val Gln Ser
385                 390                 395                 400 ggc tct aac gat atc gcc acc gcc gcc gtc aaa ctg gcc tgt ggc gaa      1248
Gly Ser Asn Asp Ile Ala Thr Ala Ala Val Lys Leu Ala Cys Gly Glu
                405                 410                 415 gaa gtc aaa gca gaa gcc gcc aac ggt aac ggt ccg gtc gat gcc gtc      1296
Glu Val Lys Ala Glu Ala Ala Asn Gly Asn Gly Pro Val Asp Ala Val
        420                 425                 430 tat cag gca att aac cgc atc act gaa tat aac gtc gaa ctg gtg aaa      1344
Tyr Gln Ala Ile Asn Arg Ile Thr Glu Tyr Asn Val Glu Leu Val Lys
    435                 440                 445 tac agc ctg acc gcc aaa ggc cac ggt aaa gat gcg ctg ggt cag gtg      1392
Tyr Ser Leu Thr Ala Lys Gly His Gly Lys Asp Ala Leu Gly Gln Val
450                 455                 460 gat atc gtc gct aac tac aac ggt cgc cgc ttc cac ggc gtc ggc ctg      1440
Asp Ile Val Ala Asn Tyr Asn Gly Arg Arg Phe His Gly Val Gly Leu
465                 470                 475                 480 gct acc gat att gtc gag tca tct gcc aaa gcc atg gtg cac gtt ctg      1488
Ala Thr Asp Ile Val Glu Ser Ser Ala Lys Ala Met Val His Val Leu
                485                 490                 495 aac aat atc tgg cgt gcc gca gaa gtc gaa aaa gag ttg caa cgc aaa      1536
Asn Asn Ile Trp Arg Ala Ala Glu Val Glu Lys Glu Leu Gln Arg Lys
        500                 505                 510 gct caa cac aac gaa aac aac aag gaa acc gtg tga                      1572
Ala Gln His Asn Glu Asn Asn Lys Glu Thr Val
    515                 520

<210> SEQ ID NO 24
<211> LENGTH: 523
<212> TYPE: PRT
<213> ORGANISM: Escherichia coli

<400> SEQUENCE: 24

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
                20                  25                  30

Leu Ala Leu Glu Arg Met Gly Val Asp Val Met Glu Val Gly Phe Pro
            35                  40                  45

Val Ser Ser Pro Gly Asp Phe Glu Ser Val Gln Thr Ile Ala Arg Gln
        50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95
```

-continued

```
His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
            115                 120                 125

Ala Arg Asn Tyr Thr Asp Asp Val Glu Phe Ser Cys Glu Asp Ala Gly
            130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                    165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
            195                 200                 205

Leu Ala Val Gly Asn Ser Leu Ala Ala Val His Ala Gly Ala Arg Gln
            210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                    245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
            275                 280                 285

Gly Ser Gly Ala Phe Ala His Ser Ser Gly Ile His Gln Asp Gly Val
            290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                    325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Gly Lys Gln
            370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                    405                 410                 415

Glu Val Lys Ala Glu Ala Asn Gly Asn Gly Pro Val Asp Ala Val
            420                 425                 430

Tyr Gln Ala Ile Asn Arg Ile Thr Glu Tyr Asn Val Glu Leu Val Lys
            435                 440                 445

Tyr Ser Leu Thr Ala Lys Gly His Gly Lys Asp Ala Leu Gly Gln Val
            450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                    485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
```

<210> SEQ ID NO 25
<211> LENGTH: 1095
<212> TYPE: DNA
<213> ORGANISM: Escherichia coli
<220> FEATURE:
<221> NAME/KEY: CDS
<222> LOCATION: (1)..(1095)

<400> SEQUENCE: 25

| | | | | | | | | | | | | | | | | |
|---|---|---|---|---|---|---|---|---|---|---|---|---|---|---|---|---|
| gtg | atg | tcg | aag | aat | tac | cat | att | gcc | gta | ttg | ccg | ggg | gac | ggt | att | 48 |
| Val | Met | Ser | Lys | Asn | Tyr | His | Ile | Ala | Val | Leu | Pro | Gly | Asp | Gly | Ile | |
| 1 | | | | 5 | | | | | 10 | | | | | 15 | | |
| ggt | ccg | gaa | gtg | atg | acc | cag | gcg | ctg | aaa | gtg | ctg | gat | gcc | gtg | cgc | 96 |
| Gly | Pro | Glu | Val | Met | Thr | Gln | Ala | Leu | Lys | Val | Leu | Asp | Ala | Val | Arg | |
| | | | 20 | | | | | 25 | | | | | 30 | | | |
| aac | cgc | ttt | gcg | atg | cgc | atc | acc | acc | agc | cat | tac | gat | gta | ggc | ggc | 144 |
| Asn | Arg | Phe | Ala | Met | Arg | Ile | Thr | Thr | Ser | His | Tyr | Asp | Val | Gly | Gly | |
| | | 35 | | | | | 40 | | | | | 45 | | | | |
| gca | gcc | att | gat | aac | cac | ggg | caa | cca | ctg | ccg | cct | gcg | acg | gtt | gaa | 192 |
| Ala | Ala | Ile | Asp | Asn | His | Gly | Gln | Pro | Leu | Pro | Pro | Ala | Thr | Val | Glu | |
| | 50 | | | | | 55 | | | | | 60 | | | | | |
| ggt | tgt | gag | caa | gcc | gat | gcc | gtg | ctg | ttt | ggc | tcg | gta | ggc | ggc | ccg | 240 |
| Gly | Cys | Glu | Gln | Ala | Asp | Ala | Val | Leu | Phe | Gly | Ser | Val | Gly | Gly | Pro | |
| 65 | | | | | 70 | | | | | 75 | | | | | 80 | |
| aag | tgg | gaa | cat | tta | cca | cca | gac | cag | caa | cca | gaa | cgc | ggc | gcg | ctg | 288 |
| Lys | Trp | Glu | His | Leu | Pro | Pro | Asp | Gln | Gln | Pro | Glu | Arg | Gly | Ala | Leu | |
| | | | | 85 | | | | | 90 | | | | | 95 | | |
| ctg | cct | ctg | cgt | aag | cac | ttc | aaa | tta | ttc | agc | aac | ctg | cgc | ccg | gca | 336 |
| Leu | Pro | Leu | Arg | Lys | His | Phe | Lys | Leu | Phe | Ser | Asn | Leu | Arg | Pro | Ala | |
| | | | | 100 | | | | | 105 | | | | | 110 | | |
| aaa | ctg | tat | cag | ggg | ctg | gaa | gca | ttc | tgt | ccg | ctg | cgt | gca | gac | att | 384 |
| Lys | Leu | Tyr | Gln | Gly | Leu | Glu | Ala | Phe | Cys | Pro | Leu | Arg | Ala | Asp | Ile | |
| | | | 115 | | | | | 120 | | | | | 125 | | | |
| gcc | gca | aac | ggc | ttc | gac | atc | ctg | tgt | gtg | cgc | gaa | ctg | acc | ggc | ggc | 432 |
| Ala | Ala | Asn | Gly | Phe | Asp | Ile | Leu | Cys | Val | Arg | Glu | Leu | Thr | Gly | Gly | |
| | | 130 | | | | | 135 | | | | | 140 | | | | |
| atc | tat | ttc | ggt | cag | cca | aaa | ggc | cgc | gaa | ggt | agc | gga | caa | tat | gaa | 480 |
| Ile | Tyr | Phe | Gly | Gln | Pro | Lys | Gly | Arg | Glu | Gly | Ser | Gly | Gln | Tyr | Glu | |
| 145 | | | | | 150 | | | | | 155 | | | | | 160 | |
| aaa | gcc | ttt | gat | acc | gag | gtg | tat | cac | cgt | ttt | gag | atc | gaa | cgt | atc | 528 |
| Lys | Ala | Phe | Asp | Thr | Glu | Val | Tyr | His | Arg | Phe | Glu | Ile | Glu | Arg | Ile | |
| | | | | 165 | | | | | 170 | | | | | 175 | | |
| gcc | cgc | atc | gcg | ttt | gaa | tct | gct | cgc | aag | cgt | cgc | cac | aaa | gtg | acg | 576 |
| Ala | Arg | Ile | Ala | Phe | Glu | Ser | Ala | Arg | Lys | Arg | Arg | His | Lys | Val | Thr | |
| | | | 180 | | | | | 185 | | | | | 190 | | | |
| tcg | atc | gat | aaa | gcc | aac | gtg | ctg | caa | tcc | tct | att | tta | tgg | cgg | gag | 624 |
| Ser | Ile | Asp | Lys | Ala | Asn | Val | Leu | Gln | Ser | Ser | Ile | Leu | Trp | Arg | Glu | |
| | | 195 | | | | | 200 | | | | | 205 | | | | |
| atc | gtt | aac | gag | atc | gcc | acg | gaa | tac | ccg | gat | gtc | gaa | ctg | gcg | cat | 672 |
| Ile | Val | Asn | Glu | Ile | Ala | Thr | Glu | Tyr | Pro | Asp | Val | Glu | Leu | Ala | His | |
| | 210 | | | | | 215 | | | | | 220 | | | | | |
| atg | tac | atc | gac | aac | gcc | acc | atg | cag | ctg | att | aaa | gat | cca | tca | cag | 720 |
| Met | Tyr | Ile | Asp | Asn | Ala | Thr | Met | Gln | Leu | Ile | Lys | Asp | Pro | Ser | Gln | |
| 225 | | | | | 230 | | | | | 235 | | | | | 240 | |
| ttt | gac | gtt | ctg | ctg | tgc | tcc | aac | ctg | ttt | ggc | gac | att | ctg | tct | gac | 768 |
| Phe | Asp | Val | Leu | Leu | Cys | Ser | Asn | Leu | Phe | Gly | Asp | Ile | Leu | Ser | Asp | |
| | | | | 245 | | | | | 250 | | | | | 255 | | |
| gag | tgc | gca | atg | atc | act | ggc | tcg | atg | ggg | atg | ttg | cct | tcc | gcc | agc | 816 |
| Glu | Cys | Ala | Met | Ile | Thr | Gly | Ser | Met | Gly | Met | Leu | Pro | Ser | Ala | Ser | |

```
                 260                 265                 270
ctg aac gag caa ggt ttt gga ctg tat gaa ccg gcg ggc ggc tcg gca         864
Leu Asn Glu Gln Gly Phe Gly Leu Tyr Glu Pro Ala Gly Gly Ser Ala
        275                 280                 285 cca gat atc gca ggc aaa aac atc gcc aac ccg att gca caa atc ctt         912
Pro Asp Ile Ala Gly Lys Asn Ile Ala Asn Pro Ile Ala Gln Ile Leu
290                 295                 300 tcg ctg gca ctg ctg ctg cgt tac agc ctg gat gcc gat gat gcg gct         960
Ser Leu Ala Leu Leu Leu Arg Tyr Ser Leu Asp Ala Asp Asp Ala Ala
305                 310                 315                 320 tgc gcc att gaa cgc gcc att aac cgc gca tta gaa gaa ggc att cgc        1008
Cys Ala Ile Glu Arg Ala Ile Asn Arg Ala Leu Glu Glu Gly Ile Arg
            325                 330                 335 acc ggg gat tta gcc cgt ggc gct gcc gcc gtt agt acc gat gaa atg        1056
Thr Gly Asp Leu Ala Arg Gly Ala Ala Ala Val Ser Thr Asp Glu Met
        340                 345                 350 ggc gat atc att gcc cgc tat gta gca gaa ggg gtg taa                    1095
Gly Asp Ile Ile Ala Arg Tyr Val Ala Glu Gly Val
                355                 360

<210> SEQ ID NO 26
<211> LENGTH: 364
<212> TYPE: PRT
<213> ORGANISM: Escherichia coli

<400> SEQUENCE: 26

Val Met Ser Lys Asn Tyr His Ile Ala Val Leu Pro Gly Asp Gly Ile
1               5                   10                  15

Gly Pro Glu Val Met Thr Gln Ala Leu Lys Val Leu Asp Ala Val Arg
                20                  25                  30

Asn Arg Phe Ala Met Arg Ile Thr Thr Ser His Tyr Asp Val Gly Gly
            35                  40                  45

Ala Ala Ile Asp Asn His Gly Gln Pro Leu Pro Pro Ala Thr Val Glu
        50                  55                  60

Gly Cys Glu Gln Ala Asp Ala Val Leu Phe Gly Ser Val Gly Gly Pro
65                  70                  75                  80

Lys Trp Glu His Leu Pro Pro Asp Gln Pro Glu Arg Gly Ala Leu
                85                  90                  95

Leu Pro Leu Arg Lys His Phe Lys Leu Phe Ser Asn Leu Arg Pro Ala
            100                 105                 110

Lys Leu Tyr Gln Gly Leu Glu Ala Phe Cys Pro Leu Arg Ala Asp Ile
        115                 120                 125

Ala Ala Asn Gly Phe Asp Ile Leu Cys Val Arg Glu Leu Thr Gly Gly
    130                 135                 140

Ile Tyr Phe Gly Gln Pro Lys Gly Arg Glu Gly Ser Gly Gln Tyr Glu
145                 150                 155                 160

Lys Ala Phe Asp Thr Glu Val Tyr His Arg Phe Glu Ile Glu Arg Ile
                165                 170                 175

Ala Arg Ile Ala Phe Glu Ser Ala Arg Lys Arg Arg His Lys Val Thr
            180                 185                 190

Ser Ile Asp Lys Ala Asn Val Leu Gln Ser Ser Ile Leu Trp Arg Glu
        195                 200                 205

Ile Val Asn Glu Ile Ala Thr Glu Tyr Pro Asp Val Glu Leu Ala His
    210                 215                 220

Met Tyr Ile Asp Asn Ala Thr Met Gln Leu Ile Lys Asp Pro Ser Gln
225                 230                 235                 240
```

```
Phe Asp Val Leu Leu Cys Ser Asn Leu Phe Gly Asp Ile Leu Ser Asp
                245                 250                 255

Glu Cys Ala Met Ile Thr Gly Ser Met Gly Met Leu Pro Ser Ala Ser
            260                 265                 270

Leu Asn Glu Gln Gly Phe Gly Leu Tyr Glu Pro Ala Gly Gly Ser Ala
        275                 280                 285

Pro Asp Ile Ala Gly Lys Asn Ile Ala Asn Pro Ile Ala Gln Ile Leu
    290                 295                 300

Ser Leu Ala Leu Leu Arg Tyr Ser Leu Asp Ala Asp Ala Ala
305                 310                 315                 320

Cys Ala Ile Glu Arg Ala Ile Asn Arg Ala Leu Glu Glu Gly Ile Arg
                325                 330                 335

Thr Gly Asp Leu Ala Arg Gly Ala Ala Ala Val Ser Thr Asp Glu Met
            340                 345                 350

Gly Asp Ile Ile Ala Arg Tyr Val Ala Glu Gly Val
        355                 360

<210> SEQ ID NO 27
<211> LENGTH: 1401
<212> TYPE: DNA
<213> ORGANISM: Escherichia coli
<220> FEATURE:
<221> NAME/KEY: CDS
<222> LOCATION: (1)..(1401)

<400> SEQUENCE: 27 atg gct aag acg tta tac gaa aaa ttg ttc gac gct cac gtt gtg tac     48
Met Ala Lys Thr Leu Tyr Glu Lys Leu Phe Asp Ala His Val Val Tyr
1               5                   10                  15 gaa gcc gaa aac gaa acc cca ctg tta tat atc gac cgc cac ctg gtg    96
Glu Ala Glu Asn Glu Thr Pro Leu Leu Tyr Ile Asp Arg His Leu Val
                20                  25                  30 cat gaa gtg acc tca ccg cag gcg ttc gat ggt ctg cgc gcc cac ggt   144
His Glu Val Thr Ser Pro Gln Ala Phe Asp Gly Leu Arg Ala His Gly
            35                  40                  45 cgc ccg gta cgt cag ccg ggc aaa acc ttc gct acc atg gat cac aac   192
Arg Pro Val Arg Gln Pro Gly Lys Thr Phe Ala Thr Met Asp His Asn
        50                  55                  60 gtc tct acc cag acc aaa gac att aat gcc tgc ggt gaa atg gcg cgt   240
Val Ser Thr Gln Thr Lys Asp Ile Asn Ala Cys Gly Glu Met Ala Arg
65                  70                  75                  80 atc cag atg cag gaa ctg atc aaa aac tgc aaa gaa ttt ggc gtc gaa   288
Ile Gln Met Gln Glu Leu Ile Lys Asn Cys Lys Glu Phe Gly Val Glu
                85                  90                  95 ctg tat gac ctg aat cac ccg tat cag ggg atc gtc cac gta atg ggg   336
Leu Tyr Asp Leu Asn His Pro Tyr Gln Gly Ile Val His Val Met Gly
                100                 105                 110 ccg gaa cag ggc gtc acc ttg ccg ggg atg acc att gtc tgc ggc gac   384
Pro Glu Gln Gly Val Thr Leu Pro Gly Met Thr Ile Val Cys Gly Asp
            115                 120                 125 tcg cat acc gcc acc cac ggc gcg ttt ggc gca ctg gcc ttt ggt atc   432
Ser His Thr Ala Thr His Gly Ala Phe Gly Ala Leu Ala Phe Gly Ile
        130                 135                 140 ggc act tcc gaa gtt gaa cac gta ctg gca acg caa acc ctg aaa cag   480
Gly Thr Ser Glu Val Glu His Val Leu Ala Thr Gln Thr Leu Lys Gln
145                 150                 155                 160 ggc cgc gca aaa acc atg aaa att gaa gtc cag ggc aaa gcc gcg ccg   528
Gly Arg Ala Lys Thr Met Lys Ile Glu Val Gln Gly Lys Ala Ala Pro
                165                 170                 175
```

```
ggc att acc gca aaa gat atc gtg ctg gca att atc ggt aaa acc ggt       576
Gly Ile Thr Ala Lys Asp Ile Val Leu Ala Ile Ile Gly Lys Thr Gly
            180                 185                 190 agc gca ggc ggc acc ggg cat gtg gtg gag ttt tgc ggc gaa gca atc       624
Ser Ala Gly Gly Thr Gly His Val Val Glu Phe Cys Gly Glu Ala Ile
        195                 200                 205 cgt gat tta agc atg gaa ggt cgt atg acc ctg tgc aat atg gca atc       672
Arg Asp Leu Ser Met Glu Gly Arg Met Thr Leu Cys Asn Met Ala Ile
    210                 215                 220 gaa atg ggc gca aaa gcc ggt ctg gtt gca ccg gac gaa acc acc ttt       720
Glu Met Gly Ala Lys Ala Gly Leu Val Ala Pro Asp Glu Thr Thr Phe
225                 230                 235                 240 aac tat gtc aaa ggc cgt ctg cat gcg ccg aaa ggc aaa gat ttc gac       768
Asn Tyr Val Lys Gly Arg Leu His Ala Pro Lys Gly Lys Asp Phe Asp
                245                 250                 255 gac gcc gtt gcc tac tgg aaa acc ctg caa acc gac gaa ggc gca act       816
Asp Ala Val Ala Tyr Trp Lys Thr Leu Gln Thr Asp Glu Gly Ala Thr
            260                 265                 270 ttc gat acc gtt gtc act ctg caa gca gaa gaa att tca ccg cag gtc       864
Phe Asp Thr Val Val Thr Leu Gln Ala Glu Glu Ile Ser Pro Gln Val
        275                 280                 285 acc tgg ggc acc aat ccc ggc cag gtg att tcc gtg aac gac aat att       912
Thr Trp Gly Thr Asn Pro Gly Gln Val Ile Ser Val Asn Asp Asn Ile
    290                 295                 300 ccc gat ccg gct tcg ttt gcc gat ccg gtt gaa cgc gcg tcg gca gaa       960
Pro Asp Pro Ala Ser Phe Ala Asp Pro Val Glu Arg Ala Ser Ala Glu
305                 310                 315                 320 aaa gcg ctg gcc tat atg ggg ctg aaa ccg ggt att ccg ctg acc gaa      1008
Lys Ala Leu Ala Tyr Met Gly Leu Lys Pro Gly Ile Pro Leu Thr Glu
                325                 330                 335 gtg gct atc gac aaa gtg ttt atc ggt tcc tgt acc aac tcg cgc att      1056
Val Ala Ile Asp Lys Val Phe Ile Gly Ser Cys Thr Asn Ser Arg Ile
            340                 345                 350 gaa gat tta cgc gcg gca gcg gag atc gcc aaa ggg cga aaa gtc gcg      1104
Glu Asp Leu Arg Ala Ala Ala Glu Ile Ala Lys Gly Arg Lys Val Ala
        355                 360                 365 cca ggc gtg cag gca ctg gtg gtt ccc ggc tct ggc ccg gta aaa gcc      1152
Pro Gly Val Gln Ala Leu Val Val Pro Gly Ser Gly Pro Val Lys Ala
    370                 375                 380 cag gcg gaa gcg gaa ggt ctg gat aaa atc ttt att gaa gcc ggt ttt      1200
Gln Ala Glu Ala Glu Gly Leu Asp Lys Ile Phe Ile Glu Ala Gly Phe
385                 390                 395                 400 gaa tgg cgc ttg cct ggc tgc tca atg tgt ctg gcg atg aac aac gac      1248
Glu Trp Arg Leu Pro Gly Cys Ser Met Cys Leu Ala Met Asn Asn Asp
                405                 410                 415 cgt ctg aat ccg ggc gaa cgt tgt gcc tcc acc agc aac cgt aac ttt      1296
Arg Leu Asn Pro Gly Glu Arg Cys Ala Ser Thr Ser Asn Arg Asn Phe
            420                 425                 430 gaa ggc cgc cag ggg cgc ggc ggg cgc acg cat ctg gtc agc ccg gca      1344
Glu Gly Arg Gln Gly Arg Gly Gly Arg Thr His Leu Val Ser Pro Ala
        435                 440                 445 atg gct gcc gct gct gct gtg acc gga cat ttc gcc gac att cgc aac      1392
Met Ala Ala Ala Ala Ala Val Thr Gly His Phe Ala Asp Ile Arg Asn
    450                 455                 460 att aaa taa                                                          1401
Ile Lys
465

<210> SEQ ID NO 28
<211> LENGTH: 466
```

```
<212> TYPE: PRT
<213> ORGANISM: Escherichia coli

<400> SEQUENCE: 28

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
            20                  25                  30

His Glu Val Thr Ser Pro Gln Ala Phe Asp Gly Leu Arg Ala His Gly
        35                  40                  45

Arg Pro Val Arg Gln Pro Gly Lys Thr Phe Ala Thr Met Asp His Asn
    50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
        115                 120                 125

Ser His Thr Ala Thr His Gly Ala Phe Gly Ala Leu Ala Phe Gly Ile
    130                 135                 140

Gly Thr Ser Glu Val Glu His Val Leu Ala Thr Gln Thr Leu Lys Gln
145                 150                 155                 160

Gly Arg Ala Lys Thr Met Lys Ile Glu Val Gln Gly Lys Ala Ala Pro
                165                 170                 175

Gly Ile Thr Ala Lys Asp Ile Val Leu Ala Ile Ile Gly Lys Thr Gly
            180                 185                 190

Ser Ala Gly Gly Thr Gly His Val Val Glu Phe Cys Gly Glu Ala Ile
        195                 200                 205

Arg Asp Leu Ser Met Glu Gly Arg Met Thr Leu Cys Asn Met Ala Ile
    210                 215                 220

Glu Met Gly Ala Lys Ala Gly Leu Val Ala Pro Asp Glu Thr Thr Phe
225                 230                 235                 240

Asn Tyr Val Lys Gly Arg Leu His Ala Pro Lys Gly Lys Asp Phe Asp
                245                 250                 255

Asp Ala Val Ala Tyr Trp Lys Thr Leu Gln Thr Asp Glu Gly Ala Thr
            260                 265                 270

Phe Asp Thr Val Val Thr Leu Gln Ala Glu Glu Ile Ser Pro Gln Val
        275                 280                 285

Thr Trp Gly Thr Asn Pro Gly Gln Val Ile Ser Val Asn Asp Asn Ile
    290                 295                 300

Pro Asp Pro Ala Ser Phe Ala Asp Pro Val Glu Arg Ala Ser Ala Glu
305                 310                 315                 320

Lys Ala Leu Ala Tyr Met Gly Leu Lys Pro Gly Ile Pro Leu Thr Glu
                325                 330                 335

Val Ala Ile Asp Lys Val Phe Ile Gly Ser Cys Thr Asn Ser Arg Ile
            340                 345                 350

Glu Asp Leu Arg Ala Ala Ala Glu Ile Ala Lys Gly Arg Lys Val Ala
        355                 360                 365

Pro Gly Val Gln Ala Leu Val Val Pro Gly Ser Gly Pro Val Lys Ala
    370                 375                 380

Gln Ala Glu Ala Glu Gly Leu Asp Lys Ile Phe Ile Glu Ala Gly Phe
385                 390                 395                 400
```

```
Glu Trp Arg Leu Pro Gly Cys Ser Met Cys Leu Ala Met Asn Asn Asp
                405                 410                 415
Arg Leu Asn Pro Gly Glu Arg Cys Ala Ser Thr Ser Asn Arg Asn Phe
            420                 425                 430
Glu Gly Arg Gln Gly Arg Gly Arg Thr His Leu Val Ser Pro Ala
        435                 440                 445
Met Ala Ala Ala Ala Val Thr Gly His Phe Ala Asp Ile Arg Asn
    450                 455                 460
Ile Lys
465

<210> SEQ ID NO 29
<211> LENGTH: 606
<212> TYPE: DNA
<213> ORGANISM: Escherichia coli
<220> FEATURE:
<221> NAME/KEY: CDS
<222> LOCATION: (1)..(606)

<400> SEQUENCE: 29 atg gca gag aaa ttt atc aaa cac aca ggc ctg gtg gtt ccg ctg gat     48
Met Ala Glu Lys Phe Ile Lys His Thr Gly Leu Val Val Pro Leu Asp
1               5                   10                  15 gcc gcc aat gtc gat acc gat gca atc atc ccg aaa cag ttt ttg cag     96
Ala Ala Asn Val Asp Thr Asp Ala Ile Ile Pro Lys Gln Phe Leu Gln
                20                  25                  30 aaa gtg acc cgt acg ggt ttt ggc gcg cat ctg ttt aac gac tgg cgt    144
Lys Val Thr Arg Thr Gly Phe Gly Ala His Leu Phe Asn Asp Trp Arg
            35                  40                  45 ttt ctg gat gaa aaa ggc caa cag cca aac ccg gac ttc gtg ctg aac    192
Phe Leu Asp Glu Lys Gly Gln Gln Pro Asn Pro Asp Phe Val Leu Asn
        50                  55                  60 ttc ccg cag tat cag ggc gct tcc att ttg ctg gca cga gaa aac ttc    240
Phe Pro Gln Tyr Gln Gly Ala Ser Ile Leu Leu Ala Arg Glu Asn Phe
65                  70                  75                  80 ggc tgt ggc tct tcg cgt gag cac gcg ccc tgg gca ttg acc gac tac    288
Gly Cys Gly Ser Ser Arg Glu His Ala Pro Trp Ala Leu Thr Asp Tyr
                85                  90                  95 ggt ttt aaa gtg gtg att gcg ccg agt ttt gct gac atc ttc tac ggc    336
Gly Phe Lys Val Val Ile Ala Pro Ser Phe Ala Asp Ile Phe Tyr Gly
            100                 105                 110 aat agc ttt aac aac cag ctg ctg ccg gtg aaa tta agc gat gca gaa    384
Asn Ser Phe Asn Asn Gln Leu Leu Pro Val Lys Leu Ser Asp Ala Glu
        115                 120                 125 gtg gac gaa ctg ttt gcg ctg gtg aaa gct aat ccg ggg atc cat ttc    432
Val Asp Glu Leu Phe Ala Leu Val Lys Ala Asn Pro Gly Ile His Phe
130                 135                 140 gac gtg gat ctg gaa gcg caa gag gtg aaa gcg gga gag aaa acc tat    480
Asp Val Asp Leu Glu Ala Gln Glu Val Lys Ala Gly Glu Lys Thr Tyr
145                 150                 155                 160 cgc ttt acc atc gat gcc ttc cgc cgc cac tgc atg atg aac ggt ctg    528
Arg Phe Thr Ile Asp Ala Phe Arg Arg His Cys Met Met Asn Gly Leu
                165                 170                 175 gac agt att ggg ctt acc ttg cag cac gac gac gcc att gcc gct tat    576
Asp Ser Ile Gly Leu Thr Leu Gln His Asp Asp Ala Ile Ala Ala Tyr
            180                 185                 190 gaa gca aaa caa cct gcg ttt atg aat taa                            606
Glu Ala Lys Gln Pro Ala Phe Met Asn
        195                 200
```

<210> SEQ ID NO 30
<211> LENGTH: 201
<212> TYPE: PRT
<213> ORGANISM: Escherichia coli

<400> SEQUENCE: 30

```
Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200
```

<210> SEQ ID NO 31
<211> LENGTH: 1476
<212> TYPE: DNA
<213> ORGANISM: Methanococcus jannaschii
<220> FEATURE:
<221> NAME/KEY: CDS
<222> LOCATION: (1)..(1476)

<400> SEQUENCE: 31

```
atg atg gta agg ata ttt gat aca aca ctt aga gat gga gag caa aca      48
Met Met Val Arg Ile Phe Asp Thr Thr Leu Arg Asp Gly Glu Gln Thr
1               5                   10                  15 cca gga gtt tct tta aca cca aat gat aag tta gag ata gca aaa aaa      96
Pro Gly Val Ser Leu Thr Pro Asn Asp Lys Leu Glu Ile Ala Lys Lys
            20                  25                  30 ttg gat gag ctt gga gtt gat gtt ata gag gca ggt tca gct ata act     144
Leu Asp Glu Leu Gly Val Asp Val Ile Glu Ala Gly Ser Ala Ile Thr
        35                  40                  45 tca aaa gga gag aga gaa gga ata aaa tta ata aca aaa gaa ggt tta     192
Ser Lys Gly Glu Arg Glu Gly Ile Lys Leu Ile Thr Lys Glu Gly Leu
    50                  55                  60 aat gca gaa atc tgc tca ttt gtt aga gct tta cct gta gat att gat     240
Asn Ala Glu Ile Cys Ser Phe Val Arg Ala Leu Pro Val Asp Ile Asp
65                  70                  75                  80 gct gcc tta gaa tgt gat gta gat agt gtc cat tta gta gtg cca aca     288
```

```
                Ala Ala Leu Glu Cys Asp Val Asp Ser Val His Leu Val Val Pro Thr
                                 85              90              95 tct cca ata cac atg aaa tat aag ctt aga aaa aca gaa gat gag gtt         336
Ser Pro Ile His Met Lys Tyr Lys Leu Arg Lys Thr Glu Asp Glu Val
            100             105             110 tta gag aca gct tta aag gct gta gag tat gct aaa gaa cat gga ttg         384
Leu Glu Thr Ala Leu Lys Ala Val Glu Tyr Ala Lys Glu His Gly Leu
        115             120             125 att gtt gag tta tct gca gag gat gca aca aga agt gat gta aat ttc         432
Ile Val Glu Leu Ser Ala Glu Asp Ala Thr Arg Ser Asp Val Asn Phe
    130             135             140 tta ata aaa cta ttt aat gaa ggg gaa aag gtt gga gca gac aga gtt         480
Leu Ile Lys Leu Phe Asn Glu Gly Glu Lys Val Gly Ala Asp Arg Val
145             150             155             160 tgt gtt tgt gac aca gta gga gtt tta act cca caa aag agt cag gaa         528
Cys Val Cys Asp Thr Val Gly Val Leu Thr Pro Gln Lys Ser Gln Glu
                165             170             175 tta ttt aaa aaa ata act gaa aat gtt aat tta ccg gtc tca gtt cat         576
Leu Phe Lys Lys Ile Thr Glu Asn Val Asn Leu Pro Val Ser Val His
            180             185             190 tgc cac aac gac ttt gga atg gct act gct aat act tgc tca gca gtt         624
Cys His Asn Asp Phe Gly Met Ala Thr Ala Asn Thr Cys Ser Ala Val
        195             200             205 tta ggt gga gct gtt cag tgc cac gta aca gtt aat ggt att gga gag         672
Leu Gly Gly Ala Val Gln Cys His Val Thr Val Asn Gly Ile Gly Glu
    210             215             220 aga gca gga aat gcc tca ttg gaa gag gtt gtt gct gct tta aaa ata         720
Arg Ala Gly Asn Ala Ser Leu Glu Glu Val Val Ala Ala Leu Lys Ile
225             230             235             240 ctc tat ggc tat gat act aag ata aag atg gaa aag tta tat gag gtt         768
Leu Tyr Gly Tyr Asp Thr Lys Ile Lys Met Glu Lys Leu Tyr Glu Val
                245             250             255 tca aga att gtc tca aga ttg atg aaa ctt cct gtt cca cca aat aaa         816
Ser Arg Ile Val Ser Arg Leu Met Lys Leu Pro Val Pro Pro Asn Lys
            260             265             270 gca att gtt ggg gac aat gca ttt gct cat gaa gca gga ata cat gtt         864
Ala Ile Val Gly Asp Asn Ala Phe Ala His Glu Ala Gly Ile His Val
        275             280             285 gat gga tta ata aaa aat act gaa acc tat gag cca ata aaa cca gaa         912
Asp Gly Leu Ile Lys Asn Thr Glu Thr Tyr Glu Pro Ile Lys Pro Glu
    290             295             300 atg gtt ggg aat aga aga aga att att ttg ggt aag cat tct ggt aga         960
Met Val Gly Asn Arg Arg Arg Ile Ile Leu Gly Lys His Ser Gly Arg
305             310             315             320 aaa gct tta aaa tac aaa ctt gat ttg atg ggc ata aac gtt agt gat        1008
Lys Ala Leu Lys Tyr Lys Leu Asp Leu Met Gly Ile Asn Val Ser Asp
                325             330             335 gag caa tta aat aaa ata tat gaa aga gtt aaa gaa ttt ggg gat ttg        1056
Glu Gln Leu Asn Lys Ile Tyr Glu Arg Val Lys Glu Phe Gly Asp Leu
            340             345             350 ggt aaa tac att tca gac gct gat ttg ttg gct ata gtt aga gaa gtt        1104
Gly Lys Tyr Ile Ser Asp Ala Asp Leu Leu Ala Ile Val Arg Glu Val
        355             360             365 act gga aaa ttg gta gaa gag aaa atc aaa tta gat gaa tta act gtt        1152
Thr Gly Lys Leu Val Glu Glu Lys Ile Lys Leu Asp Glu Leu Thr Val
    370             375             380 gta tct gga aat aaa ata aca cca att gca tct gtt aaa ctc cat tat        1200
Val Ser Gly Asn Lys Ile Thr Pro Ile Ala Ser Val Lys Leu His Tyr
385             390             395             400
```

-continued

| | | | | | | | | | | | | | | | | |
|---|---|---|---|---|---|---|---|---|---|---|---|---|---|---|---|---|
| aaa | gga | gaa | gat | ata | act | tta | ata | gaa | act | gct | tat | ggt | gtt | gga | ccg | 1248 |
| Lys | Gly | Glu | Asp | Ile | Thr | Leu | Ile | Glu | Thr | Ala | Tyr | Gly | Val | Gly | Pro | |
| | | | 405 | | | | | 410 | | | | | 415 | | | |
| gta | gat | gca | gca | ata | aat | gct | gtg | aga | aag | gca | ata | agt | gga | gtt | gca | 1296 |
| Val | Asp | Ala | Ala | Ile | Asn | Ala | Val | Arg | Lys | Ala | Ile | Ser | Gly | Val | Ala | |
| | | | 420 | | | | | 425 | | | | | 430 | | | |
| gat | att | aag | ttg | gta | gag | tat | aga | gtt | gaa | gca | att | ggt | gga | gga | act | 1344 |
| Asp | Ile | Lys | Leu | Val | Glu | Tyr | Arg | Val | Glu | Ala | Ile | Gly | Gly | Gly | Thr | |
| | | | 435 | | | | | 440 | | | | | 445 | | | |
| gat | gcg | tta | ata | gag | gtt | gtt | gtt | aaa | tta | aga | aaa | gga | act | gaa | att | 1392 |
| Asp | Ala | Leu | Ile | Glu | Val | Val | Val | Lys | Leu | Arg | Lys | Gly | Thr | Glu | Ile | |
| | | | 450 | | | | | 455 | | | | | 460 | | | |
| gtt | gaa | gtt | aga | aaa | tca | gac | gct | gat | ata | ata | agg | gct | tct | gta | gat | 1440 |
| Val | Glu | Val | Arg | Lys | Ser | Asp | Ala | Asp | Ile | Ile | Arg | Ala | Ser | Val | Asp | |
| | 465 | | | | | 470 | | | | | 475 | | | | 480 | |
| gct | gta | atg | gaa | gga | atc | aat | atg | tta | ttg | aat | taa | | | | | 1476 |
| Ala | Val | Met | Glu | Gly | Ile | Asn | Met | Leu | Leu | Asn | | | | | | |
| | | | 485 | | | | | 490 | | | | | | | | |

<210> SEQ ID NO 32
<211> LENGTH: 491
<212> TYPE: PRT
<213> ORGANISM: Methanococcus jannaschii

<400> SEQUENCE: 32

Met Met Val Arg Ile Phe Asp Thr Thr Leu Arg Asp Gly Glu Gln Thr
1               5                   10                  15

Pro Gly Val Ser Leu Thr Pro Asn Asp Lys Leu Glu Ile Ala Lys Lys
            20                  25                  30

Leu Asp Glu Leu Gly Val Asp Val Ile Glu Ala Gly Ser Ala Ile Thr
        35                  40                  45

Ser Lys Gly Glu Arg Glu Gly Ile Lys Leu Ile Thr Lys Glu Gly Leu
    50                  55                  60

Asn Ala Glu Ile Cys Ser Phe Val Arg Ala Leu Pro Val Asp Ile Asp
65                  70                  75                  80

Ala Ala Leu Glu Cys Asp Val Asp Ser Val His Leu Val Val Pro Thr
                85                  90                  95

Ser Pro Ile His Met Lys Tyr Lys Leu Arg Lys Thr Glu Asp Glu Val
            100                 105                 110

Leu Glu Thr Ala Leu Lys Ala Val Glu Tyr Ala Lys Glu His Gly Leu
        115                 120                 125

Ile Val Glu Leu Ser Ala Glu Asp Ala Thr Arg Ser Asp Val Asn Phe
    130                 135                 140

Leu Ile Lys Leu Phe Asn Glu Gly Glu Lys Val Gly Ala Asp Arg Val
145                 150                 155                 160

Cys Val Cys Asp Thr Val Gly Val Leu Thr Pro Gln Lys Ser Gln Glu
                165                 170                 175

Leu Phe Lys Lys Ile Thr Glu Asn Val Asn Leu Pro Val Ser Val His
            180                 185                 190

Cys His Asn Asp Phe Gly Met Ala Thr Ala Asn Thr Cys Ser Ala Val
        195                 200                 205

Leu Gly Gly Ala Val Gln Cys His Val Thr Val Asn Gly Ile Gly Glu
    210                 215                 220

Arg Ala Gly Asn Ala Ser Leu Glu Glu Val Val Ala Ala Leu Lys Ile
225                 230                 235                 240

Leu Tyr Gly Tyr Asp Thr Lys Ile Lys Met Glu Lys Leu Tyr Glu Val
                245                 250                 255

```
Ser Arg Ile Val Ser Arg Leu Met Lys Leu Pro Val Pro Asn Lys
            260                 265                 270

Ala Ile Val Gly Asp Asn Ala Phe Ala His Glu Ala Gly Ile His Val
        275                 280                 285

Asp Gly Leu Ile Lys Asn Thr Glu Thr Tyr Glu Pro Ile Lys Pro Glu
    290                 295                 300

Met Val Gly Asn Arg Arg Ile Ile Leu Gly Lys His Ser Gly Arg
305                 310                 315                 320

Lys Ala Leu Lys Tyr Lys Leu Asp Leu Met Gly Ile Asn Val Ser Asp
                325                 330                 335

Glu Gln Leu Asn Lys Ile Tyr Glu Arg Val Lys Glu Phe Gly Asp Leu
            340                 345                 350

Gly Lys Tyr Ile Ser Asp Ala Asp Leu Leu Ala Ile Val Arg Glu Val
        355                 360                 365

Thr Gly Lys Leu Val Glu Glu Lys Ile Lys Leu Asp Glu Leu Thr Val
    370                 375                 380

Val Ser Gly Asn Lys Ile Thr Pro Ile Ala Ser Val Lys Leu His Tyr
385                 390                 395                 400

Lys Gly Glu Asp Ile Thr Leu Ile Glu Thr Ala Tyr Gly Val Gly Pro
                405                 410                 415

Val Asp Ala Ala Ile Asn Ala Val Arg Lys Ala Ile Ser Gly Val Ala
            420                 425                 430

Asp Ile Lys Leu Val Glu Tyr Arg Val Glu Ala Ile Gly Gly Gly Thr
        435                 440                 445

Asp Ala Leu Ile Glu Val Val Lys Leu Arg Lys Gly Thr Glu Ile
    450                 455                 460

Val Glu Val Arg Lys Ser Asp Ala Asp Ile Ile Arg Ala Ser Val Asp
465                 470                 475                 480

Ala Val Met Glu Gly Ile Asn Met Leu Leu Asn
                485                 490

<210> SEQ ID NO 33
<211> LENGTH: 264
<212> TYPE: DNA
<213> ORGANISM: Escherichia coli
<220> FEATURE:
<221> NAME/KEY: CDS
<222> LOCATION: (1)..(264)

<400> SEQUENCE: 33 atg atg caa cat cag gtc aat gta tcg gct cgc ttc aat cca gaa acc    48
Met Met Gln His Gln Val Asn Val Ser Ala Arg Phe Asn Pro Glu Thr
1               5                   10                  15 tta gaa cgt gtt tta cgc gtg gtg cgt cat cgt ggt ttc cac gtc tgc    96
Leu Glu Arg Val Leu Arg Val Val Arg His Arg Gly Phe His Val Cys
            20                  25                  30 tca atg aat atg gcc gcc gcc agc gat gca caa aat ata aat atc gaa   144
Ser Met Asn Met Ala Ala Ala Ser Asp Ala Gln Asn Ile Asn Ile Glu
        35                  40                  45 ttg acc gtt gcc agc cca cgg tcg gtc gac tta ctg ttt agt cag tta   192
Leu Thr Val Ala Ser Pro Arg Ser Val Asp Leu Leu Phe Ser Gln Leu
    50                  55                  60 aat aaa ctg gtg gac gtc gca cac gtt gcc atc tgc cag agc aca acc   240
Asn Lys Leu Val Asp Val Ala His Val Ala Ile Cys Gln Ser Thr Thr
65                  70                  75                  80 aca tca caa caa atc cgc gcc tga                                   264
Thr Ser Gln Gln Ile Arg Ala
```

<210> SEQ ID NO 34
<211> LENGTH: 87
<212> TYPE: PRT
<213> ORGANISM: Escherichia coli

<400> SEQUENCE: 34

Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
            20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85

<210> SEQ ID NO 35
<211> LENGTH: 582
<212> TYPE: DNA
<213> ORGANISM: Escherichia coli
<220> FEATURE:
<221> NAME/KEY: CDS
<222> LOCATION: (1)..(582)

<400> SEQUENCE: 35 ttg ttg tta aaa caa ctg tcg gat cgt aaa cct gcg gat tgc gtc gtg     48
Leu Leu Leu Lys Gln Leu Ser Asp Arg Lys Pro Ala Asp Cys Val Val
1               5                   10                  15 acc aca gat gtg ggg cag cac cag atg tgg gct gcg cag cac atc gcc     96
Thr Thr Asp Val Gly Gln His Gln Met Trp Ala Ala Gln His Ile Ala
            20                  25                  30 cac act cgc ccg gaa aat ttc atc acc tcc agc ggt tta ggt acc atg    144
His Thr Arg Pro Glu Asn Phe Ile Thr Ser Ser Gly Leu Gly Thr Met
        35                  40                  45 ggt ttt ggt tta ccg gcg gcg gtt ggc gca caa gtc gcg cga ccg aac    192
Gly Phe Gly Leu Pro Ala Ala Val Gly Ala Gln Val Ala Arg Pro Asn
    50                  55                  60 gat acc gtt gtc tgt atc tcc ggt gac ggc tct ttc atg atg aat gtg    240
Asp Thr Val Val Cys Ile Ser Gly Asp Gly Ser Phe Met Met Asn Val
65                  70                  75                  80 caa gag ctg ggc acc gta aaa cgc aag cag tta ccg ttg aaa atc gtc    288
Gln Glu Leu Gly Thr Val Lys Arg Lys Gln Leu Pro Leu Lys Ile Val
                85                  90                  95 tta ctc gat aac caa cgg tta ggg atg gtt cga caa tgg cag caa ctg    336
Leu Leu Asp Asn Gln Arg Leu Gly Met Val Arg Gln Trp Gln Gln Leu
            100                 105                 110 ttt ttt cag gaa cga tac agc gaa acc acc ctt act gat aac ccc gat    384
Phe Phe Gln Glu Arg Tyr Ser Glu Thr Thr Leu Thr Asp Asn Pro Asp
        115                 120                 125 ttc ctc atg tta gcc agc gcc ttc ggc atc cat ggc caa cac atc acc    432
Phe Leu Met Leu Ala Ser Ala Phe Gly Ile His Gly Gln His Ile Thr
    130                 135                 140 cgg aaa gac cag gtt gaa gcg gca ctc gac acc atg ctg aac agt gat    480
Arg Lys Asp Gln Val Glu Ala Ala Leu Asp Thr Met Leu Asn Ser Asp
145                 150                 155                 160

```
ggg cca tac ctg ctt cat gtc tca atc gac gaa ctt gag aac gtc tgg    528
Gly Pro Tyr Leu Leu His Val Ser Ile Asp Glu Leu Glu Asn Val Trp
            165                 170                 175 ccg ctg gtg ccg cct ggc gcc agt aat tca gaa atg ttg gag aaa tta    576
Pro Leu Val Pro Pro Gly Ala Ser Asn Ser Glu Met Leu Glu Lys Leu
        180                 185                 190 tca tga                                                             582
Ser

<210> SEQ ID NO 36
<211> LENGTH: 193
<212> TYPE: PRT
<213> ORGANISM: Escherichia coli

<400> SEQUENCE: 36

Leu Leu Leu Lys Gln Leu Ser Asp Arg Lys Pro Ala Asp Cys Val Val
1               5                   10                  15

Thr Thr Asp Val Gly Gln His Gln Met Trp Ala Ala Gln His Ile Ala
            20                  25                  30

His Thr Arg Pro Glu Asn Phe Ile Thr Ser Ser Gly Leu Gly Thr Met
        35                  40                  45

Gly Phe Gly Leu Pro Ala Ala Val Gly Ala Gln Val Ala Arg Pro Asn
    50                  55                  60

Asp Thr Val Val Cys Ile Ser Gly Asp Gly Ser Phe Met Met Asn Val
65                  70                  75                  80

Gln Glu Leu Gly Thr Val Lys Arg Lys Gln Leu Pro Leu Lys Ile Val
                85                  90                  95

Leu Leu Asp Asn Gln Arg Leu Gly Met Val Arg Gln Trp Gln Gln Leu
            100                 105                 110

Phe Phe Gln Glu Arg Tyr Ser Glu Thr Thr Leu Thr Asp Asn Pro Asp
        115                 120                 125

Phe Leu Met Leu Ala Ser Ala Phe Gly Ile His Gly Gln His Ile Thr
    130                 135                 140

Arg Lys Asp Gln Val Glu Ala Ala Leu Asp Thr Met Leu Asn Ser Asp
145                 150                 155                 160

Gly Pro Tyr Leu Leu His Val Ser Ile Asp Glu Leu Glu Asn Val Trp
                165                 170                 175

Pro Leu Val Pro Pro Gly Ala Ser Asn Ser Glu Met Leu Glu Lys Leu
            180                 185                 190

Ser

<210> SEQ ID NO 37
<211> LENGTH: 291
<212> TYPE: DNA
<213> ORGANISM: Escherichia coli
<220> FEATURE:
<221> NAME/KEY: CDS
<222> LOCATION: (1)..(291)

<400> SEQUENCE: 37 atg caa aac aca act cat gac aac gta att ctg gag ctc acc gtt cgc     48
Met Gln Asn Thr Thr His Asp Asn Val Ile Leu Glu Leu Thr Val Arg
1               5                   10                  15 aac cat ccg ggc gta atg acc cac gtt tgt ggc ctt ttt gcc cgc cgc     96
Asn His Pro Gly Val Met Thr His Val Cys Gly Leu Phe Ala Arg Arg
            20                  25                  30 gct ttt aac gtt gaa ggc att ctt tgt ctg ccg att cag gac agc gac    144
Ala Phe Asn Val Glu Gly Ile Leu Cys Leu Pro Ile Gln Asp Ser Asp
        35                  40                  45
```

```
aaa agc cat atc tgg cta ctg gtc aat gac gac cag cgt ctg gag cag        192
Lys Ser His Ile Trp Leu Leu Val Asn Asp Asp Gln Arg Leu Glu Gln
 50                  55                  60 atg ata agc caa atc gat aag ctg gaa gat gtc gtg aaa gtg cag cgt        240
Met Ile Ser Gln Ile Asp Lys Leu Glu Asp Val Val Lys Val Gln Arg
 65                  70                  75                  80 aat cag tcc gat ccg acg atg ttt aac aag atc gcg gtg ttt ttt cag        288
Asn Gln Ser Asp Pro Thr Met Phe Asn Lys Ile Ala Val Phe Phe Gln
                 85                  90                  95 taa                                                                    291

<210> SEQ ID NO 38
<211> LENGTH: 96
<212> TYPE: PRT
<213> ORGANISM: Escherichia coli

<400> SEQUENCE: 38

Met Gln Asn Thr Thr His Asp Asn Val Ile Leu Glu Leu Thr Val Arg
 1               5                  10                  15

Asn His Pro Gly Val Met Thr His Val Cys Gly Leu Phe Ala Arg Arg
                20                  25                  30

Ala Phe Asn Val Glu Gly Ile Leu Cys Leu Pro Ile Gln Asp Ser Asp
             35                  40                  45

Lys Ser His Ile Trp Leu Leu Val Asn Asp Asp Gln Arg Leu Glu Gln
 50                  55                  60

Met Ile Ser Gln Ile Asp Lys Leu Glu Asp Val Val Lys Val Gln Arg
 65                  70                  75                  80

Asn Gln Ser Asp Pro Thr Met Phe Asn Lys Ile Ala Val Phe Phe Gln
                 85                  90                  95

<210> SEQ ID NO 39
<211> LENGTH: 1689
<212> TYPE: DNA
<213> ORGANISM: Escherichia coli
<220> FEATURE:
<221> NAME/KEY: CDS
<222> LOCATION: (1)..(1689)

<400> SEQUENCE: 39 atg gca agt tcg ggc aca aca tcg acg cgt aag cgc ttt acc ggc gca         48
Met Ala Ser Ser Gly Thr Thr Ser Thr Arg Lys Arg Phe Thr Gly Ala
 1               5                  10                  15 gaa ttt atc gtt cat ttc ctg gaa cag cag ggc att aag att gtg aca         96
Glu Phe Ile Val His Phe Leu Glu Gln Gln Gly Ile Lys Ile Val Thr
                20                  25                  30 ggc att ccg ggc ggt tct atc ctg cct gtt tac gat gcc tta agc caa        144
Gly Ile Pro Gly Gly Ser Ile Leu Pro Val Tyr Asp Ala Leu Ser Gln
             35                  40                  45 agc acg caa atc cgc cat att ctg gcc cgt cat gaa cag ggc gcg ggc        192
Ser Thr Gln Ile Arg His Ile Leu Ala Arg His Glu Gln Gly Ala Gly
 50                  55                  60 ttt atc gct cag gga atg gcg cgc acc gac ggt aaa ccg gcg gtc tgt        240
Phe Ile Ala Gln Gly Met Ala Arg Thr Asp Gly Lys Pro Ala Val Cys
 65                  70                  75                  80 atg gcc tgt agc gga ccg ggt gcg act aac ctg gtg acc gcc att gcc        288
Met Ala Cys Ser Gly Pro Gly Ala Thr Asn Leu Val Thr Ala Ile Ala
                 85                  90                  95 gat gcg cgg ctg gac tcc atc ccg ctg att tgc atc act ggt cag gtt        336
Asp Ala Arg Leu Asp Ser Ile Pro Leu Ile Cys Ile Thr Gly Gln Val
                100                 105                 110
```

```
ccc gcc tcg atg atc ggc acc gac gcc ttc cag gaa gtg gac acc tac    384
Pro Ala Ser Met Ile Gly Thr Asp Ala Phe Gln Glu Val Asp Thr Tyr
        115                 120                 125 ggc atc tct atc ccc atc acc aaa cac aac tat ctg gtc aga cat atc    432
Gly Ile Ser Ile Pro Ile Thr Lys His Asn Tyr Leu Val Arg His Ile
130                 135                 140 gaa gaa ctc ccg cag gtc atg agc gat gcc ttc cgc att gcg caa tca    480
Glu Glu Leu Pro Gln Val Met Ser Asp Ala Phe Arg Ile Ala Gln Ser
145                 150                 155                 160 ggc cgc cca ggc ccg gtg tgg ata gac att cct aag gat gtg caa acg    528
Gly Arg Pro Gly Pro Val Trp Ile Asp Ile Pro Lys Asp Val Gln Thr
                165                 170                 175 gca gtt ttt gag att gaa aca cag ccc gct atg gca gaa aaa gcc gcc    576
Ala Val Phe Glu Ile Glu Thr Gln Pro Ala Met Ala Glu Lys Ala Ala
            180                 185                 190 gcc ccc gcc ttt agc gaa gaa agc att cgt gac gca gcg gcg atg att    624
Ala Pro Ala Phe Ser Glu Glu Ser Ile Arg Asp Ala Ala Ala Met Ile
        195                 200                 205 aac gct gcc aaa cgc ccg gtg ctt tat ctg ggc ggc ggt gtg atc aat    672
Asn Ala Ala Lys Arg Pro Val Leu Tyr Leu Gly Gly Gly Val Ile Asn
210                 215                 220 gcg ccc gca cgg gtg cgt gaa ctg gcg gag aaa gcg caa ctg cct acc    720
Ala Pro Ala Arg Val Arg Glu Leu Ala Glu Lys Ala Gln Leu Pro Thr
225                 230                 235                 240 acc atg act tta atg gcg ctg ggc atg ttg cca aaa gcg cat ccg ttg    768
Thr Met Thr Leu Met Ala Leu Gly Met Leu Pro Lys Ala His Pro Leu
                245                 250                 255 tcg ctg ggt atg ctg ggg atg cac ggc gtg cgc agc acc aac tat att    816
Ser Leu Gly Met Leu Gly Met His Gly Val Arg Ser Thr Asn Tyr Ile
            260                 265                 270 ttg cag gag gcg gat ttg ttg ata gtg ctc ggt gcg cgt ttt gat gac    864
Leu Gln Glu Ala Asp Leu Leu Ile Val Leu Gly Ala Arg Phe Asp Asp
        275                 280                 285 cgg gcg att ggc aaa acc gag cag ttc tgt ccg aat gcc aaa atc att    912
Arg Ala Ile Gly Lys Thr Glu Gln Phe Cys Pro Asn Ala Lys Ile Ile
290                 295                 300 cat gtc gat atc gac cgt gca gag ctg ggt aaa atc aag cag ccg cac    960
His Val Asp Ile Asp Arg Ala Glu Leu Gly Lys Ile Lys Gln Pro His
305                 310                 315                 320 gtg gcg att cag gcg gat gtt gat gac gtg ctg gcg cag ttg atc ccg   1008
Val Ala Ile Gln Ala Asp Val Asp Asp Val Leu Ala Gln Leu Ile Pro
                325                 330                 335 ctg gtg gaa gcg caa ccg cgt gca gag tgg cac cag ttg gta gcg gat   1056
Leu Val Glu Ala Gln Pro Arg Ala Glu Trp His Gln Leu Val Ala Asp
            340                 345                 350 ttg cag cgt gag ttt ccg tgt cca atc ccg aaa gcg tgc gat ccg tta   1104
Leu Gln Arg Glu Phe Pro Cys Pro Ile Pro Lys Ala Cys Asp Pro Leu
        355                 360                 365 agc cat tac ggc ctg atc aac gcc gtt gcc gcc tgt gtc gat gac aat   1152
Ser His Tyr Gly Leu Ile Asn Ala Val Ala Ala Cys Val Asp Asp Asn
370                 375                 380 gca att atc acc acc gac gtt ggt cag cat cag atg tgg acc gcg caa   1200
Ala Ile Ile Thr Thr Asp Val Gly Gln His Gln Met Trp Thr Ala Gln
385                 390                 395                 400 gct tat ccg ctc aat cgc cca cgc cag tgg ctg acc tcc ggt ggg ctg   1248
Ala Tyr Pro Leu Asn Arg Pro Arg Gln Trp Leu Thr Ser Gly Gly Leu
                405                 410                 415 ggc acg atg ggt ttt ggc ctg cct gcg gcg att ggc gct gcg ctg gcg   1296
Gly Thr Met Gly Phe Gly Leu Pro Ala Ala Ile Gly Ala Ala Leu Ala
```

```
                    420              425              430
aac ccg gat cgc aaa gtg ttg tgt ttc tcc ggc gac ggc agc ctg atg       1344
Asn Pro Asp Arg Lys Val Leu Cys Phe Ser Gly Asp Gly Ser Leu Met
            435                 440                 445 atg aat att cag gag atg gcg acc gcc agt gaa aat cag ctg gat gtc       1392
Met Asn Ile Gln Glu Met Ala Thr Ala Ser Glu Asn Gln Leu Asp Val
    450                 455                 460 aaa atc att ctg atg aac aac gaa gcg ctg ggg ctg gtg cat cag caa       1440
Lys Ile Ile Leu Met Asn Asn Glu Ala Leu Gly Leu Val His Gln Gln
465                 470                 475                 480 cag agt ctg ttc tac gag caa ggc gtt ttt gcc gcc acc tat ccg ggc       1488
Gln Ser Leu Phe Tyr Glu Gln Gly Val Phe Ala Ala Thr Tyr Pro Gly
                485                 490                 495 aaa atc aac ttt atg cag att gcc gcc gga ttc ggc ctc gaa acc tgt       1536
Lys Ile Asn Phe Met Gln Ile Ala Ala Gly Phe Gly Leu Glu Thr Cys
            500                 505                 510 gat ttg aat aac gaa gcc gat ccg cag gct tca ttg cag gaa atc atc       1584
Asp Leu Asn Asn Glu Ala Asp Pro Gln Ala Ser Leu Gln Glu Ile Ile
    515                 520                 525 aat cgc cct ggc ccg gcg ctg atc cat gtg cgc att gat gcc gaa gaa       1632
Asn Arg Pro Gly Pro Ala Leu Ile His Val Arg Ile Asp Ala Glu Glu
530                 535                 540 aaa gtt tac ccg atg gtg ccg cca ggt gcg gcg aat act gaa atg gtg       1680
Lys Val Tyr Pro Met Val Pro Pro Gly Ala Ala Asn Thr Glu Met Val
545                 550                 555                 560 ggg gaa taa                                                           1689
Gly Glu <210> SEQ ID NO 40
<211> LENGTH: 562
<212> TYPE: PRT
<213> ORGANISM: Escherichia coli

<400> SEQUENCE: 40

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
            20                  25                  30

Gly Ile Pro Gly Gly Ser Ile Leu Pro Val Tyr Asp Ala Leu Ser Gln
        35                  40                  45

Ser Thr Gln Ile Arg His Ile Leu Ala Arg His Glu Gln Gly Ala Gly
    50                  55                  60

Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
```

```
            180                 185                 190
Ala Pro Ala Phe Ser Glu Glu Ser Ile Arg Asp Ala Ala Met Ile
            195                 200                 205

Asn Ala Ala Lys Arg Pro Val Leu Tyr Leu Gly Gly Val Ile Asn
            210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
            245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
            275                 280                 285

Arg Ala Ile Gly Lys Thr Glu Gln Phe Cys Pro Asn Ala Lys Ile Ile
            290                 295                 300

His Val Asp Ile Asp Arg Ala Glu Leu Gly Lys Ile Lys Gln Pro His
305                 310                 315                 320

Val Ala Ile Gln Ala Asp Val Asp Asp Val Leu Ala Gln Leu Ile Pro
            325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
            355                 360                 365

Ser His Tyr Gly Leu Ile Asn Ala Val Ala Ala Cys Val Asp Asp Asn
            370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
            405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
            435                 440                 445

Met Asn Ile Gln Glu Met Ala Thr Ala Ser Glu Asn Gln Leu Asp Val
            450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
            485                 490                 495

Lys Ile Asn Phe Met Gln Ile Ala Ala Gly Phe Gly Leu Glu Thr Cys
            500                 505                 510

Asp Leu Asn Asn Glu Ala Asp Pro Gln Ala Ser Leu Gln Glu Ile Ile
            515                 520                 525

Asn Arg Pro Gly Pro Ala Leu Ile His Val Arg Ile Asp Ala Glu Glu
            530                 535                 540

Lys Val Tyr Pro Met Val Pro Pro Gly Ala Ala Asn Thr Glu Met Val
545                 550                 555                 560

Gly Glu

<210> SEQ ID NO 41
<211> LENGTH: 2577
<212> TYPE: DNA
<213> ORGANISM: Clostridium acetobutylicum
<220> FEATURE:
```

-continued

<221> NAME/KEY: CDS
<222> LOCATION: (1)..(2577)

<400> SEQUENCE: 41

```
atg aaa gtt aca aat caa aaa gaa cta aaa caa aag cta aat gaa ttg      48
Met Lys Val Thr Asn Gln Lys Glu Leu Lys Gln Lys Leu Asn Glu Leu
1               5                   10                  15 aga gaa gcg caa aag aag ttt gca acc tat act caa gag caa gtt gat      96
Arg Glu Ala Gln Lys Lys Phe Ala Thr Tyr Thr Gln Glu Gln Val Asp
                20                  25                  30 aaa att ttt aaa caa tgt gcc ata gcc gca gct aaa gaa aga ata aac     144
Lys Ile Phe Lys Gln Cys Ala Ile Ala Ala Ala Lys Glu Arg Ile Asn
        35                  40                  45 tta gct aaa tta gca gta gaa gaa aca gga ata ggt ctt gta gaa gat     192
Leu Ala Lys Leu Ala Val Glu Glu Thr Gly Ile Gly Leu Val Glu Asp
    50                  55                  60 aaa att ata aaa aat cat ttt gca gca gaa tat ata tac aat aaa tat     240
Lys Ile Ile Lys Asn His Phe Ala Ala Glu Tyr Ile Tyr Asn Lys Tyr
65                  70                  75                  80 aaa aat gaa aaa act tgt ggc ata ata gac cat gac gat tct tta ggc     288
Lys Asn Glu Lys Thr Cys Gly Ile Ile Asp His Asp Asp Ser Leu Gly
                85                  90                  95 ata aca aag gtt gct gaa cca att gga att gtt gca gcc ata gtt cct     336
Ile Thr Lys Val Ala Glu Pro Ile Gly Ile Val Ala Ala Ile Val Pro
                100                 105                 110 act act aat cca act tcc aca gca att ttc aaa tca tta att tct tta     384
Thr Thr Asn Pro Thr Ser Thr Ala Ile Phe Lys Ser Leu Ile Ser Leu
        115                 120                 125 aaa aca aga aac gca ata ttc ttt tca cca cat cca cgt gca aaa aaa     432
Lys Thr Arg Asn Ala Ile Phe Phe Ser Pro His Pro Arg Ala Lys Lys
    130                 135                 140 tct aca att gct gca gca aaa tta att tta gat gca gct gtt aaa gca     480
Ser Thr Ile Ala Ala Ala Lys Leu Ile Leu Asp Ala Ala Val Lys Ala
145                 150                 155                 160 gga gca cct aaa aat ata ata ggc tgg ata gat gag cca tca ata gaa     528
Gly Ala Pro Lys Asn Ile Ile Gly Trp Ile Asp Glu Pro Ser Ile Glu
                165                 170                 175 ctt tct caa gat ttg atg agt gaa gct gat ata ata tta gca aca gga     576
Leu Ser Gln Asp Leu Met Ser Glu Ala Asp Ile Ile Leu Ala Thr Gly
                180                 185                 190 ggt cct tca atg gtt aaa gcg gcc tat tca tct gga aaa cct gca att     624
Gly Pro Ser Met Val Lys Ala Ala Tyr Ser Ser Gly Lys Pro Ala Ile
        195                 200                 205 ggt gtt gga gca gga aat aca cca gca ata ata gat gag agt gca gat     672
Gly Val Gly Ala Gly Asn Thr Pro Ala Ile Ile Asp Glu Ser Ala Asp
    210                 215                 220 ata gat atg gca gta agc tcc ata att tta tca aag act tat gac aat     720
Ile Asp Met Ala Val Ser Ser Ile Ile Leu Ser Lys Thr Tyr Asp Asn
225                 230                 235                 240 gga gta ata tgc gct tct gaa caa tca ata tta gtt atg aat tca ata     768
Gly Val Ile Cys Ala Ser Glu Gln Ser Ile Leu Val Met Asn Ser Ile
                245                 250                 255 tac gaa aaa gtt aaa gag gaa ttt gta aaa cga gga tca tat ata ctc     816
Tyr Glu Lys Val Lys Glu Glu Phe Val Lys Arg Gly Ser Tyr Ile Leu
                260                 265                 270 aat caa aat gaa ata gct aaa ata aaa gaa act atg ttt aaa aat gga     864
Asn Gln Asn Glu Ile Ala Lys Ile Lys Glu Thr Met Phe Lys Asn Gly
        275                 280                 285 gct att aat gct gac ata gtt gga aaa tct gct tat ata att gct aaa     912
Ala Ile Asn Ala Asp Ile Val Gly Lys Ser Ala Tyr Ile Ile Ala Lys
```

```
            290                 295                 300
atg gca gga att gaa gtt cct caa act aca aag ata ctt ata ggc gaa    960
Met Ala Gly Ile Glu Val Pro Gln Thr Thr Lys Ile Leu Ile Gly Glu
305                 310                 315                 320 gta caa tct gtt gaa aaa agc gag ctg ttc tca cat gaa aaa cta tca   1008
Val Gln Ser Val Glu Lys Ser Glu Leu Phe Ser His Glu Lys Leu Ser
                325                 330                 335 cca gta ctt gca atg tat aaa gtt aag gat ttt gat gaa gct cta aaa   1056
Pro Val Leu Ala Met Tyr Lys Val Lys Asp Phe Asp Glu Ala Leu Lys
            340                 345                 350 aag gca caa agg cta ata gaa tta ggt gga agt gga cac acg tca tct   1104
Lys Ala Gln Arg Leu Ile Glu Leu Gly Gly Ser Gly His Thr Ser Ser
        355                 360                 365 tta tat ata gat tca caa aac aat aag gat aaa gtt aaa gaa ttt gga   1152
Leu Tyr Ile Asp Ser Gln Asn Asn Lys Asp Lys Val Lys Glu Phe Gly
370                 375                 380 tta gca atg aaa act tca agg aca ttt att aac atg cct tct tca cag   1200
Leu Ala Met Lys Thr Ser Arg Thr Phe Ile Asn Met Pro Ser Ser Gln
385                 390                 395                 400 gga gca agc gga gat tta tac aat ttt gcg ata gca cca tca ttt act   1248
Gly Ala Ser Gly Asp Leu Tyr Asn Phe Ala Ile Ala Pro Ser Phe Thr
                405                 410                 415 ctt gga tgc ggc act tgg gga gga aac tct gta tcg caa aat gta gag   1296
Leu Gly Cys Gly Thr Trp Gly Gly Asn Ser Val Ser Gln Asn Val Glu
            420                 425                 430 cct aaa cat tta tta aat att aaa agt gtt gct gaa aga agg gaa aat   1344
Pro Lys His Leu Leu Asn Ile Lys Ser Val Ala Glu Arg Arg Glu Asn
        435                 440                 445 atg ctt tgg ttt aaa gtg cca caa aaa ata tat ttt aaa tat gga tgt   1392
Met Leu Trp Phe Lys Val Pro Gln Lys Ile Tyr Phe Lys Tyr Gly Cys
450                 455                 460 ctt aga ttt gca tta aaa gaa tta aaa gat atg aat aag aaa aga gcc   1440
Leu Arg Phe Ala Leu Lys Glu Leu Lys Asp Met Asn Lys Lys Arg Ala
465                 470                 475                 480 ttt ata gta aca gat aaa gat ctt ttt aaa ctt gga tat gtt aat aaa   1488
Phe Ile Val Thr Asp Lys Asp Leu Phe Lys Leu Gly Tyr Val Asn Lys
                485                 490                 495 ata aca aag gta cta gat gag ata gat att aaa tac agt ata ttt aca   1536
Ile Thr Lys Val Leu Asp Glu Ile Asp Ile Lys Tyr Ser Ile Phe Thr
            500                 505                 510 gat att aaa tct gat cca act att gat tca gta aaa aaa ggt gct aaa   1584
Asp Ile Lys Ser Asp Pro Thr Ile Asp Ser Val Lys Lys Gly Ala Lys
        515                 520                 525 gaa atg ctt aac ttt gaa cct gat act ata atc tct att ggt ggt gga   1632
Glu Met Leu Asn Phe Glu Pro Asp Thr Ile Ile Ser Ile Gly Gly Gly
530                 535                 540 tcg cca atg gat gca gca aag gtt atg cac ttg tta tat gaa tat cca   1680
Ser Pro Met Asp Ala Ala Lys Val Met His Leu Leu Tyr Glu Tyr Pro
545                 550                 555                 560 gaa gca gaa att gaa aat cta gct ata aac ttt atg gat ata aga aag   1728
Glu Ala Glu Ile Glu Asn Leu Ala Ile Asn Phe Met Asp Ile Arg Lys
                565                 570                 575 aga ata tgc aat ttc cct aaa tta ggt aca aag gcg att tca gta gct   1776
Arg Ile Cys Asn Phe Pro Lys Leu Gly Thr Lys Ala Ile Ser Val Ala
            580                 585                 590 att cct aca act gct ggt acc ggt tca gag gca aca cct ttt gca gtt   1824
Ile Pro Thr Thr Ala Gly Thr Gly Ser Glu Ala Thr Pro Phe Ala Val
        595                 600                 605 ata act aat gat gaa aca gga atg aaa tac cct tta act tct tat gaa   1872
Ile Thr Asn Asp Glu Thr Gly Met Lys Tyr Pro Leu Thr Ser Tyr Glu
```

```
Ile Thr Asn Asp Glu Thr Gly Met Lys Tyr Pro Leu Thr Ser Tyr Glu
610                 615                 620 ttg acc cca aac atg gca ata ata gat act gaa tta atg tta aat atg      1920
Leu Thr Pro Asn Met Ala Ile Ile Asp Thr Glu Leu Met Leu Asn Met
625                 630                 635                 640 cct aga aaa tta aca gca gca act gga ata gat gca tta gtt cat gct      1968
Pro Arg Lys Leu Thr Ala Ala Thr Gly Ile Asp Ala Leu Val His Ala
            645                 650                 655 ata gaa gca tat gtt tcg gtt atg gct acg gat tat act gat gaa tta      2016
Ile Glu Ala Tyr Val Ser Val Met Ala Thr Asp Tyr Thr Asp Glu Leu
            660                 665                 670 gcc tta aga gca ata aaa atg ata ttt aaa tat ttg cct aga gcc tat      2064
Ala Leu Arg Ala Ile Lys Met Ile Phe Lys Tyr Leu Pro Arg Ala Tyr
            675                 680                 685 aaa aat ggg act aac gac att gaa gca aga gaa aaa atg gca cat gcc      2112
Lys Asn Gly Thr Asn Asp Ile Glu Ala Arg Glu Lys Met Ala His Ala
690                 695                 700 tct aat att gcg ggg atg gca ttt gca aat gct ttc tta ggt gta tgc      2160
Ser Asn Ile Ala Gly Met Ala Phe Ala Asn Ala Phe Leu Gly Val Cys
705                 710                 715                 720 cat tca atg gct cat aaa ctt ggg gca atg cat cac gtt cca cat gga      2208
His Ser Met Ala His Lys Leu Gly Ala Met His His Val Pro His Gly
                725                 730                 735 att gct tgt gct gta tta ata gaa gaa gtt att aaa tat aac gct aca      2256
Ile Ala Cys Ala Val Leu Ile Glu Glu Val Ile Lys Tyr Asn Ala Thr
            740                 745                 750 gac tgt cca aca aag caa aca gca ttc cct caa tat aaa tct cct aat      2304
Asp Cys Pro Thr Lys Gln Thr Ala Phe Pro Gln Tyr Lys Ser Pro Asn
            755                 760                 765 gct aag aga aaa tat gct gaa att gca gag tat ttg aat tta aag ggt      2352
Ala Lys Arg Lys Tyr Ala Glu Ile Ala Glu Tyr Leu Asn Leu Lys Gly
770                 775                 780 act agc gat acc gaa aag gta aca gcc tta ata gaa gct att tca aag      2400
Thr Ser Asp Thr Glu Lys Val Thr Ala Leu Ile Glu Ala Ile Ser Lys
785                 790                 795                 800 tta aag ata gat ttg agt att cca caa aat ata agt gcc gct gga ata      2448
Leu Lys Ile Asp Leu Ser Ile Pro Gln Asn Ile Ser Ala Ala Gly Ile
                805                 810                 815 aat aaa aaa gat ttt tat aat acg cta gat aaa atg tca gag ctt gct      2496
Asn Lys Lys Asp Phe Tyr Asn Thr Leu Asp Lys Met Ser Glu Leu Ala
            820                 825                 830 ttt gat gac caa tgt aca aca gct aat cct agg tat cca ctt ata agt      2544
Phe Asp Asp Gln Cys Thr Thr Ala Asn Pro Arg Tyr Pro Leu Ile Ser
            835                 840                 845 gaa ctt aag gat atc tat ata aaa tca ttt taa                          2577
Glu Leu Lys Asp Ile Tyr Ile Lys Ser Phe
            850                 855

<210> SEQ ID NO 42
<211> LENGTH: 858
<212> TYPE: PRT
<213> ORGANISM: Clostridium acetobutylicum

<400> SEQUENCE: 42

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
                20                  25                  30

Lys Ile Phe Lys Gln Cys Ala Ile Ala Ala Ala Lys Glu Arg Ile Asn
        35                  40                  45
```

```
Leu Ala Lys Leu Ala Val Glu Glu Thr Gly Ile Gly Leu Val Glu Asp
        50                  55                  60

Lys Ile Ile Lys Asn His Phe Ala Ala Glu Tyr Ile Tyr Asn Lys Tyr
 65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
    130                 135                 140

Ser Thr Ile Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
450                 455                 460
```

-continued

```
Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
            485                 490                 495

Ile Thr Lys Val Leu Asp Glu Ile Asp Ile Lys Tyr Ser Ile Phe Thr
        500                 505                 510

Asp Ile Lys Ser Asp Pro Thr Ile Asp Ser Val Lys Lys Gly Ala Lys
    515                 520                 525

Glu Met Leu Asn Phe Glu Pro Asp Thr Ile Ile Ser Ile Gly Gly Gly
530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
                725                 730                 735

Ile Ala Cys Ala Val Leu Ile Glu Glu Val Ile Lys Tyr Asn Ala Thr
            740                 745                 750

Asp Cys Pro Thr Lys Gln Thr Ala Phe Pro Gln Tyr Lys Ser Pro Asn
        755                 760                 765

Ala Lys Arg Lys Tyr Ala Glu Ile Ala Glu Tyr Leu Asn Leu Lys Gly
    770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                805                 810                 815

Asn Lys Lys Asp Phe Tyr Asn Thr Leu Asp Lys Met Ser Glu Leu Ala
            820                 825                 830

Phe Asp Asp Gln Cys Thr Thr Ala Asn Pro Arg Tyr Pro Leu Ile Ser
        835                 840                 845

Glu Leu Lys Asp Ile Tyr Ile Lys Ser Phe
    850                 855

<210> SEQ ID NO 43
<211> LENGTH: 1551
<212> TYPE: DNA
```

<213> ORGANISM: Leptospira interrogans
<220> FEATURE:
<221> NAME/KEY: CDS
<222> LOCATION: (1)..(1551)

<400> SEQUENCE: 43

```
atg aca aaa gta gaa act cga ttg gaa att tta gac gta act ttg aga        48
Met Thr Lys Val Glu Thr Arg Leu Glu Ile Leu Asp Val Thr Leu Arg
1               5                  10                  15 gac ggg gag cag acc aga ggg gtc agt ttt tcc act tcc gaa aaa cta        96
Asp Gly Glu Gln Thr Arg Gly Val Ser Phe Ser Thr Ser Glu Lys Leu
            20                  25                  30 aat atc gca aaa ttt cta tta caa aaa cta aat gta gat cgg gta gag       144
Asn Ile Ala Lys Phe Leu Leu Gln Lys Leu Asn Val Asp Arg Val Glu
        35                  40                  45 att gcg tct gca aga gtt tct aaa ggg gaa ttg gaa acg gtc caa aaa       192
Ile Ala Ser Ala Arg Val Ser Lys Gly Glu Leu Glu Thr Val Gln Lys
    50                  55                  60 atc atg gaa tgg gct gca aca gaa cag ctt acg gaa aga atc gaa atc       240
Ile Met Glu Trp Ala Ala Thr Glu Gln Leu Thr Glu Arg Ile Glu Ile
65                  70                  75                  80 tta ggt ttt gta gac ggg aat aaa acc gta gat tgg atc aaa gat agt       288
Leu Gly Phe Val Asp Gly Asn Lys Thr Val Asp Trp Ile Lys Asp Ser
                85                  90                  95 ggg gct aag gtt tta aat ctt ttg act aag gga tcg ctt cat cat tta       336
Gly Ala Lys Val Leu Asn Leu Leu Thr Lys Gly Ser Leu His His Leu
            100                 105                 110 gaa aaa caa tta ggc aaa act ccg aaa gaa ttc ttt aca gac gtt tct       384
Glu Lys Gln Leu Gly Lys Thr Pro Lys Glu Phe Phe Thr Asp Val Ser
        115                 120                 125 ttt gta ata gaa tac gcg atc aaa agc gga ctt aaa ata aac gta tat       432
Phe Val Ile Glu Tyr Ala Ile Lys Ser Gly Leu Lys Ile Asn Val Tyr
    130                 135                 140 tta gaa gat tgg tcc aac ggt ttc aga aac agt cca gat tac gtc aaa       480
Leu Glu Asp Trp Ser Asn Gly Phe Arg Asn Ser Pro Asp Tyr Val Lys
145                 150                 155                 160 tcg ctc gta gaa cat cta agt aaa gaa cat ata gaa aga att ttt ctt       528
Ser Leu Val Glu His Leu Ser Lys Glu His Ile Glu Arg Ile Phe Leu
                165                 170                 175 cca gac acg tta ggc gtt ctt tcg cca gaa gag acg ttt caa gga gtg       576
Pro Asp Thr Leu Gly Val Leu Ser Pro Glu Glu Thr Phe Gln Gly Val
            180                 185                 190 gat tca ctc att caa aaa tac ccg gat att cat ttt gaa ttt cac gga       624
Asp Ser Leu Ile Gln Lys Tyr Pro Asp Ile His Phe Glu Phe His Gly
        195                 200                 205 cat aac gac tac gat ctt tcc gtg gca aat agt ctt caa gcg att cgt       672
His Asn Asp Tyr Asp Leu Ser Val Ala Asn Ser Leu Gln Ala Ile Arg
    210                 215                 220 gcc gga gtc aaa ggt ctt cac gct tct ata aat ggt ctc gga gaa aga       720
Ala Gly Val Lys Gly Leu His Ala Ser Ile Asn Gly Leu Gly Glu Arg
225                 230                 235                 240 gcc gga aat act ccg ttg gaa gca ctc gta acc acg att cat gat aag       768
Ala Gly Asn Thr Pro Leu Glu Ala Leu Val Thr Thr Ile His Asp Lys
                245                 250                 255 tct aac tct aaa acg aac ata aac gaa att gca att acg gaa gca agc       816
Ser Asn Ser Lys Thr Asn Ile Asn Glu Ile Ala Ile Thr Glu Ala Ser
            260                 265                 270 cgt ctt gta gaa gta ttc agc gga aaa aga att tct gca aat aga ccg       864
Arg Leu Val Glu Val Phe Ser Gly Lys Arg Ile Ser Ala Asn Arg Pro
        275                 280                 285
```

| | | | | | | | | | | | | | | | |
|---|---|---|---|---|---|---|---|---|---|---|---|---|---|---|---|
| atc | gta | gga | gaa | gac | gtg | ttt | act | cag | acc | gcg | gga | gta | cac | gca | gac | 912 |
| Ile | Val | Gly | Glu | Asp | Val | Phe | Thr | Gln | Thr | Ala | Gly | Val | His | Ala | Asp | |
| | | 290 | | | | | 295 | | | | | 300 | | | | | atc gta gga gaa gac gtg ttt act cag acc gcg gga gta cac gca gac    912
Ile Val Gly Glu Asp Val Phe Thr Gln Thr Ala Gly Val His Ala Asp
        290                 295                 300 gga gac aaa aaa gga aat tta tac gca aat cct att tta ccg gaa aga    960
Gly Asp Lys Lys Gly Asn Leu Tyr Ala Asn Pro Ile Leu Pro Glu Arg
305                 310                 315                 320 ttt ggt agg aaa aga agt tac gcg tta ggc aaa ctt gca ggt aag gcg    1008
Phe Gly Arg Lys Arg Ser Tyr Ala Leu Gly Lys Leu Ala Gly Lys Ala
                325                 330                 335 agt atc tcc gaa aat gta aaa caa ctc gga atg gtt tta agt gaa gtg    1056
Ser Ile Ser Glu Asn Val Lys Gln Leu Gly Met Val Leu Ser Glu Val
            340                 345                 350 gtt tta caa aag gtt tta gaa agg gtg atc gaa tta gga gat cag aat    1104
Val Leu Gln Lys Val Leu Glu Arg Val Ile Glu Leu Gly Asp Gln Asn
        355                 360                 365 aaa cta gtg aca cct gaa gat ctt cca ttt atc att gcg gac gtt tct    1152
Lys Leu Val Thr Pro Glu Asp Leu Pro Phe Ile Ile Ala Asp Val Ser
370                 375                 380 gga aga acc gga gaa aag gta ctt aca atc aaa tct tgt aat att cat    1200
Gly Arg Thr Gly Glu Lys Val Leu Thr Ile Lys Ser Cys Asn Ile His
385                 390                 395                 400 tcc gga att gga att cgt cct cac gca caa att gaa ttg gaa tat cag    1248
Ser Gly Ile Gly Ile Arg Pro His Ala Gln Ile Glu Leu Glu Tyr Gln
                405                 410                 415 gga aag att cat aag gaa att tct gaa gga gac gga ggg tat gat gcg    1296
Gly Lys Ile His Lys Glu Ile Ser Glu Gly Asp Gly Gly Tyr Asp Ala
            420                 425                 430 ttt atg aat gca ctt act aaa att acg aat cgc ctc ggt att agt att    1344
Phe Met Asn Ala Leu Thr Lys Ile Thr Asn Arg Leu Gly Ile Ser Ile
        435                 440                 445 cct aaa ttg ata gat tac gaa gta agg att cct cct ggt gga aaa aca    1392
Pro Lys Leu Ile Asp Tyr Glu Val Arg Ile Pro Pro Gly Gly Lys Thr
450                 455                 460 gat gca ctt gta gaa act agg atc acc tgg aac aag tcc tta gat tta    1440
Asp Ala Leu Val Glu Thr Arg Ile Thr Trp Asn Lys Ser Leu Asp Leu
465                 470                 475                 480 gaa gag gac cag act ttc aaa acg atg gga gtt cat ccg gat caa acg    1488
Glu Glu Asp Gln Thr Phe Lys Thr Met Gly Val His Pro Asp Gln Thr
                485                 490                 495 gtt gca gcg gtt cat gca act gaa aag atg ctc aat caa att cta caa    1536
Val Ala Ala Val His Ala Thr Glu Lys Met Leu Asn Gln Ile Leu Gln
            500                 505                 510 cca tgg caa atc taa                                                 1551
Pro Trp Gln Ile
        515

<210> SEQ ID NO 44
<211> LENGTH: 516
<212> TYPE: PRT
<213> ORGANISM: Leptospira interrogans

<400> SEQUENCE: 44

Met Thr Lys Val Glu Thr Arg Leu Glu Ile Leu Asp Val

-continued

```
Ile Met Glu Trp Ala Ala Thr Glu Gln Leu Thr Glu Arg Ile Glu Ile
 65              70                  75                  80

Leu Gly Phe Val Asp Gly Asn Lys Thr Val Asp Trp Ile Lys Asp Ser
             85                  90                  95

Gly Ala Lys Val Leu Asn Leu Leu Thr Lys Gly Ser Leu His His Leu
            100                 105                 110

Glu Lys Gln Leu Gly Lys Thr Pro Lys Glu Phe Phe Thr Asp Val Ser
            115                 120                 125

Phe Val Ile Glu Tyr Ala Ile Lys Ser Gly Leu Lys Ile Asn Val Tyr
            130                 135                 140

Leu Glu Asp Trp Ser Asn Gly Phe Arg Asn Ser Pro Tyr Val Lys
145             150                 155                 160

Ser Leu Val Glu His Leu Ser Lys Glu His Ile Glu Arg Ile Phe Leu
                165                 170                 175

Pro Asp Thr Leu Gly Val Leu Ser Pro Glu Thr Phe Gln Gly Val
            180                 185                 190

Asp Ser Leu Ile Gln Lys Tyr Pro Asp Ile His Phe Glu Phe His Gly
            195                 200                 205

His Asn Asp Tyr Asp Leu Ser Val Ala Asn Ser Leu Gln Ala Ile Arg
210             215                 220

Ala Gly Val Lys Gly Leu His Ala Ser Ile Asn Gly Leu Gly Glu Arg
225                 230                 235                 240

Ala Gly Asn Thr Pro Leu Glu Ala Leu Val Thr Thr Ile His Asp Lys
                245                 250                 255

Ser Asn Ser Lys Thr Asn Ile Asn Glu Ile Ala Ile Thr Glu Ala Ser
            260                 265                 270

Arg Leu Val Glu Val Phe Ser Gly Lys Arg Ile Ser Ala Asn Arg Pro
            275                 280                 285

Ile Val Gly Glu Asp Val Phe Thr Gln Thr Ala Gly Val His Ala Asp
            290                 295                 300

Gly Asp Lys Lys Gly Asn Leu Tyr Ala Asn Pro Ile Leu Pro Glu Arg
305                 310                 315                 320

Phe Gly Arg Lys Arg Ser Tyr Ala Leu Gly Lys Leu Ala Gly Lys Ala
                325                 330                 335

Ser Ile Ser Glu Asn Val Lys Gln Leu Gly Met Val Leu Ser Glu Val
            340                 345                 350

Val Leu Gln Lys Val Leu Glu Arg Val Ile Glu Leu Gly Asp Gln Asn
            355                 360                 365

Lys Leu Val Thr Pro Glu Asp Leu Pro Phe Ile Ile Ala Asp Val Ser
            370                 375                 380

Gly Arg Thr Gly Glu Lys Val Leu Thr Ile Lys Ser Cys Asn Ile His
385                 390                 395                 400

Ser Gly Ile Gly Ile Arg Pro His Ala Gln Ile Glu Leu Glu Tyr Gln
                405                 410                 415

Gly Lys Ile His Lys Glu Ile Ser Glu Gly Asp Gly Tyr Asp Ala
            420                 425                 430

Phe Met Asn Ala Leu Thr Lys Ile Thr Asn Arg Leu Gly Ile Ser Ile
            435                 440                 445

Pro Lys Leu Ile Asp Tyr Glu Val Arg Ile Pro Pro Gly Gly Lys Thr
            450                 455                 460

Asp Ala Leu Val Glu Thr Arg Ile Thr Trp Asn Lys Ser Leu Asp Leu
465                 470                 475                 480
```

```
Glu Glu Asp Gln Thr Phe Lys Thr Met Gly Val His Pro Asp Gln Thr
                485                 490                 495

Val Ala Ala Val His Ala Thr Glu Lys Met Leu Asn Gln Ile Leu Gln
            500                 505                 510

Pro Trp Gln Ile
        515

<210> SEQ ID NO 45
<211> LENGTH: 1398
<212> TYPE: DNA
<213> ORGANISM: Leptospira interrogans
<220> FEATURE:
<221> NAME/KEY: CDS
<222> LOCATION: (1)..(1398)

<400> SEQUENCE: 45 atg aag aca atg ttc gaa aaa att tgg gaa gat cat cta gtc gga gaa      48
Met Lys Thr Met Phe Glu Lys Ile Trp Glu Asp His Leu Val Gly Glu
1               5                   10                  15 cta gat gct gga tcc tat cta atc tat ata gat cgc cat ctc att cat      96
Leu Asp Ala Gly Ser Tyr Leu Ile Tyr Ile Asp Arg His Leu Ile His
            20                  25                  30 gaa gtt aca agt cct cag gcg ttt gaa gga ctt aaa ctt gca ggc aga      144
Glu Val Thr Ser Pro Gln Ala Phe Glu Gly Leu Lys Leu Ala Gly Arg
        35                  40                  45 aag gtt cgt cgt cct gaa gct act ttt gcc aca atg gat cat aac gtt      192
Lys Val Arg Arg Pro Glu Ala Thr Phe Ala Thr Met Asp His Asn Val
    50                  55                  60 tct act aga aca cgt gat tta agt ctg gcc gat cct gtt tcc gca att      240
Ser Thr Arg Thr Arg Asp Leu Ser Leu Ala Asp Pro Val Ser Ala Ile
65                  70                  75                  80 caa atg cag act tta aaa aag aac tgc gac gaa aac gga atc cgc gtt      288
Gln Met Gln Thr Leu Lys Lys Asn Cys Asp Glu Asn Gly Ile Arg Val
                85                  90                  95 tat gat ttt caa aac cct gac caa gga atc att cac gta atc gct cct      336
Tyr Asp Phe Gln Asn Pro Asp Gln Gly Ile Ile His Val Ile Ala Pro
            100                 105                 110 gaa atg gga ctg act cat cct gga atg aca atc gta tgc gga gat tct      384
Glu Met Gly Leu Thr His Pro Gly Met Thr Ile Val Cys Gly Asp Ser
        115                 120                 125 cat act tct aca cac ggt gcg ttt ggt gcg ctt gct ttc ggg atc gga      432
His Thr Ser Thr His Gly Ala Phe Gly Ala Leu Ala Phe Gly Ile Gly
    130                 135                 140 acc agc gaa gta gag cac gtt ctt gcg act caa acc tta gtt caa aaa      480
Thr Ser Glu Val Glu His Val Leu Ala Thr Gln Thr Leu Val Gln Lys
145                 150                 155                 160 aga gca aaa aca atg gag att aga gtc gat gga aaa ctt tcc gat aag      528
Arg Ala Lys Thr Met Glu Ile Arg Val Asp Gly Lys Leu Ser Asp Lys
                165                 170                 175 gtc aca gca aaa gac atc att ctt gcg atc att gga aaa att gga acc      576
Val Thr Ala Lys Asp Ile Ile Leu Ala Ile Ile Gly Lys Ile Gly Thr
            180                 185                 190 gca ggt gcg aca ggt tat gtg atc gaa tat aga ggt tct gca att caa      624
Ala Gly Ala Thr Gly Tyr Val Ile Glu Tyr Arg Gly Ser Ala Ile Gln
        195                 200                 205 gcc ctc agt atg gaa gct aga atg act att tgt aat atg tct atc gaa      672
Ala Leu Ser Met Glu Ala Arg Met Thr Ile Cys Asn Met Ser Ile Glu
    210                 215                 220 gcg gga gct aga gca ggt tta atc gca cca gat gaa act act ttt aat      720
Ala Gly Ala Arg Ala Gly Leu Ile Ala Pro Asp Glu Thr Thr Phe Asn
225                 230                 235                 240
```

```
tat att caa gga aag gac ttt tct cca aaa gga gtc gaa tgg gat ctt      768
Tyr Ile Gln Gly Lys Asp Phe Ser Pro Lys Gly Val Glu Trp Asp Leu
                245                 250                 255 gcg gtc aaa aaa tgg aaa cac tat gta acg gac gaa ggt gct aaa ttt      816
Ala Val Lys Lys Trp Lys His Tyr Val Thr Asp Glu Gly Ala Lys Phe
            260                 265                 270 gat aga acc gta att ctt cat gca gat gaa atc gct cct atg gta act      864
Asp Arg Thr Val Ile Leu His Ala Asp Glu Ile Ala Pro Met Val Thr
        275                 280                 285 tgg gga act tct ccc agt cag gtt gtt tcg ata aaa gga gtc gtt cca      912
Trp Gly Thr Ser Pro Ser Gln Val Val Ser Ile Lys Gly Val Val Pro
    290                 295                 300 gat cca aaa gat gca aat gat ccg gtg gaa aaa att gga att gag tct      960
Asp Pro Lys Asp Ala Asn Asp Pro Val Glu Lys Ile Gly Ile Glu Ser
305                 310                 315                 320 gcg ctt aaa tat atg gat ctc aaa tcg ggc cag aag ata gaa gac att     1008
Ala Leu Lys Tyr Met Asp Leu Lys Ser Gly Gln Lys Ile Glu Asp Ile
                325                 330                 335 tca att aat aaa gtg ttt atc ggt tcc tgt act aat tct aga atc gaa     1056
Ser Ile Asn Lys Val Phe Ile Gly Ser Cys Thr Asn Ser Arg Ile Glu
            340                 345                 350 gat tta aga gcg gcc gct gct acc gta aaa gga aaa aaa gtt tcc tct     1104
Asp Leu Arg Ala Ala Ala Ala Thr Val Lys Gly Lys Lys Val Ser Ser
        355                 360                 365 aag gtt cag gcg att gtg gtt ccc ggt tca ggc aga gtc aaa cgt cag     1152
Lys Val Gln Ala Ile Val Val Pro Gly Ser Gly Arg Val Lys Arg Gln
    370                 375                 380 gcg gaa caa gaa ggt ctg gat aaa att ttt acc gcg gcc ggt ttt gaa     1200
Ala Glu Gln Glu Gly Leu Asp Lys Ile Phe Thr Ala Ala Gly Phe Glu
385                 390                 395                 400 tgg aga aat cca ggc tgt tct atg tgt ctt gcg atg aac gac gac gta     1248
Trp Arg Asn Pro Gly Cys Ser Met Cys Leu Ala Met Asn Asp Asp Val
                405                 410                 415 tta gaa ccg gga gat cgt tgt gct tct act tct aac cga aac ttt gaa     1296
Leu Glu Pro Gly Asp Arg Cys Ala Ser Thr Ser Asn Arg Asn Phe Glu
            420                 425                 430 ggt cgt caa gga aaa gga gga aga acc cat cta gta gga ccg gaa atg     1344
Gly Arg Gln Gly Lys Gly Gly Arg Thr His Leu Val Gly Pro Glu Met
        435                 440                 445 gcc gcc gcc gcg gct atc gaa ggc cat ttt gtg gat att cga aac tgg     1392
Ala Ala Ala Ala Ala Ile Glu Gly His Phe Val Asp Ile Arg Asn Trp
    450                 455                 460 aaa taa                                                              1398
Lys
465

<210> SEQ ID NO 46
<211> LENGTH: 465
<212> TYPE: PRT
<213> ORGANISM: Leptospira interrogans

<400> SEQUENCE: 46

Met Lys Thr Met Phe Glu Lys Ile Trp Glu Asp His Leu Val Gly Glu
1               5                   10                  15

Leu Asp Ala Gly Ser Tyr Leu Ile Tyr Ile Asp Arg His Leu Ile His
                20                  25                  30

Glu Val Thr Ser Pro Gln Ala Phe Glu Gly Leu Lys Leu Ala Gly Arg
            35                  40                  45

Lys Val Arg Arg Pro Glu Ala Thr Phe Ala Thr Met Asp His Asn Val
```

```
                    50                  55                  60
Ser Thr Arg Thr Arg Asp Leu Ser Leu Ala Asp Pro Val Ser Ala Ile
 65                      70                  75                  80

Gln Met Gln Thr Leu Lys Lys Asn Cys Asp Glu Asn Gly Ile Arg Val
                     85                  90                  95

Tyr Asp Phe Gln Asn Pro Asp Gln Gly Ile Ile His Val Ile Ala Pro
                100                 105                 110

Glu Met Gly Leu Thr His Pro Gly Met Thr Ile Val Cys Gly Asp Ser
                115                 120                 125

His Thr Ser Thr His Gly Ala Phe Gly Ala Leu Ala Phe Gly Ile Gly
                130                 135                 140

Thr Ser Glu Val Glu His Val Leu Ala Thr Gln Thr Leu Val Gln Lys
145                 150                 155                 160

Arg Ala Lys Thr Met Glu Ile Arg Val Asp Gly Lys Leu Ser Asp Lys
                165                 170                 175

Val Thr Ala Lys Asp Ile Ile Leu Ala Ile Ile Gly Lys Ile Gly Thr
                180                 185                 190

Ala Gly Ala Thr Gly Tyr Val Ile Glu Tyr Arg Gly Ser Ala Ile Gln
                195                 200                 205

Ala Leu Ser Met Glu Ala Arg Met Thr Ile Cys Asn Met Ser Ile Glu
                210                 215                 220

Ala Gly Ala Arg Ala Gly Leu Ile Ala Pro Asp Glu Thr Thr Phe Asn
225                 230                 235                 240

Tyr Ile Gln Gly Lys Asp Phe Ser Pro Lys Gly Val Glu Trp Asp Leu
                245                 250                 255

Ala Val Lys Lys Trp Lys His Tyr Val Thr Asp Glu Gly Ala Lys Phe
                260                 265                 270

Asp Arg Thr Val Ile Leu His Ala Asp Glu Ile Ala Pro Met Val Thr
                275                 280                 285

Trp Gly Thr Ser Pro Ser Gln Val Val Ser Ile Lys Gly Val Val Pro
                290                 295                 300

Asp Pro Lys Asp Ala Asn Asp Pro Val Glu Lys Ile Gly Ile Glu Ser
305                 310                 315                 320

Ala Leu Lys Tyr Met Asp Leu Lys Ser Gly Gln Lys Ile Glu Asp Ile
                325                 330                 335

Ser Ile Asn Lys Val Phe Ile Gly Ser Cys Thr Asn Ser Arg Ile Glu
                340                 345                 350

Asp Leu Arg Ala Ala Ala Thr Val Lys Gly Lys Lys Val Ser Ser
                355                 360                 365

Lys Val Gln Ala Ile Val Val Pro Gly Ser Gly Arg Val Lys Arg Gln
                370                 375                 380

Ala Glu Gln Glu Gly Leu Asp Lys Ile Phe Thr Ala Ala Gly Phe Glu
385                 390                 395                 400

Trp Arg Asn Pro Gly Cys Ser Met Cys Leu Ala Met Asn Asp Val
                405                 410                 415

Leu Glu Pro Gly Asp Arg Cys Ala Ser Thr Ser Asn Arg Asn Phe Glu
                420                 425                 430

Gly Arg Gln Gly Lys Gly Gly Arg Thr His Leu Val Gly Pro Glu Met
                435                 440                 445

Ala Ala Ala Ala Ala Ile Glu Gly His Phe Val Asp Ile Arg Asn Trp
                450                 455                 460

Lys
465
```

<210> SEQ ID NO 47
<211> LENGTH: 621
<212> TYPE: DNA
<213> ORGANISM: Leptospira interrogans
<220> FEATURE:
<221> NAME/KEY: CDS
<222> LOCATION: (1)..(621)

<400> SEQUENCE: 47

| atg | aaa | ccc | ttt | act | ata | tta | aat | gga | att | gcc | gcc | tta | ctg | gac | aga | 48 |
| Met | Lys | Pro | Phe | Thr | Ile | Leu | Asn | Gly | Ile | Ala | Ala | Leu | Leu | Asp | Arg | |
| 1 | | | | 5 | | | | | 10 | | | | | 15 | | |

| ccc | aac | gtg | gat | acg | gat | cag | atc | att | cca | aaa | caa | ttt | tta | cgg | aag | 96 |
| Pro | Asn | Val | Asp | Thr | Asp | Gln | Ile | Ile | Pro | Lys | Gln | Phe | Leu | Arg | Lys | |
| | | | 20 | | | | | 25 | | | | | 30 | | | |

| ata | gaa | cga | acc | ggt | ttc | gga | gtt | cat | ctg | ttt | cac | gat | tgg | aga | tac | 144 |
| Ile | Glu | Arg | Thr | Gly | Phe | Gly | Val | His | Leu | Phe | His | Asp | Trp | Arg | Tyr | |
| | | 35 | | | | | 40 | | | | | 45 | | | | |

| tta | gac | gac | gcg | ggt | acc | aaa | ctc | aat | cct | gat | ttt | tcc | ctc | aat | caa | 192 |
| Leu | Asp | Asp | Ala | Gly | Thr | Lys | Leu | Asn | Pro | Asp | Phe | Ser | Leu | Asn | Gln | |
| 50 | | | | | 55 | | | | | 60 | | | | | | |

| gaa | cga | tat | aag | gga | gct | tct | atc | ctt | atc | acc | aga | gat | aac | ttt | ggt | 240 |
| Glu | Arg | Tyr | Lys | Gly | Ala | Ser | Ile | Leu | Ile | Thr | Arg | Asp | Asn | Phe | Gly | |
| 65 | | | | 70 | | | | | 75 | | | | | 80 | | |

| tgt | gga | tct | tcc | aga | gaa | cac | gct | cct | tgg | gct | tta | gaa | gac | tac | ggg | 288 |
| Cys | Gly | Ser | Ser | Arg | Glu | His | Ala | Pro | Trp | Ala | Leu | Glu | Asp | Tyr | Gly | |
| | | | 85 | | | | | 90 | | | | | 95 | | | |

| ttt | agg | gca | atc | att | gct | cct | tct | tac | gcg | gat | att | ttt | ttc | aac | aac | 336 |
| Phe | Arg | Ala | Ile | Ile | Ala | Pro | Ser | Tyr | Ala | Asp | Ile | Phe | Phe | Asn | Asn | |
| | | 100 | | | | | 105 | | | | | 110 | | | | |

| tgc | ttt | aaa | aac | gga | atg | ctt | cca | gtc | att | tta | aaa | tcg | gaa | gaa | gta | 384 |
| Cys | Phe | Lys | Asn | Gly | Met | Leu | Pro | Val | Ile | Leu | Lys | Ser | Glu | Glu | Val | |
| | 115 | | | | | 120 | | | | | 125 | | | | | |

| gaa | gag | ctg | ttc | cat | ttg | gtt | tcg | act | aac | gta | gga | gcg | aaa | gtc | ata | 432 |
| Glu | Glu | Leu | Phe | His | Leu | Val | Ser | Thr | Asn | Val | Gly | Ala | Lys | Val | Ile | |
| 130 | | | | | 135 | | | | | 140 | | | | | | |

| gtg | gat | ctg | gac | aaa | caa | act | gta | acc | gga | ccg | act | gga | aaa | ata | tat | 480 |
| Val | Asp | Leu | Asp | Lys | Gln | Thr | Val | Thr | Gly | Pro | Thr | Gly | Lys | Ile | Tyr | |
| 145 | | | | | 150 | | | | | 155 | | | | | 160 | |

| tat | ttt | gaa | gtg | gat | tct | ttt | cgt | aaa | tac | tgt | ctt | tat | aac | gga | ctt | 528 |
| Tyr | Phe | Glu | Val | Asp | Ser | Phe | Arg | Lys | Tyr | Cys | Leu | Tyr | Asn | Gly | Leu | |
| | | | | 165 | | | | | 170 | | | | | 175 | | |

| gat | gac | ata | ggt | cta | act | cta | aaa | caa | gaa | agt | aaa | att | gga | gag | ttt | 576 |
| Asp | Asp | Ile | Gly | Leu | Thr | Leu | Lys | Gln | Glu | Ser | Lys | Ile | Gly | Glu | Phe | |
| | | | 180 | | | | | 185 | | | | | 190 | | | |

| gaa | aaa | aag | cag | aaa | gaa | gtt | gaa | cct | tgg | tta | tac | gcc | ata | taa | | 621 |
| Glu | Lys | Lys | Gln | Lys | Glu | Val | Glu | Pro | Trp | Leu | Tyr | Ala | Ile | | | |
| | 195 | | | | | 200 | | | | | 205 | | | | | |

<210> SEQ ID NO 48
<211> LENGTH: 206
<212> TYPE: PRT
<213> ORGANISM: Leptospira interrogans

<400> SEQUENCE: 48

| Met | Lys | Pro | Phe | Thr | Ile | Leu | Asn | Gly | Ile | Ala | Ala | Leu | Leu | Asp | Arg |
| 1 | | | | 5 | | | | | 10 | | | | | 15 | |

| Pro | Asn | Val | Asp | Thr | Asp | Gln | Ile | Ile | Pro | Lys | Gln | Phe | Leu | Arg | Lys |
| | | | 20 | | | | | 25 | | | | | 30 | | |

| Ile | Glu | Arg | Thr | Gly | Phe | Gly | Val | His | Leu | Phe | His | Asp | Trp | Arg | Tyr |

```
                35                  40                  45
Leu Asp Asp Ala Gly Thr Lys Leu Asn Pro Asp Phe Ser Leu Asn Gln
    50                  55                  60

Glu Arg Tyr Lys Gly Ala Ser Ile Leu Ile Thr Arg Asp Asn Phe Gly
65                  70                  75                  80

Cys Gly Ser Ser Arg Glu His Ala Pro Trp Ala Leu Glu Asp Tyr Gly
                85                  90                  95

Phe Arg Ala Ile Ile Ala Pro Ser Tyr Ala Asp Ile Phe Phe Asn Asn
            100                 105                 110

Cys Phe Lys Asn Gly Met Leu Pro Val Ile Leu Lys Ser Glu Glu Val
        115                 120                 125

Glu Glu Leu Phe His Leu Val Ser Thr Asn Val Gly Ala Lys Val Ile
    130                 135                 140

Val Asp Leu Asp Lys Gln Thr Val Thr Gly Pro Thr Gly Lys Ile Tyr
145                 150                 155                 160

Tyr Phe Glu Val Asp Ser Phe Arg Lys Tyr Cys Leu Tyr Asn Gly Leu
                165                 170                 175

Asp Asp Ile Gly Leu Thr Leu Lys Gln Glu Ser Lys Ile Gly Glu Phe
            180                 185                 190

Glu Lys Lys Gln Lys Glu Val Glu Pro Trp Leu Tyr Ala Ile
        195                 200                 205

<210> SEQ ID NO 49
<211> LENGTH: 1077
<212> TYPE: DNA
<213> ORGANISM: Leptospira interrogans
<220> FEATURE:
<221> NAME/KEY: CDS
<222> LOCATION: (1)..(1077)

<400> SEQUENCE: 49 atg aag aat gta gca gta ctt tca gga gac gga atc gga ccg gaa gtc      48
Met Lys Asn Val Ala Val Leu Ser Gly Asp Gly Ile Gly Pro Glu Val
1               5                   10                  15 atg gag ata gcc atc tcc gtt ttg aaa aag gct ctc ggt gca aaa gtt      96
Met Glu Ile Ala Ile Ser Val Leu Lys Lys Ala Leu Gly Ala Lys Val
            20                  25                  30 tcc gag ttt caa ttt aaa gaa gga ttt gta ggt gga atc gca atc gat     144
Ser Glu Phe Gln Phe Lys Glu Gly Phe Val Gly Gly Ile Ala Ile Asp
        35                  40                  45 aaa act gga cac cca ctt cca ccg gaa act ctt aaa cta tgt gaa gaa     192
Lys Thr Gly His Pro Leu Pro Pro Glu Thr Leu Lys Leu Cys Glu Glu
    50                  55                  60 tct tcc gca att ctt ttc gga agt gtg gga ggt cct aaa tgg gaa aca     240
Ser Ser Ala Ile Leu Phe Gly Ser Val Gly Gly Pro Lys Trp Glu Thr
65                  70                  75                  80 ctc cct ccg gaa aaa caa ccg gaa cga ggg gca ctt cta cct ttg aga     288
Leu Pro Pro Glu Lys Gln Pro Glu Arg Gly Ala Leu Leu Pro Leu Arg
                85                  90                  95 aaa cat ttt gat cta ttt gca aac tta aga cct gcg atc att tat cca     336
Lys His Phe Asp Leu Phe Ala Asn Leu Arg Pro Ala Ile Ile Tyr Pro
            100                 105                 110 gag ttg aaa aat gct tct cca gtt cgt tct gat att att gga aac gga     384
Glu Leu Lys Asn Ala Ser Pro Val Arg Ser Asp Ile Ile Gly Asn Gly
        115                 120                 125 tta gat att ctc ata tta aga gag tta acc gga gga att tat ttt gga     432
Leu Asp Ile Leu Ile Leu Arg Glu Leu Thr Gly Gly Ile Tyr Phe Gly
    130                 135                 140
```

-continued

| | | |
|---|---|---|
| caa cca aaa gga aga gaa gga tca ggt cag gaa gaa ttt gca tac gac<br>Gln Pro Lys Gly Arg Glu Gly Ser Gly Gln Glu Glu Phe Ala Tyr Asp<br>145                                  150                            155                          160 | | 480 |
| acg atg aag tat tcc aga aga gaa atc gaa agg att gct aaa gtc gca<br>Thr Met Lys Tyr Ser Arg Arg Glu Ile Glu Arg Ile Ala Lys Val Ala<br>                        165                            170                            175 | | 528 |
| ttc cag gcg gcc aga aaa aga aat aat aaa gtg act agt atc gat aaa<br>Phe Gln Ala Ala Arg Lys Arg Asn Asn Lys Val Thr Ser Ile Asp Lys<br>                 180                            185                            190 | | 576 |
| gca aac gtc ttg act act tcc gtt ttt tgg aag gaa gta gta atc gaa<br>Ala Asn Val Leu Thr Thr Ser Val Phe Trp Lys Glu Val Val Ile Glu<br>195                                  200                            205 | | 624 |
| ttg cat aag aaa gaa ttt tca gac gtc caa ttg aat cat ctt tat gtg<br>Leu His Lys Lys Glu Phe Ser Asp Val Gln Leu Asn His Leu Tyr Val<br>        210                            215                            220 | | 672 |
| gac aat gcg gcg atg cag tta atc gta aat ccg aaa caa ttc gac gtg<br>Asp Asn Ala Ala Met Gln Leu Ile Val Asn Pro Lys Gln Phe Asp Val<br>225                                  230                            235                        240 | | 720 |
| gtt ctt tgt gag aat atg ttt ggt gat att ctt tcg gac gag gct tcc<br>Val Leu Cys Glu Asn Met Phe Gly Asp Ile Leu Ser Asp Glu Ala Ser<br>                        245                            250                            255 | | 768 |
| atc att acg ggt tca atc gga atg ctt cct tct gcc tct ctt tcc gaa<br>Ile Ile Thr Gly Ser Ile Gly Met Leu Pro Ser Ala Ser Leu Ser Glu<br>                 260                            265                            270 | | 816 |
| tct gga ttt gga ttg tat gaa cct tct ggt ggt tct gcg ccg gac ata<br>Ser Gly Phe Gly Leu Tyr Glu Pro Ser Gly Gly Ser Ala Pro Asp Ile<br>275                                  280                            285 | | 864 |
| gcc gga aaa gga gtg gca aat ccg att gct caa gta ttg agt gcg gcg<br>Ala Gly Lys Gly Val Ala Asn Pro Ile Ala Gln Val Leu Ser Ala Ala<br>        290                            295                            300 | | 912 |
| ttg atg tta cgt tat tct ttt tct atg gaa gaa gaa gca aac aag ata<br>Leu Met Leu Arg Tyr Ser Phe Ser Met Glu Glu Glu Ala Asn Lys Ile<br>305                                  310                            315                        320 | | 960 |
| gaa acc gcc gtg cgt aaa acg att gcc tcc gga aaa aga acc aga gac<br>Glu Thr Ala Val Arg Lys Thr Ile Ala Ser Gly Lys Arg Thr Arg Asp<br>                        325                            330                            335 | | 1008 |
| ata gcg gaa gta gga tct acg atc gta gga act aaa gaa atc ggt caa<br>Ile Ala Glu Val Gly Ser Thr Ile Val Gly Thr Lys Glu Ile Gly Gln<br>        340                            345                            350 | | 1056 |
| ttg atc gaa tcc ttt ctc taa<br>Leu Ile Glu Ser Phe Leu<br>        355 | | 1077 |

<210> SEQ ID NO 50
<211> LENGTH: 358
<212> TYPE: PRT
<213> ORGANISM: Leptospira interrogans

<400> SEQUENCE: 50

Met Lys Asn Val Ala Val Leu Ser Gly Asp Gly Ile Gly Pro Glu Val
1                   5                    10                  15

Met Glu Ile Ala Ile Ser Val Leu Lys Lys Ala Leu Gly Ala Lys Val
                  20                        25                    30

Ser Glu Phe Gln Phe Lys Glu Gly Phe Val Gly Gly Ile Ala Ile Asp
                  35                        40                    45

Lys Thr Gly His Pro Leu Pro Pro Glu Thr Leu Lys Leu Cys Glu Glu
      50                            55                            60

Ser Ser Ala Ile Leu Phe Gly Ser Val Gly Gly Pro Lys Trp Glu Thr
65                                70                            75                    80

-continued

```
Leu Pro Pro Glu Lys Gln Pro Glu Arg Gly Ala Leu Leu Pro Leu Arg
                 85                  90                  95

Lys His Phe Asp Leu Phe Ala Asn Leu Arg Pro Ala Ile Ile Tyr Pro
            100                 105                 110

Glu Leu Lys Asn Ala Ser Pro Val Arg Ser Asp Ile Ile Gly Asn Gly
        115                 120                 125

Leu Asp Ile Leu Ile Leu Arg Glu Leu Thr Gly Gly Ile Tyr Phe Gly
    130                 135                 140

Gln Pro Lys Gly Arg Glu Gly Ser Gly Gln Glu Phe Ala Tyr Asp
145                 150                 155                 160

Thr Met Lys Tyr Ser Arg Arg Glu Ile Glu Arg Ile Ala Lys Val Ala
                165                 170                 175

Phe Gln Ala Ala Arg Lys Arg Asn Asn Lys Val Thr Ser Ile Asp Lys
            180                 185                 190

Ala Asn Val Leu Thr Thr Ser Val Phe Trp Lys Glu Val Val Ile Glu
        195                 200                 205

Leu His Lys Lys Glu Phe Ser Asp Val Gln Leu Asn His Leu Tyr Val
    210                 215                 220

Asp Asn Ala Ala Met Gln Leu Ile Val Asn Pro Lys Gln Phe Asp Val
225                 230                 235                 240

Val Leu Cys Glu Asn Met Phe Gly Asp Ile Leu Ser Asp Glu Ala Ser
                245                 250                 255

Ile Ile Thr Gly Ser Ile Gly Met Leu Pro Ser Ala Ser Leu Ser Glu
            260                 265                 270

Ser Gly Phe Gly Leu Tyr Glu Pro Ser Gly Gly Ser Ala Pro Asp Ile
        275                 280                 285

Ala Gly Lys Gly Val Ala Asn Pro Ile Ala Gln Val Leu Ser Ala Ala
    290                 295                 300

Leu Met Leu Arg Tyr Ser Phe Ser Met Glu Glu Glu Ala Asn Lys Ile
305                 310                 315                 320

Glu Thr Ala Val Arg Lys Thr Ile Ala Ser Gly Lys Arg Thr Arg Asp
                325                 330                 335

Ile Ala Glu Val Gly Ser Thr Val Gly Thr Lys Glu Ile Gly Gln
            340                 345                 350

Leu Ile Glu Ser Phe Leu
        355

<210> SEQ ID NO 51
<211> LENGTH: 1161
<212> TYPE: DNA
<213> ORGANISM: Escherichia coli
<220> FEATURE:
<221> NAME/KEY: CDS
<222> LOCATION: (1)..(1161)

<400> SEQUENCE: 51 atg aca tcg gaa aac ccg tta ctg gcg ctg cga gag aaa atc agc gcg     48
Met Thr Ser Glu Asn Pro Leu Leu Ala Leu Arg Glu Lys Ile Ser Ala
1               5                   10                  15 ctg gat gaa aaa tta tta gcg tta ctg gca gaa cgg cgc gaa ctg gcc     96
Leu Asp Glu Lys Leu Leu Ala Leu Leu Ala Glu Arg Arg Glu Leu Ala
            20                  25                  30 gtc gag gtg gga aaa gcc aaa ctg ctc tcg cat cgc ccg gta cgt gat    144
Val Glu Val Gly Lys Ala Lys Leu Leu Ser His Arg Pro Val Arg Asp
        35                  40                  45 att gat cgt gaa cgc gat ttg ctg gaa aga tta att acg ctc ggt aaa    192
Ile Asp Arg Glu Arg Asp Leu Leu Glu Arg Leu Ile Thr Leu Gly Lys
```

```
                    50                   55                    60
gcg cac cat ctg gac gcc cat tac att act cgc ctg ttc cag ctc atc      240
Ala His His Leu Asp Ala His Tyr Ile Thr Arg Leu Phe Gln Leu Ile
 65              70                   75                      80 att gaa gat tcc gta tta act cag cag gct ttg ctc caa caa cat ctc      288
Ile Glu Asp Ser Val Leu Thr Gln Gln Ala Leu Leu Gln Gln His Leu
                    85                   90                   95 aat aaa att aat ccg cac tca gca cgc atc gct ttt ctc ggc ccc aaa      336
Asn Lys Ile Asn Pro His Ser Ala Arg Ile Ala Phe Leu Gly Pro Lys
                100                  105                 110 ggt tct tat tcc cat ctt gcg gcg cgc cag tat gct gcc cgt cac ttt      384
Gly Ser Tyr Ser His Leu Ala Ala Arg Gln Tyr Ala Ala Arg His Phe
                115                  120                 125 gag caa ttc att gaa agt ggc tgc gcc aaa ttt gcc gat att ttt aat      432
Glu Gln Phe Ile Glu Ser Gly Cys Ala Lys Phe Ala Asp Ile Phe Asn
       130                  135                  140 cag gtg gaa acc ggc cag gcc gac tat gcc gtc gta ccg att gaa aat      480
Gln Val Glu Thr Gly Gln Ala Asp Tyr Ala Val Val Pro Ile Glu Asn
145                  150                  155                 160 acc agc tcc ggt gcc ata aac gac gtt tac gat ctg ctg caa cat acc      528
Thr Ser Ser Gly Ala Ile Asn Asp Val Tyr Asp Leu Leu Gln His Thr
                        165                  170                 175 agc ttg tcg att gtt ggc gag atg acg tta act atc gac cat tgt ttg      576
Ser Leu Ser Ile Val Gly Glu Met Thr Leu Thr Ile Asp His Cys Leu
                180                  185                 190 ttg gtc tcc ggc act act gat tta tcc acc atc aat acg gtc tac agc      624
Leu Val Ser Gly Thr Thr Asp Leu Ser Thr Ile Asn Thr Val Tyr Ser
                195                  200                 205 cat ccg cag cca ttc cag caa tgc agc aaa ttc ctt aat cgt tat ccg      672
His Pro Gln Pro Phe Gln Gln Cys Ser Lys Phe Leu Asn Arg Tyr Pro
        210                  215                 220 cac tgg aag att gaa tat acc gaa agt acg tct gcg gca atg gaa aag      720
His Trp Lys Ile Glu Tyr Thr Glu Ser Thr Ser Ala Ala Met Glu Lys
225                  230                  235                 240 gtt gca cag gca aaa tca ccg cat gtt gct gcg ttg gga agc gaa gct      768
Val Ala Gln Ala Lys Ser Pro His Val Ala Ala Leu Gly Ser Glu Ala
                        245                  250                 255 ggc ggc act ttg tac ggt ttg cag gta ctg gag cgt att gaa gca aat      816
Gly Gly Thr Leu Tyr Gly Leu Gln Val Leu Glu Arg Ile Glu Ala Asn
                260                  265                 270 cag cga caa aac ttc acc cga ttt gtg gtg ttg gcg cgt aaa gcc att      864
Gln Arg Gln Asn Phe Thr Arg Phe Val Val Leu Ala Arg Lys Ala Ile
            275                  280                 285 aac gtg tct gat cag gtt ccg gcg aaa acc acg ttg tta atg gcg acc      912
Asn Val Ser Asp Gln Val Pro Ala Lys Thr Thr Leu Leu Met Ala Thr
290                  295                  300 ggg caa caa gcc ggt gcg ctg gtt gaa gcg ttg ctg gta ctg cgc aac      960
Gly Gln Gln Ala Gly Ala Leu Val Glu Ala Leu Leu Val Leu Arg Asn
305                  310                  315                 320 cac aat ctg att atg acc cgt ctg gaa tca cgc ccg att cac ggt aat     1008
His Asn Leu Ile Met Thr Arg Leu Glu Ser Arg Pro Ile His Gly Asn
                        325                  330                 335 cca tgg gaa gag atg ttc tat ctg gat att cag gcc aat ctt gaa tca     1056
Pro Trp Glu Glu Met Phe Tyr Leu Asp Ile Gln Ala Asn Leu Glu Ser
                340                  345                 350 gcg gaa atg caa aaa gca ttg aaa gag tta ggg gaa atc acc cgt tca     1104
Ala Glu Met Gln Lys Ala Leu Lys Glu Leu Gly Glu Ile Thr Arg Ser
            355                  360                 365 atg aag gta ttg ggc tgt tac cca agt gag aac gta gtg cct gtt gat     1152
```

```
              Met Lys Val Leu Gly Cys Tyr Pro Ser Glu Asn Val Pro Val Asp
                  370                 375                 380 cca acc tga                                                              1161
Pro Thr
385

<210> SEQ ID NO 52
<211> LENGTH: 386
<212> TYPE: PRT
<213> ORGANISM: Escherichia coli

<400> SEQUENCE: 52

Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
                20                  25                  30

Val Glu Val Gly Lys Ala Lys Leu Leu Ser His Arg Pro Val Arg Asp
            35                  40                  45

Ile Asp Arg Glu Arg Asp Leu Leu Glu Arg Leu Ile Thr Leu Gly Lys
        50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
                100                 105                 110

Gly Ser Tyr Ser His Leu Ala Ala Arg Gln Tyr Ala Ala Arg His Phe
            115                 120                 125

Glu Gln Phe Ile Glu Ser Gly Cys Ala Lys Phe Ala Asp Ile Phe Asn
        130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
```

```
                340              345              350
Ala Glu Met Gln Lys Ala Leu Lys Glu Leu Gly Glu Ile Thr Arg Ser
            355              360              365
Met Lys Val Leu Gly Cys Tyr Pro Ser Glu Asn Val Pro Val Asp
        370              375              380
Pro Thr
385

<210> SEQ ID NO 53
<211> LENGTH: 1122
<212> TYPE: DNA
<213> ORGANISM: Escherichia coli
<220> FEATURE:
<221> NAME/KEY: CDS
<222> LOCATION: (1)..(1122)

<400> SEQUENCE: 53 atg gtt gct gaa ttg acc gca tta cgc gat caa att gat gaa gtc gat        48
Met Val Ala Glu Leu Thr Ala Leu Arg Asp Gln Ile Asp Glu Val Asp
1               5                  10                  15 aaa gcg ctg ctg aat tta tta gcg aag cgt ctg gaa ctg gtt gct gaa        96
Lys Ala Leu Leu Asn Leu Leu Ala Lys Arg Leu Glu Leu Val Ala Glu
            20                  25                  30 gtg ggc gag gtg aaa agc cgc ttt gga ctg cct att tat gtt ccg gag       144
Val Gly Glu Val Lys Ser Arg Phe Gly Leu Pro Ile Tyr Val Pro Glu
        35                  40                  45 cgc gag gca tct atg ttg gcc tcg cgt cgt gca gag gcg gaa gct ctg       192
Arg Glu Ala Ser Met Leu Ala Ser Arg Arg Ala Glu Ala Glu Ala Leu
    50                  55                  60 ggt gta ccg cca gat ctg att gag gat gtt ttg cgt cgg gtg atg cgt       240
Gly Val Pro Pro Asp Leu Ile Glu Asp Val Leu Arg Arg Val Met Arg
65                  70                  75                  80 gaa tct tac tcc agt gaa aac gac aaa gga ttt aaa aca ctt tgt ccg       288
Glu Ser Tyr Ser Ser Glu Asn Asp Lys Gly Phe Lys Thr Leu Cys Pro
                85                  90                  95 tca ctg cgt ccg gtg gtt atc gtc ggc ggt ggc ggt cag atg gga cgc       336
Ser Leu Arg Pro Val Val Ile Val Gly Gly Gly Gly Gln Met Gly Arg
            100                 105                 110 ctg ttc gag aag atg ctg acc ctc tcg ggt tat cag gtg cgg att ctg       384
Leu Phe Glu Lys Met Leu Thr Leu Ser Gly Tyr Gln Val Arg Ile Leu
        115                 120                 125 gag caa cat gac tgg gat cga gcg gct gat att gtt gcc gat gcc gga       432
Glu Gln His Asp Trp Asp Arg Ala Ala Asp Ile Val Ala Asp Ala Gly
    130                 135                 140 atg gtg att gtt agt gtg cca atc cac gtt act gag caa gtt att ggc       480
Met Val Ile Val Ser Val Pro Ile His Val Thr Glu Gln Val Ile Gly
145                 150                 155                 160 aaa tta ccg cct tta ccg aaa gat tgt att ctg gtc gat ctg gca tca       528
Lys Leu Pro Pro Leu Pro Lys Asp Cys Ile Leu Val Asp Leu Ala Ser
                165                 170                 175 gtg aaa aat ggg cca tta cag gcc atg ctg gtg gcg cat gat ggt ccg       576
Val Lys Asn Gly Pro Leu Gln Ala Met Leu Val Ala His Asp Gly Pro
            180                 185                 190 gtg ctg ggg cta cac ccg atg ttc ggt ccg gac agc ggt agc ctg gca       624
Val Leu Gly Leu His Pro Met Phe Gly Pro Asp Ser Gly Ser Leu Ala
        195                 200                 205 aag caa gtt gtg gtc tgg tgt gat gga cgt aaa ccg gaa gca tac caa       672
Lys Gln Val Val Val Trp Cys Asp Gly Arg Lys Pro Glu Ala Tyr Gln
    210                 215                 220 tgg ttt ctg gag caa att cag gtc tgg ggc gct cgg ctg cat cgt att       720
Trp Phe Leu Glu Gln Ile Gln Val Trp Gly Ala Arg Leu His Arg Ile
```

```
Trp Phe Leu Glu Gln Ile Gln Val Trp Gly Ala Arg Leu His Arg Ile
225                 230                 235                 240 agc gcc gtc gag cac gat cag aat atg gcg ttt att cag gca ctg cgc    768
Ser Ala Val Glu His Asp Gln Asn Met Ala Phe Ile Gln Ala Leu Arg
                        245                 250                 255 cac ttt gct act ttt gct tac ggg ctg cac ctg gca gaa gaa aat gtt    816
His Phe Ala Thr Phe Ala Tyr Gly Leu His Leu Ala Glu Glu Asn Val
                260                 265                 270 cag ctt gag caa ctt ctg gcg ctc tct tcg ccg att tac cgc ctt gag    864
Gln Leu Glu Gln Leu Leu Ala Leu Ser Ser Pro Ile Tyr Arg Leu Glu
        275                 280                 285 ctg gcg atg gtc ggg cga ctg ttt gct cag gat ccg cag ctt tat gcc    912
Leu Ala Met Val Gly Arg Leu Phe Ala Gln Asp Pro Gln Leu Tyr Ala
    290                 295                 300 gac atc att atg tcg tca gag cgt aat ctg gcg tta atc aaa cgt tac    960
Asp Ile Ile Met Ser Ser Glu Arg Asn Leu Ala Leu Ile Lys Arg Tyr
305                 310                 315                 320 tat aag cgt ttc ggc gag gcg att gag ttg ctg gag cag ggc gat aag   1008
Tyr Lys Arg Phe Gly Glu Ala Ile Glu Leu Leu Glu Gln Gly Asp Lys
                325                 330                 335 cag gcg ttt att gac agt ttc cgc aag gtg gag cac tgg ttc ggc gat   1056
Gln Ala Phe Ile Asp Ser Phe Arg Lys Val Glu His Trp Phe Gly Asp
            340                 345                 350 tac gca cag cgt ttt cag agt gaa agc cgc gtg tta ttg cgt cag gcg   1104
Tyr Ala Gln Arg Phe Gln Ser Glu Ser Arg Val Leu Leu Arg Gln Ala
        355                 360                 365 aat gac aat cgc cag taa                                            1122
Asn Asp Asn Arg Gln
    370

<210> SEQ ID NO 54
<211> LENGTH: 373
<212> TYPE: PRT
<213> ORGANISM: Escherichia coli

<400> SEQUENCE: 54

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175
```

```
Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
        370

<210> SEQ ID NO 55
<211> LENGTH: 1716
<212> TYPE: DNA
<213> ORGANISM: Bacillus subtilis
<220> FEATURE:
<221> NAME/KEY: CDS
<222> LOCATION: (1)..(1716)

<400> SEQUENCE: 55 atg ttg aca aaa gca aca aaa gaa caa aaa tcc ctt gtg aaa aac aga      48
Met Leu Thr Lys Ala Thr Lys Glu Gln Lys Ser Leu Val Lys Asn Arg
1               5                   10                  15 ggg gcg gag ctt gtt gtt gat tgc tta gtg gag caa ggt gtc aca cat      96
Gly Ala Glu Leu Val Val Asp Cys Leu Val Glu Gln Gly Val Thr His
            20                  25                  30 gta ttt ggc att cca ggt gca aaa att gat gcg gta ttt gac gct tta     144
Val Phe Gly Ile Pro Gly Ala Lys Ile Asp Ala Val Phe Asp Ala Leu
        35                  40                  45 caa gat aaa gga cct gaa att atc gtt gcc cgg cac gaa caa aac gca     192
Gln Asp Lys Gly Pro Glu Ile Ile Val Ala Arg His Glu Gln Asn Ala
    50                  55                  60 gca ttc atg gcc caa gca gtc ggc cgt tta act gga aaa ccg gga gtc     240
Ala Phe Met Ala Gln Ala Val Gly Arg Leu Thr Gly Lys Pro Gly Val
65                  70                  75                  80 gtg tta gtc aca tca gga ccg ggt gcc tct aac ttg gca aca ggc ctg     288
Val Leu Val Thr Ser Gly Pro Gly Ala Ser Asn Leu Ala Thr Gly Leu
                85                  90                  95 ctg aca gcg aac act gaa gga gac cct gtc gtt gcg ctt gct gga aac     336
Leu Thr Ala Asn Thr Glu Gly Asp Pro Val Val Ala Leu Ala Gly Asn
            100                 105                 110
```

```
gtg atc cgt gca gat cgt tta aaa cgg aca cat caa tct ttg gat aat     384
Val Ile Arg Ala Asp Arg Leu Lys Arg Thr His Gln Ser Leu Asp Asn
        115                 120                 125 gcg gcg cta ttc cag ccg att aca aaa tac agt gta gaa gtt caa gat     432
Ala Ala Leu Phe Gln Pro Ile Thr Lys Tyr Ser Val Glu Val Gln Asp
        130                 135                 140 gta aaa aat ata ccg gaa gct gtt aca aat gca ttt agg ata gcg tca     480
Val Lys Asn Ile Pro Glu Ala Val Thr Asn Ala Phe Arg Ile Ala Ser
145                 150                 155                 160 gca ggg cag gct ggg gcc gct ttt gtg agc ttt ccg caa gat gtt gtg     528
Ala Gly Gln Ala Gly Ala Ala Phe Val Ser Phe Pro Gln Asp Val Val
                165                 170                 175 aat gaa gtc aca aat acg aaa aac gtg cgt gct gtt gca gcg cca aaa     576
Asn Glu Val Thr Asn Thr Lys Asn Val Arg Ala Val Ala Ala Pro Lys
            180                 185                 190 ctc ggt cct gca gca gat gat gca atc agt gcg gcc ata gca aaa atc     624
Leu Gly Pro Ala Ala Asp Asp Ala Ile Ser Ala Ala Ile Ala Lys Ile
        195                 200                 205 caa aca gca aaa ctt cct gtc gtt ttg gtc ggc atg aaa ggc gga aga     672
Gln Thr Ala Lys Leu Pro Val Val Leu Val Gly Met Lys Gly Gly Arg
        210                 215                 220 ccg gaa gca att aaa gcg gtt cgc aag ctt ttg aaa aag gtt cag ctt     720
Pro Glu Ala Ile Lys Ala Val Arg Lys Leu Leu Lys Lys Val Gln Leu
225                 230                 235                 240 cca ttt gtt gaa aca tat caa gct gcc ggt acc ctt tct aga gat tta     768
Pro Phe Val Glu Thr Tyr Gln Ala Ala Gly Thr Leu Ser Arg Asp Leu
                245                 250                 255 gag gat caa tat ttt ggc cgt atc ggt ttg ttc cgc aac cag cct ggc     816
Glu Asp Gln Tyr Phe Gly Arg Ile Gly Leu Phe Arg Asn Gln Pro Gly
            260                 265                 270 gat tta ctg cta gag cag gca gat gtt gtt ctg acg atc ggc tat gac     864
Asp Leu Leu Leu Glu Gln Ala Asp Val Val Leu Thr Ile Gly Tyr Asp
        275                 280                 285 ccg att gaa tat gat ccg aaa ttc tgg aat atc aat gga gac cgg aca     912
Pro Ile Glu Tyr Asp Pro Lys Phe Trp Asn Ile Asn Gly Asp Arg Thr
        290                 295                 300 att atc cat tta gac gag att atc gct gac att gat cat gct tac cag     960
Ile Ile His Leu Asp Glu Ile Ile Ala Asp Ile Asp His Ala Tyr Gln
305                 310                 315                 320 cct gat ctt gaa ttg atc ggt gac att ccg tcc acg atc aat cat atc    1008
Pro Asp Leu Glu Leu Ile Gly Asp Ile Pro Ser Thr Ile Asn His Ile
                325                 330                 335 gaa cac gat gct gtg aaa gtg gaa ttt gca gag cgt gag cag aaa atc    1056
Glu His Asp Ala Val Lys Val Glu Phe Ala Glu Arg Glu Gln Lys Ile
            340                 345                 350 ctt tct gat tta aaa caa tat atg cat gaa ggt gag cag gtg cct gca    1104
Leu Ser Asp Leu Lys Gln Tyr Met His Glu Gly Glu Gln Val Pro Ala
        355                 360                 365 gat tgg aaa tca gac aga gcg cac cct ctt gaa atc gtt aaa gag ttg    1152
Asp Trp Lys Ser Asp Arg Ala His Pro Leu Glu Ile Val Lys Glu Leu
        370                 375                 380 cgt aat gca gtc gat gat cat gtt aca gta act tgc gat atc ggt tcg    1200
Arg Asn Ala Val Asp Asp His Val Thr Val Thr Cys Asp Ile Gly Ser
385                 390                 395                 400 cac gcc att tgg atg tca cgt tat ttc cgc agc tac gag ccg tta aca    1248
His Ala Ile Trp Met Ser Arg Tyr Phe Arg Ser Tyr Glu Pro Leu Thr
                405                 410                 415 tta atg atc agt aac ggt atg caa aca ctc ggc gtt gcg ctt cct tgg    1296
Leu Met Ile Ser Asn Gly Met Gln Thr Leu Gly Val Ala Leu Pro Trp
            420                 425                 430
```

```
gca atc ggc gct tca ttg gtg aaa ccg gga gaa aaa gtg gtt tct gtc    1344
Ala Ile Gly Ala Ser Leu Val Lys Pro Gly Glu Lys Val Val Ser Val
        435                 440                 445 tct ggt gac ggc ggt ttc tta ttc tca gca atg gaa tta gag aca gca    1392
Ser Gly Asp Gly Gly Phe Leu Phe Ser Ala Met Glu Leu Glu Thr Ala
    450                 455                 460 gtt cga cta aaa gca cca att gta cac att gta tgg aac gac agc aca    1440
Val Arg Leu Lys Ala Pro Ile Val His Ile Val Trp Asn Asp Ser Thr
465                 470                 475                 480 tat gac atg gtt gca ttc cag caa ttg aaa aaa tat aac cgt aca tct    1488
Tyr Asp Met Val Ala Phe Gln Gln Leu Lys Lys Tyr Asn Arg Thr Ser
                485                 490                 495 gcg gtc gat ttc gga aat atc gat atc gtg aaa tat gcg gaa agc ttc    1536
Ala Val Asp Phe Gly Asn Ile Asp Ile Val Lys Tyr Ala Glu Ser Phe
            500                 505                 510 gga gca act ggc ttg cgc gta gaa tca cca gac cag ctg gca gat gtt    1584
Gly Ala Thr Gly Leu Arg Val Glu Ser Pro Asp Gln Leu Ala Asp Val
        515                 520                 525 ctg cgt caa ggc atg aac gct gaa ggt cct gtc atc atc gat gtc ccg    1632
Leu Arg Gln Gly Met Asn Ala Glu Gly Pro Val Ile Ile Asp Val Pro
    530                 535                 540 gtt gac tac agt gat aac att aat tta gca agt gac aag ctt ccg aaa    1680
Val Asp Tyr Ser Asp Asn Ile Asn Leu Ala Ser Asp Lys Leu Pro Lys
545                 550                 555                 560 gaa ttc ggg gaa ctc atg aaa acg aaa gct ctc tag                    1716
Glu Phe Gly Glu Leu Met Lys Thr Lys Ala Leu
                565                 570

<210> SEQ ID NO 56
<211> LENGTH: 571
<212> TYPE: PRT
<213> ORGANISM: Bacillus subtilis

<400> SEQUENCE: 56

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
```

-continued

```
                180                 185                 190
Leu Gly Pro Ala Ala Asp Asp Ala Ile Ser Ala Ala Ile Ala Lys Ile
            195                 200                 205

Gln Thr Ala Lys Leu Pro Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
            245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
            275                 280                 285

Pro Ile Glu Tyr Asp Pro Lys Phe Trp Asn Ile Asn Gly Asp Arg Thr
            290                 295                 300

Ile Ile His Leu Asp Glu Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
            370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
            450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
            485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
            530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570
```

ELECTRO-AUTOTROPHIC SYNTHESIS OF HIGHER ALCOHOLS

CROSS-REFERENCE TO RELATED APPLICATION

This application claims priority under 35 U.S.C. §119 to U.S. Provisional Application No. 61/295,656, filed Jan. 15, 2010, the disclosure of which is incorporated herein by reference.

STATEMENT OF GOVERNMENT LICENSE RIGHTS

This invention was made with Government support under Grant No. DE-AR0000085awarded by the United States Department of Energy. The Government has certain rights in this invention.

BACKGROUND

Biofuels are an alternative for fossil fuels. For example, isobutanol can be used as a high octane fuel for four-stroke internal combustion engines, as a pure component or in any portion as a mixture with gasoline. It has a high energy density (36 MJ/Kg) and low heat of vaporization (0.43 MJ/Kg), both of which satisfy the requirements (energy density ≥32 MJ/Kg, heat of vaporization <0.5 MJ/Kg) specified by this FOA. The research octane number of isobutanol is 110, which also satisfies the requirement (>85).

SUMMARY

The disclosure provides recombinant microorganisms that take advantage of the biological C—C bond formation capability without relying on inefficient photoenergy conversion (see, e.g., FIG. 1). Instead, reducing power is generated from electricity (including sunlight) to drive the metabolic process that forms C—C bonds necessary for liquid fuel synthesis. Thus, the microorganism of the disclosure utilizes man-made photoconversion and the biological C—C bond synthesis to make liquid fuels. The pathways engineered into microorganisms as described herein utilize electrically generated reducing mediators ($H_2$ or formate) to drive the "dark reaction" of $CO_2$ fixation. Both $H_2$ and formate can be used to reduce NAD(P)+ to NAD(P)H, which is then used as the reducing equivalent in $CO_2$ reduction, fuel synthesis, and ATP synthesis (FIG. 1C). Once $CO_2$ is fixed in a metabolic intermediate, such as pyruvate, it can be diverted to make isobutanol and other biofuels. The biological processes ($H_2$ or formate utilization, $CO_2$ fixation, fuel synthesis) can be independently or all engineered into the same cell so long as the pathway comprises $CO_2$ fixation and utilizes reducing mediators along with the specific biofuel pathway. Furthermore, bioreactors and electrolysis units can be integrated to form an electro-bio reaction unit.

The disclosure provides a recombinant microorganism capable of using $H_2$ or formate for reduction of $CO_2$ and wherein the microorganism produces an alcohol selected from the group consisting of 1-propanol, isobutanol, 1-butanol, 2-methyl 1-butanol, 3-methyl 1-butanol and 2-phenylethanol from $CO_2$ as the carbon source, wherein the alcohol is produced from a metabolite comprising a 2-keto acid. In one embodiment, the microorganism has a naturally occurring $H_2$ and/or formate reduction pathway and at least one recombinant enzyme for the production of an intermediate in the synthesis of the alcohol. In another embodiment, the microorganism comprises expression of a heterologous or overexpression of an endogenous carbon-fixation enzyme and heterologous or overexpression of a hydrogenase and/or formate dehydrogenase such that the microorganism can utilize $H_2$ and/or formate as a reducing metabolite. In any of the foregoing embodiments, the alcohol can be isobutanol. In yet another embodiment, the recombinant microorganism is obtained from a *Ralstonia* sp. parental organism. In another embodiment, the 2-keto acid is selected from the group consisting of 2-ketobutyrate, 2-ketoisovalerate, 2-ketovalerate, 2-keto 3-methylvalerate, 2-keto 4-methyl-pentanoate, and phenylpyruvate. In one embodiment, the microorganism comprises elevated expression or activity of a 2-keto-acid decarboxylase and an alcohol dehydrogenase, as compared to a parental microorganism. In one embodiment, the 2-keto-acid decarboxylase is selected from the group consisting of Pdc6, Aro10, Thi3, Kivd, and Pdc, or homolog thereof. In yet another embodiment, the 2-keto-acid decarboxylase is encoded by a nucleic acid sequence derived from a gene selected from the group consisting of PDC6, ARO10, THI3, kivd, and pdc, or homolog thereof. In a specific embodiment, the 2-keto-acid decarboxylase is encoded by a nucleic acid sequence derived from the kivd gene, or homolog thereof. In one embodiment, the alcohol dehydrogenase is Adh2, or homolog thereof. In another embodiment, the alcohol dehydrogenase is encoded by a nucleic acid sequence derived from the ADH2 gene, or homolog thereof. In another embodiment, the microorganism is selected from a genus of *Escherichia, Corynebacterium, Lactobacillus, Lactococcus, Salmonella, Enterobacter, Enterococcus, Erwinia, Pantoea, Morganella, Pectobacterium, Proteus, Ralstonia, Serratia, Shigella, Klebsiella, Citrobacter, Saccharomyces, Dekkera, Klyveromyces,* and *Pichia*. In one embodiment, not only does the organism comprise a pathway for utilizing H2 or formate but the organism also has a modification in the biosynthetic pathway for the production of an amino acid to produce the alcohol. The microorganism can also have reduced ethanol production capability compared to a parental microorganism. For examples, the microorganism comprises a reduction or inhibition in the conversion of acetyl-coA to ethanol. The microorganism can comprise a reduction of an ethanol dehydrogenase thereby providing a reduced ethanol production capability. In specific embodiments of any of the foregoing the microorganism produces greater than 100 mg/L of isobutanol in 40 hours from sugar. In another specific embodiments of any of the foregoing, the microorganism produces greater than 150 mg/L of 3-methyl-1-butanol in 40 hours from sugar. In another embodiment, the microorganism produces 120 mg/L of isobutanol or 180 mg/L of 3-methyl-1-butanol.

The disclosure also provides a method of producing a biofuel, comprising culturing a microorganism of any of the foregoing embodiments under conditions and in the presence or a suitable carbon source and reducing agent and isolating the biofuel. In one embodiment, the biofuel is isobutanol. In another embodiment, the reducing agent is formate or $H_2$. In yet a further embodiment, the microorganism is obtained from a *Ralstonia* sp. parental organism.

The disclosure also provides a bioreactor system comprising a source of H2 or formate, a source of energy to generate H2 or a combination thereof, a source of CO2 and a recombinant microorganism of the disclosure. In one embodiment, the disclosure can comprise a light source for photosynthesis.

DESCRIPTION OF THE FIGURES

FIG. 2A-G shows isobutyraldehyde, isobutanol production and cell growth in microorganism of the disclosure. FIGS. 2A-B show production directly from $CO_2$ using engineered cyanobacterium *S. elogatus*. A. cumulative production of isobutyraldehyde and B. Daily production of isobutyraldehyde. C. shows characterization of the enhanced enzyme activities for 2-KIV production. D. shows expression system for 2-KIV conversion into isobutanol. E. shows autotrophic production of isobutanol using recombinant *Ralstonia eutropha* LH74. F. shows the effect of different AHAS genes on isobutanol production in *Ralstonia*. G. shows autotrophic growth fo *R. eutropha* H16 on formate.

FIG. 3 depicts a nucleic acid sequence (SEQ ID NO:1) derived from a kivd gene encoding a polypeptide having 2-keto-acid decarboxylase activity.

FIG. 4 depicts a nucleic acid sequence (SEQ ID NO:3) derived from a PDC6 gene encoding a polypeptide having 2-keto-acid decarboxylase activity.

FIG. 5 depicts a nucleic acid sequence (SEQ ID NO:5) derived from an ARO10 gene encoding a polypeptide having 2-keto-acid decarboxylase activity.

FIG. 6 depicts a nucleic acid sequence (SEQ ID NO:7) derived from a THI3 gene encoding a polypeptide having 2-keto-acid decarboxylase activity.

FIG. 7 depicts a nucleic acid sequence (SEQ ID NO:9) derived from a pdc gene encoding a polypeptide having 2-keto-acid decarboxylase activity.

FIG. 8 depicts a nucleic acid sequence (SEQ ID NO:11) derived from an ADH2 gene encoding a polypeptide having alcohol dehydrogenase activity.

FIG. 9 depicts a nucleic acid sequence (SEQ ID NO:13) derived from an ilvIgene encoding a polypeptide having acetolactate synthase large subunit activity.

FIG. 10 depicts a nucleic acid sequence (SEQ ID NO:15) derived from an ilvH gene encoding a polypeptide having acetolactate synthase small subunit activity.

FIG. 11 depicts a nucleic acid sequence (SEQ ID NO:17) derived from an ilvC gene encoding a polypeptide having acetohydroxy acid isomeroreductase activity.

FIG. 12 depicts a nucleic acid sequence (SEQ ID NO:19) derived from an ilvD gene encoding a polypeptide having dihydroxy-acid dehydratase activity.

FIG. 13 depicts a nucleic acid sequence (SEQ ID NO:21) derived from an ilvA gene encoding a polypeptide having threonine dehydratase activity.

FIG. 14 depicts a nucleic acid sequence (SEQ ID NO:23) derived from a leuA gene encoding a polypeptide having 2-isopropylmalate synthase activity.

FIG. 15 depicts a nucleic acid sequence (SEQ ID NO:25) derived from a leuB gene encoding a polypeptide having beta-isopropylmalate dehydrogenase activity.

FIG. 16 depicts a nucleic acid sequence (SEQ ID NO:27) derived from a leuC gene encoding a polypeptide having isopropylmalate isomerase large subunit activity.

FIG. 17 depicts a nucleic acid sequence (SEQ ID NO:29) derived from a leuD gene encoding a polypeptide having isopropylmalate isomerase small subunit activity.

FIG. 18 depicts a nucleic acid sequence (SEQ ID NO:31) derived from a cimA gene encoding a polypeptide having alpha-isopropylmalate synthase activity.

FIG. 19 depicts a nucleic acid sequence (SEQ ID NO:33) derived from an ilvM gene encoding a polypeptide having acetolactate synthase large subunit activity.

FIG. 20 depicts a nucleic acid sequence (SEQ ID NO:35) derived from an ilvG gene encoding a polypeptide having acetolactate synthase small subunit activity.

FIG. 21 depicts a nucleic acid sequence (SEQ ID NO:37) derived from an ilvN gene encoding a polypeptide having acetolactate synthase large subunit activity.

FIG. 22 depicts a nucleic acid sequence (SEQ ID NO:39) derived from an ilvB gene encoding a polypeptide having acetolactate synthase small subunit activity.

FIG. 23 depicts. a nucleic acid sequence (SEQ ID NO:41) derived from an adhE2 gene encoding a polypeptide having alcohol dehydrogenase activity.

FIG. 24 depicts a nucleic acid sequence (SEQ ID NO:43) derived from a Li-cimA gene encoding a polypeptide having alpha-isopropylmalate synthase activity.

FIG. 25 depicts a nucleic acid sequence (SEQ ID NO:45) derived from a Li-leuC gene encoding a polypeptide having isopropylmalate isomerase large subunit activity.

FIG. 26 depicts a nucleic acid sequence (SEQ ID NO:47) derived from a Li-leuD gene encoding a polypeptide having isopropylmalate isomerase small subunit activity.

FIG. 27 depicts a nucleic acid sequence (SEQ ID NO:49) derived from a Li-leuB gene encoding a polypeptide having beta-isopropylmalate dehydrogenase activity.

FIG. 28 depicts a nucleic acid sequence (SEQ ID NO:51) derived from a pheA gene encoding a polypeptide having chorismate mutase P/prephenate dehydratase activity.

FIG. 29 depicts a nucleic acid sequence (SEQ ID NO:53) derived from a TyrA gene encoding a polypeptide having chorismate mutase T/prephenate dehydratase activity.

FIG. 30 depicts a nucleic acid sequence (SEQ ID NO:55) derived from an alsS gene encoding a polypeptide having acetolactate synthase activity.

DETAILED DESCRIPTION

Figure 1A:
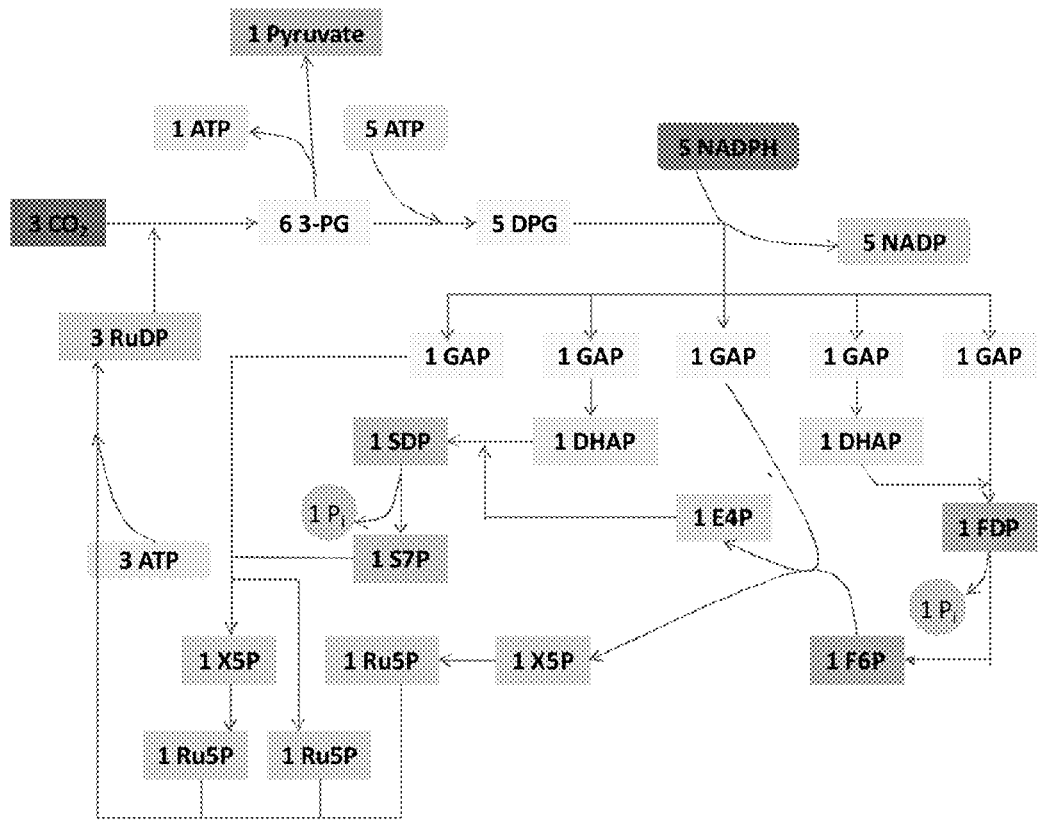
FIG. 1A-F shows various pathways described in the disclosure. A) shows $CO_2$ fixation to produce pyruvate via the CBB cycle. B) shows a general pathway for producing isobutanol from pyruvate. C) shows an electro-autotrophic pathway of the disclosure. D) shows various pathways for the production of biofuels. E) shows production of various keto acids from pyruvate. F) shows valine biosynthetic pathways used in *Ralstonia* eutropha.

As used herein and in the appended claims, the singular forms "a," "and," and "the" include plural referents unless the context clearly dictates otherwise. Thus, for example, reference to "a microorganism" includes a plurality of such microorganisms and reference to "the polypeptide" includes reference to one or more polypeptides known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of"

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The fixation of $CO_2$ into longer chain chemicals suitable for use as liquid fuels requires 1) formation of C—C bond, and 2) reduction of carbon. In plants and photosynthetic microorganisms, $CO_2$ fixation (the dark reaction) is coupled with the light reaction of photosynthesis, which produces the reducing power (NADPH) and energy (ATP). However, in various photosynthetic systems light penetration in culture environments can be limiting, reducing efficiency and fuel production.

Nature has evolved organisms that have decoupled the photosynthesis process required for producing reducing power. A group of microbes derive energy and reducing power from chemicals (chemoautotrophs) such as formate, or inorganics (lithoautotrophs) such as $H_2$ to drive $CO_2$ fixation. Examples of these organisms include *Ralstonia* (formerly *Alcaligenes*) and *Xanthobacter*. In particular, *Ralstonia eutropha* has been extensively studied for the production of polyhydroxyalkanoate (PHA) industrially. It is metabolically active and versatile, and grows reasonably fast. *Ralstonia* can use either $H_2$ or formate to drive $CO_2$ fixation through the CBB cycle. These organisms have hydrogenases and formate dehydrogenase to derive NAD(P)H from $H_2$ and formate, respectively. Thus, the NAD(P)H and ATP that are needed to drive $CO_2$ fixation are obtained either via the CBB or rTCA cycles. For example, NADH can be derived from $H_2$ via hydrogenases or formate via formate dehydrogenases. NADH can then be converted to NADPH via transhydrogenases. ATP is generated via the electron transport chain using $O_2$ as the terminal electron acceptor.

The disclosure provides methods and compositions for the production of higher alcohols using a culture of microorganisms that utilizes $CO_2$ as a carbon source and utilizes a non-light or light and non-light produced reducing agent for production of NADPH (e.g., chemoautotrophs, lithoautotrophes, photoautotrophs and any combination thereof).

The disclosure utilizes recombinant mioorganisms and engineered metabolic pathways for microbial production of higher alcohols. These pathways can be engineered into *E. coli*, *Saccharomyces cerevisiae*, *Bacillus subtilis*, *Clostridia*, *Ralstonia* (formerly *Alcaligenes*), *Xanthobacter* and *Corynebacteria*.

Examples of microorganisms that utilize $CO_2$ as a carbon source include photoautotrophs, chemoautotrophs and lithoautotrophs. In some embodiments, that methods and compositions comprise a co-culture of autotrophs, photoautotrophs and a photoheterotroph or a photoautotroph and a microorganism that cannot utilize $CO_2$ as a carbon source.

*S. elongatus* does not utilize $H_2$ or formate as an electron donor. In one embodiment, the disclosure provides recombinant microorganisms that comprise an engineered pathway (e.g., comprising a hydrogenase or formate dehydrogenase) to utilize $H_2$ or formate as an electron donor. In one embodiment, *S. elongatus* is engineered to utilize these electron sources and alter its innate regulation networks to fix $CO_2$ in the dark. On the other hand, *Ra. eutropha* and *Rh. palustris* are able to utilize $H_2$ or formate as electron sources to fix $CO_2$ in the dark. In these organisms, a biofuel production pathway that converts pyruvate or other suitable intermediate into the biofuel (e.g., isobutanol) is engineered into these microorganisms in an efficient way.

*E. coli*, for example, has three hydrogenases, of which at least one hydrogenase has been shown to be reversible. By using the native reversible hydrogenase of *E. coli* under high pressure of hydrogen in the culture or by overexpressing hydrogenases from other species (e.g., *Ra. eutropha*), *E. coli* can be engineered to harness the power of hydrogenase to use hydrogen as an energy source.

The disclosure can utilize such parental organisms with heterologous polynucleotides to promote the biosynthetic pathway for the production of biofuels. In one embodiment, *Ralstonia eutropha* is used as a host organism for isobutanol production. In other embodiments, the disclosure provides a recombinant microorganism that comprises a heterologous $CO_2$ fixation enzyme and a non-light producing reducing agent.

$H_2$ and formate are used as exemplary reducing mediators. $H_2$ can be generated from water hydrolysis, and formate can be generated by electrochemical reduction of $CO_2$. The former process has been extensively studied and industrial processes have been developed. Formate can be used as the electron mediator to circumvent the safety issue of $H_2$ utilization. $H_2$ can be transferred to the microbes, and the reducing power can be extracted by hydrogenase to drive the $CO_2$ fixation process. Formate can also be taken up by cells and produce NAD(P)H and $CO_2$ by formate dehydrogenase. NAD(P)H is then used to drive $CO_2$ fixation. $O_2$ is chosen as the terminal electron acceptor, as it is most environmentally friendly. Any other electron acceptors will cause too much environmental upset to be scalable.

The yield of isobutanol from sugar has already reached industrial level. Since the pathways developed take advantage of the keto acid chemistry, which is used in amino acid biosynthesis, they are readily compatible with many organisms. Furthermore, the pathway platform has been engineered in a photosynthetic microorganism, *Synechococcus elongatus* PCC7942, to produce isobutyraldehyde and isobutanol directly from $CO_2$ (see, e.g., FIG. 1). The engineered strain produced isobutanol with a production rate higher than those reported for ethanol, hydrogen, or lipid production from cyanobacteria or algae (FIG. 2).

This disclosure demonstrates that alternative reducing processes, other than photosynthesis light reactions, can be used. For example, $H_2$, formate and electricity can be used instead of photosynthesis to deliver chemical reducing power to drive $CO_2$ fixation using the Calvin-Benson-Bassham (CBB) cycle and the biosynthesis of isobutanol. The chemical redox mediator ($H_2$ or formate). $H_2$ and formate can be evenly distributed in a large volume to promote redox avoiding problems associated with light-penetration associated with photosynthesis.

$H_2$ and formic acid can be used as the reducing mediators. The selection will depend on efficiency of the overall process. $H_2$ can be generated from water hydrolysis, and formic acid can be generated by electrochemical reduction of $CO_2$. Both of these processes have been extensively studied and industrial processes have been developed. The efficiencies of these processes are similar. $H_2$ can be transferred to the microbes, and the reducing power can be extracted by hydrogenase to drive the $CO_2$ fixing process. Formic acid is the primary product of $CO_2$ reduction electrochemically with the highest current efficiency. It can also be taken up by cells and produce NAD(P)H and CO, by formate dehydrogenase. NAD(P)H is then used to drive $CO_2$ fixation.

The generation of $H_2$ and biochemical utilization are relatively straightforward. These two redox mediators are relatively inexpensive and can be dispersed in large volumes without high surface areas. $H_2$ and formate are produced from water and $CO_2$, respectively, and they are cycled back as such.

Competing alternatives include i) direct electrode coupling to cells such as *Geobactor*, ii) metal ions as mediators, iii)

other organic compounds as mediators. Direct electrode coupling requires high electrode surface areas to drive the slow biological reaction.

The cyanobacterium, *S. elongates*, can be engineered to accept $H_2$ and formate as electron donors, and to decouple the CBB cycle from the light reaction. The advantage of cyanobacteia is that they can also harvest sun light and thus can use photosynthesis wherever light is available and use reducing mediator wherever light is unavailable. This strategy allows the organism to use both solar energy directly or indirectly through mediators and solves the problem of large light area requirement of photosynthesis. Another advantage of cyanobacteria is that synthesis of isobutanol and isobutyraldehyde can be achieved in relatively high productivity.

TABLE 1

Reducing equivalent "[$H_2$]" and ATP equivalent "~P" needed for each $CO_2$ fixing pathway. "[$H_2$]" represents a two-electron donor, such as NAD(P)H, Flavin-$H_2$, or 2 reduced Ferredoxins. Total "[$H_2$]" = "[$H_2$]" + "~P"/2, with an assumption that P/O ration equals 2.

| Pathways | $CO_2$ | $H_2CO_3$ | "[$H_2$]" | "~P" | Total "[$H_2$]" |
|---|---|---|---|---|---|
| CBB | 6 | 0 | 12 | 14 | 19 |
| 3HP/glyoxylate | 0 | 6 | 12 | 14 | 19 |
| 3HP/4HB | 2 | 4 | 12 | 12 | 18 |
| reductive TCA | 6 | 0 | 12 | 4 | 14 |
| Wood-Ljundahl | 6 | 0 | 12 | 2 | 13 |

However, other pathways are typically used by thermophiles (Table 2).

TABLE 2

Comparison of different $CO_2$ fixation organisms

| Pathways | Organisms | litho/chemo autotrophic? | existing electon donor | growth temp | O2 sensitive? | doubling time | genetic tools | Comments |
|---|---|---|---|---|---|---|---|---|
| CBB | *Synechococcus elongatus* | to be engineered | photosynthesis | 30 C. | no | 4 h | available | produce isobtuanol |
|  | *Ralstonia eutropha* | yes | H2, Formate | 30 C. | no | 5-10 h | available | produce PHA |
| Reductive TCA | *Hydrogenobacter thermophilus* | yea | H2 | 70 C. | no | 15 h | no | low density culture |
|  | *Chlorobium limicola* | yes | thiosulfate | 26-29 C. | yes | 15-20 h | no | low density culture |
| Wood-Ljundahl | *Moorella thermoacetica* | yes | H2, formate | 55-60 C. | somewhat | 15-20 h | no | low density culture |

For example, $CO_2$ is converted to pyruvate, which is then converted to isobutanol via the keto acid pathway (FIG. 4). AlsS (from *B. subtilis*) and ilvCD (from *E. coli*), and kivd (from *Lactococcus lactis*) are the most effective in producing isobutanol and isobutyraldehyde, from keto acids and can be readily expressed in multiple organisms. These genes can be used initially to achieve isobutanol production.

The overall reaction of $CO_2$ fixation to isobutanol via the CBB cycle is calculated as follows:

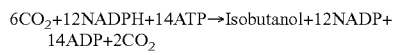

$6CO_2+12NADPH+14ATP \rightarrow Isobutanol+12NADP+14ADP+2CO_2$

The ATP expenditure is slightly better than the $CO_2$ production to glucose on a per carbon basis.

The CBB cycle is the most common and best studied pathway for $CO_2$ fixation. However, its energy expenditure is the highest, because it uses the high energy phospho-group to activate intermediates. Other competing pathways include the Wood-Ljundahl (reductive acetyl coA) pathway, the reductive TCA cycle, the 3-hydroxypropionate (3HP)/glyoxylate cycle, and the 3HP/4-hydroxybutyrate (4HP) cycle.

The overall reducing equivalent requirement and ATP equivalent requirement of each pathway are summarized in Table 1. Note that these pathways all have the same requirement for reducing equivalent, as it is dictated by the chemical structures of the substrate and the product. However, CBB and 3HP/glyoxylate are the most energy intensive, while the reductive TCA and Wood-Ljundahl pathways are most energy efficient. If the P/O ratio is assumed to be 2, the total reducing equivalent required by using CBB, pathway is 19, while the reduced TCA or Wood-Ljundahl pathways use 14 and 13 total reducing equivalents, respectively. The energy saving by using these more efficient pathways amounts to 26-30%.

For the above reasons, suitable hosts includes, for example, cyanobacteria, *S. elongates* and *R. eutropha*. *R. eutropha* can already use $H_2$ and formate as electron donors for $CO_2$ fixation, and has been used industrially for PHA synthesis. Its growth rate is acceptable and genetic tools are available. The isobutanol pathway genes (FIG. 4) can be expressed in *R. eutropha* to produce isobutanol from $CO_2$ and $H_2$ and formate. *S. elongates* has been used for isobutanol production from $CO_2$ with high productivity. *S. elongates* can be engineered to use $H_2$ or formate as electron donors by expressing hydrogenase and formate dehydrogenase. The organism can also be engineered to further inactivate innate regulations that coordinate the light reaction with the dark reaction. The resulting organism can use either light or electron mediators ($H_2$ or formate) to drive isobutanol production from $CO_2$.

In the recombinant microorganisms of the disclosure the CBB pathway genes are amplified and deregulated so that they are not subject to transcription level or protein level control. The use of electron mediators in low $O_2$ environment also reduces photorespiration of Rubisco, which is a major efficiency loss in photosynthesis. Ribulose-1,5-bisphosphate carboxylase oxygenase, most commonly known by the shorter name RuBisCO, is an enzyme (EC 4.1.1.39) that is used in the Calvin cycle to catalyze the first major step of carbon fixation, a process by which the atoms of atmospheric carbon dioxide are made available to organisms in the form of energy-rich molecules such as sucrose. RuBisCO catalyzes either the carboxylation or the oxygenation of ribulose-1,5-bisphosphate (also known as RuBP) with carbon dioxide or oxygen.

RuBisCO is one of the most abundant proteins on Earth. Accordingly, a number of homologs and variants of RuBisCO have been identified and generated. RuBisCo usually consists of two types of protein subunit, called the large chain (L, about 55,000 Da) and the small chain (S, about 13,000 Da). The enzymatically active substrate (ribulose 1,5-bisphosphate) binding sites are located in the large chains that form dimers in which amino acids from each large chain contribute to the binding sites. A total of eight large-chain dimers and eight small chains assemble into a larger complex of about 540,000 Da. In some proteobacteria and dinoflagellates, enzymes consisting of only large subunits have been found.

Magnesium ions ($Mg^{2+}$) are needed for enzymatic activity. Correct positioning of $Mg^{2+}$ in the active site of the enzyme involves addition of an "activating" carbon dioxide molecule ($CO_2$) to a lysine in the active site (forming a carbamate). Formation of the carbamate is favored by an alkaline pH. The pH and the concentration of magnesium ions in the fluid compartment (in plants, the stroma of the chloroplast) increases in the light.

During carbon fixation, the substrate molecules for RuBisCO are ribulose 1,5-bisphosphate, carbon dioxide and water. RuBisCO can also allow a reaction to occur with molecular oxygen ($O_2$) instead of carbon dioxide ($CO_2$).

When carbon dioxide is the substrate, the product of the carboxylase reaction is a highly unstable six-carbon phosphorylated intermediate known as 3-keto-2-carboxyarabinitol 1,5-bisphosphate, which decays into two molecules of glycerate 3-phosphate. The 3-phosphoglycerate can be used to produce larger molecules such as glucose. When molecular oxygen is the substrate, the products of the oxygenase reaction are phosphoglycolate and 3-phosphoglycerate. Phosphoglycolate initiates a sequence of reactions called photorespiration, which involves enzymes and cytochromes located in the mitochondria and peroxisomes. In this process, two molecules of phosphoglycolate are converted to one molecule of carbon dioxide and one molecule of 3-phosphoglycerate, which can reenter the Calvin cycle. Some of the phosphoglycolate entering this pathway can be retained by plants to produce other molecules such as glycine. Some plants, many algae, and photosynthetic bacteria have overcome this limitation by devising means to increase the concentration of carbon dioxide around the enzyme, including C4 carbon fixation, crassulacean acid metabolism and using pyrenoid.

RuBisCO is usually active only during the day because ribulose 1,5-bisphosphate is not being produced in the dark, due to the regulation of several other enzymes in the Calvin cycle. In addition, the activity of RuBisCO is coordinated with that of the other enzymes of the Calvin cycle.

In plants and some algae, another enzyme, RuBisCO activase is used in the formation of the carbamate in the active site of RuBisCO. Ribulose 1,5-bisphosphate (RuBP) substrate binds more strongly to the active sites lacking the carbamate and markedly slows down the "activation" process. In the light, RuBisCO activase promotes the release of the inhibitory RuBP from the catalytic sites. CA1P binds tightly to the active site of carbamoylated RuBisCO and inhibits catalytic activity. In the light, RuBisCO activase also promotes the release of CA1P from the catalytic sites. After the CA1P is released from RuBisCO, it is rapidly converted to a non-inhibitory form by a light-activated CA1P-phosphatase.

The removal of the inhibitory RuBP, CA1P, and the other inhibitory substrate analogs by activase requires the consumption of ATP. This reaction is inhibited by the presence of ADP, and, thus, activase activity depends on the ratio of these compounds in the chloroplast stroma. Furthermore, in most plants, the sensitivity of activase to the ratio of ATP/ADP is modified by the stromal reduction/oxidation (redox) state through another small regulatory protein, thioredoxin. In this manner, the activity of activase and the activation state of RuBisCO can be modulated in response to light intensity and, thus, the rate of formation of the ribulose 1,5-bisphosphate substrate.

In cyanobacteria, inorganic phosphate ($P_i$) participates in the coordinated regulation of photosynthesis. $P_i$ binds to the RuBisCO active site and to another site on the large chain where it can influence transitions between activated and less active conformations of the enzyme. Activation of bacterial RuBisCO might be particularly sensitive to $P_i$ levels which can act in the same way as RuBisCO activase in higher plants.

The disclosure provides, in some embodiments, recombinant microorganisms that utilize upregulated RuBisCO to promote carbon fixation and alcohol production in photosynthetic organism as described herein, while comprising a recombinant non-light engineered redox pathway for NADPH production and utilization.

Figure 1B:
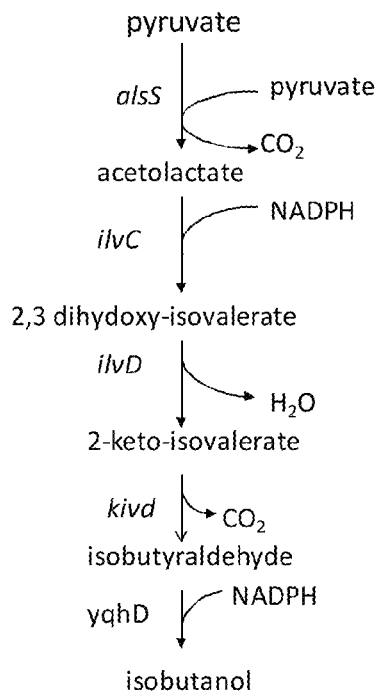
Figure 1C:
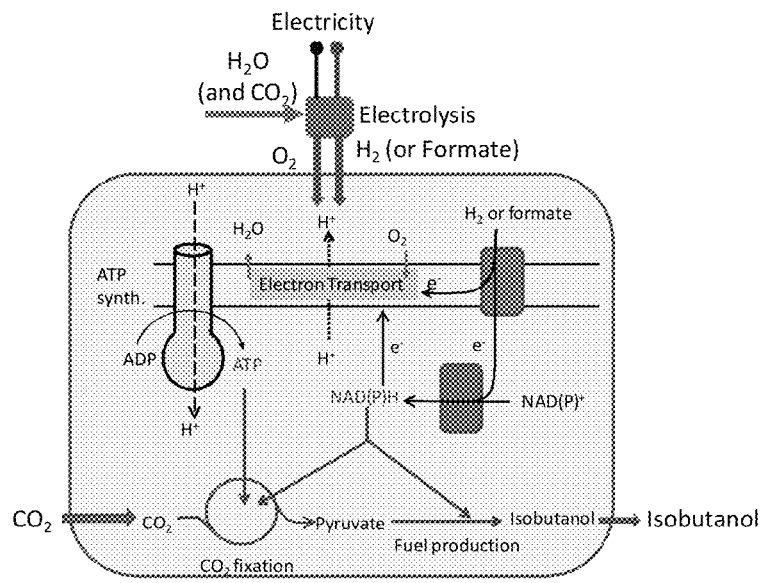
Figure 1D:
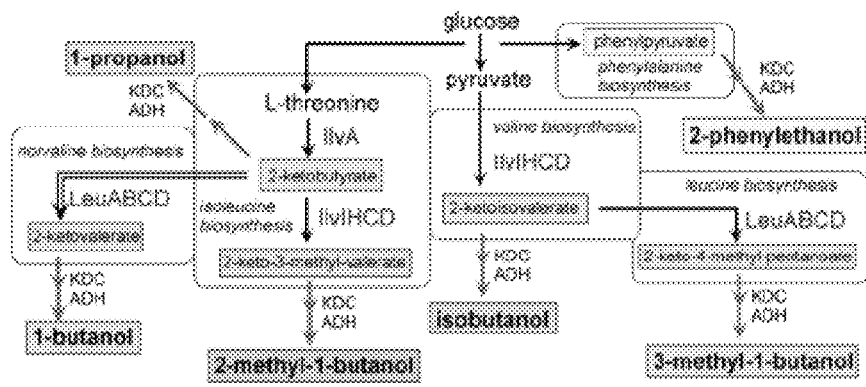
Figure 1E:
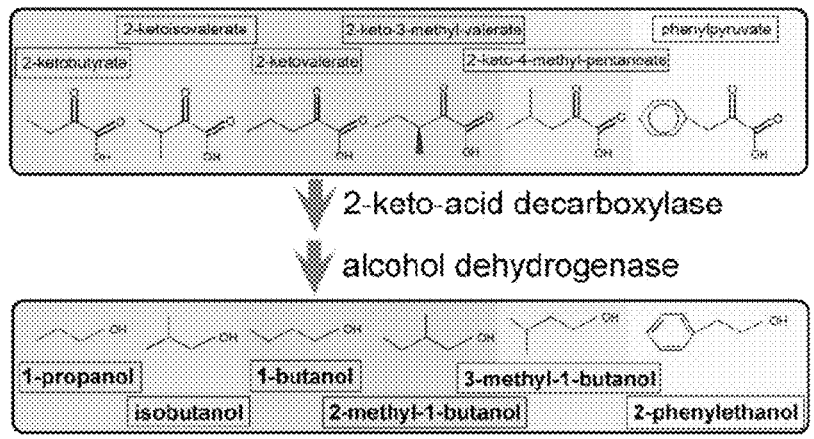

FIG. 1A shows a $CO_2$ fixation pathway to produce pyruvate via the CBB cycle. FIG. 1B shows a general pathway for production of isobutanol from pyruvate in a recombinant microorganism. FIG. 1C shows pathways for the production of various keto acids from pyruvate. Exemplary metabolites include glucose, pyruvate, 1-propanol, isobutanol, 1-butanol, 2-methyl 1-butanol, 3-methyl 1-butanol or 2-phenylethanol, and 2-keto acids. As depicted in FIG. 1C, exemplary 2-keto acids include 2-ketobutyrate, 2-ketoisovalerate, 2-ketovalerate, 2-keto 3-methylvalerate, 2-keto 4-methyl-pentanoate and phenylpyruvate. The exemplary 2-keto acids shown in FIG. 1C may be used as metabolic intermediates in the production of 1-propanol, isobutanol, 1-butanol, 2-methyl 1-butanol, 3-methyl 1-butanol or 2-phenylethanol. For example, as shown in FIG. 1C a recombinant microorganism metabolically engineered to provide elevated expression of enzymes encoded by LeuABCD produces 2-ketovalerate from 2-ketobutyrate. The 2-ketovalerate metabolite may be used to produce 1-butanol by additional enzymes produced by the metabolically modified microorganism. Additionally, 1-propanol and 2-methyl 1-butanol can be produced from 2-ketobutyrate and 2-keto-3-methyl-valerate by a recombinant microorganism metabolically engineered to express or over-express enzymes encoded by ilvIHDC, KDC and ADH genes. Further, the metabolite 2-ketoisovalerate can be produced by a recombinant microorganism metabolically engineered to express or over-express enzymes encoded by ilvIHCD genes. This metabolite can then be used in the production of isobutanol or 3-methyl 1-butanol. The metabolites pyruvate and phenylpyruvate can be used to produce 2-phenylethanol by a recombinant microorganism metabolically engineered to express or over-express enzymes encoded by KDC and ADH. Additional metabolites and genes are shown in FIG. 1C.

In various embodiments the metabolically engineered microorganisms or combination cultures provided herein include biochemical pathways for the production of higher alcohols including isobutanol, 1-butanol, 1-propanol, 2-methyl-1-butanol, 3-methyl-1-butanol and 2-phenylethanol from a suitable substrate. In various embodiments a recombinant microorganism provided herein includes the elevated expression or expression of a heterologous polypeptide of at least one target enzyme as compared to a parental microorganism. The recombinant microorganism also produces at least one metabolite involved in a biosynthetic pathway for the production of isobutanol, 1-butanol, 1-propanol, 2-methyl-1-butanol, 3-methyl-1-butanol or 2-phenylethanol. In general, the microorganisms or combination culture provided herein include at least one recombinant metabolic pathway that includes a target enzyme. The pathway acts to modify a substrate or metabolic intermediate in the production of isobutanol, 1-butanol, 1-propanol, 2-methyl-1-butanol, 3-methyl-1-butanol or 2-phenylethanol. The target enzyme is encoded by, and expressed from, a nucleic acid sequence derived from a suitable biological source. In some embodiments the polynucleotide is a gene derived from a bacterial or yeast source.

As used herein, the term "metabolically engineered" or "metabolic engineering" involves rational pathway design and assembly of biosynthetic genes, genes associated with operons, and control elements of such nucleic acid sequences, for the production of a desired metabolite, such as a 2-keto acid or high alcohol, in a microorganism. "Metabolically engineered" can further include optimization of metabolic flux by regulation and optimization of transcription, translation, protein stability and protein functionality using genetic engineering and appropriate culture condition. The biosynthetic genes can be heterologous to the host (e.g., microorganism), either by virtue of being foreign to the host, or being modified by mutagenesis, recombination, and/or association with a heterologous expression control sequence in an endogenous host cell. Appropriate culture conditions are conditions of culture medium pH, ionic strength, nutritive content, etc.; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. In an illustrative embodiment, the introduction of genetic material into a parental microorganism results in a new or modified ability to produce an alcohol such as 1-propanol, isobutanol, 1-butanol, 2-methyl 1-butanol, 3-methyl 1-butanol or 2-phenylethanol. The genetic material introduced into the parental microorganism contains gene(s), or parts of genes, coding for one or more of the enzymes involved in a biosynthetic pathway for the production of an alcohol and may also include additional elements for the expression and/or regulation of expression of these genes, e.g. promoter sequences.

Microorganisms provided herein are modified to produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate) in production of an intermediate (e.g., 2-keto acid) or in production of an end product (e.g., 1-propanol, isobutanol, 1-butanol, 2-methyl 1-butanol, 3-methyl 1-butanol or 2-phenylethanol) of metabolism. Metabolites can be used to construct more complex molecules, or they can be broken down into simpler ones. Intermediate metabolites may be synthesized from other metabolites used, for example, to make more complex substances, or broken down into simpler compounds, often with the release of chemical energy. End products of metabolism are the final result of the breakdown of other metabolites.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein. A "biomass derived sugar" includes, but is not limited to, molecules such as glucose, mannose, xylose, and arabinose or sugars or intermediates produced by a photosynthetic microorganism. The term biomass derived sugar encompasses suitable carbon substrates ordinarily used by microorganisms, such as 6 carbon sugars, including but not limited to glucose, lactose, sorbose, fructose, idose, galactose and mannose all in either D or L form, or a combination of 6 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

The term "alcohol" includes for example 1-propanol, isobutanol, 1-butanol, 2-methyl 1-butanol, 3-methyl 1-butanol or 2-phenylethanol. The term "1-butanol" generally refers to a straight chain isomer with the alcohol functional group at the terminal carbon. The straight chain isomer with the alcohol at an internal carbon is sec-butanol or 2-butanol. The branched isomer with the alcohol at a terminal carbon is isobutanol, and the branched isomer with the alcohol at the internal carbon is tert-butanol.

Accordingly, provided herein are recombinant microorganisms that produce isobutanol and in some embodiments may include the elevated expression of target enzymes such as acetohydroxy acid synthase (ilvIH operon), acetohydroxy acid isomeroreductase (ilvC), dihydroxy-acid dehydratase (ilvD), 2-keto-acid decarboxylase (PDC6, ARO10, THI3, kivd, or pdc), RuBisCo, furmate dehydrogenase and/or a hydrogenase, and alcohol dehydrogenase (ADH2). The microorganism may further include the deletion or inhibition of expression of an adh (e.g., an adhE), ldh (e.g., an ldhA), frd (e.g., an frdB, an frdC or an frdBC), fnr, pflB, or pta gene, or any combination thereof, to increase the availability of pyruvate. In some embodiments the recombinant microorganism may include the elevated expression of acetolactate synthase (alsS), acteohydroxy acid isomeroreductase (ilvC), dihydroxy-acid dehydratase (ilvD), 2-keto acid decarboxylase (PDC6, ARO10, TH13, kivd, or pdc), and alcohol dehydrogenase (ADH2). In one embodiment, the recombinant microorganism is an autophototroph or may be a non-photosynthetic organism recombinantly engineered to produce the alcohol that is cultured in combination with a autophototroph to fix $CO_2$. In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

Also provided are recombinant microorganisms that produce 1-butanol and may include the elevated expression of target enzymes such as 2-isopropylmalate synthase (leuA), beta-isopropylmalate dehydrogenase (leuB), isopropylmalate isomerase (leuCD operon), threonine dehydratase (ilvA). The microorganism may be a autophotroph microorganism or a non-photosynthetic or heterotrophic microorganism. The microorganism may further include decreased levels of 2-ketoisovalerate, 2-keto-3-methyl-valerate, or 2-keto-4-methyl-pentanoate, or any combination thereof, as compared to a parental microorganism. In addition, the microorganism may include the deletion or inhibition of expression of an ilvD gene, as compared to a parental microorganism. A recombinant microorganism that produces 1-butanol and may include further elevated expression or activity of pyruvate carboxylase, aspartate aminotransferase, homoserine dehydrogenase, aspartate-semialdehyde dehydrogenase, homoserine kinase, threonine synthase, L-serine dehydratase, and/or threonine dehydratase, encoded by a nucleic acid sequences derived from the ppc, pyc, aspC, thrA, asd, thrB, thrC, sdaAB, and tdcB genes, respectively. In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

Also provided are recombinant microorganisms that produce 1-propanol and may include the elevated expression of target enzymes such as alpha-isopropylmalate synthase (cimA), beta-isopropylmalate dehydrogenase (leuB), isopropylmalate isomerase (leuCD operon) and threonine dehydratase. In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

Also provided are recombinant microorganisms that produce 2-methyl 1-butanol and may include the elevated expression of target enzymes such as threonine dehydratase (ilvA or tdcB), acetohydroxy acid synthase (ilvIH operon), acetohydroxy acid isomeroreductase (ilvC), dihydroxy-acid dehydratase (ilvD), 2-keto-acid decarboxylase (PDC6, ARO10, THI3, kivd, and/or pdc, and alcohol dehydrogenase (ADH2). In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

Also provided are recombinant photoautotroph microorganism(s) or culture comprising a photoautotroph and a recombinant non-photosynthetic or photoheterotroph microorganism that produce 3-methyl 1-butanol and may include the elevated expression of target enzymes such as acetolactate synthase (alsS), acetohydroxy acid synthase (ilvIH), acetolactate synthase (ilvMG) or (ilvNB), acetohydroxy acid isomeroreductase (ilvC), dihydroxy-acid dehydratase (ilvD), 2-isopropylmalate synthase (leuA), isopropylmalate isomerase (leuCD operon), beta-isopropylmalate dehydrogenase (leuB), 2-keto-acid decarboxylase (kivd, PDC6, or THI3), and alcohol dehydrogenase (ADH2). In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

Also provided are recombinant photoautotroph microorganism(s) or culture comprising a photoautotroph and a recombinant non-photosynthetic or photoheterotroph microorganism that produce phenylethanol and may include the elevated expression of target enzymes such as chorismate mutase P/prephenate dehydratase (pheA), chorismate mutase T/prephenate dehydrogenase (tyrA), 2-keto-acid decarboxylase (kivd, PDC6, or THI3), and alcohol dehydrogenase (ADH2). In another embodiment, the recombinant microorganism is a photosynthetic microorganism comprising a decoupled light and dark reaction, wherein the dark reaction comprises a recombinant pathway that utilizes $H_2$ or formate as a reducing agent. In one embodiment, the microorganism comprise a heterologous hydrogenase and/or formate dehydrogenase. In another embodiment, the recombinant microorganism comprises a recombinant pathway that utilizes $H_2$ or formate as a reducing agent. In one embodiment, the microorganism comprise a heterologous hydrogenase and/or formate dehydrogenase.

As previously noted the target enzymes described throughout this disclosure generally produce metabolites. For example, the enzymes 2-isopropylmalate synthase (leuA), beta-isopropylmalate dehydrogenase (leuB), and isopropylmalate isomerase (leuCD operon) may produce 2-ketovalerate from a substrate that includes 2-ketobutyrate. In addition, the target enzymes described throughout this disclosure are encoded by nucleic acid sequences. For example, threonine dehydratase can be encoded by a nucleic acid sequence derived from an ilvA gene. Acetohydroxy acid synthase can be encoded by a nucleic acid sequence derived from an ilvIH operon. Acetohydroxy acid isomeroreductase can be encoded by a nucleic acid sequence derived from an ilvC gene. Dihydroxy-acid dehydratase can be encoded by a nucleic acid sequence derived from an ilvD gene. 2-keto-acid decarboxylase can be encoded by a nucleic acid sequence derived from a PDC6, ARO10, THI3, kivd, and/or pdc gene. Alcohol dehydrogenase can be encoded by a nucleic acid sequence derived from an ADH2 gene. Additional enzymes and exemplary genes are described throughout this document. Homologs of the various polypeptides and nucleic acid sequences can be derived from any biologic source that provides a suitable nucleic acid sequence encoding a suitable enzyme.

It is understood that a range of microorganisms can be modified to include a recombinant metabolic pathway suitable for the production of e.g., 1-propanol, isobutanol, 1-butanol, 2-methyl 1-butanol, 3-methyl 1-butanol or 2-phenylethanol. It is also understood that various microorganisms can act as "sources" for genetic material encoding target enzymes suitable for use in a recombinant microorganism provided herein. The term "microorganism" includes prokaryotic and eukaryotic photosynthetic microbial species and non-photosynthetic species. The terms "microbial cells" and "microbes" are used interchangeably with the term microorganism.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus*, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) Bacteroides, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Ralstonia, Rickettsia, Treponema,* and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces*.

Photoautotrophic bacteria are typically Gram-negative rods which obtain their energy from sunlight through the processes of photosynthesis. In this process, sunlight energy is used in the synthesis of carbohydrates, which in recombinant photoautotrophs can be further used as intermediates in the synthesis of biofuels. In other embodiment, the photoautotrophs serve as a source of carbohydrates for use by non-photosynthetic microorganism (e.g., recombinant *E. coli*) to produce biofuels by a metabolically engineered microorganism. Certain photoautotrophs called anoxygenic photoautotrophs grow only under anaerobic conditions and neither use water as a source of hydrogen nor produce oxygen from photosynthesis. Other photoautotrophic bacteria are oxygenic photoautotrophs. These bacteria are typically cyanobacteria. They use chlorophyll pigments and photosynthesis in photosynthetic processes resembling those in algae and complex plants. During the process, they use water as a source of hydrogen and produce oxygen as a product of photosynthesis.

Cyanobacteria include various types of bacterial rods and cocci, as well as certain filamentous forms. The cells contain thylakoids, which are cytoplasmic, platelike membranes containing chlorophyll. The organisms produce heterocysts, which are specialized cells believed to function in the fixation of nitrogen compounds.

The term "recombinant microorganism" and "recombinant host cell" are used interchangeably herein and refer to microorganisms that have been genetically modified to express or over-express endogenous nucleic acid sequences, or to express non-endogenous sequences, such as those included in a vector. The nucleic acid sequence generally encodes a target enzyme involved in a metabolic pathway for producing a desired metabolite as described above. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

A "parental microorganism" refers to a cell used to generate a recombinant microorganism. The term "parental microorganism" describes a cell that occurs in nature, i.e. a "wild-type" cell that has not been genetically modified. The term "parental microorganism" also describes a cell that has been genetically modified but which does not express or over-express a target enzyme e.g., an enzyme involved in the biosynthetic pathway for the production of a desired metabolite such as 1-propanol, isobutanol, 1-butanol, 2-methyl 1-butanol, 3-methyl 1-butanol or 2-phenylethanol. For example, a wild-type microorganism can be genetically modified to express or over express a first target enzyme such as thiolase. This microorganism can act as a parental microorganism in the generation of a microorganism modified to express or over-express a second target enzyme e.g., hydroxybutyryl CoA dehydrogenase. In turn, the microorganism modified to express or over express e.g., thiolase and hydroxybutyryl CoA dehydrogenase can be modified to express or over express a third target enzyme e.g., crotonase. Accordingly, a parental microorganism functions as a reference cell for successive genetic modification events. Each modification event can be accomplished by introducing a nucleic acid molecule in to the reference cell. The introduction facilitates the expression or over-expression of a target enzyme. It is understood that the term "facilitates" encompasses the activation of endogenous nucleic acid sequences encoding a target enzyme through genetic modification of e.g., a promoter sequence in a parental microorganism. It is further understood that the term "facilitates" encompasses the introduction of exogenous nucleic acid sequences encoding a target enzyme in to a parental microorganism.

In another embodiment a method of producing a recombinant microorganism that converts a suitable carbon substrate (including $CO_2$) to e.g., 1-propanol, isobutanol, 1-butanol, 2-methyl 1-butanol, 3-methyl 1-butanol or 2-phenylethanol is provided. The method includes transforming a microorganism with one or more recombinant nucleic acid sequences encoding polypeptides that include e.g., a hydrogenase and/or a formate dehydrogenase, acetohydroxy acid synthase operon), acetohydroxy acid isomeroreductase (ilvC), dihydroxy-acid dehydratase (ilvD), 2-keto-acid decarboxylase (PDC6, ARO10, THI3, kivd, or pdc), 2-isopropylmalate synthase (leuA), beta-isopropylmalate dehydrogenase (leuB), isopropylmalate isomerase (leuCD operon), threonine dehydratase (ilvA), alpha-isopropylmalate synthase (cimA), beta-isopropylmalate dehydrogenase (leuB), isopropylmalate isomerase (leuCD operon), threonine dehydratase (ilvA), acetolactate synthase (ilvMG or ilvNB), acetohydroxy acid isomeroreductase (ilvC), dihydroxy-acid dehydratase (ilvD), beta-isopropylmalate dehydrogenase (leuB), chorismate mutase P/prephenate dehydratase (pheA), chorismate mutase T/prephenate dehydrogenase (tyrA), 2-keto-acid decarboxylase (kivd, PDC6, or THI3), and alcohol dehydrogenase activity. Nucleic acid sequences that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. It is understood that the addition of sequences which do not alter the encoded activity of a nucleic acid molecule, such as the addition of a non-functional or non-coding sequence, is a conservative variation of the basic nucleic acid. The "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

A "protein" or "polypeptide", which terms are used interchangeably herein, comprises one or more chains of chemical building blocks called amino acids that are linked together by chemical bonds called peptide bonds. An "enzyme" means any substance, composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

Accordingly, homologs of enzymes useful for generating metabolites (e.g., keto thiolase, acetyl-CoA acetyltransferase, hydroxybutyryl CoA dehydrogenase, crotonase, crotonyl-CoA reductase, butyryl-coA dehydrogenase, alcohol dehydrogenase (ADH)) are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm when comparing a inhibitory molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

It is understood that the nucleic acid sequences described above include "genes" and that the nucleic acid molecules described above include "vectors" or "plasmids." For example, a nucleic acid sequence encoding a keto thiolase can be encoded by an atoB gene or homolog thereof, or an fadA gene or homolog thereof. Accordingly, the term "gene", also called a "structural gene" refers to a nucleic acid sequence that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence. The term "nucleic acid" or "recombinant nucleic acid" refers to polynucleotides such as deoxyribonucleic acid (DNA), and, where appropriate, ribonucleic acid (RNA). The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The term "operon" refers two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

Those of skill in the art will recognize that, due to the degenerate nature of the genetic code, a variety of DNA compounds differing in their nucleotide sequences can be used to encode a given amino acid sequence of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate embodiments of the disclosure.

The disclosure provides nucleic acid molecules in the form of recombinant DNA expression vectors or plasmids, as described in more detail below, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) forms.

Provided herein are methods for the heterologous expression of one or more of the biosynthetic genes involved in 1-propanol, isobutanol, 1-butanol, 2-methyl 1-butanol, 3-methyl 1-butanol, and/or 2-phenylethanol biosynthesis and recombinant DNA expression vectors useful in the method. Thus, included within the scope of the disclosure are recombinant expression vectors that include such nucleic acids. The term expression vector refers to a nucleic acid that can be introduced into a host microorganism or cell-free transcription and translation system. An expression vector can be maintained permanently or transiently in a microorganism, whether as part of the chromosomal or other DNA in the microorganism or in any cellular compartment, such as a replicating vector in the cytoplasm. An expression vector also comprises a promoter that drives expression of an RNA, which typically is translated into a polypeptide in the microorganism or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host microorganisms containing the vector can be identified and/or selected, may also be present in an expression vector. Selectable markers, i.e., genes that confer antibiotic resistance or sensitivity, are used and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433) can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

Due to the inherent degeneracy of the genetic code, other nucleic acid sequences which encode substantially the same or a functionally equivalent amino acid sequence can also be used to clone and express the polynucleotides encoding such enzymes. As previously noted, the term "host cell" is used interchangeably with the term "recombinant microorganism" and includes any cell type which is suitable for producing e.g., 1-propanol, isobutanol, 1-butanol, 2-methyl 1-butanol, 3-methyl 1-butanol and/or 2-phenylethanol and susceptible to transformation with a nucleic acid construct such as a vector or plasmid.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

A nucleic acid of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated nucleic acid molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment a method for producing e.g., 1-propanol, isobutanol, 1-butanol, 2-methyl 1-butanol, 3-methyl 1-butanol or 2-phenylethanol is provided. The method includes culturing a recombinant photoautotroph microorganism(s) or culture comprising a photoautotroph and a recombinant non-photosynthetic or photoheterotroph microorganism as provided herein in the presence of a suitable substrate (e.g., $CO_2$) and under conditions suitable for the conversion of the substrate to 1-propanol, isobutanol, 1-butanol, 2-methyl 1-butanol, 3-methyl 1-butanol or 2-phenylethanol. The alcohol produced by a microorganism or culture provided herein can be detected by any method known to the skilled artisan. Culture conditions suitable for the growth and maintenance of a recombinant microorganism provided herein are described in the Examples below. The skilled artisan will recognize that such conditions can be modified to accommodate the requirements of each microorganism.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Several thousand Ribulose-1,5-bisphosphate carbxylase/oxygenase and other $CO_2$ fixation enzymes are known and their sequences are readily available in the art using various search criteria and web-sites. For example, the methods and compositions of the disclosure may utilize Ribulose-1,5-bisphosphate carboxylase/oxygenase (RubisCo)—small subunit—cbbS, Ribulose-1,5-bisphosphate carbyxlase/oxygenase (RubisCo)—large subunit cbbL, Rubisco activase, rbcL, rbcS and variants and homologs thereof in the disclosure. In yet other related embodiments, the engineered can further comprise engineered rbcL nucleic acid, engineered rbcS nucleic acid, and engineered phosphoribulokinase. Rubisco polypeptides of the useful in the disclosure include Rubisco large subunit polypeptides ("rbcL"), Rubisco small subunit polypeptides ("rbcS"), and Rubisco large/small polypeptides ("rbcLS"). Large and small subunits may be combined in different combinations with each other together in a single enzyme having Rubisco specific activity. Alternatively, the large and small subunits of the may be combined with the large and small subunits from a wild type Rubisco polypeptides to form a polypeptide having Rubisco activity. Exemplary ribulose-1,5-bisphosophate carboxylase/oxygenases include spinach form I Rubisco Spinacia oleracea; gi:7636117; CAB88737, Archaeoglobus fulgidus DSM 4304 rbcL-1 (gi:2648975; AAB86661); Sinorhizobium meliloti 1021 (gi:15140252; CAC48779); Mesorhizobium loti MAFF303099 (gi:14026595; BAB53192); Chlorobium limicola f. thiosulfatophilum (gi:13173182; AAK14332); C. tepidum TLS (gi:21647784; AAM72993); R. palustris (gi:78490428; ZP_00842677); R. palustris (gi:77687805; ZP_00802991); R. rubrum (gi:48764419; ZP_00268971); Bordetella bronchiseptica RB50 (gi:33567621; CAE31534); Burkholderia fungorum LB400 (gi:48788861; ZP_00284840); B. clausii KSM-K16 (gi:56909783; BAD64310); Bacillus thuringiensis serovar konkukian strain 97-27 (gi:49333072; AAT63718); Geobacillus kaustophilus HTA426 (gi:56379330; BAD75238); Bacillus licheniformis ATCC14580 (gi:52003120; AAU23062); Bacillus anthracis strain A2012 (gi:65321428; ZP_00394387); Bacillus cereus E33L (gi:51974924; AAU16474); B. subtilis subsp. subtilis strain 168 (gi:2633730; CAB 13232). Accession numbers are from GenBank and sequences associated with those accession numbers are incorporated herein by reference. In addition, variants comprising RuBisCo activity and having at least 85%, 90%, 95%, 98%, 99% identity to any of the foregoing sequences is also encompassed by the disclosure.

Ethanol Dehydrogenase (also referred to as Aldehyde-alcohol dehydrogenase) is encoded in E. coli by adhE. adhE comprises three activities: alcohol dehydrogenase (ADH); acetaldehyde/acetyl-CoA dehydrogenase (ACDH); pyruvate-formate-lyase deactivase (PFL deactivase); PFL deactivase activity catalyzes the quenching of the pyruvate-formate-lyase catalyst in an iron, NAD, and CoA dependent reaction. Homologs are known in the art (see, e.g., aldehyde-alcohol dehydrogenase (Polytomella sp. Pringsheim 198.80) gi|40644910|emb|CAD42653.2|(40644910); aldehyde-alcohol dehydrogenase (Clostridium botulinum A str. ATCC 3502) gi|148378348|ref|YP_001252889.1|(148378348); aldehyde-alcohol dehydrogenase (Yersinia pestis CO92) gi|16122410|ref|NP_405723.1|(16122410); aldehyde-alcohol dehydrogenase (Yersinia pseudotuberculosis IP 32953) gi|51596429|ref|YP_070620.1|(51596429); aldehyde-alcohol dehydrogenase (Yersinia pestis CO92) gi|115347889|emb|CAL20810.1|(115347889); aldehyde-alcohol dehydrogenase (Yersinia pseudotuberculosis IP 32953) gi|51589711|emb|CAH21341.1|(51589711); Aldehyde-alcohol dehydrogenase (Escherichia coli CFT073) gi|26107972|gb|AAN80172.1|AE016760_3|(26107972); aldehyde-alcohol dehydrogenase (Yersinia pestis biovar Microtus str. 91001) gi|45441777|ref|NP_993316.1|(45441777); aldehyde-alcohol dehydrogenase (Yersinia pestis biovar Microtus str. 91001) gi|45436639|gb|AAS62193.1|(45436639); aldehyde-alcohol dehydrogenase (Clostridium perfringens ATCC 13124) gi|10798574|ref|YP_697219.1|(110798574); aldehyde-alcohol dehydrogenase (Shewanella oneidensis MR-1)gi|24373696|ref|NP_717739.1|(24373696); aldehyde-alcohol dehydrogenase (Clostridium botulinum A str. ATCC 19397) gi|153932445|ref|YP_001382747.1|(153932445); aldehyde-alcohol dehydrogenase (Yersinia pestis biovar Antigua str. E1979001) gi|165991833|gb|EDR44134.1|(165991833); aldehyde-alcohol dehydrogenase (Clostridium botulinum A str. Hall) gi|153937530|ref|YP_001386298.1|(153937530); aldehyde-alcohol dehydrogenase (Clostridium perfringens ATCC 13124) gi|110673221|gb|ABG82208.1|(110673221); aldehyde-alcohol dehydrogenase (Clostridium botulinum A str. Hall) gi|152933444|gb|ABS38943.1|(152933444); aldehyde-alcohol dehydrogenase (Yersinia pestis biovar Orientalis str. F1991016) gi|165920640|gb|EDR37888.1|(165920640); aldehyde-alcohol dehydrogenase (Yersinia pestis biovar Orientalis str. IP275) gi|165913933|gb|EDR32551.1|(165913933); aldehyde-alcohol dehydrogenase (Yersinia pestis Angola) gi|162419116|ref|YP_001606617.1|(162419116); aldehyde-alcohol dehydrogenase (Clostridium botulinum F str. Langeland) gi|153940830|ref|YP_001389712.1|(153940830); aldehyde-alcohol dehydrogenase (Escherichia coli HS) gi|157160746|ref|YP_001458064.1|(157160746); aldehyde-alcohol dehydrogenase (Escherichia coli E24377A) gi|157155679|ref|YP_001462491.1|(157155679); aldehyde-alcohol dehydrogenase (Yersinia enterocolitica subsp. enterocolitica 8081) gi|123442494|ref|YP_001006472.1|(123442494); aldehyde-alcohol dehydrogenase (Synechococcus sp. JA-3-3Ab) gi|86605191|ref|YP_473954.1|(86605191); aldehyde-alcohol dehydrogenase (Listeria monocytogenes str. 4b F2365) gi|46907864|ref|YP_014253.1|(46907864); aldehyde-alcohol dehydrogenase (Enterococcus faecalis V583) gi|29375484|ref|NP_814638.1|(29375484); aldehyde-alcohol dehydrogenase (Streptococcus agalactiae 2603V/R) gi|22536238|ref|NP_687089.1|(22536238); aldehyde-alcohol dehydrogenase (Clostridium botulinum A str. ATCC 19397) gi|152928489|gb|ABS33989.1|(152928489); aldehyde-alcohol dehydrogenase (Escherichia coli E24377A) gi|157077709|gb|ABV17417.1|(157077709); aldehyde-alcohol dehydrogenase (Escherichia coli HS) gi|157066426|gb|ABV05681.1|(157066426); aldehyde-alcohol dehydrogenase (Clostridium botulinum F str. Langeland) gi|152936726|gb|ABS42224.1|(152936726); aldehyde-alcohol dehydrogenase (Yersinia pestis CA88-4125) gi|149292312|gb|EDM42386.1|(149292312); aldehyde-alcohol dehydrogenase (Yersinia enterocolitica subsp. enterocolitica 8081) gi|122089455|emb|CAL12303.1|(122089455); aldehyde-alcohol dehydrogenase (Chlamydomonas reinhardtii) gi|92084840|emb|CAF04128.1|(92084840); aldehyde-alcohol dehydrogenase (Synechococcus sp. JA-3-3Ab) gi|86553733|gb|ABC98691.1|(86553733); aldehyde-alcohol dehydrogenase (Shewanella oneidensis MR-1) gi|24348056|gb|AAN55183.1|AE015655_9(24348056); aldehyde-alcohol dehydrogenase (Enterococcus faecalis V583) gi|29342944|gb|AAO80708.1|(29342944); aldehyde-alcohol dehydrogenase (Listeria monocytogenes str. 4b F2365) gi|46881133|gb|AAT04430.1|(46881133); aldehyde-alcohol dehydrogenase (Listeria monocytogenes str. 1/2a F6854) gi|47097587|ref|ZP_00235115.1|(47097587); aldehyde-alcohol dehydrogenase (Listeria monocytogenes str. 4b H7858) gi|47094265|ref|ZP_00231973.1|(47094265); aldehyde-alcohol dehydrogenase (Listeria monocytogenes str. 4b H7858)

gi|47017355|gb|EAL08180.1|(47017355); aldehyde-alcohol dehydrogenase (*Listeria monocytogenes* str. 1/2a F6854) gi|47014034|gb|EAL05039.1|(47014034); aldehyde-alcohol dehydrogenase (*Streptococcus agalactiae* 2603V/R) gi|22533058|gb|AAM98961.1|AE014194_6(22533058)p; aldehyde-alcohol dehydrogenase (*Yersinia pestis* biovar Antigua str. E1979001) gi|166009278|ref|ZP_02230176.1|(166009278); aldehyde-alcohol dehydrogenase (*Yersinia pestis* biovar Orientalis str. IP275) gi|165938272|ref|ZP_02226831.1|(165938272); aldehyde-alcohol dehydrogenase (*Yersinia pestis* biovar Orientalis str. F1991016) gi|165927374|ref|ZP_02223206.1|(165927374); aldehyde-alcohol dehydrogenase (*Yersinia pestis* Angola) gi|162351931|gb|ABX85879.1|(162351931); aldehyde-alcohol dehydrogenase (*Yersinia pseudotuberculosis* IP 31758) gi|153949366|ref|YP_001400938.1|(153949366); aldehyde-alcohol dehydrogenase (*Yersinia pseudotuberculosis* IP 31758) gi|152960861|gb|ABS48322.1|(152960861); aldehyde-alcohol dehydrogenase (*Yersinia pestis* CA88-4125) gi|149365899|ref|ZP_01887934.1|(149365899); Acetaldehyde dehydrogenase (acetylating) (*Escherichia coli* CFT073) gi|26247570|ref|NP_753610.1|(26247570); aldehyde-alcohol dehydrogenase (includes: alcohol dehydrogenase; acetaldehyde dehydrogenase (acetylating) (EC 1.2.1.10) (acdh); pyruvate-formate-lyase deactivase (pfl deactivase)) (*Clostridium botulinum* A str. ATCC 3502) gi|148287832|emb|CAL81898.1|(148287832); aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152980|sp|P0A9Q7.2|ADHE_ECOLI(71152980); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCR11043) gi|50121254|ref|YP_050421.1|(50121254); aldehyde-alcohol dehydrogenase (includes: alcohol dehydrogenase and acetaldehyde dehydrogenase, and pyruvate-formate-lyase deactivase (*Erwinia carotovora* subsp. *atroseptica* SCR11043) gi|49611780|emb|CAG75229.1|(49611780); Aldehyde-alcohol dehydrogenase (Includes: Alcohol dehydrogenase (ADH); Acetaldehyde dehydrogenase (acetylating) (ACDH)) gi|19858620|sp|P33744.3|ADHE_CLOAB(19858620); Aldehyde-alcohol dehydrogenase (Includes: Alcohol dehydrogenase (ADH); Acetaldehyde dehydrogenase (acetylating) (ACDH); Pyruvate-formate-lyase deactivase (PFL deactivase)) gi|71152683|sp|P0A9Q8.2|ADHE_ECO57 (71152683); aldehyde-alcohol dehydrogenase (includes: alcohol dehydrogenase; acetaldehyde dehydrogenase (acetylating); pyruvate-formate-lyase deactivase (*Clostridium difficile* 630) gi|126697906|ref|YP_001086803.1|(126697906); aldehyde-alcohol dehydrogenase (includes: alcohol dehydrogenase; acetaldehyde dehydrogenase (acetylating); pyruvate-formate-lyase deactivase (*Clostridium difficile* 630) gi|115249343|emb|CAJ67156.1|(115249343); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|37526388|ref|NP_929732.1|(37526388); aldehyde-alcohol dehydrogenase 2 (includes: alcohol dehydrogenase; acetaldehyde dehydrogenase) (*Streptococcus pyogenes* str. Manfredo) gi|134271169|emb|CAM29381.1|(134271169); Aldehyde-alcohol dehydrogenase (includes: alcohol dehydrogenase (ADH) and acetaldehyde dehydrogenase (acetylating) (ACDH); pyruvate-formate-lyase deactivase (PFL deactivase)) (*Photorhabdus luminescens* subsp. *laumondii* TTO1) gi|136785819|emb|CAE14870.1|(36785819); aldehyde-alcohol dehydrogenase (includes: alcohol dehydrogenase and pyruvate-formate-lyase deactivase (*Clostridium difficile* 630) gi|126700586|ref|YP_001089483.1|(126700586); aldehyde-alcohol dehydrogenase (includes: alcohol dehydrogenase and pyruvate-formate-lyase deactivase (*Clostridium difficile* 630) gi|115252023|emb|CAJ69859.1|(115252023); aldehyde-alcohol dehydrogenase 2 (*Streptococcus pyogenes* str. Manfredo) gi|139472923|ref|YP_001127638.1|(139472923); aldehyde-alcohol dehydrogenase E (*Clostridium perfringens* str. 13) gi|18311513|ref|NP_563447.1|(18311513); aldehyde-alcohol dehydrogenase E (*Clostridium perfringens* str. 13) gi|18146197|dbj|BAB82237.1|(18146197); Aldehyde-alcohol dehydrogenase, ADHE1 (*Clostridium acetobutylicum* ATCC 824) gi|15004739|ref|NP_149199.1|(15004739); Aldehyde-alcohol dehydrogenase, ADHE1 (*Clostridium acetobutylicum* ATCC 824) gi|14994351|gb|AAK76781.1|AE001438_34(14994351); Aldehyde-alcohol dehydrogenase 2 (Includes: Alcohol dehydrogenase (ADH); acetaldehyde/acetyl-CoA dehydrogenase (ACDH)) gi|2492737|sp|Q24803.1|ADH2_ENTHI (2492737); alcohol dehydrogenase (*Salmonella enterica* subsp. *enterica* serovar Typhi str. CT18) gi|16760134|ref|NP_455751.1|(16760134); and alcohol dehydrogenase (*Salmonella enterica* subsp. *enterica* serovar Typhi) gi|16502428|emb|CAD08384.1|(16502428)), each sequence associated with the accession number is incorporated herein by reference in its entirety.

Lactate Dehydrogenase (also referred to as D-lactate dehydrogenase and fermentive dehydrognase) is encoded in *E. coli* by ldhA and catalyzes the NADH-dependent conversion of pyruvate to D-lactate. ldhA homologs and variants are known. In fact there are currently 1664 bacterial lactate dehydrogenases available through NCBI. For example, such homologs and variants include, for example, D-lactate dehydrogenase (D-LDH) (Fermentative lactate dehydrogenase) gi|1730102|sp|P52643.1|LDHD_ECOLI(1730102); D-lactate dehydrogenase gi|1049265|gb|AAB51772.1|(1049265); D-lactate dehydrogenase (*Escherichia coli* APEC O1) gi|117623655|ref|YP_852568.1|(117623655); D-lactate dehydrogenase (*Escherichia coli* CFT073) gi|26247689|ref|NP_753729.1|(26247689); D-lactate dehydrogenase (*Escherichia coli* O157:H7 EDL933) gi|15801748|ref|NP_287766.1|(15801748); D-lactate dehydrogenase (*Escherichia coli* APEC O1) gi|115512779|gb|ABJ00854.1|(115512779); D-lactate dehydrogenase (*Escherichia coli* CFT073) gi|26108091|gb|AAN80291.1|AE016760_150(26108091); fermentative D-lactate dehydrogenase, NAD-dependent (*Escherichia coli* K12) gi|16129341|ref|NP_415898.1|(16129341); fermentative D-lactate dehydrogenase, NAD-dependent (*Escherichia coli* UTI89) gi|91210646|ref|IP_540632.1|(91210646); fermentative D-lactate dehydrogenase, NAD-dependent (*Escherichia coli* K12) gi|1787645|gb|AAC74462.1|(1787645); fermentative D-lactate dehydrogenase, NAD-dependent (*Escherichia coli* W3110) gi|89108227|ref|AP_002007.1|(89108227); fermentative D-lactate dehydrogenase, NAD-dependent (*Escherichia coli* W3110) gi|1742259|dbj|BAA14990.1|(1742259); fermentative D-lactate dehydrogenase, NAD-dependent (*Escherichia coli* UTI89) gi|91072220|gb|ABE07101.1|(91072220); fermentative D-lactate dehydrogenase, NAD-dependent (*Escherichia coli* O157:H7 EDL933) gi|12515320|gb|AAG56380.1|AE005366_6(12515320); fermentative D-lactate dehydrogenase. (*Escherichia coli*

O157:H7 str. Sakai) gi|13361468|dbj|BAB35425.1| (13361468); COG1052: Lactate dehydrogenase and related dehydrogenases (*Escherichia coli* 101-1) gi|83588593|ref|ZP_00927217.1|(83588593); COG1052: Lactate dehydrogenase and related dehydrogenases (*Escherichia coli* 53638) gi|75515985|ref|ZP_00738103.1| (75515985); COG1052: Lactate dehydrogenase and related dehydrogenases (*Escherichia coli* E22) gi|75260157|ref|ZP_00731425.1|(75260157); COG1052: Lactate dehydrogenase and related dehydrogenases (*Escherichia coli* F11) gi|75242656|ref|ZP_00726400.1| (75242656); COG1052: Lactate dehydrogenase and related dehydrogenases (*Escherichia coli* E110019) gi|75237491|ref|ZP_00721524.1|(75237491); COG1052: Lactate dehydrogenase and related dehydrogenases (*Escherichia coli* B7A) gi|75231601|ref|ZP_00717959.1| (75231601); and COG1052: Lactate dehydrogenase and related dehydrogenases (*Escherichia coli* B171) gi|75211308|ref|ZP_00711407.1|(75211308), each sequence associated with the accession number is incorporated herein by reference in its entirety.

Two membrane-bound, FAD-containing enzymes are responsible for the catalysis of fumarate and succinate interconversion; the fumarate reductase is used in anaerobic growth, and the succinate dehydrogenase is used in aerobic growth. Fumarate reductase comprises multiple subunits (e.g., frdA, B, and C in *E. coli*). Modification of any one of the subunits can result in the desired activity herein. For example, a knockout of frdB, frdC or frdBC is useful in the methods of the disclosure. Frd homologs and variants are known. For example, homologs and variants includes, for example, Fumarate reductase subunit D (Fumarate reductase 13 kDa hydrophobic protein) gi|67463543|sp|P0A8Q3.1|FRDD_ECOLI(67463543); Fumarate reductase subunit C (Fumarate reductase 15 kDa hydrophobic protein) gi|1346037|sp|P20923.2|FRDC_PROVU(1346037); Fumarate reductase subunit D (Fumarate reductase 13 kDa hydrophobic protein) gi|120499|sp|P20924.1|FRDD_PROVU (120499); Fumarate reductase subunit C (Fumarate reductase 15 kDa hydrophobic protein) gi|67463538|sp|P0A8Q0.1|FRDC_ECOLI(67463538); fumarate reductase iron-sulfur subunit (*Escherichia coli*) gi|145264|gb|AAA23438.1|(145264); fumarate reductase flavoprotein subunit (*Escherichia coli*) gi|145263|gb|AAA23437.1|(145263); Fumarate reductase flavoprotein subunit gi|37538290|sp|P17412.3|FRDA_WOLSU(37538290); Fumarate reductase flavoprotein subunit gi|120489|sp|P00363.3|FRDA_ECOLI(120489); Fumarate reductase flavoprotein subunit gi|120490|sp|P20922.1|FRDA_PROVU(120490); Fumarate reductase flavoprotein subunit precursor (Flavocytochrome c) (Flavocytochrome c3) (Fcc3) gi|119370087|sp|Q07WU7.2|FRDA_SHEFN(119370087); Fumarate reductase iron-sulfur subunit gi|81175308|sp|P0AC47.2|FRDB_ECOLI(81175308); Fumarate reductase flavoprotein subunit (Flavocytochrome c) (Flavocytochrome c3) (Fcc3) gi|119370088|sp|P0C278.1|FRDA_SHEFR(119370088); Frd operon uncharacterized protein C gi|140663|sp|P20927.1|YFRC_PROVU(140663); Frd operon probable iron-sulfur subunit A gi|140661|sp|P20925.1|YFRA_PROVU(140661); Fumarate reductase iron-sulfur subunit gi|120493|sp|P20921.2|FRDB_PROVU(120493); Fumarate reductase flavoprotein subunit gi|2494617|sp|O06913.2|FRDA_HELPY(2494617); Fumarate reductase flavoprotein subunit precursor (Iron(III)-induced flavocytochrome C3) (Ifc3) gi|13878499|sp|Q9Z4P0.1|FRD2_SHEFN(13878499); Fumarate reductase flavoprotein subunit gi|54041009|sp|P64174.1|FRDA_MYCTU(54041009); Fumarate reductase flavoprotein subunit gi|54037132|sp|P64175.1|FRDA_MYCBO(54037132); Fumarate reductase flavoprotein subunit gi|12230114|sp|Q9ZMP0.1|FRDA_HELPJ(12230114); Fumarate reductase flavoprotein subunit gi|1169737|sp|P44894.1|FRDA_HAEIN(1169737); fumarate reductase flavoprotein subunit (*Wolinella succinogenes*) gi|13160058|emb|CAA04214.2|(13160058); Fumarate reductase flavoprotein subunit precursor (Flavocytochrome c) (FL cyt) gi|25452947|sp|P83223.2|FRDA_SHEON (25452947); fumarate reductase iron-sulfur subunit (*Wolinella succinogenes*) gi|2282000|emb|CAA04215.1| (2282000); and fumarate reductase cytochrome b subunit (*Wolinella succinogenes*) gi|2281998|emb|CAA04213.1| (2281998), each sequence associated with the accession number is incorporated herein by reference in its entirety.

Acetate kinase is encoded in *E. coli* by ackA. AckA is involved in conversion of acetyl-coA to acetate. Specifically, ackA catalyzes the conversion of acetyl-phosphate to acetate. AckA homologs and variants are known. The NCBI database list approximately 1450 polypeptides as bacterial acetate kinases. For example, such homologs and variants include acetate kinase (*Streptomyces coelicolor* A3(2)) gi|21223784|ref|NP_629563.1|(21223784); acetate kinase (*Streptomyces coelicolor* A3(2)) gi|6808417|emb|CAB70654.1|(6808417); acetate kinase (*Streptococcus pyogenes* M1 GAS) gi|15674332|ref|NP_268506.1|(15674332); acetate kinase (*Campylobacter jejuni* subsp. *jejuni* NCTC 11168) gi|15792038|ref|NP_281861.1| (15792038); acetate kinase (*Streptococcus pyogenes* M1 GAS) gi|13621416|gb|AAK33227.1|(13621416); acetate kinase (*Rhodopirellula baltica* SH 1) gi|32476009|ref|NP_869003.1|(32476009); acetate kinase (Rhodopirellula baltica SH 1) gi|32472045|ref|NP_865039.1|(32472045); acetate kinase (*Campylobacter jejuni* subsp. *jejuni* NCTC 11168) gi|112360034|emb|CAL34826.1|(112360034); acetate kinase (*Rhodopirellula baltica* SH 1) gi|32446553|emb|CAD76388.1|(32446553); acetate kinase (*Rhodopirellula baltica* SH 1) gi|32397417|emb|CAD72723.1|(32397417); AckA (*Clostridium kluyveri* DSM 555) gi|153954016|ref|YP_001394781.1|(153954016); acetate kinase (*Bifidobacterium longum* NCC2705) gi|23465540|ref|NP_696143.1| (23465540); AckA (*Clostridium kluyveri* DSM 555) gi|146346897|gb|EDK33433.1|(146346897); Acetate kinase (*Corynebacterium diphtheriae*) gi|38200875|emb|CAE50580.1|(38200875); acetate kinase (*Bifidobacterium longum* NCC2705) gi|23326203|gb|AAN24779.1|(23326203); Acetate kinase (Acetokinase) gi|67462089|sp|P0A6A3.1|ACKA_ECOLI (67462089); and AckA (*Bacillus licheniformis* DSM 13) gi|52349315|gb|AAU41949.1|(52349315), the sequences associated with such accession numbers are incorporated herein by reference.

Phosphate acetyltransferase is encoded in *E. coli* by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (*Rick-* ettsia felis URRWXCal2) gi|67004021|gb|AAY60947.1| (67004021); phosphate acetyltransferase (*Buchnera aphidicola* str. Cc (Cinara cedri)) gi|116256910|gb|ABJ90592.1| (116256910); pta (*Buchnera aphidicola* str. Cc (Cinara cedri)) gi|116515056|ref|YP_802685.1|(116515056); pta (*Wigglesworthia glossinidia endosymbiont* of *Glossina brevipalpis*) gi|125166135|dbj|BAC24326.1|(25166135); Pta (*Pasteurella multocida* subsp. *multocida* str. Pm70) gi|12720993|gb|AAK02789.1|(12720993); Pta (*Rhodospirillum rubrum*) gi|125989720|gb|AAN75024.1|(25989720); pta (*Listeria welshimeri* serovar 6b str. SLCC5334) gi|116742418|emb|CAK21542.1|(116742418); Pta (*Mycobacterium avium* subsp. *paratuberculosis* K-10) gi|41398816|gb|AAS06435.1|(41398816); phosphate acetyltransferase (pta) (*Borrelia burgdorferi* B31) gi|5594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|1574131|gb|AAC22857.1|(1574131); Phosphate acetyltransferase Pta (*Rickettsia bellii* RML369-C) gi|91206026|ref|YP_538381.1|(91206026); Phosphate acetyltransferase Pta (*Rickettsia bellii* RML369-C) gi|91206025|ref|YP_538380.1|(91206025); phosphate acetyltransferase pta (*Mycobacterium tuberculosis* F11) gi|148720131|gb|ABR04756.1|(148720131); phosphate acetyltransferase pta (*Mycobacterium tuberculosis* str. Haarlem) gi|134148886|gb|EBA40931.1|(134148886); phosphate acetyltransferase pta (*Mycobacterium tuberculosis* C) gi|124599819|gb|EAY58829.1|(124599819); Phosphate acetyltransferase Pta (*Rickettsia bellii* RML369-C) gi|91069570|gb|ABE05292.1|(91069570); Phosphate acetyltransferase Pta (*Rickettsia bellii* RML369-C) gi|91069569|gb|ABE05291.1|(91069569); phosphate acetyltransferase (pta) (*Treponema pallidum* subsp. *pallidum* str. Nichols) gi|15639088|ref|NP_218534.1|(15639088); and phosphate acetyltransferase (pta) (*Treponema pallidum* subsp. *pallidum* str. Nichols) gi|3322356|gb|AAC65090.1| (3322356), each sequence associated with the accession number is incorporated herein by reference in its entirety.

Pyruvate-formate lyase (Formate acetylytransferase) is an enzyme that catalyzes the conversion of pyruvate to acetyl)-coA and formate. It is induced by pfl-activating enzyme under anaerobic conditions by generation of an organic free radical and decreases significantly during phosphate limitation. Formate acetylytransferase is encoded in *E. coli* by pflB. PFLB homologs and variants are known. For examples, such homologs and variants include, for example, Formate acetyltransferase 1 (Pyruvate formate-lyase 1) gi|129879|sp|P09373.21 PFLB_ECOLI(129879); formate acetyltransferase 1 (*Yersinia pestis* CO92) gi|16121663|ref|NP_404976.1|(16121663); formate acetyltransferase 1 (*Yersinia pseudotuberculosis* IP 32953) gi|51595748|ref|YP_069939.1|(51595748); formate acetyltransferase 1 (*Yersinia pestis* biovar Microtus str. 91001) gi|45441037|ref|NP_992576.1|(45441037); formate acetyltransferase 1 (*Yersinia pestis* CO92) gi|115347142|emb|CAL20035.1|(115347142); formate acetyltransferase 1 (*Yersinia pestis* biovar Microtus str. 91001) gi|45435896|gb|AAS61453.1|(45435896); formate acetyltransferase 1 (*Yersinia pseudotuberculosis* IP 32953) gi|51589030|emb|CAH20648.1|(51589030); formate acetyltransferase 1 (*Salmonella enterica* subsp. *enterica* serovar Typhi str. CT18) gi|16759843|ref|NP_455460.1| (16759843); formate acetyltransferase 1 (*Salmonella enterica* subsp. *enterica* serovar *Paratyphi* A str. ATCC 9150) gi|56413977|ref|YP_151052.1|(56413977); formate acetyltransferase 1 (*Salmonella enterica* subsp. *enterica* serovar Typhi) gi|16502136|emb|CAD05373.1|(16502136); formate acetyltransferase 1 (*Salmonella enterica* subsp. *enterica* serovar Paratyphi A str. ATCC 9150) gi|56128234|gb|AAV77740.1|(56128234); formate acetyltransferase 1 (*Shigella dysenteriae* Sd197) gi|82777577|ref|YP_403926.1|(82777577); formate acetyltransferase 1 (*Shigella flexneri* 2a str. 2457T) gi|30062438|ref|NP_836609.1|(30062438); formate acetyltransferase 1 (*Shigella flexneri* 2a str. 2457T) gi|30040684|gb|AAP16415.1|(30040684); formate acetyltransferase 1 (*Shigella flexneri* 5 str. 8401) gi|110614459|gb|ABF03126.1|(110614459); formate acetyltransferase 1 (*Shigella dysenteriae* Sd197) gi|81241725|gb|ABB62435.1|(81241725); formate acetyltransferase 1 (*Escherichia coli* O157:H7 EDL933) gi|12514066|gb|AAG55388.1|AE005279_8(12514066); formate acetyltransferase 1 (*Yersinia pestis* KIM) gi|22126668|ref|NP_670091.1|(22126668); formate acetyltransferase 1 (*Streptococcus agalactiae* A909) gi|176787667|ref|YP_330335.1|(76787667); formate acetyltransferase 1 (*Yersinia pestis* KIM) gi|21959683|gb|AAM86342.1|AE013882_3(21959683); formate acetyltransferase 1 (*Streptococcus agalactiae* A909) gi|76562724|gb|ABA45308.1|(76562724); formate acetyltransferase 1 (*Yersinia enterocolitica* subsp. *enterocolitica* 8081) gi|123441844|ref|YP_001005827.1|(123441844); formate acetyltransferase 1 (*Shigella flexneri* 5 str. 8401) gi|110804911|ref|YP_688431.1|(110804911); formate acetyltransferase 1 (*Escherichia coli* UTI89) gi|191210004|ref|YP_539990.1|(91210004); formate acetyltransferase 1Sb227) (*Shigella boydii* Sb227) gi|82544641|ref|YP_408588.1|(82544641); formate acetyltransferase 1 (*Shigella sonnei* Ss046) gi|74311459|ref|YP_309878.1|(74311459); formate acetyltransferase 1 (*Klebsiella pneumoniae* subsp. *pneumoniae* MGH 78578) gi|152969488|ref|YP_001334597.1|(152969488); formate acetyltransferase 1 (*Salmonella enterica* subsp. *enterica* serovar Typhi Ty2) gi|29142384|ref|NP_805726.1| (29142384) formate acetyltransferase 1 (*Shigella flexneri* 2a str. 301) gi|24112311|ref|NP_706821.1|(24112311); formate acetyltransferase 1 (*Escherichia coli* O157:H7 EDL933) gi|15800764|ref|NP_286778.1|(15800764); formate acetyltransferase 1 (*Klebsiella pneumoniae* subsp. *pneumoniae* MGH 78578) gi|150954337|gb|ABR76367.1| (150954337); formate acetyltransferase 1 (*Yersinia pestis* CA88-4125) gi|149366640|ref|ZP_01888674.1| (149366640); formate acetyltransferase 1 (*Yersinia pestis* CA88-4125) gi|149291014|gb|EDM41089.1|(149291014); formate acetyltransferase 1 (*Yersinia enterocolitica* subsp. *enterocolitica* 8081) gi|122088805|emb|CAL11611.1| (122088805); formate acetyltransferase 1 (*Shigella sonnei* Ss046) gi|73854936|gb|AAZ87643.1|(73854936); formate acetyltransferase 1 (*Escherichia coli* UT189) gi|91071578|gb|ABE06459.1|(91071578); formate acetyltransferase 1 (*Salmonella enterica* subsp. *enterica* serovar Typhi Ty2) gi|29138014|gb|AAO69575.1|(29138014); formate acetyltransferase 1 (*Shigella boydii* Sb227) gi|81246052|gb|ABB66760.1|(81246052); formate acetyltransferase 1 (*Shigella flexneri* 2a str. 301) gi|24051169|gb|AAN42528.1|(24051169); formate acetyltransferase 1 (*Escherichia coli* O157:H7 str. Sakai) gi|13360445|dbj|BAB34409.1|(13360445); formate acetyltransferase 1 (*Escherichia coli* O157:H7 str. Sakai) gi|15830240|ref|NP_309013.1|(15830240); formate acetyltransferase 1 (pyruvate formate-lyase 1) (*Photorhabdus luminescens* subsp. *laumondii* TTO1)

gi|36784986|emb|CAE13906.1|(36784986); formate. acetyltransferase 1 (pyruvate formate-lyase 1) (Photorhabdus luminescens subsp. *laumondii* TTO1) gi|37525558|ref|NP_928902.1|(37525558); formate acetyltransferase (*Staphylococcus aureus* subsp. *aureus* Mu50) gi|14245993|dbj|BAB56388.1|(14245993); formate acetyltransferase (*Staphylococcus aureus* subsp. *aureus* Mu50) gi|15923216|ref|NP_370750.1|(15923216); Formate acetyltransferase (Pyruvate formate-lyase) gi|81706366|sp|Q7A7X6.1|PFLB_STAAN(81706366); Formate acetyltransferase (Pyruvate formate-lyase) gi|81782287|sp|Q99WZ7.1|PFLB_STAAM(81782287); Formate acetyltransferase (Pyruvate formate-lyase) gi|81704726|sp|Q7A1W9.1|PFLB_STAAW(81704726); formate acetyltransferase (*Staphylococcus aureus* subsp. *aureus* Mu3) gi|156720691|dbj|BAF77108.1|(156720691); formate acetyltransferase (*Erwinia carotovora* subsp. *atroseptica* SCR11043) gi|50121521|ref|YP_050688.1|(50121521); formate acetyltransferase (Erwinia carotovora subsp. atroseptica SCR11043) gi|49612047|emb|CAG75496.1|(49612047); formate acetyltransferase (*Staphylococcus aureus* subsp. *aureus* str. Newman) gi|150373174|dbj|BAF66434.1|(150373174); formate acetyltransferase (Shewanella oneidensis MR-1) gi|24374439|ref|NP_718482.1|(24374439); formate acetyltransferase (*Shewanella oneidensis* MR-1) gi|124349015|gb|AAN55926.1|AE015730_3(24349015); formate acetyltransferase (*Actinobacillus pleuropneumoniae* serovar 3 str. JL03) gi|165976461|ref|YP_001652054.1|(165976461); formate acetyltransferase (*Actinobacillus pleuropneumoniae* serovar 3 str. JL03) gi|165876562|gb|ABY69610.1|(165876562); formate acetyltransferase (*Staphylococcus aureus* subsp. *aureus* MW2) gi|21203365|dbj|BAB94066.1|(21203365); formate acetyltransferase (*Staphylococcus aureus* subsp. *aureus* N315) gi|13700141|dbj|BAB41440.1|(13700141); formate acetyltransferase (*Staphylococcus aureus* subsp. *aureus* str. Newman) gi|151220374|ref|YP_001331197.1|(151220374); formate acetyltransferase (*Staphylococcus aureus* subsp. *aureus* Mu3) gi|156978556|ref|YP_001440815.1|(156978556); formate acetyltransferase (*Synechococcus* sp. JA-2-3B' a(2-13)) gi|86607744|ref|YP_476506.1|(86607744); formate acetyltransferase (*Synechococcus* sp. JA-3-3Ab) gi|86605195|ref|YP_473958.1|(86605195); formate acetyltransferase (*Streptococcus pneumoniae* D39) gi|116517188|ref|YP_815928.1|(116517188); formate acetyltransferase (*Synechococcus* sp. JA-2-3B' a(2-13)) gi|86556286|gb|ABD01243.1|(86556286); formate acetyltransferase (*Synechococcus* sp. JA-3-3Ab) gi|86553737|gb|ABC98695.1|(86553737); formate acetyltransferase (*Clostridium novyi* NT) gi|118134908|gb|ABK61952.1|(118134908); formate acetyltransferase (*Staphylococcus aureus* subsp. *aureus* MRSA252) gi|49482458|ref|YP_039682.1|(49482458); and formate acetyltransferase (*Staphylococcus aureus* subsp. *aureus* MRSA252) gi|49240587|emb|CAG39244.1|(49240587), each sequence associated with the accession number is incorporated herein by reference in its entirety.

Alpha isopropylmalate synthase (EC 2.3.3.13, sometimes referred to a 2-isopropylmalate synthase, alpha-IPM synthetase) catalyzes the condensation of the acetyl group of acetyl-CoA with 3-methyl-2-oxobutanoate (2-oxoisovalerate) to form 3-carboxy-3-hydroxy-4-methylpentanoate (2-isopropylmalate). Alpha isopropylmalate synthase is encoded in *E. coli* by leuA. LeuA homologs and variants are known. For example, such homologs and variants include, for example, 2-isopropylmalate synthase (*Corynebacterium glutamicum*) gi|452382|emb|CAA50295.1|(452382); 2-isopropylmalate synthase (*Escherichia coli* K12) gi|116128068|ref|NP_414616.1|(16128068); 2-isopropylmalate synthase (*Escherichia coli* K12) gi|1786261|gb|AAC73185.1|(1786261); 2-isopropylmalate synthase (*Arabidopsis thaliana*) gi|15237194|ref|NP_197692.1|(15237194); 2-isopropylmalate synthase (*Arabidopsis thaliana*) gi|42562149|ref|NP_173285.2|(42562149); 2-isopropylmalate synthase (*Arabidopsis thaliana*) gi|15221125|ref|NP_177544.1|(15221125); 2-isopropylmalate synthase (*Streptomyces coelicolor* A3(2)) gi|32141173|ref|NP_733575.1|(32141173); 2-isopropylmalate synthase (Rhodopirellula baltica SH 1) gi|32477692|ref|NP_870686.1|(32477692); 2-isopropylmalate synthase (Rhodopirellula baltica SH 1) gi|32448246|emb|CAD77763.1|(32448246); 2-isopropylmalate synthase (*Akkermansia muciniphila* ATCC BAA-835) gi|166241432|gb|EDR53404.1|(166241432); 2-isopropylmalate synthase (*Herpetosiphon aurantiacus* ATCC 23779) gi|159900959|ref|YP_001547206.1|(159900959); 2-isopropylmalate synthase (*Dinoroseobacter shibae* DFL 12) gi|159043149|ref|YP_001531943.1|(159043149); 2-isopropylmalate synthase (*Salinispora arenicola* CNS-205) gi|159035933|ref|YP_001535186.1|(159035933); 2-isopropylmalate synthase (*Clavibacter michiganensis* subsp. *michiganensis* NCPPB 382) gi|148272757|ref|YP_001222318.1|(148272757); 2-isopropylmalate synthase (*Escherichia coli* B) gi|124530643|ref|ZP_01701227.1|(124530643); 2-isopropylmalate synthase (*Escherichia coli* C str. ATCC 8739) gi|124499067|gb|EAY46563.1|(124499067); 2-isopropylmalate synthase (*Bordetella pertussis* Tohama I) gi|33591386|ref|NP_879030.1|(33591386); 2-isopropylmalate synthase (*Polynucleobacter necessarius* STIR 1) gi|164564063|ref|ZP_02209880.1|(164564063); 2-isopropylmalate synthase (Polynucleobacter necessarius STIR1) gi|164506789|gb|EDQ94990.1|(164506789); and 2-isopropylmalate synthase (*Bacillus weihenstephanensis* KBAB4) gi|163939313|ref|YP_001644197.1|(163939313), any sequence associated with the accession number is incorporated herein by reference in its entirety.

BCAA aminotransferases catalyze the formation of branched chain amino acids (BCAA). A number of such aminotranferases are known and are exemplified by ilvE in *E. coli*. Exemplary homologs and variants include sequences designated by the following accession numbers: ilvE (Microcystic aeruginosa PCC 7806) gi|159026756|emb|CAO86637.1|(159026756); IlvE (*Escherichia coli*) gi|87117962|gb|ABD20288.1|(87117962); IlvE (*Escherichia coli*) gi|87117960|gb|ABD20287.1|(87117960); IlvE (*Escherichia coli*) gi|87117958|gb|ABD20286.1|(87117958); IlvE (*Shigella flexneri*) gi|87117956|gb|ABD20285.1|(87117956); IlvE (*Shigella flexneri*) gi|87117954|gb|ABD20284.1|(87117954); IlvE (*Shigella flexneri*) gi|87117952|gb|ABD20283.1|(87117952); IlvE (*Shigella flexneri*) gi|87117950|gb|ABD20282.1|(87117950); IlvE (*Shigella flexneri*) gi|87117948|gb|ABD20281.1|(87117948); IlvE (*Shigella flexneri*) gi|87117946|gb|ABD20280.1|(87117946); IlvE (*Shigella flexneri*) gi|87117944|gb|ABD20279.1|(87117944); IlvE (*Shigella flexneri*) gi|87117942|gb|ABD20278.1|(87117942); IlvE (*Shigella flexneri*) gi|87117940|gb|ABD20277.1|(87117940); IlvE (*Shigella flexneri*) gi|87117938|gb|ABD20276.1|(87117938); IlvE (*Shigella dysenteriae*) gi|87117936|gb|ABD20275.1|(87117936); IlvE (*Shigella dysenteriae*)

gi|87117934|gb|ABD20274.1|(87117934); IlvE (*Shigella dysenteriae*) gi|87117932|gb|ABD20273.1|(87117932); IlvE (*Shigella dysenteriae*) gi|87117930|gb|ABD20272.1| (87117930); and IlvE (*Shigella dysenteriae*) gi|87117928|gb|ABD20271.1|(87117928), each sequence associated with the accession number is incorporated herein by reference.

Tyrosine aminotransferases catalyzes transamination for both dicarboxylic and aromatic amino-acid substrates. A tyrosine aminotransferase of *E. coli* is encoded by the gene tyrB. TyrB homologs and variants are known. For example, such homologs and variants include tyrB (*Bordetella petrii*) gi|163857093|ref|YP_001631391.1|(163857093); tyrB (*Bordetella petrii*) gi|163260821|emb|CAP43123.1| (163260821); aminotransferase gi|1551844|gb|AAA24704.1|(551844); aminotransferase (*Bradyrhizobium* sp. BTAi1) gi|146404387|gb|ABQ32893.1|(146404387); tyrosine aminotransferase TyrB (*Salmonella enterica*) gi|4775574|emb|CAB40973.2|(4775574); tyrosine aminotransferase (*Salmonella typhimurium* LT2) gi|16422806|gb|AAL23072.1|(16422806); and tyrosine aminotransferase gi|148085|gb|AAA24703.1|(148085), each sequence of which is incorporated herein by reference.

Pyruvate oxidase catalyzes the conversion of pyruvate to acetate and $CO_2$. In *E. coli*, pyruvate oxidase is encoded by poxB. PoxB and homologs and variants thereof include, for example, pyruvate oxidase; PoxB (*Escherichia coli*) gi|685128|gb|AAB31180.1||bbm|34845|bbs|154716 (685128); PoxB (*Pseudomonas fluorescens*) gi|32815820|gb|AAP88293.1|(32815820); poxB (*Escherichia coli*) gi|25269169|emb|CAD57486.1|(25269169); pyruvate dehydrogenase (*Salmonella enterica* subsp. *enterica* serovar *Typhi*) gi|16502101|emb|CAD05337.1| (16502101); pyruvate oxidase (*Lactobacillus plantarum*) gi|41691702|gb|AAS10156.1|(41691702); pyruvate dehydrogenase (*Bradyrhizobium japonicum*) gi|20257167|gb|AAM12352.1|(20257167); pyruvate dehydrogenase (*Yersinia pestis* KIM) gi|22126698|ref|NP_670121.1|(22126698); pyruvate dehydrogenase (cytochrome) (*Yersinia pestis* biovar Antigua str. B42003004) gi|166211240|ref|ZP_02237275.1|(166211240); pyruvate dehydrogenase (cytochrome) (*Yersinia pestis* biovar Antigua str. B42003004) gi|166207011|gb|EDR51491.1| (166207011); pyruvate dehydrogenase (*Pseudomonas syringae* pv. tomato str. DC3000) gi|28869703|ref|NP_792322.1| (28869703); pyruvate dehydrogenase (*Salmonella typhimurium* LT2) gi|16764297|ref|NP_459912.1| (16764297); pyruvate dehydrogenase (*Salmonella enterica* subsp. *enterica* serovar *Typhi* str. CT18) gi|16759808|ref|NP_455425.1|(16759808); pyruvate dehydrogenase (cytochrome) (*Coxiella burnetii* Dugway 5J108-111) gi|154706110|ref|YP_001424132.1|(154706110); pyruvate dehydrogenase (*Clavibacter michiganensis* subsp. *michiganensis* NCPPB 382) gi|148273312|ref|YP_001222873.1|(148273312); pyruvate oxidase (*Lactobacillus acidophilus* NCFM) gi|58338213|ref|YP_194798.1| (58338213); and pyruvate dehydrogenase (*Yersinia pestis* C092) gi|16121638|ref|NP_404951.1|(16121638), the sequences of each accession number are incorporated herein by reference.

L-threonine 3-dehydrogenase (EC 1.1.1.103) catalyzes the conversion of L-threonine to L-2-amino-3-oxobutanoate. The gene tdh encodes an L-threonine 3-dehydrogenase. There are approximately 700 L-threonine 3-dehydrogenases from bacterial organism recognized in NCBI. Various homologs and variants of tdh include; for example L-threonine 3-dehydrogenase gi|135560|sp|P07913.1|TDH_ECOLI(135560); L-threonine 3-dehydrogenase gi|166227854|sp|A4TSC6.1|TDH_YERPP(166227854); L-threonine 3-dehydrogenase gi|166227853|sp|A1JHX8.1|TDH_YERE8(166227853); L-threonine 3-dehydrogenase gi|166227852|sp|A6UBM6.1|TDH_SINMW(166227852); L-threonine 3-dehydrogenase gi|166227851|sp|A1RE07.1|TDH_SHESW(166227851); L-threonine 3-dehydrogenase gi|166227850|sp|A0L2Q3.1|TDH_SHESA(166227850); L-threonine 3-dehydrogenase gi|166227849|sp|A4YCC5.1|TDH_SHEPC(166227849); L-threonine 3-dehydrogenase gi|166227848|sp|A3QJC8.1|TDH_SHELP(166227848); L-threonine 3-dehydrogenase gi|166227847|sp|A6WUG6.1|TDH_SHEB8(166227847); L-threonine 3-dehydrogenase gi|166227846|sp|A3CYN0.1|TDH_SHEB5(166227846); L-threonine 3-dehydrogenase gi|166227845|sp|A1S1Q3.1|TDH_SHEAM(166227845); L-threonine 3-dehydrogenase gi|166227844|sp|A4FND4.1|TDH_SACEN(166227844); L-threonine 3-dehydrogenase gi|166227843|sp|A1SVW5.1|TDH_PSYIN(166227843); L-threonine 3-dehydrogenase gi|166227842|sp|A51GK7.1|TDH_LEGPC(166227842); L-threonine 3-dehydrogenase gi|166227841|sp|A6TFL2.1|TDH_KLEP7(166227841); L-threonine 3-dehydrogenase gi|166227840|sp|A41Z92.1|TDH_FRATW(166227840); L-threonine 3-dehydrogenase gi|166227839|sp|A0Q5K3.1|TDH_FRATN(166227839); L-threonine 3-dehydrogenase gi|166227838|sp|A7NDM9.1|TDH_FRATF(166227838); L-threonine 3-dehydrogenase gi|166227837|sp|A7MID0.1|TDH_ENTS8(166227837); and L-threonine 3-dehydrogenase gi|166227836|sp|A1AHF3.1|TDH_ECOK1(166227836), the sequences associated with each accession number are incorporated herein by reference.

Acetohydroxy acid synthases (e.g. ilvH) and acetolactate synthases (e.g., alsS, ilvB, ilvI) catalyze the synthesis of the branched-chain amino acids (valine, leucine, and isoleucine). IlvH encodes an acetohydroxy acid synthase in *E. coli* (see, e.g., acetohydroxy acid synthase AHAS III (IlvH) (*Escherichia coli*) gi|40846|emb|CAA38855.1|(40846), incorporated herein by reference). Homologs and variants as well as operons comprising ilvH are known and include, for example, ilvH (*Microcystis aeruginosa* PCC 7806) gi|159026908|emb|CAO89159.1|(159026908); IlvH (*Bacillus amyloliquefaciens* FZB42) gi|154686966|ref|YP_001422127.1|(154686966); IlvH (*Bacillus amyloliquefaciens* FZB42) gi|154352817|gb|ABS74896.1| (154352817); IlvH (*Xenorhabdus nematophila*) gi|131054140|gb|AB032787.1|(131054140); IlvH (*Salmonella typhimurium*) gi|7631124|gb|AAF65177.1|AF117227_2(7631124), ilvN (*Listeria innocua*) gi|16414606|emb|CAC97322.1| (16414606); ilvN (*Listeria monocytogenes*) gi|16411438|emb|CAD00063.1|(16411438); acetohydroxy acid synthase (*Caulobacter crescentus*) gi|408939|gb|AAA23048.1|(408939); acetohydroxy acid synthase I, small subunit (*Salmonella enterica* subsp. *enterica* serovar *Typhi*) gi|16504830|emb|CAD03199.1| (16504830); acetohydroxy acid synthase, small subunit (*Tro-* pheryma whipplei TW08/27) gi|28572714|ref|NP_789494.1|(28572714); acetohydroxy acid synthase, small subunit (Tropheryma whipplei TW08/27) gi|28410846|emb|CAD67232.1|(28410846); acetohydroxy acid synthase I, small subunit (*Salmonella enterica* subsp. *enterica* serovar *Paratyphi* A str. ATCC 9150) gi|56129933|gb|AAV79439.1|(56129933); acetohydroxy acid synthase small subunit; acetohydroxy acid synthase, small subunit gi|551779|gb|AAA62430.1|(551779); acetohydroxy acid synthase I, small subunit (*Salmonella enterica* subsp. *enterica* serovar *Typhi* Ty2) gi|29139650|gb|AA071216.1|(29139650); acetohydroxy acid synthase small subunit (*Streptomyces cinnamonensis*) gi|5733116|gb|AAD49432.1|AF175526_1|(5733116); acetohydroxy acid synthase large subunit; and acetohydroxy acid synthase, large subunit gi|400334|gb|AAA62429.1|(400334), the sequences associated with the accession numbers are incorporated herein by reference. Acetolactate synthase genes include alsS and ilvI. Homologs of ilvI and alsS are known and include, for example, acetolactate synthase small subunit (*Bifidobacterium longum* NCC2705) gi|23325489|gb|AAN24137.1|(23325489); acetolactate synthase small subunit (*Geobacillus stearothermophilus*) gi|19918933|gb|AAL99357.1|(19918933); acetolactate synthase (*Azoarcus* sp. BH72) gi|119671178|emb|CAL95091.1|(119671178); Acetolactate synthase small subunit (*Corynebacterium diphtheriae*) gi|38199954|emb|CAE49622.1|(38199954); acetolactate synthase (*Azoarcus* sp. BH72) gi|119669739|emb|CAL93652.1|(119669739); acetolactate synthase small subunit (*Corynebacterium jeikeium* K411) gi|68263981|emb|CAI37469.1|(68263981); acetolactate synthase small subunit (*Bacillus subtilis*) gi|1770067|emb|CAA99562.1|(1770067); Acetolactate synthase isozyme 1 small subunit (AHAS-I) (Acetohydroxy-acid synthase I small subunit) (ALS-I) gi|83309006|sp|P0ADF8.1|ILVN_ECOLI(83309006); acetolactate synthase large subunit (*Geobacillus stearothermophilus*) gi|19918932|gb|AAL99356.1|(19918932); and Acetolactate synthase, small subunit (*Thermoanaerobacter tengcongensis* MB4) gi|20806556|ref|NP_621727.1|(20806556), the sequences associated with the accession numbers are incorporated herein by reference. There are approximately 1120 ilvB homologs and variants listed in NCBI.

Acetohydroxy acid isomeroreductase is the second enzyme in parallel pathways for the biosynthesis of isoleucine and valine. IlvC encodes an acetohydroxy acid isomeroreductase in *E. coli*. Homologs and variants of ilvC are known and include, for example, acetohydroxyacid reductoisomerase (*Schizosaccharomyces pombe* 972h-) gi|162312317|ref|NP_001018845.2|(162312317); acetohydroxyacid reductoisomerase (*Schizosaccharomyces pombe*) gi|3116142|emb|CAA18891.1|(3116142); acetohydroxyacid reductoisomerase (*Saccharomyces cerevisiae* YJM789) gi|151940879|gb|EDN59261.1|(151940879); Ilv5p: acetohydroxy acid reductoisomerase (*Saccharomyces cerevisiae*) gi|1609403|gb|AAB67753.1|(609403); ACL198Wp (*Ashbya gossypii* ATCC 10895) gi|45185490|ref|NP_983206.1|(45185490); ACL198Wp (*Ashbya gossypii* ATCC 10895) gi|44981208|gb|AAS51030.1|(44981208); acetohydroxyacid isomeroreductase; Ilv5x (*Saccharomyces cerevisiae*) gi|957238|gb|AAB33579.1|bbm|369068|bbs|165406 (957238); acetohydroxy-acid isomeroreductase; Ilv5g (*Saccharomyces cerevisiae*) gi|957236|gb|AAB33578.1|bbm|369064|bbs|165405 (957236); and ketol-acid reductoisomerase (*Schizosaccharomyces pombe*) gi|2696654|dbj|BAA24000.1|(2696654), each sequence associated with the accession number is incorporated herein by reference.

Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. Homologs and variants of dihydroxy-acid dehydratases are known and include, for example, IlvD (*Mycobacterium leprae*) gi|2104594|emb|CAB08798.1|(2104594); dihydroxyacid dehydratase (Tropheryma whipplei TW08/27) gi|28410848|emb|CAD67234.1|(28410848); dihydroxyacid dehydratase (*Mycobacterium leprae*) gi|13093837|emb|CAC32140.1|(13093837); dihydroxyacid dehydratase (Rhodopirellula baltica SH 1) gi|32447871|emb|CAD77389.1|(32447871); and putative dihydroxy-acid dehydratase (*Staphylococcus aureus* subsp. *aureus* MRSA252) gi|49242408|emb|CAG41121.1|(49242408), each sequence associated with the accession numbers are incorporated herein by reference.

2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thl3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (*Lactococcus lactis*); gi|15004729|ref|NP_149189.1| Pyruvate decarboxylase (*Clostridium acetobutylicum* ATCC 824); gi|82749898|ref|YP_415639.1| probable pyruvate decarboxylase (*Staphylococcus aureus* RF122); gi|77961217|ref|ZP_00825060.1| COG3961: Pyruvate decarboxylase and related thiamine pyrophosphate-requiring enzymes (*Yersinia mollaretii* ATCC 43969); gi|71065418|ref|YP_264145.1| putative pyruvate decarboxylase (*Psychrobacter arcticus* 273-4); gi|16761331|ref|NP_456948.1| putative decarboxylase (*Salmonella enterica* subsp. *enterica* serovar *Typhi* str. CT18); gi|93005792|ref|YP_580229.1| Pyruvate decarboxylase (*Psychrobacter cryohalolentis* K5); gi|23129016|ref|ZP_00110850.1| COG3961: Pyruvate decarboxylase and related thiamine pyrophosphate-requiring enzymes (*Nostoc punctiforme* PCC 73102); gi|16417060|gb|AAL18557.1|AF354297_1 pyruvate decarboxylase (*Sarcina ventriculi*); gi|15607993|ref|NP_215368.1|PROBABLE PYRUVATE OR INDOLE-3-PYRUVATE DECARBOXYLASE PDC (*Mycobacterium tuberculosis* H37Rv); gi|41406881|ref|NP_959717.1|Pdc (*Mycobacterium avium* subsp. *paratuberculosis* K-10); gi|91779968|ref|YP_555176.1| putative pyruvate decarboxylase (*Burkholderia xenovorans* LB400); gi|15828161|ref|NP_302424.1| pyruvate (or indolepyruvate) decarboxylase (*Mycobacterium leprae* TN); gi|118616174|ref|YP_904506.1| pyruvate or indole-3-pyruvate decarboxylase Pdc (*Mycobacterium ulcerans* Agy99); gi|67989660|ref|NP_001018185.1| hypothetical protein SPAC3H8.01 (*Schizosaccharomyces pombe* 972h-); gi|21666011|gb|AAM73540.1|AF282847_1 pyruvate decarboxylase PdcB (*Rhizopus oryzae*); gi|69291130|ref|ZP_00619161.1| Pyruvate decarboxylase: Pyruvate decarboxylase (*Kineococcus radiotolerans* SRS30216); gi|66363022|ref|XP_628477.1| pyruvate decarboxylase (*Cryptosporidium parvum* Iowa II);

gi|70981398|ref|XP_731481.1| pyruvate decarboxylase (*Aspergillus fumigatus* Af293); gi|121704274|ref|XP_001270401.1| pyruvate decarboxylase, putative (*Aspergillus clavatus* NRRL 1); gi|119467089|ref|XP_001257351.1| pyruvate decarboxylase, putative (*Neosartorya fischeri* NRRL 181); gi|26554143|ref|NP_758077.1| pyruvate decarboxylase (*Mycoplasma penetrans* HF-2); gi|21666009|gb|AAM73539.1|AF282846_1 pyruvate decarboxylase PdcA (*Rhizopus oryzae*).

Alcohol dehydrogenases (adh) catalyze the final step of amino acid catabolism, conversion of an aldehyde to a long chain or complex alcohol. Various adh genes are known in the art. As indicated herein adh1 homologs and variants include, for example, adh2, adh3, adh4, adh5, adh 6 and sfa1 (see, e.g., SFA (*Saccharomyces cerevisiae*) gi|1288591|emb|CAA48161.1| (288591); the sequence associated with the accession number is incorporated herein by reference).

Citramalate synthase catalyzes the condensation of pyruvate and acetate. CimA encodes a citramalate synthase. Homologs and variants are known and include, for example, citramalate synthase (*Leptospira biflexa* serovar *Patoc*) gi|116664687|gb|ABK13757.1|(116664687); citramalate synthase (*Leptospira biflexa* serovar *Monteralerio*) gi|116664685|gb|ABK13756.1|(116664685); citramalate synthase (*Leptospira interrogans* serovar *Hebdomadis*) gi|116664683|gb|ABK13755.1|(116664683); citramalate synthase (*Leptospira interrogans* serovar *Pomona*) gi|116664681|gb|ABK13754.1|(116664681); citramalate synthase (*Leptospira interrogans* serovar *Australis*) gi|116664679|gb|ABK13753.1|(116664679); citramalate synthase (*Leptospira interrogans* serovar *Autumnalis*) gi|116664677|gb|ABK13752.1|(116664677); citramalate synthase (*Leptospira interrogans* serovar *Pyrogenes*) gi|116664675|gb|ABK13751.1|(116664675); citramalate synthase (*Leptospira interrogans* serovar *Canicola*) gi|116664673|gb|ABK13750.1|(116664673); citramalate synthase (*Leptospira interrogans* serovar *Lai*) gi|116664671|gb|ABK13749.1|(116664671); CimA (*Leptospira meyeri* serovar *Semaranga*) gi|119720987|gb|ABL98031.1|(119720987); (R)-citramalate synthase gi|2492795|sp|Q58787.1|CIMA_METJA (2492795); (R)-citramalate synthase gi|22095547|sp|P58966.1|CIMA_METMA(22095547); (R)-citramalate synthase gi|22001554|sp|Q8TJJ1.1|CIMA_METAC(22001554); (R)-citramalate synthase gi|22001553|sp|O26819.1|CIMA_METTH(22001553); (R)-citramalate synthase gi|22001555|sp|Q8TYB1.1|CIMA_METKA(22001555); (R)-citramalate synthase (*Methanococcus maripaludis* S2) gi|14535858|ref|NP_988138.1|(45358581); (R)-citramalate synthase (*Methanococcus maripaludis* S2) gi|44921339|emb|CAF30574.1|(44921339); and similar to (R)-citramalate synthase (*Candidatus Kuenenia* stuttgartiensis) gi|91203541|emb|CAJ71194.1|(91203541), each sequence associated with the foregoing accession numbers is incorporated herein by reference.

The proteobacterium *Ralstonia eutropha* possesses two energy-linked (NiFe) hydrogenases: a membrane hydrogenase and a cytoplasmic hydrogenase. The membrane hydrogenase is involved in electron transport-coupled phosphorylation through coupling to the respiratory chain, whereas the cytoplasmic hydrogenase is able to reduce NAD$^+$ to generate reducing equivalents (Schink et al., Biochim. Biophys. Acta 567:315-324, 1979; Schneider et al. Biochim. Biophys. Acta 452:66-80, 1976, each of which is incorporated herein by reference in its entirety). The genes encoding the two hydrogenases are clustered in two separate operons together with regulatory genes involved in hydrogenase biosynthesis on megaplasmid pHG1 (Schultz et al. Science 302:624-627, 2003; Schwartz et al. J. Bacteriol. 180:3197-3204, 1998, each of which is incorporated herein by reference in its entirety). A third hydrogenase was identified in *R. eutropha* and classified as belonging to the subclass of H$_2$-sensing (NiFe) hydrogenases (Kleihues et al., J. Bacteriol. 182:2716-2724, 2000, incorporated herein by reference in its entirety). The third hydrogenase is stable in presence of O$_2$, CO, and C$_2$H$_2$. The rate of hydrogen oxidation of this third hydrogenase is one to two orders of magnitude lower than that of standard membrane and cytoplasmic hydrogenase. The third hydrogenase contains an active size similar to the initial two hydrogenases. This third hydrogenase is encoded by the hoxB and hoxC genes (large and small subunit, respectively). The hyp genes (hypA1B1F1CDEX) are responsible for the maturation of the third hydrogenase in *R. eutropha* are located between the membrane hydrogenase genes and hoxA.

Oxygen-tolerant hydrogenases have been identified in *Bradyrhizobium japonicum* (Black et al., 1994), *Ra. eutropha* (Buhrke et al., 2005; Lenz and Friedrich, 1998), *Rhodobacter capsulatus* (Elsen et al., 1996; Vignais et al., 2002), *Thiocapsa roseopersicina* (Kovacs et al., 2005), and *Rh. palustris* (Rey et al., 2006). Significant heterologous activity of one these hydrogenases has been reported in *Synechococcus elongatus* PCC7002, with the chromosomal integration of the soluble hydrogenase and accessory maturation proteins of *Ra. eutropha* (Xu, 2009).

In a specific embodiment, a microorganism which naturally contains a CO$_2$ fixation enzyme and an ability to use H$_2$ or formate for reduction is engineered to produce an alcohol. In one embodiment, the alcohol is isobutanol. In another embodiment, the recombinant microorganism is engineered from a *Ralstonia* sp. to contain a pathway comprising the enzymes and conversion set forth in the following tables. The following tables set forth reaction pathways for various recombinant microorganism of the disclosure including a list of exemplary genes and homologs and organism source.

1-Butanol Production Pathway Via Pyruvate

| Reaction 1 |
|---|
| Pyruvate + Acetyl-CoA –> (R)-citramalate |
| Genes |
| cimA (*Methanocaldococcus jannaschii*), cimA (*Leptospira interrogans*) or homologs thereof |

| Reaction 2 |
|---|
| (R)-citramalate –> citraconate |
| Genes |
| leuCD (*Leptospira interrogans*), leuCD (*E. coli*) or homologs thereof |

| Reaction 3 |
| --- |
| citraconate –> β-methyl-D-malate<br>Genes |
| leuCD (*Leptospira interrogans*), leuCD (*E. coli*) or homologs thereof<br>Reaction 4 |
| β-methyl-D-malate –> 2-keto-butyrate<br>Genes |
| leuB (*Leptospira interrogans*), leuB (*E. coli*) or homologs thereof<br>Reaction 5 |
| 2-keto-butyrate –> 2-ethylmalate<br>Genes |
| leuA (*E. coli*) or homologs thereof<br>Reaction 3 |
| 2-ethylmalate –> 3-ethylmalate<br>Genes |
| leuCD (*E. coli*) or homologs thereof<br>Reaction 4 |
| 3-ethylmalate –> 2-ethyl-3-oxosuccinate<br>Genes |
| leuB (*E. coli*) or homologs thereof<br>Reaction 5 |
| 2-ethyl-3-oxosuccinate –> 2-keto-valerate<br>Genes |
| (spontaneous)<br>Reaction 6 |
| 2-keto-valerate –> butrylaldehyde<br>Genes |
| kivd (*Lactococcus lactis*), kdcA (*Lactococcus lactis*), PDC1 (*Saccharomyces cerevisiae*), PDC5 (*Saccharomyces cerevisiae*), PDC6 (*Saccharomyces cerevisiae*) THI3 (*Saccharomyces cerevisiae*), ARO10 (*Saccharomyces cerevisiae*) or homologs thereof<br>Reaction 7 |
| butrylaldehyde –> 1-butanol<br>Genes |
| ADH1 (*Saccharomyces cerevisiae*), ADH2 (*Saccharomyces cerevisiae*), ADH3 (*Saccharomyces cerevisiae*), ADH4 (*Saccharomyces cerevisiae*), ADH5 (*Saccharomyces cerevisiae*), ADH6 (*Saccharomyces cerevisiae*), SFA1 (*Saccharomyces cerevisiae*) or homologs thereof |

1-Propanol Production Pathway Via Pyruvate

| Reaction 1 |
| --- |
| Pyruvate + Acetyl-CoA –> (R)-citramalate<br>Genes |
| cimA (*Methanocaldococcus jannaschii*), cimA (*Leptospira interrogans*) or homologs thereof<br>Reaction 2 |
| (R)-citramalate –> citraconate<br>Genes |
| leuCD (*Leptospira interrogans*), leuCD (*E. coli*) or homologs thereof<br>Reaction 3 |
| citraconate –> β-methyl-D-malate<br>Genes |
| leuCD (*Leptospira interrogans*), leuCD (*E. coli*) or homologs thereof |

| Reaction 4 |
| --- |
| β-methyl-D-malate –> 2-keto-butyrate<br>Genes |
| leuB (*Leptospira interrogans*), leuB (*E. coli*) or homologs thereof<br>Reaction 5 |
| 2-keto-butyral –> butrylaldehyde<br>Genes |
| kivd (*Lactococcus lactis*), kdcA (*Lactococcus lactis*), PDC1 (*Saccharomyces cerevisiae*), PDC5 (*Saccharomyces cerevisiae*), PDC6 (*Saccharomyces cerevisiae*) THI3 (*Saccharomyces cerevisiae*), ARO10 (*Saccharomyces cerevisiae*) or homologs thereof<br>Reaction 7 |
| butrylaldehyde –> 1-butanol<br>Genes |
| ADH1 (*Saccharomyces cerevisiae*), ADH2 (*Saccharomyces cerevisiae*), ADH3 (*Saccharomyces cerevisiae*), ADH4 (*Saccharomyces cerevisiae*), ADH5 (*Saccharomyces cerevisiae*), ADH6 (*Saccharomyces cerevisiae*), SFA1 (*Saccharomyces cerevisiae*) or homologs thereof |

3-Methyl-1-Butanol Production Pathway (Via Pyruvate)

| Reaction 1 |
| --- |
| pyruvate –> 2-acetolactate<br>Gene |
| ilvHI (*E. coli*), ilvNB (*E. coli*), ilvGM (*E. coli*), alsS (*Bacillus subtilis*) or homologs thereof<br>Reaction 2 |
| 2-acetolactate –> 2,3-dihydroxy-isovalerate<br>Genes |
| ilvC (*E. coli*) or homologs thereof<br>Reaction 3 |
| 2,3-dihydroxy-isovalerate –> 2-keto-isovalerate<br>Genes |
| ilvD (*E. coli*) or homologs thereof<br>Reaction 4 |
| 2-keto-isovalerate –> 2-isopropylmalate<br>Genes |
| leuA (*E. coli*) or homologs thereof<br>Reaction 5 |
| 2-isopropylmalate –> 3-isopropylmalate<br>Genes |
| leuCD (*E. coli*) or homologs thereof<br>Reaction 6 |
| 3-isopropylmalate –> 2-isopropyl-3-oxosuccinate<br>Genes |
| leuB (*E. coli*) or homologs thereof<br>Reaction 7 |
| 2-isopropyl-3-oxosuccinate –> 2-ketoisocaproate<br>Gene |
| (spontaneous)<br>Reaction 8 |
| 2-ketoisocaproate –> 3-methylbutyraldehyde<br>Genes |
| kivd (*Lactococcus lactis*), kdcA (*Lactococcus lactis*), PDC1 (*Saccharomyces cerevisiae*), PDC5 (*Saccharomyces cerevisiae*), PDC6 (*Saccharomyces cerevisiae*) THI3 (*Saccharomyces cerevisiae*), ARO10 (*Saccharomyces cerevisiae*) or homologs thereof |

| Reaction 9 |
| --- |
| 3-methylbutyraldehyde –> 3-methyl-1-butanol |
| Genes |
| ADH1 (*Saccharomyces cerevisiae*), ADH2 (*Saccharomyces cerevisiae*), ADH3(*Saccharomyces cerevisiae*), ADH4 (*Saccharomyces cerevisiae*), ADH5(*Saccharomyces cerevisiae*), ADH6 (*Saccharomyces cerevisiae*), SFA1 (*Saccharomyces cerevisiae*) or homologs thereof |

Isobutanol Production Pathway (Via Pyruvate)

| Reaction 1 |
| --- |
| pyruvate –> 2-acetolactate |
| Genes |
| ilvHI (*E. coli*), ilvNB (*E. coli*), ilvGM (*E. coli*), alsS (*Bacillus subtilis*) or homologs thereof |
| Reaction 2 |
| 2-acetolactate –> 2,3-dihydroxy-isovalerate |
| Genes |
| ilvC (*E. coli*) or homologs thereof |
| Reaction 3 |
| 2,3-dihydroxy-isovalerate –> 2-keto-isovalerate |
| Genes |
| ilvD (*E. coli*) or homologs thereof |
| Reaction 4 |
| 2-keto-isovalerate –> isobutrylaldehyde |
| Genes |
| kivd (*Lactococcus lactis*), kdcA (*Lactococcus lactis*), PDC1 (*Saccharomyces cerevisiae*), PDC5 (*Saccharomyces cerevisiae*), PDC6 (*Saccharomyces cerevisiae*) THI3 (*Saccharomyces cerevisiae*), ARO10 (*Saccharomyces cerevisiae*) or homologs thereof |
| Reaction 5 |
| isobutrylaldehyde –> isobutanol |
| Genes |
| ADH1 (*Saccharomyces cerevisiae*), ADH2 (*Saccharomyces cerevisiae*), ADH3(*Saccharomyces cerevisiae*), ADH4 (*Saccharomyces cerevisiae*), ADH5(*Saccharomyces cerevisiae*), ADH6 (*Saccharomyces cerevisiae*), SFA1 (*Saccharomyces cerevisiae*) or homologs thereof |

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Q□-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

EXAMPLES

DNA polymerase KOD for PCR reactions can be purchased from EMD Chemicals (San Diego, Calif.). All restriction enzymes and Antarctic phosphatase can be obtain from New England Biolabs (Ipswich, Mass.). Rapid DNA ligation kit is available from Roche (Manheim, Germany). Oligonucleotides can be ordered from Operon (Huntsville, Ala.). All antibiotics and reagents in media are available from either Sigma Aldrich (St. Louis, Mo.) or Fisher Scientifics (Houston, Tex.).

Bacterial Strains.

Escherichia coli BW25113 ($rrnB_{T14}$ $\Delta lacZ_{WJ16}$ hsdR514 $\Delta araBAD_{AH33}$ $\Delta rhaBAD_{LD78}$) was designated as the wild-type (WT) (Datsenko and Wanner, Proc. Natl. Acad. Sci. USA 97, 6640-6645, 2000) for comparison. In some experiments for isobutanol, JCL16 ($rrnB_{T14}$ $\Delta lacZ_{WJ16}$ hsdR514$\Delta araBAD_{AH33}$ $\Delta rhaBAD_{LD78}$/F' (traD36, proAB+, lacIq Z$\Delta$11/115)) was used as wild-type (WT). Host gene deletions of metA, tdh, ilvB, ilvI, adhE, pta, ldhA, and pflP were achieved with P1 transduction using the Keio collection strains (Baba et al., Mol. Systems Biol. 2, 2006) as donor. The $kan^R$ inserted into the target gene region was removed with pCP20 (Datsenko and Wanner, supra) in between each consecutive knock out. Then, removal of the gene segment was verified by colony PCR using the appropriate primers. XL-1 Blue (Stratagene, La Jolla, Calif.) was used to propagate all plasmids.

Plasmid Construction.

pSA40, pSA55, and pSA62 were designed and constructed as described elsewhere herein. The lacI gene was amplified with primers lad SacI f and lacI SacI r from E. coli MG 1655 genomic DNA. The PCR product was then digested with SacI and ligated into the pSA55 open vector cut with the same enzyme behind the promoter of the ampicillin resistance gene, creating pSA55I.

The gene tdcB was amplified with PCR using primers tdcB f Acc65 and tdcB r SalI from the genomic DNA of E. coli BW25113 WT. The resulting PCR product was gel purified and digested with Acc65 and SalI. The digested fragment was then ligated into the pSA40 open vector cut with the same pair of enzymes, creating pCS14.

To replace the replication origin of pCS14 from colE1 to p15A, pZA31-luc was digested with SacI and AvrII. The shorter fragment was gel purified and cloned into plasmid pCS14 cut with the same enzymes, creating pCS16.

The operon leuABCD was amplified using primers A106 and A109 and E. coli BW25113 genomic DNA as the template. The PCR product was cut with SalI and BglII and ligated into pCS16 digested with SalI and BamHI, creating pCS20.

To create an expression plasmid identical to pSA40 but with p15A origin, the p15A fragment obtained from digesting pZA31-luc with SacI and AvrII was cloned into pSA40 open vector cut with the same restriction enzymes, creating pCS27.

The leuA* G462D mutant was constructed using SOE (Splice Overlap extension) with primers G462Df and G462Dr and the E. coli BW25113 WT genomic DNA as a template to obtain leuA*BCD. Then the SOE product was digested and cloned into the restriction sites Acc65 and XbaI to create PZE_leuABCD. The resulting plasmid was next used as a template to PCR out the leuA*BCD using primers A106 and A109. The product was cut with SalI and BglII and ligated into pCS27 digested with SalI and BamHI, creating pCS48.

The gene ilvA was amplified from E. coli BW25113 WT genomic DNA with primers A110 and A112. Next, it was cut with Acc65 and XhoI and ligated into the pCS48 open vector digested with Acc65 and SalI, creating pCS51.

The gene tdcB from the genomic DNA of E. coli BW25113 WT was amplified with PCR using primers tdcB f Acc65 and tdcB r SalI. The resulting PCR product was gel purified, digested with Acc65 and SalI and then ligated into the pCS48 open vector cut with the same pair of enzymes, creating pCS50.

WT thrABC was amplified by PCR using primers thrA f Acc65 and thrC r HindIII. The resulting product was digested with Acc65 and HindIII and cloned into pSA40 cut with the same pair of enzymes, creating pCS41.

To replace the replication origin of pCS41 from colE1 to pSC101, pZS24-MCS1 was digested with SacI and AvrII. The shorter fragment was gel purified and cloned into plasmid pCS41 cut with the same enzymes, creating pCS59.

The feedback resistant mutant thrA* was amplified by PCR along with thrB and thrC from the genomic DNA isolated from the threonine over-producer ATCC 21277 using primers thrA f Acc65 and thrC r HindIII. The resulting product was digested with Acc65 and HindIII and cloned into pSA40 cut with the same pair of enzymes, creating pCS43.

To replace the replication origin of pCS43 from colE1 to pSC101, pZS24-MCS1 was digested with SacI and AvrII. The shorter fragment was gel purified and cloned into plasmid pCS43 cut with the same enzymes, creating pCS49.

Branched-chain amino-acid aminotransferase (encoded by ilvE) and tyrosine aminotransferase (encoded by tyrB) were deleted by P1 transduction from strains disclosed in Baba et al.

To clone the L-valine biosynthesis genes i) ilvIHCD (EC) and ii) als (BS) along with ilvCD (EC), the low copy origin of replication (ori) from pZS24-MCS1 was removed by digestion with SacI and AvrII, and ligated into the corresponding sites of i) pSA54 and ii) pSA69 to create plasmid pIAA1 and pIAA11, respectively.

To clone kivd from L. lactis and ADH2 from S. cerevisiae, the ColE1 on of pSA55 was removed by digestion with SacI and AvrII and replaced with the p15A on of pSA54 digested with the same restriction enzymes to create pIAA13. To better control the expression of these genes, lad was amplified from E. coli MG 1655 genomic DNA with KOD polymerase using primers lacISacIf and lacISacIr and ligated into the SacI site of pCS22 to be expressed along with the ampicillin resistance gene, bla, and create plasmid pIAA12.

In order to overexpress the leuABCD operon in BW25113/F' from the chromosome, the native promoter and leader sequence was replaced with the $P_{LlacO-1}$ promoter. The $P_{LlacO-1}$ promoter was amplified from pZE12-luc with KOD polymerase using primers lacO1KanSOEf and lacO1LeuAlr. The gene encoding resistance to kanamycin, aph, was amplified from pKD13 using primers KanLeuO1f and KanlacO1SOEr. 1 μL of product from each reaction was added as template along with primers KanLeuO2f and lacO1LeuA2r, and was amplified with KOD polymerase using SOE. The new construct was amplified from the genomic DNA of kanamycin resistant clones using primers leuKOv1 and leuKOv2 and sent out for sequence verification to confirm the accuracy of cloning. To overexpress the leuABCD operon from plasmid, the p15A on from pSA54 was removed with SacI and AvrII and ligated into the corresponding sites of pCS22 (ColE1, $Cm^R$, $P_{LlacO-1}$:leuABCD) to create plasmid pIAA2. In order for tighter expression, lad was amplified and ligated as described previously for pIAA12 into pCS22 to be expressed along with the chloroamphenicol resistance gene, cat, and create plasmid pIAA15. Plasmid pIAA16 containing leuA(G1385A) encoding for IPMS (G462D) was created by ligating the 5.5 kb fragment of pIAA15 digested with XhoI and NdeI and ligating it with the 2.3 kb fragment of pZE12-leuABCD (ColE1, $Amp^R$, $P_{LlacO-1}$: leuA(G1385A)BCD) cut with the same restriction enzymes. To control for expression level, the RBS was replaced in pIAA15 to match that of pIAA16. To do this, the 5.6 kb fragment of pIAA16 from digestion with HindIII and NdeI was ligated with the 2.2 kb fragment of pIAA15 digested with the same enzymes to create pIAA17.

Media and Cultivation.

Certain strains were grown in a modified M9 medium (6 g $Na_2HPO4$, 3 g $KH_2PO_4$, 1 g $NH_4Cl$, 0.5 g NaCl, 1 mM $MgSO_4$, 1 mM $CaCl_2$, 10 mg Vitamin B1 per liter of water) containing 10 g/L of glucose, 5 g/L of yeast extract, and 1000× Trace Metals Mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water) inoculated 1% from 3 mL overnight cultures in LB into 10 mL of fresh media in 125 mL screw cap flasks and grown at 37° C. in a rotary shaker for 4 hours. The culture was then induced with 1 mM IPTG and grown at 30° C. for 18 hours. Antibiotics were added as needed (ampicillin 100 μg/mL, chloroamphenicol 35 μg/mL, kanamycin 50 μg/mL).

For some alcohol fermentation experiments, single colonies were picked from LB plates and inoculated into 3 ml of LB media with the appropriate antibiotics (ampicillin 100 μg/ml, kanamycin 50 μg/ml, and spectinomycin 50 μg/ml). The overnight culture grown in LB at 37° C. in a rotary shaker (250 rpm) was then inoculated (1% vol/vol) into 20 ml of M9 medium (6 g $Na_2HPO_4$, 3 g $KH_2PO_4$, 0.5 g NaCl, 1 g $NH_4Cl$, 1 mM $MgSO_4$, 10 mg vitamin B1 and 0.1 mM $CaCl_2$ per liter of water) containing 30 g/L glucose, 5 g/L yeast extract, appropriate antibiotics, and 1000× Trace Metal Mix A5 (2.86 g $H_3BO_3$, 1.81 g $MnCl_2.4H_2O$, 0.222 g $ZnSO_4.7H_2O$, 0.39 g $Na_2MoO_4.2H_2O$, 0.079 g $CuSO_4.5H_2O$, 49.4 mg $Co(NO_3)_2.6H_2O$ per liter water) in 250 ml conical flask. The culture was allowed to grow at 37° C. in a rotary shaker (250 rpm) to an $OD_{600}$ of 0.4~0.6, then 12 ml of the culture was transferred to a 250 ml screw capped conical flask and induced with 1 mM IPTG. The induced cultures were grown at 30° C. in a rotary shaker (240 rpm). Samples were taken throughout the next three to four days by opening the screwed caps of the flasks, and culture broths were either centrifuged or filtered to retrieve the supernatant. In some experiments as indicated, 8 g/L of threonine was added directly into the cell culture at the same time of induction.

α-keto acid experiments were done under oxygen 'rich' conditions unless otherwise noted. For oxygen rich experiments, 10 mL cultures in 250 mL baffled shake flasks were inoculated 1% from 3 mL overnight cultures in LB. For oxygen poor experiments, 10 mL cultures were inoculated in 125 mL screw caps. All cultures were grown at 37° C. for 4 hours and induced with 1 mM IPTG and harvested after 18 hrs of growth at 30° C.

Metabolite Detections.

The produced alcohol compounds can be quantified by a gas chromatograph (GC) equipped with flame ionization detector. The system includes model 5890A GC (Hewlett-Packard, Avondale, Pa.) and a model 7673A automatic injector, sampler and controller (Hewlett-Packard). Supernatant of culture broth (0.1 ml) is injected in split injection mode (1:15 split ratio) using methanol as the internal standard.

The separation of alcohol compounds is carried out by A DB-WAX capillary column (30 m, 0.32 mm-i.d., 0.50 μm-film thickness) purchased from Agilent Technologies (Santa Clara, Calif.). GC oven temperature is initially held at 40° C. for 5 min and raised with a gradient of 15° C./min until 120° C. It is then raised with a gradient of 50° C./min until 230° C. and held for 4 min. Helium is used as the carrier gas with 9.3 psi inlet pressure. The injector and detector are maintained at 225° C. 0.5 ul supernatant of culture broth is injected in split injection mode with a 1:15 split ratio. Methanol is used as the internal standard.

For other secreted metabolites, filtered supernatant is applied (20 ul) to an Agilent 1100 HPLC equipped with an auto-sampler (Agilent Technologies) and a BioRad (Biorad Laboratories, Hercules, Calif.) Aminex HPX87 column (5 mM $H_2SO_4$, 0.6 ml/min, column temperature at 65° C.). Glucose is detected with a refractive index detector, while organic acids are detected using a photodiode array detector at 210 nm. Concentrations are determined by extrapolation from standard curves.

For other secreted metabolites, filtered supernatant is applied (0.02 ml) to an Agilent 1100 HPLC equipped with an auto-sampler (Agilent Technologies) and a BioRad (Biorad Laboratories, Hercules, Calif.) Aminex HPX87 column (0.5 mM $H_2SO_4$, 0.6 mL/min, column temperature at 65° C.). Glucose is detected with a refractive index detector while organic acids are detected using a photodiode array detector at 210 nm. Concentrations are determined by extrapolation from standard curves.

Cyanobacteria encompass a large group of photosynthetic microorganisms that vary widely in morphology, habitat, and physiology. Included in this group is the unicellular *Synechococcus* sp. strain PCC 7942 (previously Anacystis nidulans R2), which is one of the few cyanobacterial strains which have been well-characterized in terms of physiology, biochemistry, and genetics. As stated previously, *S. elongatus* PCC7942 has been engineered to produce up to 1.1 g/L of isobutryaldehyde from $CO_2$ (see, e.g., Atsumi et al., 2009) by utilizing the microorganism's photosynthesis and CBB cycle. In addition to *S. elongatus* PCC7942, other cyanobacterial strains can be used. For example, *S. elongatus* PCC7002 has the ability to grow heterotrophically on glycerol and has a shorter generation time of 4 hr compared to 6.4 hr for *S. elongatus* PCC7942.

In order to engineer *S. elongatus* to utilize $H_2$ as an electron donor, strains that express hydrogenase genes from *Ra. eutropha*, *B. japonicum*, *R. capsulatus*, and *Rh. palustris* are constructed by chromosomal insertion of the expression cassettes into neutral site 1 (NSI). An expression cassette is thus created by cloning the individual genes into the NSI-targeting vector, pAM2991 under the IPTG-inducible Ptrc promoter. Methods for measuring in vitro and in vivo hydrogenase activity have been well-established (Vignais and Billoud, 2007) and can be used to determine the best hydrogenase for a particular system.

To improve the $H_2$ uptake rate of the hydrogenases error prone PCR can be used on one of the oxygen-tolerant hydrogenases (e.g., from *Ra. eutropha*). Under conditions where the photosynthetic activity of *Synechococcus* is relatively low (i.e., low light conditions), the fastest growing transformants can be analyzed for improvements in $H_2$ uptake (Vignais and Billoud, 2007). Other approaches can be used to capitalize on the loss of autotrophic growth, but maintenance of heterotrophic growth of a *Ra. eutropha* ΔhoxFUYG hydrogenase mutant (Massanz, 1998). An expression library of mutant, oxygen-tolerant hydrogenases created by error-prone PCR from *Ra. eutropha* and/or other species will be transformed into the *Ra. eutropha* ΔhoxFUYG hydrogenase mutant. Grown under lithoautotrophic conditions, the fastest growing transformants express mutant hydrogenases with improved $H_2$ uptake and/or activity, which can be ascertained by $H_2$ uptake assays (Vignais and Billoud, 2007). The genes that express these mutant hydrogenases with improved $H_2$ uptake activity can be cloned into the NSI-targeting vector and introduced into *S. elongatus* for expression.

In order to engineer *S. elongatus* to oxidize formate for the production of reducing equivalents, formate dehydrogenases (FDHs) are heterologously expressed in this microorganism. FDHs have been proven to be the most promising candidate for the development of NAD+ regeneration systems in organic synthesis for production of high-added-value products largely due to their wide pH-optimum (pH 6.0-9.0) and to the non-reversibility of enzymes (Burton, 2003; Hummel and Kula, 1989; Shaked et al., 1980; Wichmann and Vasic-Racki, 2005). Of the FDHs that have been studied, the one from *Candida boidinii* is the most commonly used for the development of NAD+ regeneration systems (Ohshima et al., 1985). Studies on *C. boidinii* FDH have identified mutations that confer altered cofactor specificity (Rozzell, 2004), improved catalytic activity (Slusarczyk, 2003), and enhanced chemical stability (Slusarczyk, 2003; Felber, 2001). Using various optimized FDH, the activity in *S. elongates* can be optimized, especially in altering the cofactor specificity from NAD(H) to NADP(H) because *S. elongatus* has a preference for NADP(H) (Tamoi et al., 2005).

Several FDHs have been integrated into the NSI site of *S. elongatus* PCC7942. The genes that encode the wild type and D195S/Y196H double mutant FDH from *C. boidinii* and the FDH from *M. thermoacetica* were each cloned into the NSI-targeting vector, under the IPTG-inducible Ptrc promoter: The D195S/Y196H double mutation was utilized because it results in a FDH with altered cofactor specificity from NAD (H) to NADP(H). The FDH gene from *Moorella thermoacetica*, encoded by Moth_2314, has been indicated to encode for an enzyme with formate:NADP+ oxidoreductase activity. This enzyme was chosen because of its cofactor preference.

In addition to the FDHs, other genes were also heterologously expressed to optimize formate utilization. To ensure efficient formate uptake, a formate transporter encoded by focA from *E. coli* was also overexpressed. Furthermore, to specifically generate NADPH from formate oxidization, several transhydrogenases including pntAB and udhA from *E. coli* have been introduced in combination with wild type NAD+-dependent *C. boidinii* FDH. By using enzymatic assays of crude cyanobacterial cell lysates, as well as HPLC measurements of formate consumption in flask culture, the co-expression of *E. coli* focA, *C. boidinii* wild type FDH, and *E. coli* pntAB enable *S. elongatus* to consume formate at a significant rate.

To improve $CO_2$ fixation, an additional copy of the CBB cycle genes, rbcLS, were integrated into the chromosome of the isobutyraldehyde *S. elongatus* PCC7942 production strain, resulting in a 2-fold increase in isobutyraldehyde (Atsumi et al., 2009). This example, along with successful examples of fructose-1,6/sedoheptulose-1,7-bisphosphatase overexpression (Miyagawa et al. 2001; Ma et al. 2005), illustrate that overexpression of CBB enzymes can enhance photosynthesis efficiency, growth characteristics, and biofuel production. Additional copies of many of the CBB cycle genes have been integrated into the NSI and NSII sites of *S. elongatus* PCC7942. Genes that have been integrated include those that encode for fructose-1-6-bisphosphatase 1 (Synpcc7942_2335), ribulose-phosphate 3-epimerase (Synpcc7942_0604), sedoheptulose bisphosphatase (Synpcc7942_0505), ribose 5-phosphate isomerase (Synpcc7942_0584), phosphoribulokinase (Synpcc7942_0977), and the *E. coli* transketolase, tktA.

In cyanobacteria and higher plants, $CO_2$ fixation is regulated by various regulation pathways, which can be divided into two major categories: transcriptional and posttranslational. In both cases, the redox status of the photosynthetic electron transportation chain has been proposed to play an important role in light sensing as the signaling input pathway (Buchanan and Balmer, 2005; Golden, 1995). Once received, the light signal is then relayed from the photosynthetic machinery to other cellular mediators, including various proteins in the ferredoxin/thioredoxin system and KaiABC oscillator system (Buchanan and Balmer, 2005; Ivleva et al., 2006; Lindahl and Florencio, 2003; Schmitz et al., 2000).

Transcription of most of the CBB cycle genes are significantly suppressed in the dark cycle (Ito et al., 2009; Nakahira et al., 2004). One of the most extensively studied regulation systems in *S. elongatus* PCC7942 is the KaiABC circadian rhythm oscillator system, which governs the global transcription profile in a diurnal cyclic fashion (Ishiura et al., 1998; Johnson et al., 2008). Recent studies have shown that transcriptional activity from most of the promoters in *S. elongatus* displayed substantial fluctuation over a day/night cycle (Ito et al., 2009; Liu et al., 1995; Smith and Williams, 2006). Moreover, the overall organization of the *S. elongatus* chromosome undergoes cyclic change (Nakahira et al., 2004; Smith and Williams, 2006), which may affect the expression level of both endogenous and genome-integrated heterogeneous production pathways. Previous studies have shown that disruption of the kaiABC gene cluster delivered the arrhythmia phenotype in *S. elongatus* PCC7942, although the average expression level of each individual gene in the genome was not dramatically altered (Ito et al., 2009). This and similar arrhythmic strains may be favored for $CO_2$ fixation in the dark, due to their steady global gene expression levels regardless of changing light condition. In addition, to maintain CBB gene expression at a high level, enzymes such as RuBisCO, phosphoribulokinase (PRK), and glyceraldehyde-3-phosphate dehydrogenase (GAPDH) can be constitutively overexpressed.

Posttranslational level (or protein level) regulation represents another layer of light/dark regulation of $CO_2$ fixation on top of transcriptional regulation. The exchange of dithiol/disulfide status controlled by the ferredoxin/thioredoxin system is one of these conserved posttranslational regulation mechanism utilized by chloroplasts of plants, algae, as well as photosynthetic microorganisms, to adjust enzyme activities according to light condition (Buchanan et al., 1980; Pfannschmidt et al., 2000; Buchanan et al., 2002; Lindahl et al., 2003). In light conditions, ferredoxin receives electrons from Photosystem I (PS I) and transfers them to thioredoxin (Trx), mediated by the enzyme ferredoxin-Trx reductase (FTR). Thioredoxin can then reduce disulfide bonds formed between cysteine residues within target enzymes and thus modulate their activities.

In contrast to higher plants, most enzymes in the CBB cycle of cyanobacterium *Synechocystis* sp. PCC 6803 are not directly regulated by the ferredoxin/thioredoxin system (Lindahl and Florencio, 2003). Specifically, although fructose-1,6-bisphosphatase (FBPase), NADP+-glycerolaldehyde-3-phosphate dehydrogenase (NADP+-GAPDH), and phosphoribulokinase (PRK) are greatly suppressed in the dark condition by redox regulation in higher plants (Buchanan, 1980), similar redox regulation of these three enzymes have been suggested to be absent in cyanobacteria *Synechocystis* sp. PCC 6803 and *Synechococcus elongatus* PCC7942 by biochemical studies (Tamoi et al., 1996; Tamoi et al., 1998). Consistently, it has also been indicated from amino acid sequence alignment that the potential regulatory cysteine residues are missing in cyanobacterial NADP+-GAPDH and FBPase (Tamoi et al., 1996; Tamoi et al., 1998).

Thus, removing ferredoxin/thioredoxin-mediated redox regulation of the CBB enzymes in cyanobacteria can be performed. RuBisCO has been suggested to be a conserved ferredoxin/thioredoxin target (Lindahl and Florencio, 2003). Fortunately, with a C172A mutation in the RuBisCO of *Synechocystis* sp. strain PCC6803, the inhibitory effect of oxidants that react with the vicinal thiols in RuBisCO is alleviated (Marcus et al., 2003). Since the regulatory cysteines are conserved among cyanobacteria species, these observations provided useful information for protein engineering in the construction of a redox-resistant RuBisCO in *S. elongatus* PCC7942.

Besides the universal redox regulation system shared by all photosynthetic organisms, cyanobacterial cells also possess other unique posttranslational mechanisms to regulate $CO_2$ fixation. For example, protein CP12 in *S. elongatus* PCC7942 has been found to form a complex with RuBisCO and GAPDH to inhibit their activities in the dark (Wedel and Soli, 1998). Furthermore, the formation of this complex is dynamically regulated by CP12, which is able to sense the NAD(H)/NADP(H) ratio under light/dark conditions (Tamoi et al., 2005). In cyanobacteria, mutations that prevent CP12 expression had no effect during conditions of continuous light, but resulted in inhibited growth in light/dark diurnal conditions presumably due to a carbon metabolism disorder related to leaky CBB cycle activity in the dark (Tamoi et al., 2005). By inactivating CP12 using genetic or protein engineering approaches, formation of the inhibitory complex could be eliminated, releasing the CBB cycle from light/dark regulation.

As a chemolithoautotroph, *Ra. eutropha* is able to derive its energy and reducing power from inorganic compounds or elements, such as $H_2$ or formate, to drive $CO_2$ fixation through the CBB cycle.

*Ra. eutropha* employs native hydrogen utilization pathways when it undergoes chemoautotrophic growth. Two types of hydrogen utilization pathways run in parallel to fuel the $CO_2$-fixing CBB cycle with ATP and NADPH: A membrane-bound hydrogenase (MBH), which oxidizes H2 and feeds electrons into the respiratory chain to generate ATP; and also a soluble hydrogenase (SH), which directly uses NAD (P)+ as an electron acceptor to produce NAD(P)H at the expense of $H_2$. In addition, several transhydrogenases convert NADH into NADPH in order to meet the NADPH needs required by the CBB cycle (Cramm, 2009; Pohlmann et al., 2006). *Ra. eutropha* hydrogenases belong to a family of (NiFe) bidirectional hydrogenases. However, unlike most of the members in the family, which are sensitive to very low oxygen concentrations, *Ra. eutropha* hydrogenases are relatively oxygen tolerant, consistent with the aerobic physiological nature of this organism.

Similarly, formate can serve as both an electron donor and carbon source to sustain autotrophic growth of *Ra. eutropha*. A membrane-bound formate dehydrogenase oxidizes formate and transports the electrons into respiratory chain; and a soluble formate dehydrogenase uses NAD+ as the electron acceptor. The $CO_2$ produced from formate oxidization is then assimilated (Cramm, 2009; Pohlmann et al., 2006).

$CO_2$ is fixed through the CBB cycle in *Ra. eutropha* to pyruvate. By engineering alsS from *B. subtilis*, ilvCD and yqhD from *E. coli*, and kivd from *L. lactis* into *Ra. eutropha* autotrophic isobutanol synthesis can be obtained.

To enhance isobutanol production efficiency, competing pathways that dissipate reducing equivalence or drain carbon flux can be eliminated. In *Ra. eutropha*, a prominent example would be the PHA production pathway. The cells can naturally accumulate up to about 70% PHA (of the cell mass), even in autotrophic conditions with $CO_2$ and $H_2$ as substrates (Tanaka et al., 1995), which utilizes a large portion of carbon source and NADPH pools. Fortunately, the PHA production pathway is very well known and genetic manipulation tools to perform knock-out studies are available.

To achieve high titer levels of isobutanol production, it is beneficial to isolate a mutant that has a higher tolerance to isobutanol. The gram-negative *Ra. eutropha* appears to have comparable solvent tolerance to that of *E. coli*. Given the success in developing and characterizing *E. coli* strains that can tolerate up to 8 g/L isobutanol, similar mutagenesis approaches can be utilized in addition to solvent challenging selection. Furthermore, based on high-throughput genomic DNA sequencing of the solvent tolerant strains generated by our group as well as others, rational strain engineering approaches may also become available.

Purple bacteria, such as *Rhodopsudomonas* and *Rhodobacter*, demonstrate lithoautotrophic and chemoautotrophic growth with many organic and inorganic electron donors, including hydrogen and formate. These microorganisms are able to grow in a mineral medium in the dark at the expense of hydrogen, oxygen, and $CO_2$. Although their growth is sensitive to $O_2$, the presence of methanol in the medium can improve oxygen tolerance (Siefert and Pfennig, 1979). Given these factorable characteristics *Rh. palustris* can be a host for isobutanol synthesis from $CO_2$ and $H_2$ or formate.

Either co-replicated plasmids or chromosome integration is used to express enzymes of the isobutanol pathway. Specifically, alsS from *B. subtilis*, ilvCD and yqhD from *E. coli*, and kivd and yqhD from *L. lactis* can be engineered into the microorganism. Functional expression of the pathway can be examined by enzyme assays and by measuring the production of isobutanol under chemoheterotrophic growth conditions. Isobutanol production in *Rh. palustris* can be investigated in electron-autotrophic conditions with hydrogen or formate as the electron donor. Electron-autotrophic biofuel production is performed in the dark under either aerobic or microaerobic conditions.

*Rh. palustris* is able to sense redox status and ATP levels, and is thus able to change metabolic modes according to changes in culture conditions (Larimer et al., 2004). Experimental evidence has shown that single-gene deletions of cbbRRS results in a significant reduction in total RuBisCO activity, which indicates that the cbbRRS is essential for RuBisCO expression (Romagnoli and Tabita, 2006). Therefore, in order to improve or maintain CBB cycle activity during different metabolic conditions, upregulation of cbbRRS by overexpression or modify the PAS domains of cbbR can be performed to make it more efficient in catalyzing the phosphorylation cascade.

To select host organisms for further development the host strain will be exposed to mutagens, and then the surviving culture will be enriched for chemoautotrophic growth. Through several generation of metabolic evolution, the fast-growing mutants will dominate the culture. Since fast growth indicates high carbon fixation rates, these mutants most likely will demonstrate improved CBB pathway efficiency and will be subject to further engineering, such as deregulation and overexpression of CBB pathway enzymes.

In addition, the metabolite profile of electron-autotrophic production conditions is analyzed with HPLC-DAD and GC-FID. Once the major by-products are confirmed, the critical genes that are responsible for their formation are identified for inactivation. The isobutanol production efficiency is also controlled by the reducing power supply. Overexpression of NAD(P)H-generating hydrogenases and formate hydrogenases can improve energy input and biofuel production efficiency in the system.

$H_2$ can be produced by the electrolysis of water. In conventional electrolyzers, 25~30% potassium hydroxide is added to facilitate the dissociation of water into H+ and OH−. It is however corrosive to operate electrolysis in a basic environment. As a result, solid polymer electrolyte membranes (SPE) or proton exchange membranes (PEM) were developed to aid in the splitting of water in a neutral environment. The SPE or PEM electrolyzer, as the name implies, contains a polymer as a membrane separating the cathode side from the anode side. The formation of $O_2$ and $H_2$ is separated into two compartments by a solid electrolyte membrane. One of the most commonly used solid electrolytes is nafion. The solvated $SO^{3-}$ ions act as the proton carriers, which carries protons from the anode to the cathode, which is later reduced to $H_2$. The efficiency of the SPE membrane electrolyzer is estimated to be about 80~94%.

The electro-autotrophic fermentation system uses gas-phase substrates to supply for carbon and reducing power needs. When the gases are fed into the bioreactor, the solubility of the gases will normally be very low. Fortunately, the electro-autotrophic organisms of the disclosure have lower metabolic activities compared to conventional sugar-based fermentations. In order to minimize energy consumption, impellers are avoided which are energy intensive. Instead, mass transfer and cell suspension will be used to optimize the gas circulation rate. The gas stream is replenished and recycled to complete a closed system with no $H_2$ outlet. In addition, the ratio of the three components ($H_2$, $O_2$, and $CO_2$) is optimized for growth and productivity. Optimization of pH, temperature, medium components (among others) is also performed and is within the skill in the art.

For isobutanol purification, several conventional n-butanol separation technologies are known (e.g. gas-stripping and adsorption).

To develop Ralstonia eutropha as an isobutanol producer the valine biosynthetic pathway was strengthened to make enough 2-KIV(2-ketoisovalerate), which is the precursor for isobutanol. The synthetic pathway genes to convert 2-KIV into isobutanol were then engineered into the microorganism.

Figure 1F:
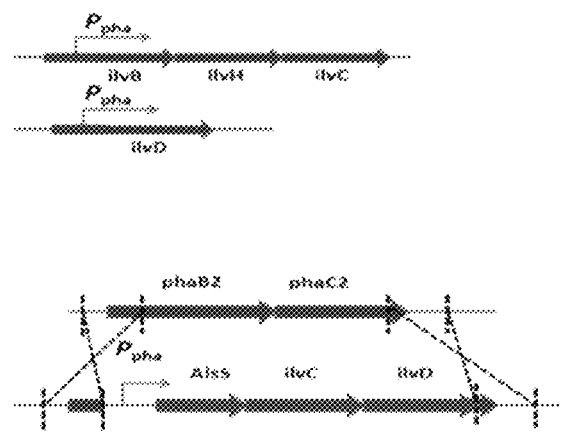

Since isobutanol is produced by decarboxylation and subsequent reduction of 2-Ketoisovalerate (2-KIV), an intermediate in valine biosynthesis, it is essential to enhance metabolic flux through valine biosynthesis pathway in the host. Two different approaches as shown in FIG. 1F were undertaken. As shown in FIG. 1F one approach taked was to strengthen natural valine biosynthetic pathway in Ralstonia, while a second approach taken was to introduce heterologous genes for valine biosynthesis pathway. In the genome of Ralstonia eutropha, the naturally existing 2-KIV biosynthesis pathway genes include ilvBHC and ilvD genes at separate loci. These natural genes were overexpressed within Ralstonia eutropha by chromosomal knocking-in of a strong phaC promoter in front of the corresponding operons as shown in FIG. 1F. Another approach introduced foreign genes for valine biosynthesis pathway. In the second method the artificial operon of alsS from B. subtilis and ilvCD from Escherichia coli was used under the phaC promoter of Ralstonia eutropha. This artificial operon was introduced into chromosomal phaB2-phaC2 loci by conjugational double-crossover integration as shown in FIG. 1F.

Figure 2C:
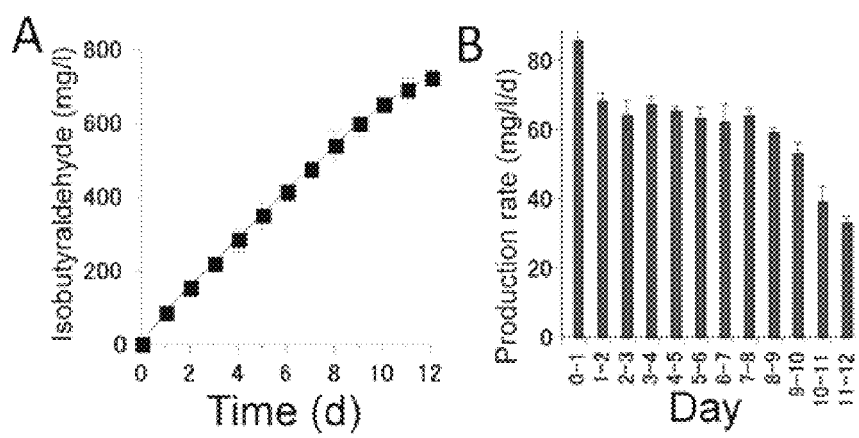
Figure 2C:
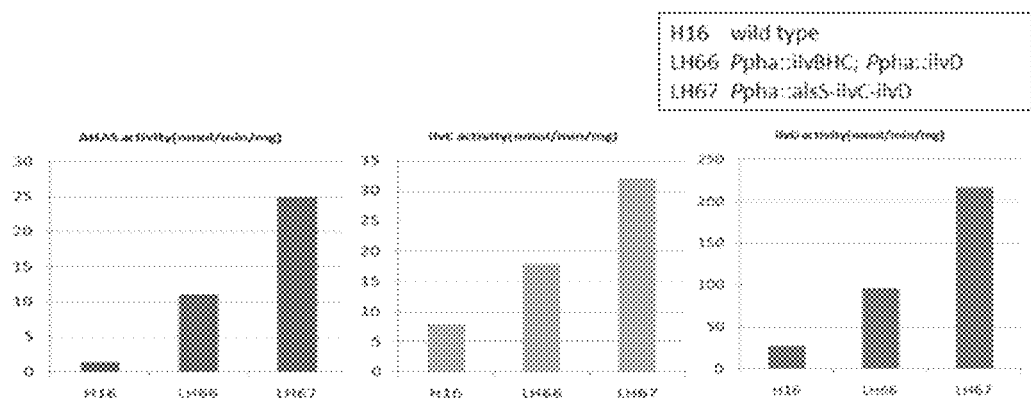

To verify the enhanced activities of 2-KIV production enzymes, the enzyme activities of these 3 enzymes was analyzed. As shown in FIG. 2C, compared to wild type Ralstonia eutropha strain H16, cells(LH66) with modifications in natural valine biosynthesis genes using the phaC promoter showed around 9 fold, 3 fold, and 4 fold increase of ilvBH, ilvC, ilvD activities, respectively. The alsS gene from Bacillus subtilis have higher catalytic activity and affinity to pyruvate and were expected to be more productive. As expected the strain (LH67), which has an integrated artificial operon of alsS from B. subtilis and ilvCD from Escherichia coli driven by phaC promoter in the genome, showed much better enzyme activities in all three enzymes. Therefore, this LH67 strain was used for the construction of isobutanol production strain in Ralstonia eutropha.

For the efficient conversion of 2-KIV into isobutanol, two more enzymatic reactions catalyzed by a 2-keto acid decarboxylase (KDC) and an alcohol dehydrogenase (ADH) were used. kivd from Lactococcus lactis was selected as the KDC for its high specificity towards 2-KIV and Adh2 from Saccharomyces cerevisiae and yqhD from E. coli were both tested as the ADH candidates for their different preference to cofactors NADH and NADPH, respectively. A plasmid containing kivd and either Adh2 or yqhD was transformed into Ralstonia cells and tested for activity to convert 2-KIV into isobutanol. Although the cells with kivd and Adh2 produced isobutanol from 2-KIV, the yqhD was a better alcohol dehydrogenase in Ralstonia to produce isobutanol efficiently. Based on these result, yqhD was shown to be more active for reducing isobutyaldehyde to isobutanol, because of the higher intracellular NADPH level than NADH in the Ralstonia eutropha.

Figure 2D:
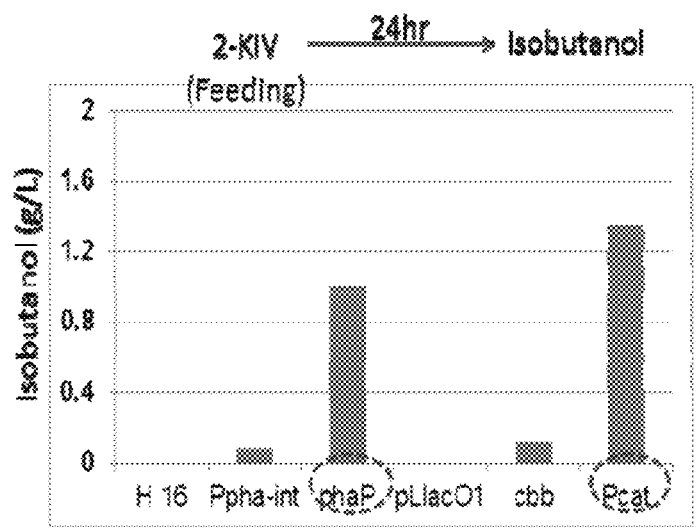

Using these two genes (kivd, yqhD), 5 different configurations were constructed for the expression of kivd and yqhD, either chromosomal or plasmid. After construction of strains, the efficiency of these enzymes expressed in Ralstonia were measured by feeding experiment of 2-KIV. After 24 hr, the isobutanol production from 2-KIV was measured from these strains. As shown in FIG. 2D, the kivd-yqhD operons driven by CAT gene promoter and phaP promoter were successful in converting 2-KIV into isobutanol. The plasmid harboring Pcat promoter version of kivd-yqhD operon was used for the construction of isobutanol production strain.

After construction of all the functionally expressed 5 genes needed for the production of isobutanol from pyruvate, the various enzymes and operons were engineered into one organism to construct an isobutanol producing Ralstonia eutropha strain. LH67, which showed the strongest enzyme activities for alsS and ilvCD, was transformed with the plasmid harboring the most efficient kivd-yqhD operon with Pcat promoter. The final strain, LH74, was tested for the production of isobutanol. In 5 L fermentor operation, this strain was found to produce 120 mg/L of isobutanol from fructose as carbon source in 40 hours. Interestingly, this strain also produced 180 mg/L of 3-Methyl-1-butanol, which is also good higher alcohol biofuel.

Figure 2E:
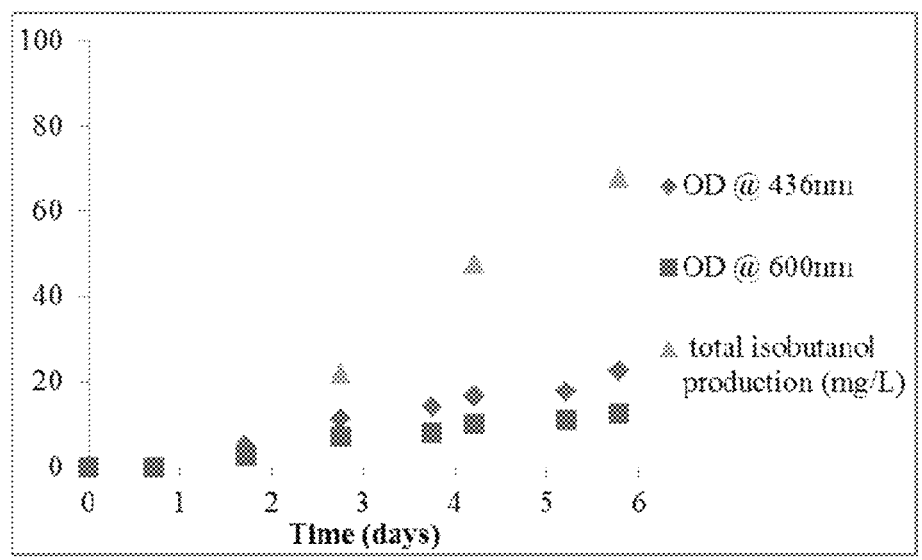

To test the electro-autotrophic production of isobutanol by R. eutropha strain LH74, the strain was cultured in minimal media using 5 L fermentor with autotrophic gas mixing condition (hydrogen, carbon dioxide, and oxygen=10:1:1). Carbon dioxide is the only carbon source provided in this fermentation. All gases were bubbled into the fermentor under atmospheric pressure and the pH of the culture was held constant at 7.0. The produced higher alcohols were collected using chilled condensing system from vent-gas line of fermentor. This fermentation was run over a 5.8 day period and produced a total 67.7 mg/L of isobutanol with a final $OD_{600nm}$ of 12.72 ($OD_{436nm}$ higher than 20) (FIG. 2E). Both the OD and the isobutanol production continued to climb over the duration of the 5.8 day fermentation. The isobutanol production showed no signs of a plateau after 5.8 days. However, under these conditions, major carbon flow from $CO_2$ fixation via CBB pathway is still directed toward cell mass production rather than biofuel production. This experiment demonstrates isobutanol production in autotrophic conditions using *R. eutropha* indicating successful electro-autotrophic production of higher alcohol.

From the intermediate 2-Ketoisovalerate (2-KIV) feeding experiment, the data suggested that the activity of the keto acid decarboxylation and reductation part of the pathway (catalyzed by kivd and yqhD) may not be the limiting factor of the production rate in vivo. Therefore, one of the hypotheses could be that the part of the pathway upstream of kivd and yqhD may be the bottleneck of isobutanol production in this strain. This part of the pathway overlaps with the native valine biosynthesis pathway and was enhanced by overexpressing alsS (*Bacillus subtilis*), ilvC (*Escherichia coli*), and ilvD (*Escherichia coli*). Although the activities of alsS, ilvC, and ilvD were measured in enzymatic assays and shown significant increased compared to wildtype strain, the absolute value of the enzymatic activity was lower than *E. coli* isobutanol production strains in other research. And because the alsS, ilvC, and ilvD operon was integrated into the *Ralstonia* chromosome with only one copy (LH74), it was reasoned that the relatively low activity of this part of the pathway may be due to the low gene dosage in the strain.

To explore this possibility, alsS, ilvC, and ilvD were also put into a multiple copy plasmid in addition to kivd and yqhD. The whole operon containing all five genes of the pathway was driven by the pPhaP promoter. After transforming this plasmid into wildtype Ralstonia cells, the resulted strain was able to produce around 200 mg/L isobutanol in one day in minimal medium with fructose as the substrate, which is over two fold of the amount produced by the previous strain in the same condition. The final titer of isobutanol can reach around 500 mg/L in minimal medium with fructose, although in these experiments the cell growth was retarded and the production limited after two days, indicating toxicity of the production pathway caused by the high level overexpression from the multiple copy plasmid.

Figure 2F:
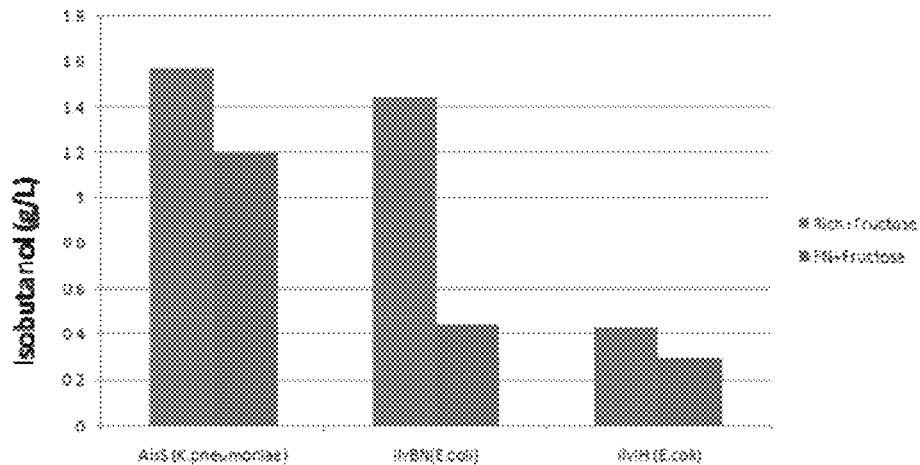

To overcome the toxicity effect while still maintaining the high gene dosage conveyed by the plasmid system, the alsS from *Bacillus subtilis* is replaced by several acetohydroxy acid synthase (AHAS) genes from different organisms in the multiple copy plasmids and tested for the activity and toxicity. The genes tested include ilvBN (*E. coli*), ilvIH (*E. coli*), and alsS (*Klebsiella pneumoniae*). The results showed that different AHAS proteins may have a broad range of activity in vivo, resulting in different isobutanol production rate and titer. For example, when alsS from *Klebsiella pneumoniae* is overexpressed, the cells were able to produce around 1.2 g/L isobutanol in minimal medium with fructose in one day as shown in FIG. 2F. However, although the AHASs tested vary in protein sequences and structures, all of them resulted in toxicity, indicating the toxicity of the pathway may not be due to the protein expression or folding problem related to one specific AHAS protein.

Figure 2G:
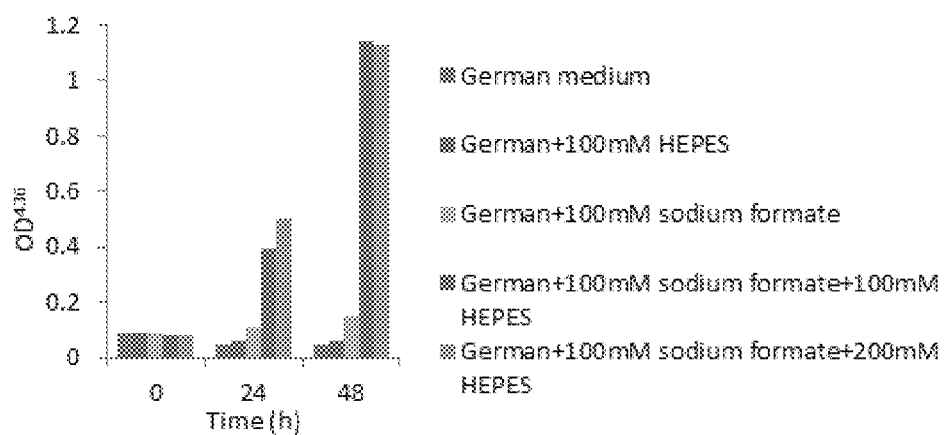

For electro-produced formate as a single carbon source, conditions for autotrophic growth on formate were developed. Under standard minimal medium (German medium) with formate, Ralstonia showed very poor growth as shown in FIG. 2G. To overcome this a buffered medium with HEPES was used to control pH during growth. Using this growth condition, more than $OD_{436nm}$ 1 was grown in 2 days.

The examples set forth above are provided to give those of ordinary skill in the art a complete disclosure and description of how to make and use the embodiments of the devices, systems and methods of the disclosure, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

Submitted on Jan. 15, 2011 along with the e-filing of this application is a .txt file of a sequence listing which is incorporated herein by reference in its entirety.

---

What is claimed is:

1. A recombinant microorganism capable of using $H_2$ or formate for reduction of $CO_2$ and wherein the microorganism produces an alcohol selected from the group consisting of 1-propanol, isobutanol, 1-butanol, 2-methyl 1-butanol, 3-methyl 1-butanol and 2-phenylethanol from $CO_2$ as the carbon source, wherein the alcohol is produced from a metabolite comprising a 2-keto acid and wherein the microorganism comprises expression of a heterologous or overexpression of an endogenous carbon-fixation enzyme and heterologous or overexpression of a hydrogenase and/or formate dehydrogenase such that the microorganism can utilize $H_2$ and/or formate as a reducing metabolite.

2. The recombinant microorganism of claim 1, wherein the microorganism has a naturally occurring $H_2$ and/or formate reduction pathway and at least one recombinant enzyme for the production of an intermediate in the synthesis of the alcohol.

3. The recombinant microorganism of claim 1, wherein the alcohol is isobutanol.

4. The recombinant microorganism of claim 1, wherein the 2-keto acid is selected from the group consisting of 2-ketobutyrate, 2-ketoisovalerate, 2-ketovalerate, 2-keto 3-methylvalerate, 2-keto 4-methyl-pentanoate, and phenylpyruvate.

5. The recombinant microorganism of claim 1, comprising elevated expression or activity of a 2-keto-acid decarboxylase and an alcohol dehydrogenase, as compared to a parental microorganism.

6. The recombinant microorganism of claim 5, wherein the 2-keto-acid decarboxylase is selected from the group consisting of Pdc6, Aro10, Thi3, Kivd, KdcA and Pdc, or homolog thereof.

7. The recombinant microorganism of claim 5, wherein the 2-keto-acid decarboxylase is encoded by a nucleic acid sequence derived from a gene selected from the group consisting of PDC6, ARO10, THI3, kivd, kdcA and pdc, or homolog thereof.

8. The recombinant microorganism of claim 7, wherein the 2-keto-acid decarboxylase is encoded by a nucleic acid sequence derived from the kivd gene, or homolog thereof.

9. The recombinant microorganism of claim 5, wherein the alcohol dehydrogenase is Adh2, YqhD, or homolog thereof.

10. The recombinant microorganism of claim 5, wherein the alcohol dehydrogenase is encoded by a nucleic acid sequence derived from the adh2 gene, the yqhD gene, or homolog thereof.

11. The recombinant microorganism of claim 1, wherein the recombinant microorganism is obtained from a parental organism of a genus selected from *Escherichia, Corynebacterium, Lactobacillus, Lactococcus, Salmonella, Enterobacter, Enterococcus, Erwinia, Pantoea, Morganella, Pectobacterium, Proteus, Serratia, Shigella, Klebsiella, Citrobacter, Saccharomyces, Dekkera, Klyveromyces, Pichia,* and *Ralstonia.*

12. The recombinant microorganism of claim 11, wherein the biosynthetic pathway for the production of an amino acid in the organism is modified for production of the alcohol.

13. The recombinant microorganism of claim 1, wherein the microorganism comprises reduced ethanol production capability compared to a parental microorganism.

14. The recombinant microorganism of claim 1 or 11, wherein the microorganism comprises a reduction or inhibition in the conversion of acetyl-coA to ethanol.

15. The recombinant microorganism of claim 1, wherein the recombinant microorganism comprises a reduction of an ethanol dehydrogenase thereby providing a reduced ethanol production capability.

16. The recombinant microorganism of claim 14, wherein the microorganism is derived from *E. coli.*

17. The recombinant microorganism of claim 14, wherein the ethanol dehydrogenase is an adhE, homolog or variant thereof.

18. The recombinant microorganism of claim 17, wherein the microorganism comprises a deletion or knockout of an adhE, homolog or variant thereof.

19. The recombinant microorganism of claim 1, wherein the microorganism comprises expression or elevated expression of an enzyme that converts pyruvate to alpha-keto-isovalerate.

20. The recombinant microorganism of claim 19, wherein the enzyme is 2-keto-acid decarboxylase.

21. The recombinant microorganism of claim 5 or 20, wherein the 2-keto-acid decarboxylase is selected from the group consisting of Pdc, Pdc1, Pdc5, Pdc6, Aro10, Thi3, Kivd, and KdcA, a homolog or variant of any of the foregoing, and a polypeptide having at least 60% identity to any one of the foregoing and having 2-keto-acid decarboxylase activity.

22. The recombinant microorganism of claim 5 or 20, wherein the 2-keto-acid decarboxylase is encoded by a polynucleotide having at least 60% identity to a nucleic acid selected from the group consisting of pdc, pdc1, pdc5, pdc6, aro10, thi3, kivd, kdcA, a homolog or variant of any of the foregoing, or a fragment thereof and wherein the polynucleotide encodes a polypeptide having 2-keto acid decarboxylase activity.

23. The recombinant microorganism of claim 22, wherein the 2-keto-acid decarboxylase is encoded by a polynucleotide derived from a kivd gene, or homolog thereof.

24. The recombinant organism of claim 5, wherein the alcohol dehydrogenase is selected from the group consisting of Adh1, Adh2, Adh3, Adh4, Adh5, Adh6, Sfa1, YqhD, a homolog or variant of any of the foregoing, and a polypeptide having at least 60% identity to any one of the foregoing and having alcohol dehydrogenase activity.

25. The recombinant microorganism of claim 5, wherein the alcohol dehydrogenase is encoded by a polynucleotide having at least 60% identity to a nucleic acid selected from the group consisting of an adh1, adh2, adh3, adh4, adh5, adh6, sfa1, yqhD gene, and a homolog of any of the foregoing and wherein the polynucleotide encodes a protein having alcohol dehydrogenase activity.

26. The recombinant microorganism of claim 11, wherein the recombinant microorganism comprises one or more deletions or knockouts in a gene encoding an enzyme that catalyzes the conversion of acetyl-coA to ethanol, catalyzes the conversion of pyruvate to lactate, catalyzes the conversion of fumarate to succinate, catalyzes the conversion of acetyl-coA and phosphate to coA and acetyl phosphate, catalyzes the conversion of acetyl-coA and formate to coA and pyruvate, condensation of the acetyl group of acetyl-CoA with 3-methyl-2-oxobutanoate (2-oxoisovalerate), isomerization between 2-isopropylmalate and 3-isopropylmalate, catalyzes the conversion of alpha-keto acid to branched chain amino acids, synthesis of Phe Tyr Asp or Leu, catalyzes the conversion of pyruvate to acetly-coA, catalyzes the formation of branched chain amino acids, catalyzes the formation of alpha-ketobutyrate from threonine, catalyzes the first step in methionine biosynthesis, and catalyzes the catabolism of threonine.

27. The recombinant microorganism of claim 1 or 26, wherein the recombinant microorganism comprises one or more gene deletions selected from the group consisting of adhE, ldhA, frdBC, fnr, pta, pflb, leuA, leuB, leuC, leuD, ilvE, tyrB, poxB, ilvB, ilvI, ilvA, metA, tdh, homologs of any of the foregoing and naturally occurring variants of any of the foregoing.

28. The recombinant microorganism of claim 1, comprising a genotype selected from the group consisting of:
(a) a deletion or knockout selected from the group consisting of ΔadhE, ΔldhA, Δpta, ΔleuA, ΔleuB, ΔleuC, ΔleuD, ΔpoxB, ΔilvB, ΔilvI, ΔmetA, Δtdh and any combination thereof and comprising an expression or increased expression of kivd, ThrABC and adh2, wherein the microorganism produces 1-propanol;
(b) a deletion or knockout selected from the group consisting of ΔadhE, ΔldhA, ΔfrdB, ΔfrdC, Δfnr, Δpta, ΔpflB, ΔleuA, ΔilvE, ΔpoxB, ΔilvA, and any combination thereof and comprising an expression or increased expression of kivd, ThrABC and adh2 wherein the microorganism produces isobutanol;
(c) a deletion or knockout selected from the group consisting of ΔadhE, ΔldhA, Δpta, ΔpoxB, ΔilvB, ΔilvI, ΔmetA, Δtdh, and any combination thereof and comprising an expression or increased expression of kivd, ThrABC and adh2 wherein the microorganism produces 1-butanol; and
(d) a deletion or knockout selected from the group consisting of ΔadhE, ΔldhA, ΔfrdB, ΔfrdC, Δfnr, Δpta, ΔpflB, ΔilvE, ΔtyrB, and any combination thereof and comprising an expression or increased expression of kivd, ThrABC and adh2 wherein the microorganism produces 3-methyl 1-butanol.

29. The recombinant microorganism of claim 3, wherein the microorganism produces greater than 100 mg/L of isobutanol in 40 hours from sugar.

30. The recombinant microorganism of claim 1, wherein the microorganism produces greater than 150 mg/L of 3-methyl-1-butanol in 40 hours from sugar.

31. The recombinant microorganism of claim 1, wherein the microorganism produces 120 mg/L of isobutanol or 180 mg/L of 3-methyl-1-butanol.

32. A method of producing a biofuel, comprising culturing a microorganism of claim 1 under conditions and in the presence of a suitable carbon source and reducing agent and isolating the biofuel.

33. The method of claim 32, wherein the biofuel is isobutanol.

34. The method of claim 32, wherein the reducing agent is formate or $H_2$.

35. The method of claim 32, wherein the microorganism is obtained from a *Ralstonia* sp. parental organism.

* * * * *